(12) United States Patent
Klaerner et al.

(10) Patent No.: US 11,311,571 B2
(45) Date of Patent: Apr. 26, 2022

(54) PROTON-BINDING POLYMERS FOR ORAL ADMINISTRATION

(71) Applicant: Tricida, Inc., South San Francisco, CA (US)

(72) Inventors: Gerrit Klaerner, Hillsborough, CA (US); Eric F. Connor, Los Gatos, CA (US); Randi K. Gbur, Brisbane, CA (US); Matthew J. Kade, Berkeley, CA (US); Paul H. Kierstead, Oakland, CA (US); Jerry M. Buysse, Los Altos, CA (US); Michael J. Cope, Berkeley, CA (US); Kalpesh N. Biyani, Dublin, CA (US); Son H. Nguyen, Milpitas, CA (US); Scott M. Tabakman, Palo Alto, CA (US)

(73) Assignee: TRICIDA, INC., South San Francisco, CA (US)

( * ) Notice: Subject to any disclaimer, the term of this patent is extended or adjusted under 35 U.S.C. 154(b) by 310 days.

(21) Appl. No.: 15/533,705

(22) PCT Filed: Dec. 10, 2015

(86) PCT No.: PCT/US2015/065041
§ 371 (c)(1),
(2) Date: Jun. 7, 2017

(87) PCT Pub. No.: WO2016/094685
PCT Pub. Date: Jun. 16, 2016

(65) Prior Publication Data
US 2018/0021370 A1 Jan. 25, 2018

Related U.S. Application Data

(60) Provisional application No. 62/090,287, filed on Dec. 10, 2014.

(51) Int. Cl.
*A61K 31/785* (2006.01)
*C08F 8/02* (2006.01)
*C08F 226/02* (2006.01)
*C08F 26/02* (2006.01)

(52) U.S. Cl.
CPC .............. *A61K 31/785* (2013.01); *C08F 8/02* (2013.01); *C08F 26/02* (2013.01); *C08F 226/02* (2013.01)

(58) Field of Classification Search
CPC ..... A61K 31/785; C08F 26/02; C08F 226/02; C08F 8/02
See application file for complete search history.

(56) References Cited

U.S. PATENT DOCUMENTS

| | | |
|---|---|---|
| 5,496,545 A | 3/1996 | Holmes-Farley et al. |
| 5,643,951 A | 7/1997 | Stacpoole et al. |
| 5,648,355 A | 7/1997 | Theoharides |
| 5,667,775 A | 9/1997 | Holmes-Farley et al. |
| 5,679,717 A | 10/1997 | Mandeville, III et al. |
| 5,753,706 A | 5/1998 | Hsu |
| 6,271,264 B1 | 8/2001 | Dhal et al. |
| 6,444,221 B1 | 9/2002 | Shapiro |
| 6,468,964 B1 | 10/2002 | Rowe |
| 6,485,703 B1 | 11/2002 | Cote et al. |
| 6,726,905 B1 | 4/2004 | Mandeveille, III et al. |
| 6,733,780 B1 | 5/2004 | Tyler et al. |
| 6,877,408 B2 | 4/2005 | Kubota et al. |
| 7,335,795 B2 | 2/2008 | Chang et al. |
| 7,342,083 B2 | 3/2008 | Chang et al. |
| 7,449,605 B2 | 11/2008 | Chang et al. |
| 7,459,502 B2 | 12/2008 | Connor et al. |
| 7,608,674 B2 | 10/2009 | Connor et al. |
| 7,754,199 B2 | 7/2010 | Chang et al. |
| 7,767,229 B1 | 8/2010 | Milne et al. |
| 7,767,768 B2 | 8/2010 | Chang et al. |
| 7,767,851 B2 | 8/2010 | Kwok et al. |
| 7,815,898 B2 | 10/2010 | Savica |
| 7,846,425 B2 | 12/2010 | Hedge et al. |
| 7,964,182 B2 | 6/2011 | Omray et al. |
| 7,985,418 B2 | 7/2011 | Bhagat et al. |
| 8,003,600 B2 | 8/2011 | Hageman |
| 8,084,397 B2 | 12/2011 | Li et al. |

(Continued)

FOREIGN PATENT DOCUMENTS

| | | |
|---|---|---|
| CN | 1503676 | 6/2004 |
| CN | 1878822 | 12/2006 |

(Continued)

OTHER PUBLICATIONS

Inoue et al., Highly selective and low-swelling phosphate-binding polymer for hyperphosphatema therapy, Chem. Letters, 2012, 41, 932-933.
Kioussis et al., Reactive nitrogen and phosphorus removal from aquaculture wastewater effluents using polymer hydrogels, Aquacultural Engineering, 2000, 23: 315-332.
Kioussis et al., Phosphate binding polymeric hydrogels for aquaculture wastewater remediation, Aquacultural Engineering, 1999, 19: 163-178.
Kioussis et al., Selective anion sorption and recovery from wastewater by polyelectrolyte hydrogels, Polymer Preprints, 2000, 41(2): 1679-1680.
Patent Cooperation Treaty, International Search Report for PCT/US2015/065041, dated Mar. 22, 2016, 5 pgs.

(Continued)

*Primary Examiner* — Hasan S Ahmed
(74) *Attorney, Agent, or Firm* — Bryan Cave Leighton Paisner LLP

(57) ABSTRACT

Pharmaceutical compositions for and methods of treating an animal, including a human, and methods of preparing such compositions. The pharmaceutical compositions contain crosslinked amine polymers and may be used, for example, to treat diseases or other metabolic conditions in which removal of protons and/or chloride ions from the gastrointestinal tract would provide physiological benefits such as normalizing serum bicarbonate concentrations and the blood pH in an animal, including a human.

11 Claims, 3 Drawing Sheets

(56) References Cited

U.S. PATENT DOCUMENTS

| | | |
|---|---|---|
| 8,163,799 B2 | 4/2012 | Dhal et al. |
| 8,187,634 B2 | 5/2012 | Hedge et al. |
| 8,273,384 B2 | 9/2012 | Wurzberger |
| 8,349,305 B2 | 1/2013 | Chang et al. |
| 8,394,416 B2 | 3/2013 | Bianchi et al. |
| 8,399,025 B2 | 3/2013 | Roy et al. |
| 8,445,014 B2 | 5/2013 | Charmot et al. |
| 8,530,519 B2 | 9/2013 | Ueno |
| 8,586,097 B2 | 11/2013 | Liu et al. |
| 8,842,086 B2 | 9/2014 | Ogg |
| 8,986,669 B2 | 3/2015 | Huval et al. |
| 9,205,107 B2 | 12/2015 | Klaerner et al. |
| 9,925,214 B2 | 3/2018 | Klaerner et al. |
| 9,993,500 B2 | 6/2018 | Klaerner et al. |
| 10,363,268 B2 | 7/2019 | Klaerner et al. |
| 10,369,169 B1 | 8/2019 | Klaerner et al. |
| 10,391,118 B2 | 8/2019 | Klaerner et al. |
| 2002/0110560 A1 | 8/2002 | Demuth et al. |
| 2002/0159968 A1 | 10/2002 | Petersen et al. |
| 2003/0039627 A1 | 2/2003 | Holmes-Farley et al. |
| 2003/0091530 A1 | 5/2003 | Goto et al. |
| 2003/0092782 A1 | 5/2003 | Goto et al. |
| 2004/0059065 A1 | 3/2004 | Goto et al. |
| 2005/0090553 A1 | 4/2005 | Shapiro |
| 2005/0131138 A1* | 6/2005 | Connor ............... A61P 3/12 524/612 |
| 2005/0220750 A1 | 10/2005 | Robert et al. |
| 2005/0220751 A1 | 10/2005 | Charmot et al. |
| 2005/0220752 A1 | 10/2005 | Charmot et al. |
| 2005/0220889 A1 | 10/2005 | Charmot et al. |
| 2005/0220890 A1 | 10/2005 | Charmot et al. |
| 2005/0234129 A1 | 10/2005 | Sutton et al. |
| 2006/0024336 A1 | 2/2006 | Charmot et al. |
| 2006/0034847 A1 | 2/2006 | Yun et al. |
| 2007/0098678 A1 | 5/2007 | Bhagat et al. |
| 2007/0135335 A1 | 6/2007 | Collier et al. |
| 2007/0293429 A1 | 12/2007 | Nestor |
| 2008/0200533 A1 | 8/2008 | Krishnan |
| 2008/0207766 A1 | 8/2008 | Devane |
| 2008/0214440 A1 | 9/2008 | Nestor |
| 2008/0248012 A1 | 10/2008 | Suematsu |
| 2008/0317729 A1 | 12/2008 | Kasch et al. |
| 2009/0053317 A1 | 2/2009 | Vigo et al. |
| 2009/0131338 A1 | 5/2009 | Saou et al. |
| 2009/0155368 A1 | 6/2009 | Holmes-Farley et al. |
| 2009/0155370 A1 | 6/2009 | Cope et al. |
| 2009/0156647 A1 | 6/2009 | Molino et al. |
| 2009/0162314 A1 | 6/2009 | Huval et al. |
| 2009/0325860 A1 | 12/2009 | Costantino et al. |
| 2010/0008988 A1 | 1/2010 | Mehta et al. |
| 2010/0035992 A1 | 2/2010 | Bhushan et al. |
| 2010/0080858 A1 | 4/2010 | Satou et al. |
| 2010/0104527 A1 | 4/2010 | Mansky et al. |
| 2010/0111891 A1 | 5/2010 | Albrecht et al. |
| 2010/0113479 A1 | 5/2010 | Choudhury et al. |
| 2010/0124542 A1 | 5/2010 | Dhal et al. |
| 2010/0129309 A1 | 5/2010 | Dhal et al. |
| 2010/0135950 A1 | 6/2010 | Huval et al. |
| 2010/0166616 A1 | 7/2010 | Dhal et al. |
| 2010/0166861 A1 | 7/2010 | Lynch |
| 2010/0189679 A1 | 7/2010 | Inoue et al. |
| 2010/0234309 A1 | 9/2010 | Cooper et al. |
| 2010/0316589 A1 | 12/2010 | Charmot et al. |
| 2011/0064820 A1 | 3/2011 | Omray et al. |
| 2011/0081413 A1 | 4/2011 | Omray |
| 2011/0142952 A1 | 6/2011 | Harris et al. |
| 2011/0189121 A1 | 8/2011 | Genth et al. |
| 2011/0263493 A1 | 10/2011 | Dugi et al. |
| 2011/0268666 A1 | 11/2011 | Friedman et al. |
| 2012/0219626 A1 | 8/2012 | Osinga |
| 2012/0259098 A1 | 10/2012 | Baker, Jr. et al. |
| 2012/0288471 A1 | 11/2012 | Huval et al. |
| 2013/0022570 A1 | 1/2013 | Kopping et al. |
| 2013/0130995 A1 | 5/2013 | Currie et al. |
| 2013/0131202 A1 | 5/2013 | Albrecht et al. |
| 2013/0137772 A1 | 5/2013 | Bergeron |
| 2013/0156720 A1 | 6/2013 | Currie |
| 2013/0189215 A1 | 7/2013 | Lees et al. |
| 2013/0189216 A1 | 7/2013 | Albrecht et al. |
| 2013/0251667 A1 | 9/2013 | Dhal et al. |
| 2013/0266533 A1 | 10/2013 | Dhal et al. |
| 2013/0345303 A1 | 12/2013 | Poradosu et al. |
| 2014/0105848 A1 | 4/2014 | Klaerner et al. |
| 2015/0056451 A1 | 2/2015 | Klaerner et al. |
| 2016/0074430 A1 | 3/2016 | Klaerner et al. |
| 2017/0095441 A1 | 4/2017 | Kwok et al. |
| 2018/0021370 A1 | 1/2018 | Klaerner et al. |
| 2018/0280428 A1 | 10/2018 | Klaerner et al. |
| 2019/0134075 A1 | 5/2019 | Klaerner et al. |
| 2019/0209607 A1 | 7/2019 | Klaerner et al. |
| 2021/0187011 A1 | 6/2021 | Klaerner et al. |
| 2021/0347925 A1 | 11/2021 | Klaerner et al. |

FOREIGN PATENT DOCUMENTS

| | | | |
|---|---|---|---|
| CN | 101687961 | 3/2010 | |
| CN | 105377270 | 3/2016 | |
| EP | 2168992 | 3/2010 | |
| EP | 1931689 | 2/2015 | |
| RU | 2160742 | 12/2000 | |
| RU | 2008136081 | 3/2010 | |
| RU | 2392926 | 6/2010 | |
| WO | 9940990 | 8/1999 | |
| WO | 2005041900 | 5/2005 | |
| WO | 2005041902 | 5/2005 | |
| WO | 2005092039 | 10/2005 | |
| WO | 2007022435 | 2/2007 | |
| WO | 2007038801 | 4/2007 | |
| WO | 2007056405 | 5/2007 | |
| WO | 2008011047 | 1/2008 | |
| WO | 2008027551 | 3/2008 | |
| WO | 2008103368 | 8/2008 | |
| WO | 2009023544 | 2/2009 | |
| WO | 2009097127 | 8/2009 | |
| WO | 2009125443 | 10/2009 | |
| WO | WO/2009/125433 | * 10/2009 | ........... A61K 31/785 |
| WO | 2012011063 | 1/2012 | |
| WO | 2014197725 | 12/2014 | |
| WO | 2015066593 | 2/2015 | |
| WO | 2016096685 | 6/2016 | |
| WO | 2017193024 | 11/2017 | |
| WO | 2017193050 | 11/2017 | |
| WO | 2017193064 | 11/2017 | |
| WO | 2019090176 | 5/2019 | |
| WO | 2019090177 | 5/2019 | |
| WO | 2019236124 | 12/2019 | |
| WO | 2019236636 | 12/2019 | |
| WO | 2019236639 | 12/2019 | |

OTHER PUBLICATIONS

Patent Cooperation Treaty, Written Opinion issued for PCT/US2015/065041, dated Mar. 22, 2016, 8 pgs.

European Patent Office, Extended European Search Report issued for App. No. 17177221.3, dated Jan. 23, 2018, 8 pgs.

Akizawa et al., Bixalomer in Hyperphosphatemic Patients With Chronic Kidney Disease Not on Dialysis: Phase 3 Randomized Trial, Therapeutic Apheresis and Dialysis, 2016, 10 pgs.

Akizawa et al., Randomized Controlled Trial of Bixalomer Versus Sevelamer Hydrochloride in Hemodialysis Patients With Hyperphosphatemia, Therapeutic Aphreresis and Dialysis, 2014, 18(2): 122-131.

Akizawa et al., Long-Term Safety and Efficacy of Bixalomer in Hyperphosphatemic Patients With Chronic Kidney Disease Not on Dialysis, Therapeutic Apheresis and Dialysis, 2017, 7pgs.

Beaubien-Souligny et al., The effect of lanthanum carbonate on metabolic acidosis in patients with chronic kidney disease stage IV, V and V-D, Int Urol Nephrol, 2015, 7pgs.

Bezzaoucha et al., The role of sevelamer carbonate in increasing serum bicarbonate in hyperphosphatemic pre-dialysis patients who have metabolic acidosis, Intern. Journal of Clinical Pharmacology and Therapeutics, 2013, 51: 989-990.

(56) References Cited

OTHER PUBLICATIONS

Bushinsky et al., Randomized, Controlled Trial of TRC101 to Increase Serum Bicarbonate in Patients with CKD, Clin J Am Soc Nephrol, 2018, 10pgs.
Chen et al., Epidemiology of Acid-Base Derangements in CKD, Adv Chronic Kidney Dis., 2017, 24(5):280-288.
Garneata et al., Ketoanalogue-Supplemented Vegetarian Very Low-Protein Diet and CKD Progression, J Am Soc Nephrol., 2016, 27:2164-2176.
Pai et al., Comparison of Sevelamer Hydrochloride and Sevelamer Carbonate: Risk of Metabolic Acidosis and Clinical Implications, Pharmacotherapy, 2009, 29(5):554-561.
Mahajan et al., Daily oral sodium bicarbonate preserves glomerular filtration rate by slowing its decline in early hypertensive nephropathy, Kidney International, 2010, 78, 303-309.
Goraya et al., Treatment of metabolic acidosis in patients with stage 3 chronic kidney disease with fruits and vegetables or oral bicarbonate reduces urine angiotensinogen and preserves glomerular filtration rate, Kidney International, 2014, 86:1031-1038.
Goraya et al., Management of the Metabolic Acidosis of Chronic Kidney Disease, Adv Chronic Kidney Dis., 2017, 24(5):298-304.
Goraya et al., A Comparison of Treating Metabolic Acidosis in CKD Stage 4 Hypertensive Kidney Disease with Fruits and Vegetables or Sodium Bicarbonate, Clin J Am Soc Nephrol, 2013, 8: 371-381.
Hatakeyama et al., Switching hemodialysis patients from sevelamer hydrochloride to bixalomer: a single-center, non-randomized analysis of efficacy and effects on gastrointestinal symptoms and metabolic acidosis, BMC Nephrology, 2013, 14:222-229.
Husted et al., NaHC03 and NaCl tolerance in chronic renal failure II, Clinical Nephrology, 1977, 7(1):21-25.
Lindley et al., Correction of metabolic acidosis after conversion from sevelamer hydrochloride to lanthanum carbonate, NDT Plus, 2008, 3:196.
Raphael, K.L., Metabolic Acidosis and Subclinical Metabolic Acidosis in CKD, J Am Soc Nephrol 29, 2017, 7pgs.
Thet et al., Differential effects of phosphate binders on pre-dialysis serum bicarbonate in end-stage kidney disease patients on maintenance haemodialysis, BMC Nephrology, 2013, 14:205-215.
Rombola et al., Lanthanum carbonate: a postmarketing observational study of efficacy and safety, Jour Nephrol, 2012, 25(4): 490-496.
Susantitaphong et al., Short- and Long-Term Effects of Alkali Therapy in Chronic Kidney Disease: A Systematic Review. Am J Nephrol, 2012, 35:540-547.
Steed et al., Supramolecular Chemistry, 2nd Edition, John Wiley & Sons, Ltd. West Sussex, United Kingdom, 216-279.
Adrogue et al., Respiratory Acidosis, Respiratory Alkalosis, and Mixed Disorders in Comprehensive Clinical Nephrology, 4th Edition, 2010, Elsevier Saunders, St. Louis, Missouri, Ch. 14, 176-189.
Ballmer et al., Chronic metabolic acidosis decreases albumin synthesis and induces negative nitrogen balance in humans. The Journal of Clinical Investigation, 1995, 95: 39-45.
Brezina et al., Acid loading during treatment with sevelamer hydrocholoride: Mechanisms and clinical implications, Kidney International, 2004, 66(90): S39-S45.
Chmelarova, Short chain fatty acids and colonic health, Bratisl Lek Listy, 2007, 108(8): 354-358.
D'Agostino et al., Alterations in the ionic composition of icotonic saline solutins instilled into the colon, The Journal of Clinical Investigation, 1953, 32(5): 444-448.
Davis et al. Evaluation of Chlorida/Biocarbonate exchange in the human colon in vivo, The Journal of Clinical Investigation, 1983, 71:201-207.
De Brito-Ashurst et al, Bicarbonate Supplementation Slows Progression of CKD and Improves Nutritional Status, J Am Soc Nephrol, 2009, 20(9): 2075-2084.
Dobre et al., Association of Serum Bicarbonate With Risk of Renal and Cardiovascular Outcomes in CKD: A Report From the Chronic Renal Insufficiency Cohort (CRIC) Study, American Journal of Kidney Diseases, 2013, 62(4) 670-678.

Dubose, Jr., et al., Renal Tubular Acidosis in Acid Base and Electrolyte Disorders: A Companion to Brenner & Rector's The Kidney, Elsevier Health Sciences, 2002, Ch. 11, 189-206.
Farwell et al., Serum anion gap, bicarbonate and biomarkers of inflammation in healthy individuals in a national survey, Canadian Medical Association Journal, 2010, 182(2): 137-141.
Fortran et al., Ionic constituents and osmolality of gastric and small-intestinal fluids after eating, New Series, 1966, 11(7):503-521.
Goldberg, Approach to Acid-Base Disorders, Ch 11, 2005, 104-109.
Heart Failure Society of America, HFSA 2010 Guideline Executive Summary Executive Summary: HFSA 2010 Comprehensive Heart Failure Practice Guideline, Journal of Cardiac Failure, 2010, 16(6), 259 pages.
Hospria Sodium Bicarb IV ANDA labels and packaging, 5 pages.
Kielland, J., Individual Activity Coefficients of Ions in Aqueous Solutions, 1937, 59, 1675-1678, retrieved from www.ufscar.br.
Lemann, Jr., et al., Bone buffering of acid and base in humans, Am J Physiol Renal Physiol, 2003, 285:F811-F832.
Lemann, Jr., et al., The Effects of Chronic Acid Loads in Normal Man: Further Evidence for the Participation of Bone Mineral in the Defense against Chronic Metabolic Acidosis, Journal of Clinical Investigation, 1966, 45(10):1608-1614.
Mitch, W. E., Influence of Metabolic Acidosis on Nutrition, American Journal of Kidney Diseases, 29(5):xlvi-xlviii.
National Kidney Foundation, K/DOQI Clinical Practice Guidelines for Bone Metabolism and Disease in Chronic Kidney Disease, 2003, 42(4), Supp. 3.
National Kidney Foundation, K/DOQI Nutrition Guidelines, American Journal of Kidney Diseases, 2000, 35(6), Supp. 2.
Phisitkul et al., Dietary protein causes a decline in the glomerular filtration rate of the remnant kidney mediated by metabolic acidosis and endothelin receptors, Kidney International, 2008, 73: 192-199.
Raphael et al., Serum bicarbonate and mortality in adults in NHANES III, Nephrol Dial Transplant, 2013, 28: 1207-1213.
Shannon, R.D., Revised Effective Ionic Radii and Systematic Studies of Interatomie Distances in Halides and Chaleogenides, Acta Cryst., 1976, A32: 751-767.
Stevens et al., Electrolyte composition of endoscopically collected duodenal drainage fluid after synthetic porcine secretin stimulation in healthy subjects, Gastrointestinal Endoscopy, 2004, 60(3): 351-355.
Sullivan et al., Halogenated Solvents, Trichloroethylene, and Methylene Chloride in Clinical Environmental Health and Toxic Exposures, 2nd Ed., Ch. 58, 1999, Lippincott Williams & Wilkins, Philadelphia, PA.
Szerlip, Metabolic Acidosis, Ch. 8, p. 74-89.
Widmer et al., Serum Electrolyte and Acid Base Composition, Arch Intern Med, 1979, 139, 1099-1102.
Wrong et al., In Vivo dialysis of faeces as a method of stool analysis, Clinical Science, 1967, 33(1): 89-100.
Yaqoob, M. M., Acidosis and progression of chronic kidney disease, Current Opinion in Nephrology and Hypertension, 2010, 19:489-492.
Remington, The Science and Practice of Pharmacy, 21st Ed., Edited by D. B. Troy, p. 317-318 and 745-775, Lippincott Williams & Wilkins, Baltimore, Maryland.
Patent Cooperation Treaty, International Search Report and Written Opinion for PCT/US2014/041152, dated Nov. 27, 2014, 10 pages.
Nakaki et al., Effect of fatty acids on the phosphate binding of TRK-390, a novel, highly selective phosphate-binding polymer, European Journal of Pharmacology, 2013, 714(1-3): 312-317.
Akizawa, et al., Long-Term Treatment of Hyperphosphatemia With Bixalomer in Japanese Hemodialysis Patients, Therapeutic Apheresis and Dialysis, 2013, 17(6): 612-619.
Ito et al., Treatment of Hyperphosphatemia With Bixalomer in Japanese Patients on Long-Term Hemodialysis With Gastrointestinal Symptoms, Therapeutic Apheresis and Dialysis, 2014; 18(Supplement 2):19-23.
Shima et al., Clinical Experiences of Bixalomer Usage at Our Hospital, Therapeutic Apheresis and Dialysis 2014; 18 (Supplement 2): 13-18.

(56) References Cited

OTHER PUBLICATIONS

Patent Cooperation Treaty, International Search Report for PCT/US2017/031395, 6 pages dated Aug. 8, 2017.
Patent Cooperation Treaty, International Search Report for PCT/US2017/031344, 5 pages dated Aug. 8, 2017.
Franch et al., Catabolism in Uremia: The Impact of Metabolic Acidosis, J. Am. Soc. Nephrol., 9: S78-S81 1998.
Patent Cooperation Treaty, International Search Report for PCT/US2017/031378, 5 pages dated Sep. 20, 2017.
Navaneethan et al., Serum Bicarbonate and Mortality in Stage 3 and Stage 4 Chronic Kidney Disease, Clinical Journal of the American Society of Nephrology, 6(10): 2395-2402 Oct. 1, 2011.
Russian Federal Institute of Industrial Property, Search Report for 2015155596, 2 pages dated May 8, 2018.
Patent Cooperation Treaty, International Search Report for PCT/US2018/059092, 3pgs. dated Jan. 8, 2019.
Kraut, Disturbances in Acid-Base, Potassium, and Sodium Balance in Patients With CKD: New Insights and Novel Therapies, Adv Chronic Kidney Dis., 2017, 24(5): 272-273 2017.
Patent Cooperation Treaty, International Search Report for PCT/US2018/059093, 3pgs. dated Jan. 8, 2019.
Wesson et al., Veverimer versus placebo in patients with metabolic acidosis associated with chronic kidney disease: a multicentre, randomised, double-blind, controlled, phase 3 trial, The Lancet, 11 pgs. Mar. 8, 2019.
Remuzzi G.., Role of Endothelin in the Development of Glomerulosclerosis, Kidney and Blodd Ress Res., 19: 182-183 1996.
Ruiz-Ortega et al., Involvement of angiotensin II and endothelin in matrix protein production and renal sclerosis, Jour. Hypertension, 12: S51-S58 1994.
Seccia et al., Role of angiotensin II, endothelin-1 and L-type calcium channel in the development of glomerular, tubulointerstitial and perivascular fibrosis, Journal of Hypertension, 26:2022-2029 2008.
Shah et al., Serum Bicarbonate Levels and the Progression of Kidney Disease: A Cohort Study, Am J Kidney Dis 54:270-277 2009.
Stein et al., Role of an improvement in acid-base status and nutrition in CAPD patients, Kidney International, 52: 1089-1095 1997.
Szeto et al., Oral Sodium Bicarbonate for the Treatment of Metabolic Acidosis in Peritoneal Dialysis Patients: A Randomized Placebo-Control Trial, J Am Soc Nephrol 14: 2119-2126 2003.
Tangri et al., A Predictive Model for Progression of Chronic Kidney Disease to Kidney Failure, JAMA, 305(15): 1553-1559 2011.
Wesson D. E., Endogenous Endothelins Mediate Increased Acidification in Remnant Kidneys, J Am Soc Nephrol 12: 1826-1835 2001.
Wesson et al., Angiotensin II receptors mediate increased distal nephron acidification caused by acid retention, Kidney International, 82: 1184-1194 2012.
Wesson et al., Angiotensin II—mediated GFR decline in subtotal nephrectomy is due to acid retention associated with reduced GFR, Nephrol Dial Transplant, 30: 762-770 2015.
European Patent Office, Extended Search Report for EP App. 17793497.3, 11 pages dated Mar. 17, 2020.
Anonymous, Tricida Announces Positive Topline Phase 1/2 Clinical Trial Results for TRC101 in 135 Subjects with Chronic Kidney Disease and Metabolic Acidosis, Business Wire, 2 pages Jan. 9, 2017.
Abramowitz et al., Effects of Oral Sodium Bicarbonate in Patients with CKD, Clin J Am Soc Nephrol, 8: 714-720 2013.
Abramowitz, M.K., Acid-Base Balance and Physical Function, Clin J Am Soc Nephrol, 9: 2030-2032 2014.
Abramowitz, M.K., Metabolic Acidosis and Cardiovascular Disease Risk in CKD, Clin J Am Soc Nephrol, 13, 2 pgs. 2018.
Aronson et al., Effects of pH on Potassium: New Explanations for Old Observations, J Am Soc Nephrol, 22: 1981-1989 2011.
Ballasi et al., Correction of metabolic acidosis improves insulin resistance in chronic kidney disease, BMC Nephrology, 17: 158-167 2016.
Wolf et al., The Renin-Angiotensin System and Progression of Renal Disease: From Hemodynamics to Cell Biology, Nephron Physiol, 93: 3-13 2003.
Witham, BiCARB results, 9 pgs. 2019.
Williams et al., Failure of Dietary Protein and Phosphate Restriction to Retard the Rate of Progression of Chronic Renal Failure: A Prospective, Randomized, Controlled Trial, 81(294): 837-855 1991.
Wesson et al., Long-term safety and efficacy of veverimer in patients with metabolic acidosis in chronic kidney disease: a multicentre, randomised, blinded, placebo-controlled, 40-week extension, Lancet, 11 pgs. 2019.
Biggar et al., Sevelamer carbonate for the treatment of hyperphosphatemia in patients with kidney failure (CKD III-V), Expert Opin. Pharmacother, 11(16): 2739-2750 2010.
Bushinsky, D. A., Tolerance to Sodium in Patients With CKD-Induced Metabolic Acidosis: Does the Accompanying Anion Matter?, 73(6): 858-865 2019.
Chen et al., Is an Increased Serum Bicarbonate Concentration during Hemodialysis Associated with an Increased Risk of Death?. Semin. Dial., 27(3): 259-262 2014.
Chen et al., Advances in management of chronic metabolic acidosis in chronic kidney disease, Pharm. Thera., 28: 8 pgs 2019.
Dawson-Hughes et al., Impact of supplementation with bicarbonate on lower-extremity muscle performance in older men and women, Osteoporos Int., 21(7): 1171-1179 2010.
De Brito-Ashurst et al., Acidosis: progression of chronic kidney disease and quality of life, Pediatr Nephrol, 30: 873-879 2015.
De Iorio et al., Very Low-Protein Diet (VLPD) Reduces Metabolic Acidosis in Subjects with Chronic Kidney Disease The "Nutritional Light Signal" of the Renal Acid Load, Nutrients, 9: 69-82 2017.
De Iorio et al., Treatment of metabolic acidosis with sodium bicarbonate delays progression of chronic kidney disease: the UBI Study, Journal of Nephrology, 32: 989-1001 2019.
Disthabanchong et al., Oral Sodium Bicarbonate Improves Thyroid Function in Predialysis Chronic Kidney Disease, Am J Nephrol., 32: 549-556 2010.
Dobre et al., Serum bicarbonate and cardiovascular events in hypertensive adults: results from the Systolic Blood Pressure Intervention Trial, Nephrol Dial Transplant, 1-8 2019.
Dobre et al., Current Status of Bicarbonate in CKD, J Am Soc Nephrol., 26(3): 515-523 2015.
Dobre et al., Persistent High Serum Bicarbonate and the Risk of Heart Failure in Patients With Chronic Kidney Disease (CKD): A Report From the Chronic Renal Insufficiency Cohort (CRIC) Study, J Am Heart Assoc., 17 pgs. 2015.
Dobre et al., Serum Bicarbonate and Structural and Functional Cardiac Abnormalities in Chronic Kidney Disease—A Report from the Chronic Renal Insufficiency Cohort Study, Am J Nephrol., 43: 411-420 2016.
Dobre et al., Serum Bicarbonate Concentration and Cognitive Function in Hypertensive Adults, Clin J Am Soc Nephrol., 13(4): 596-603 2018.
Domrongkitchaipron et al., Bone histology and bone mineral density after correction of acidosis in distal renal tubular acidosis, Kidney International, 62: 2160-2166 2002.
Dubey et al., Correction of metabolic acidosis improves muscle mass and renal function in chronic kidney disease stages 3 and 4: a randomized controlled trial, Nephrol Dial Transplant, 9 pgs 2018.
Fan et al., A randomized, crossover design study of sevelamer carbonate powder and sevelamer hydrochloride tablets in chronic kidney disease patients on haemodialysis, European Renal Association European, 5 pgs. 2011.
Gennari et al., Effect of Dietary Protein Intake on Serum Total CO2 Concentration in Chronic Kidney Disease: Modification of Diet in Renal Disease Study Findings, Clin J Am Soc Nephrol., 1: 52-57 2006.
Gonzalez et al., Sevelamer carbonate increases serum bicarbonate in pediatric dialysis patients, Pediatr Nephrol., 25: 373-375 2010.
Greene et al., Role of Aldosterone in the Remnant Kidney Model in the Rat, J. Clin. Invest., 98(4): 1063-1068 1996.

(56) References Cited

OTHER PUBLICATIONS

Halperin et al., Ammonium Excretion in Chronic Metabolic Acidosis: Benefits and Risks, American Journal of Kidney Diseases, 14(4): 267-271 1989.
Harris et al., Mechanism of Hyperkalemia-Induced Metabolic Acidosis, J Am Soc Nephrol, 29: 1411-1425 2018.
Jeong et al., Effect of Bicarbonate Supplementation on Renal Function and Nutritional Indices in Predialysis Advanced Chronic Kidney Disease, Electrolyte Blood Press, 12: 80-87 2014.
Ketteler et al., Efficacy and Tolerability of Sevelamer Carbonate in Hyperphosphatemic Patients Who Have Chronic Kidney Disease and Are Not on Dialysis, Clin J Am Soc Nephrol, 3: 1125-1130 2008.
Kittiskulnam et al., Impact of Serum Bicarbonate Levels on Muscle Mass and Kidney Function in Pre-Dialysis Chronic Kidney Disease Patients, Am J Nephrol., 11 pgs 2019.
Kraut et al., Metabolic acidosis: pathophysiology, diagnosis and management, Nature Reviews Nephrology, 6: 274-285 2010.
Mathur et al., Effects of Correction of Metabolic Acidosis on Blood Urea and Bone Metabolism in Patients with Mild to Moderate Chronic Kidney Disease: A Prospective Randomized Single Blind Controlled Trial, Renal Failure, 28: 1-5, 2006.
Melamed et al., Effects of Sodium Bicarbonate in CKD Stages 3 and 4: A Randomized, Placebo-Controlled, Multicenter Clinical Trial, Am J Kidney Dis., 10pgs 2019.
Mircescu et al., Effects of a Supplemented Hypoproteic Diet in Chronic Kidney Disease, Journal of Renal Nutrition, 17(3): 179-188 2007.
Nath et al., Increased Ammoniagenesis as a Determinant of Progressive Renal Injury, Am. Jour. Kid. Dis. 17(6): 354-657 1991.
Nathan et al., The effect of intensive treatment of diabetes on the development and progression of long-term complications in insulin-dependent diabetes mellitus, New Eng. Jour. Med., 329(14): 977-986 1993.
Navaneethan et al., Effects of Treatment of Metabolic Acidosis in CKD A Systematic Review and Meta-Analysis, CJASN, 14: 10 pgs 2019.
Perry et al., Sevelamer Carbonate: A Review in Hyperphosphataemia in Adults with Chronic Kidney Disease, Drugs, 74: 771-792 2014.
Phisitkul et al., Amelioration of metabolic acidosis in patients with low GFR reduced kidney endothelin production and kidney injury, and better preserved GFR, Kidney International, 77: 617-623 2010.
Pisani et al., 6-tips diet: a simplified dietary approach in patients with chronic renal disease. A clinical randomized trial, Clin Exp Nephrol, 10 pgs 2015.
Mount, D. B., Potassium balance in acid-base disorders, retrieved from www.uptodate.com/contents/potassium-balance-in-acid-base-disorders?search=hyperkalemia%20and%20metabolic%20acidosis&source=search_result&selectedTitle=1~150&usage_type=default&display_rank, 5 pgs 2018.
Raphael et al., Higher serum bicarbonate levels within the normal range are associated with better survival and renal outcomes in African Americans Kidney International, 79: 356-362 2011.
Raphael et al., Bicarbonate Concentration, Acid-Base Status, and Mortality in the Health, Aging, and Body Composition Study, Clin J Am Soc Nephrol, 11: 9 pgs 2016.
Raphael et al., Urine Ammonium Predicts Clinical Outcomes in Hypertensive Kidney Disease, J Am Soc Nephrol 28: 2483-2490 2017.
Raphael et al., A Randomized Trial Comparing the Safety, Adherence, and Pharmacodynamics Profiles of Two Doses of Sodium Bicarbonate in CKD: the BASE Pilot Trial, JASN 31: 14 pgs 2020.
Raphael K. L., Metabolic Acidosis in CKD: Core Curriculum 2019, AJKD, 13 pgs 2019.
Kovacic et al., Metabolic Acidosis of Chronically Hemodialyzed Patients, Am J Nephrol 23:158-164 Mar. 21, 2003.
Witham et al., Clinical and cost-effectiveness of oral sodium bicarbonate therapy for older patients with chronic kidney disease and low-grade acidosis (BiCARB): a pragmatic randomised, double-blind, placebo-controlled trial, BMC Medicine, 18:91, 16 pages 2020.
European Patent Office, Extended European Search Report for App. No. 20204589.4, 12 pages dated Apr. 30, 2021.
Kovesdy et al., Association of serum bicarbonate levels with mortality in patients with non-dialysis-dependent CKD, Nephrology Dialysis Transplantation, 4(24): 1232-1237 2008.
Inker et al., GFR Decline as an Alternative End Point to Kidney Failure in Clinical Trials: A Meta-analysis of Treatment Effects From 37 Randomized Trials, American Journal of Kidney Diseases, 64(4): 848-859 2014.
Wesson, D. E., The Continuum of Acid Stress, Clinical Journal of the American Society of Nephrology, 16: 1292-1299 2021.
Madias, N. E., Metabolic Acidosis and CKD Progression, Clinical Journal of the American Society of Nephrology, 16: 310-312 2021.

\* cited by examiner

PROTON-BINDING POLYMERS FOR ORAL ADMINISTRATION

The present invention generally relates to proton-binding polymers for oral administration that may be used in the treatment of metabolic acidosis.

Metabolic acidosis is the result of metabolic and dietary processes that in various disease states create a condition in which non-volatile acids accumulate in the body, causing a net addition of protons (H+) or the loss of bicarbonate ($HCO_3^-$). Metabolic acidosis occurs when the body accumulates acid from metabolic and dietary processes and the excess acid is not completely removed from the body by the kidneys. Chronic kidney disease is often accompanied by metabolic acidosis due to the reduced capacity of the kidney to excrete hydrogen ions secondary to an inability to reclaim filtered bicarbonate ($HCO_3^-$), synthesize ammonia (ammoniagenesis), and excrete titratable acids. Clinical practice guidelines recommend initiation of alkali therapy in patients with non-dialysis-dependent chronic kidney disease (CKD) when the serum bicarbonate level is <22 mEq/L to prevent or treat complications of metabolic acidosis. (Clinical practice guidelines for nutrition in chronic renal failure, K/DOQI, National Kidney Foundation, Am. J. Kidney Dis. 2000; 35:S1-140; Raphael, K L, Zhang, Y, Wei, G, et al. 2013, Serum bicarbonate and mortality in adults in NHANES III, Nephrol. Dial. Transplant 28: 1207-1213). These complications include malnutrition and growth retardation in children, exacerbation of bone disease, increased muscle degradation, reduced albumin synthesis, and increased inflammation. (Leman, J, Litzow, J R, Lennon, E J. 1966. The effects of chronic acid loads in normal man: further evidence for the participation of bone mineral in the defense against chronic metabolic acidosis, J. Clin. Invest. 45: 1608-1614; Franch H A, Mitch W E, 1998, Catabolism in uremia: the impact of metabolic acidosis, J. Am. Soc. Nephroi. 9: S78-81; Ballmer, P E, McNurlan, M A, Hulter, H N, et al., 1995, Chronic metabolic acidosis decreases albumin synthesis and induces negative nitrogen balance in humans, J. Clin. Invest. 95: 39-45; Farwell, W R, Taylor, E N, 2010, Serum anion gap, bicarbonate and biomarkers of inflammation in healthy individuals in a national survey, CMAJ 182:137-141). Overt metabolic acidosis is present in a large proportion of patients when the estimated glomerular filtration rate is below 30 ml/min/1.73 m$^2$. (KDOQI bone guidelines: American Journal of Kidney Diseases (2003) 42:S1-S201. (suppl); Widmer B, Gerhardt R E, Harrington J T, Cohen J J, Serum electrolyte and acid base composition: The influence of graded degrees of chronic renal failure, Arch Intern Med 139:1099-1102, 1979; Dobre M, Yang, W, Chen J, et. al., Association of serum bicarbonate with risk of renal and cardiovascular outcomes in CKD: a report from the chronic renal insufficiency cohort (CRIC) study. Am. J. Kidney Dis. 62: 670-678, 2013; Yaqoob, M M. Acidosis and progression of chronic kidney disease. Curr. Opin. Nephrol. Hypertens. 19: 489-492, 2010).

Metabolic acidosis, regardless of etiology, lowers extracellular fluid bicarbonate and, thus, decreases extracellular pH. The relationship between serum pH and serum bicarbonate is described by the Henderson-Hasselbalch equation $$pH = pK' + \log[HCO_3^-]/[(0.03 \times PaCO_2)]$$

where 0.03 is the physical solubility coefficient for $CO_2$, [$HCO_3^-$] and $PaCO_2$ are the concentrations of bicarbonate and the partial pressure of carbon dioxide, respectively.

There are several laboratory tests that can be used to define metabolic acidosis. The tests fundamentally measure either bicarbonate ($HCO_3^-$) or proton (H$^+$) concentration in various biological samples, including venous or arterial blood.

The most useful measurements for the determination of acidosis rely on a measurement of the venous plasma bicarbonate (or total carbon dioxide [$tCO_2$]), serum electrolytes Cl$^-$, K$^+$, and Na$^+$, and a determination of the anion gap. In the clinical laboratory, measurement of venous plasma or serum electrolytes includes an estimation of the $tCO_2$. This measurement reflects the sum of circulating $CO_2$ [i.e., the total $CO_2$ represented by bicarbonate ($HCO_3^-$), carbonic acid, ($H_2CO_3$) and dissolved $CO_2$ ($0.03 \times PCO_2$)]. tCO2 can also be related to $HCO_3^-$ by using a simplified and standardized form of the Henderson-Hasselbalch equation: $tCO_2 = HCO_3^- + 0.03\ PCO_2$, where $PCO_2$ is the measured partial pressure of $CO_2$. Since $HCO_3^-$ concentration is greater than 90% of the $tCO_2$, and there are small amounts of $H_2CO_3$, then venous $tCO_2$ is often used as a reasonable approximation of the venous $HCO_3^-$ concentration in the blood. Especially during chronic kidney disease, an abnormal plasma $HCO_3^-$ value <22 mEq/L generally indicates metabolic acidosis.

Changes in serum Cl$^-$ concentration can provide additional insights into possible acid-base disorders, particularly when they are disproportionate to changes in serum Na$^+$ concentration. When this occurs, the changes in serum Cl$^-$ concentration are typically associated with reciprocal changes in serum bicarbonate. Thus, in metabolic acidosis with normal anion gap, serum Cl$^-$ increases >105 mEq/L as serum bicarbonate decreases <22 mEq/L.

Calculation of the anion gap [defined as the serum Na$^+$—(Cl$^-$+$HCO_3^-$)] is an important aspect of the diagnosis of metabolic acidosis. Metabolic acidosis may be present with a normal or an elevated anion gap. However, an elevated anion gap commonly signifies the presence of metabolic acidosis, regardless of the change in serum $HCO_3^-$. An anion gap greater than 20 mEq/L (normal anion gap is 8 to 12 mEq/L) is a typical feature of metabolic acidosis.

Arterial blood gases are used to identify the type of an acid-base disorder and to determine if there are mixed disturbances. In general, the result of arterial blood gas measures should be coordinated with history, physical exam and the routine laboratory data listed above. An arterial blood gas measures the arterial carbon dioxide tension ($P_aCO_2$), acidity (pH), and the oxygen tension ($P_aO_2$). The $HCO_3^-$ concentration is calculated from the pH and the $PaCO_2$. Hallmarks of metabolic acidosis are a pH<7.35, $P_aCO_2$<35 mm Hg and $HCO_3^-$<22 mEq/L. The value of $P_aO_2$ (normal 80-95 mmHg) is not used in making the diagnosis of metabolic acidosis but may be helpful in determining the cause. Acid-base disturbance are first classified as respiratory or metabolic. Respiratory disturbances are those caused by abnormal pulmonary elimination of $CO_2$, producing an excess (acidosis) or deficit (alkalosis) of $CO_2$ (carbon dioxide) in the extracellular fluid. In respiratory acid-base disorders, changes in serum bicarbonate ($HCO_3^-$) are initially a direct consequence of the change in $Pco_2$ with a greater increase in $Pco_2$ resulting in an increase in $HCO_3^-$. (Adrogue H J, Madias N E, 2003, Respiratory acidosis, respiratory alkalosis, and mixed disorders, in Johnson R J, Feehally J (eds): Comprehensive Clinical Nephrology. London, C V Mosby, pp. 167-182). Metabolic disturbances are those caused by excessive intake of, or metabolic production or losses of, nonvolatile acids or bases in the extracellular fluid. These changes are reflected by changes in the concentration of bicarbonate anion ($HCO_3^-$) in the blood; adaptation in this case involves both buffering (immediate), respiratory (hours to days) and renal (days) mechanisms. (DuBose T D, MacDonald G A: renal tubular acidosis, 2002, in DuBose T D, Hamm L L (eds): Acid-base and electrolyte disorders: A companion to Brenners and Rector's the Kidney, Philadelphia, W B Saunders, pp. 189-206).

The overall hydrogen ion concentration in the blood is defined by the ratio of two quantities, the serum $HCO_3^-$ content (regulated by the kidneys) and the $PCO_2$ content (regulated by the lungs) and is expressed as follows:

$$[H^+] \propto (PCO_2/[HCO_3^-])$$

The consequence of an increase in the overall hydrogen ion concentration is a decline in the major extracellular buffer, bicarbonate. Normal blood pH is between 7.38 and 7.42, corresponding to a hydrogen ion ($H^+$) concentration of 42 to 38 nmol/L (Goldberg M: Approach to Acid-Base Disorders. 2005. In Greenberg A, Cheung A K (eds) Primer on Kidney Diseases, National Kidney Foundation, Philadelphia, Elsevier-Saunders, pp. 104-109.). Bicarbonate ($HCO_3^-$) is an anion that acts to buffer against pH disturbances in the body, and normal levels of plasma bicarbonate range from 22-26 mEq/L (Szerlip H M: Metabolic Acidosis, 2005, in Greenberg A, Cheung A K (eds) Primer on Kidney Diseases, National Kidney Foundation, Philadelphia, Elsevier-Saunders, pp. 74-89.). Acidosis is the process which causes a reduction in blood pH (acidemia) and reflects the accumulation of hydrogen ion (Ht) and its consequent buffering by bicarbonate ion ($HCO_3^-$) resulting in a decrease in serum bicarbonate. Metabolic acidosis can be represented as follows:

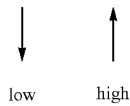

(Clinical practice guidelines for nutrition in chronic renal failure. K/DOQI, National Kidney Foundation. Am. J. Kidney Dis. 2000; 35:S1-140). Using this balance equation, the loss of one $HCO_3^-$ is equivalent to the addition of one $H^+$ and conversely, the gain of one $HCO_3^-$ is equivalent to the loss of one $H^+$. Thus, changes in blood pH, particularly increases in $H^+$ (lower pH, acidosis) can be corrected by increasing serum $HCO_3^-$ or, equivalently, by decreasing serum $H^+$.

In order to maintain extracellular pH within the normal range, the daily production of acid must be excreted from the body. Acid production in the body results from the metabolism of dietary carbohydrates, fats and amino acids. Complete oxidation of these metabolic substrates produces water and $CO_2$. The carbon dioxide generated by this oxidation (~20,000 mmol/day) is efficiently exhaled by the lungs, and represents the volatile acid component of acid-base balance.

In contrast, nonvolatile acids (~50-100 mEq/day) are produced by the metabolism of sulfate- and phosphate-containing amino acids and nucleic acids. Additional nonvolatile acids (lactic acid, butyric acid, acetic acid, other organic acids) arise from the incomplete oxidation of fats and carbohydrates, and from carbohydrate metabolism in the colon, where bacteria residing in the colon lumen convert the substrates into small organic acids that are then absorbed into the bloodstream. The impact of short chain fatty acids on acidosis is somewhat minimized by anabolism, for example into long-chain fatty acids, or catabolism to water and $CO_2$.

The kidneys maintain pH balance in the blood through two mechanisms: reclaiming filtered $HCO_3^-$ to prevent overall bicarbonate depletion and the elimination of nonvolatile acids in the urine. Both mechanisms are necessary to prevent bicarbonate depletion and acidosis.

In the first mechanism, the kidneys reclaim $HCO_3^-$ that is filtered by the glomerulus. This reclamation occurs in the proximal tubule and accounts for ~4500 mEq/day of reclaimed $HCO_3^-$. This mechanism prevents $HCO_3^-$ from being lost in the urine, thus preventing metabolic acidosis. In the second mechanism, the kidneys eliminate enough $H^+$ to equal the daily nonvolatile acid production through metabolism and oxidation of protein, fats and carbohydrates. Elimination of this acid load is accomplished by two distinct routes in the kidney, comprising active secretion of $H^+$ ion and ammoniagenesis. The net result of these two interconnected processes is the elimination of the 50-100 mEq/day of nonvolatile acid generated by normal metabolism.

Thus, normal renal function is needed to maintain acid-base balance. During chronic kidney disease, filtration and reclamation of $HCO_3^-$ is impaired as is generation and secretion of ammonia. These deficits rapidly lead to chronic metabolic acidosis which is, itself, a potent antecedent to end-stage renal disease. With continued acid production from metabolism, a reduction in acid elimination will disturb the $H^+/HCO_3^-$ balance such that blood pH falls below the normal value of pH=7.38-7.42.

Treatment of metabolic acidosis by alkali therapy is usually indicated to raise and maintain the plasma pH to greater than 7.20. Sodium bicarbonate ($NaHCO_3$) is the agent most commonly used to correct metabolic acidosis. $NaHCO_3$ can be administered intravenously to raise the serum $HCO_3^-$ level adequately to increase the pH to greater than 7.20. Further correction depends on the individual situation and may not be indicated if the underlying process is treatable or the patient is asymptomatic. This is especially true in certain forms of metabolic acidosis. For example, in high-anion gap (AG) acidosis secondary to accumulation of organic acids, lactic acid, and ketones, the cognate anions are eventually metabolized to $HCO_3^-$. When the underlying disorder is treated, the serum pH corrects; thus, caution should be exercised in these patients when providing alkali to raise the pH much higher than 7.20, to prevent an increase in bicarbonate above the normal range (>26 mEq/L).

Citrate is an appropriate alkali therapy to be given orally or IV, either as the potassium or sodium salt, as it is metabolized by the liver and results in the formation of three moles of bicarbonate for each mole of citrate. Potassium citrate administered IV should be used cautiously in the presence of renal impairment and closely monitored to avoid hyperkalemia.

Intravenous sodium bicarbonate ($NaHCO_3$) solution can be administered if the metabolic acidosis is severe or if correction is unlikely to occur without exogenous alkali administration. Oral alkali administration is the preferred route of therapy in persons with chronic metabolic acidosis. The most common alkali forms for oral therapy include $NaHCO_3$ tablets where 1 g of $NaHCO_3$ is equal to 11.9 mEq of $HCO_3^-$. However, the oral form of $NaHCO_3$ is not approved for medical use and the package insert of the intravenous sodium bicarbonate solution includes the following contraindications, warnings and precautions (Hospira label for NDC 0409-3486-16):

Contraindications: Sodium Bicarbonate Injection, USP is contraindicated in patients who are losing chloride by vomiting or from continuous gastrointestinal suction, and in patients receiving diuretics known to produce a hypochloremic alkalosis.

Warnings: Solutions containing sodium ions should be used with great care, if at all, in patients with congestive heart failure, severe renal insufficiency and in clinical states in which there exists edema with sodium retention. In patients with diminished renal function, administration of solutions containing sodium ions may result in sodium retention. The intravenous administration of these solutions can cause fluid and/or solute overloading resulting in dilution of serum electrolyte concentrations, overhydration, congested states or pulmonary edema.

Precautions: [ . . . ] The potentially large loads of sodium given with bicarbonate require that caution be exercise in the use of sodium bicarbonate in patients with congestive heart failure or other edematous or sodium-retaining states, as well as in patients with oliguria or anuria.

Acid-base disorders are common in chronic kidney disease and heart failure patients. Chronic kidney disease (CKD) progressively impairs renal excretion of the approximately 1 mmol/kg body weight of hydrogen ions generated in healthy adults (Yaqoob, M M. 2010, Acidosis and progression of chronic kidney disease, Curr. Opin. Nephrol. Hyperten. 19:489-492.). Metabolic acidosis, resulting from the accumulation of acid ($H^+$) or depletion of base ($HCO_3^-$) in the body, is a common complication of patients with CKD, particularly when the glomerular filtration rate (GFR, a measure of renal function) falls below 30 ml/min/1.73 $m^2$. Metabolic acidosis has profound long term effects on protein and muscle metabolism, bone turnover and the development of renal osteodystrophy. In addition, metabolic acidosis influences a variety of paracrine and endocrine functions, again with long term consequences such as increased inflammatory mediators, reduced leptin, insulin resistance, and increased corticosteroid and parathyroid hormone production (Mitch W E, 1997, Influence of metabolic acidosis on nutrition, Am. J. Kidney Dis. 29:46-48.). The net effect of sustained metabolic acidosis in the CKD patient is loss of bone and muscle mass, a negative nitrogen balance, and the acceleration of chronic renal failure due to hormonal and cellular abnormalities (De Brito-Ashurst I, Varagunam M, Raftery M J, et al, 2009, Bicarbonate supplementation slows progression of CKD and improves nutritional status, J. Am. Soc. Nephrol. 20: 2075-2084). Conversely, the potential concerns with alkali therapy in CKD patients include expansion of extracellular fluid volume associated with sodium ingestion, resulting in the development or aggravation of hypertension, facilitation of vascular calcification, and the decompensation of existing heart failure. CKD patients of moderate degree (GFR at 20-25% of normal) first develop hyperchloremic acidosis with a normal anion gap due to the inability to reclaim filtered bicarbonate and excrete proton and ammonium cations. As they progress toward the advanced stages of CKD the anion gap increases, reflective of the continuing degradation of the kidney's ability to excrete the anions that were associated with the unexcreted protons. Serum bicarbonate in these patients rarely goes below 15 mmol/L with a maximum elevated anion gap of approximately 20 mmol/L. The non-metabolizable anions that accumulate in CKD are buffered by alkaline salts from bone (Lemann J Jr, Bushinsky D A, Hamm L L Bone buffering of acid and base in humans. Am. J. Physiol Renal Physiol. 2003 November, 285(5):F811-32).

The majority of patients with chronic kidney disease have underlying diabetes (diabetic nephropathy) and hypertension, leading to deterioration of renal function. In almost all patients with hypertension a high sodium intake will worsen the hypertension. Accordingly, kidney, heart failure, diabetes and hypertensive guidelines strictly limit sodium intake in these patients to less than 1.5 g or 65 mEq per day (HFSA 2010 guidelines, Lindenfeld 2010, J Cardiac Failure V16 No 6 P475). Chronic anti-hypertensive therapies often induce sodium excretion (diuretics) or modify the kidney's ability to excrete sodium and water (such as, for example, Renin Angiotensin Aldosterone System inhibiting "RAASi" drugs). However, as kidney function deteriorates, diuretics become less effective due to an inability of the tubule to respond. The RAASi drugs induce life-threatening hyperkalemia as they inhibit renal potassium excretion. Given the additional sodium load, chronically treating metabolic acidosis patients with amounts of sodium-containing base that often exceed the total daily recommended sodium intake is not a reasonable practice. As a consequence, oral sodium bicarbonate is not commonly prescribed chronically in these diabetic nephropathy patients. Potassium bicarbonate is also not acceptable as patients with CKD are unable to readily excrete potassium, leading to severe hyperkalemia.

Despite these shortcomings, the role of oral sodium bicarbonate has been studied in the small subpopulation of non-hypertensive CKD patients. As part of the Kidney Research National Dialogue, alkali therapy was identified as having the potential to slow the progression of CKD, as well as to correct metabolic acidosis. The annual age-related decline in glomerular filtration rate (GFR) after the age of 40 is 0.75-1.0 ml/min/1.73 $m^2$ in normal individuals. In CKD patients with fast progression, a steeper decline of >4 ml/min/1.73 $m^2$ annually can be seen.

In one outcome study, De Brito-Ashurst et al showed that bicarbonate supplementation preserves renal function in CKD (De Brito-Ashurst I, Varagunam M, Raftery M J, et al, 2009, Bicarbonate supplementation slows progression of CKD and improves nutritional status, J. Am. Soc. Nephrol. 20: 2075-2084). The study randomly assigned 134 adult patients with CKD (creatinine clearance [CrCl] 15 to 30 ml/min per 1.73 $m^2$) and serum bicarbonate 16 to 20 mmol/L to either supplementation with oral sodium bicarbonate or standard of care for 2 years. The average dose of bicarbonate in this study was 1.82 g/day, which provides 22 mEq of bicarbonate per day. The primary end points were rate of CrCl decline, the proportion of patients with rapid decline of CrCl (>3 ml/min per 1.73 $m^2$/yr), and end-stage renal disease ("ESRD") (CrCl<10 ml/min). Compared with the control group, decline in CrCl was slower with bicarbonate supplementation (decrease of 1.88 ml/min per 1.73 $m^2$ for patients receiving bicarbonate versus a decrease of 5.93 ml/min per 1.73 $m^2$ for control group; P<0.0001). Patients supplemented with bicarbonate were significantly less likely to experience rapid progression (9% versus 45%; relative risk 0.15; 95% confidence interval 0.06 to 0.40; P <0.0001). Similarly, fewer patients supplemented with bicarbonate developed ESRD (6.5% versus 33%; relative risk 0.13; 95% confidence interval 0.04 to 0.40; P<0.001).

Hyperphosphatemia is a common co-morbidity in patients with CKD, particularly in those with advanced or end-stage renal disease. Sevelamer hydrochloride is a commonly used ion-exchange resin that reduces serum phosphate concentration. However, reported drawbacks of this agent include metabolic acidosis apparently due to the net absorption of HCl in the process of binding phosphate in the small intestine. Several studies in patients with CKD and hyperphosphatemia who received hemodialysis or peritoneal dialysis found decreases in serum bicarbonate concentrations with the use of sevelamer hydrochloride (Brezina, 2004 Kidney Int. V66 S90 (2004) S39-S45; Fan, 2009 Nephrol Dial Transplant (2009) 24:3794).

Among the various aspects of the present invention, therefore, may be noted compositions for and methods of treating an animal, including a human, and methods of preparing such compositions. The compositions comprise crosslinked amine polymers and may be used, for example, to treat diseases or other metabolic conditions in which removal of protons and/or chloride ions from the gastrointestinal tract would provide physiological benefits. For example, the polymers described herein may be used to regulate acid-base related diseases in an animal, including a human. In one such embodiment, the polymers described herein may be used to normalize serum bicarbonate concentrations and the blood pH in an animal, including a human. By way of further example, the polymers described herein may be used in the treatment of acidosis. There are several distinct physiologic conditions that describe this imbalance, each of which can be treated by a polymer that binds and removes HCl.

Metabolic acidosis resulting from a net gain of acid includes processes that increase endogenous hydrogen ion production, such as ketoacidosis, L-lactic acidosis, D-lactic acidosis and salicylate intoxication. Metabolism of ingested toxins such as methanol, ethylene glycol and paraldehyde can also increase hydrogen ion concentration. Decreased renal excretion of hydrogen ions as in uremic acidosis and distal (type I) renal tubular acidosis is another cause of net gain of acid in the body resulting in metabolic acidosis. Metabolic acidosis resulting from a loss of bicarbonate is a hallmark of proximal (type II) renal tubular acidosis. In addition, gastrointestinal loss of bicarbonate in acute or chronic diarrhea also results in metabolic acidosis. Primary or secondary hypoaldosteronism are common disorders causing hyperkalemia and metabolic acidosis and underlie the classification of type IV renal tubular acidosis. Hyporeninemic hypoaldosteronism is the most frequently encountered variety of this disorder.

Another way of describing metabolic acidosis is in terms of the anion gap. Causes of high anion gap acidosis include diabetic ketoacidosis, L-lactic acidosis, D-lactic acidosis, alcoholic ketoacidosis, starvation ketoacidosis, uremic acidosis associated with advanced renal failure (CKD Stages 4-5), salicylate intoxication, and selected toxin exposure due to ingestion including methanol, ethylene, propylene glycol and paraldehyde. Causes of normal anion gap acidosis include early stage renal failure (CKD Stages 1-3), gastrointestinal loss of bicarbonate due to acute or chronic diarrhea, distal (type I) renal tubular acidosis, proximal (type II) renal tubular acidosis, type IV renal tubular acidosis, dilutional acidosis associated with large volume intravenous fluid administration, and treatment of diabetic ketoacidosis resulting from ketones lost in the urine.

With regard to lactic acidosis, hypoxic lactic acidosis results from an imbalance between oxygen balance and oxygen supply and is associated with tissue ischemia, seizure, extreme exercise, shock, cardiac arrest, low cardiac output and congestive heart failure, severe anemia, severe hypoxemia and carbon monoxide poisoning, vitamin deficiency and sepsis. In other types of lactic acidosis, oxygen delivery is normal but oxidative phosphorylation is impaired, often the result of cellular mitochondrial defects. This is commonly seen in inborn errors of metabolism or from the ingestion of drugs or toxins. Alternate sugars used for tube feedings or as irrigants during surgery (e.g., fructose, sorbitol) can also result in metabolism that triggers lactic acidosis.

There are three main classifications of renal tubular acidosis, each with distinctive etiologies with several subtypes. Distal (type I) renal tubular acidosis can be caused by hereditary and genomic changes, particularly mutation in the $HCO_3^-/Cl^-$ exchanger (AEI) or 11+/ATPase. Examples of acquired distal (type 1) renal tubular acidosis include hyperparathyroidism, Sjogren's syndrome, medullary sponge kidney, cryoglobulinemia, systemic lupus erythematosus, kidney transplant rejection, chronic tubulointerstitial disease and exposure to various drugs including amphotericin B, lithium, ifosfamide, foscarnet, toluene and vanadium. A special classification of distal (type IV) renal tubular acidosis with hyperkalemia is found in lupus nephritis, obstructive nephropathy, sickle cell anemia, and voltage defects. Hereditary examples include pseudohypoaldosteronism type I and pseudohypoaldosteronism type II (Gordon's disease) and exposure to certain drugs (amiloride, triamterene, trimethoprim, and pentamidine) can also result in distal (type IV) renal tubular acidosis with hyperkalemia. Proximal (type II) renal tubular acidosis can be caused by hereditary or acquired causes. Hereditary causes include Wilson's disease and Lowe's syndrome. Acquired causes include cystinosis, galactosemia, multiple myeloma, light chain disease, amyloidosis, vitamin D deficiency, lead and mercury ingestion, and exposure to certain drugs including ifosfamide, cidofovir, aminoglycosides, and acetazolamide. Isolated defects in bicarbonate reabsorption can be a cause of proximal (type II) renal tubular acidosis; example of such defects include exposure to carbonic anhydrase inhibitors, acetazolamide, topiramate, sulfamylon and carbonic anhydrase deficiency. Combined proximal and distal renal tubular acidosis (type III) is uncommon and results from defects in both proximal bicarbonate reabsorption and distal proton secretion. Mutations in the gene for cystolic carbonic anhydrase can cause the defect, as well as certain drugs including ifosfamide. Type IV renal tubular acidosis with hyperkalemia is a cause of metabolic acidosis. The main etiology behind this type of acidosis is aldosterone deficiency; hypoaldosteronism results from primary adrenal failure, the syndrome of hyporeninemic hypoaldosteronism (Type IV RTA) commonly seen in elderly individuals, Addison's disease, and pseudohypoaldosteronism type I due to mineralocorticoid resistance. Chronic interstitial nephritis due to analgesic nephropathy, chronic pyelonephritis, obstructive nephropathy and sickle cell disease can also create an acidosis with hyperkalemia. Finally, drugs such as amiloride, spironolactone, triamterene, trimethoprim, heparin therapy, NSAIDs, angiotensin receptor blockers and angiotensin-converting enzyme inhibitors can induce metabolic acidosis accompanied by hyperkalemia.

All of the above causes and etiologies of metabolic acidosis are treatable with a polymer designed to bind and remove HCl in the gastrointestinal tract.

The method of treatment generally involves administering a therapeutically effective amount of a crosslinked amine polymer having the capacity to remove protons and chloride ions from the gastrointestinal tract of an animal, such as a human. In general, such crosslinked amine polymers may have advantageous characteristics such as relatively low swelling, relatively high proton and chloride ion binding, and/or relatively low binding of interfering anions such as phosphate, bicarbonate, citrate, short chain fatty acids and bile acids.

In general, it is preferable for the polymers, once they become protonated, to bind chloride as a counter ion rather than, for example, the other "interfering" anions listed above, because these interfering anions may be metabolically equivalent to bicarbonate in a patient in need of treatment. Removal of chloride along with proton from the body through being bound to an amine polymer of the present disclosure will have an alkalinizing effect, while removal of an interfering anion may have less or even no alkalinizing effect.

In certain embodiments, the polymers preferably bind and maintain their ability to bind proton and anions at the physiological conditions found along the gastrointestinal (GI) lumen. These conditions can change according to dietary intake (see, for example, Fordtran J, Locklear T. Ionic constituents and osmolality of gastric and small-intestinal fluids after eating. Digest Dis Sci. 1966; 11(7): 503-21) and location along the GI tract (Binder, H et al. Chapters 41-45 in "Medical Physiology", 2nd Edition, Elsevier [2011]. Boron and Boulpaep [Ed.]). Rapid binding of proton and chloride in the stomach and small intestine is desirable. High binding levels and selectivity for chloride later in the GI tract (lower small intestine and large intestine) is also desirable. In general, the polymers also preferably have a $pK_a$ such that the majority of amines are protonated under the various pH and electrolyte conditions encountered along the GI tract and are thereby capable of removing proton, along with an appropriate counter anion (preferably chloride), from the body into the feces.

Since the stomach is an abundant source of HCl, and the stomach is the first site of potential HCl binding (after the mouth), and since residence time in the stomach is short (gastric residence half-life of approximately 90 minutes), compared to the rest of the GI tract (small intestine transit time of approximately 4 hours; whole gut transit time of 2-3 days; Read, N W et al. Gastroenterology [1980] 79:1276), it is desirable for the polymer of the present disclosure to demonstrate rapid kinetics of proton and chloride binding in the lumen of this organ, as well as in in vitro conditions designed to mimic the stomach lumen (e.g. SGF). Phosphate is a potential interfering anion for chloride binding in the stomach and small intestine, where phosphate is mostly absorbed (Cross, H S et al Miner Electrolyte Metab [1990] 16:115-24). Therefore rapid and preferential binding of chloride over phosphate is desirable in the small intestine and in in vitro conditions designed to mimic the small intestine lumen (e.g. SIB). Since the transit time of the colon is slow (2-3 days) relative to the small intestine, and since conditions in the colon will not be encountered by an orally administered polymer until after stomach and small intestine conditions have been encountered, kinetics of chloride binding by a polymer of the present disclosure do not have to be as rapid in the colon or in in vitro conditions designed to mimic the late small intestine/colon (e.g. SOB). It is, however, important that chloride binding and selectivity over other interfering anions is high, for example, at 24 and/or 48 hours or longer In one embodiment, the crosslinked amine polymer is administered as a pharmaceutical composition comprising the crosslinked amine polymer and, optionally, a pharmaceutically acceptable carrier, diluent or excipient, or combination thereof that do not significantly interfere with the proton and/or chloride binding characteristics of the crosslinked amine polymer in vivo. Optionally, the pharmaceutical composition may also comprise an additional therapeutic agent.

A further aspect of the present disclosure is a process for the preparation of a crosslinked amine polymer that may be administered as a pharmaceutical composition. The process comprises crosslinking a preformed amine polymer in a reaction mixture containing the preformed amine polymer, a solvent, a crosslinking agent, and a swelling agent for the preformed amine polymer. The swelling agent is preferably immiscible with the solvent, the preformed amine polymer has an absorption capacity for the swelling agent, and the amount of swelling agent in the reaction mixture is less than the absorption capacity of the preformed amine polymer for the swelling agent.

A further aspect of the present disclosure is a process for the preparation of a crosslinked amine polymer that may be administered as a pharmaceutical composition. The process comprises crosslinking a preformed amine polymer in a reaction mixture containing the preformed amine polymer, a solvent, and a crosslinking agent to form a crosslinked amine polymer. Prior to the crosslinking step, the preformed amine polymer binds a first amount of chloride and competing anions (e.g., phosphate, citrate and/or taurocholate) and after the crosslinking step, the crosslinked amine polymer binds a second (different) amount of chloride and competing anions (e.g., phosphate, citrate and/or taurocholate) in an appropriate assay (e.g., SIB or SOB). For example, in one such embodiment, the second amount of the competing anions (e.g., phosphate, citrate and/or taurocholate) bound is relatively less than the first amount of the competing anions.

Amine monomers are typically polymerized in radical polymerizations via their protonated form because the free amine induces chain transfer reactions and often limits the degree of polymerization to low molecular weights. In order to crosslink beyond the limit of electrostatic repulsion and achieve a degree of crosslinking within a crosslinked particle, two discrete polymerization/crosslinking steps are performed in accordance with one aspect of the present disclosure. In the first step, a preformed amine polymer is prepared. The preformed amine polymer is deprotonated and further crosslinked in a second polymerization/crosslinking step to form a post-polymerization crosslinked polymer. Advantageously, the primary crosslinking reaction is between carbon atoms (i.e., carbon-carbon crosslinking) in the first step, whereas crosslinking is primarily between amine moieties comprised by the preformed amine polymer in the second step.

A further aspect of the present disclosure is a process for the preparation of a crosslinked amine polymer comprising two discrete polymerization/crosslinking steps. In the first step, a preformed amine polymer having a chloride binding capacity of at least 10 mmol/g in Simulated Gastric Fluid ("SGF") and a Swelling Ratio in the range of 2 to 10 is formed. In the second step, the preformed amine polymer is crosslinked with a crosslinker containing amine reactive moieties to form a post-polymerization crosslinked amine polymer. The resulting post-polymerization crosslinked amine polymer has a binding capacity for competing anions (e.g., phosphate, citrate and/or taurocholate) in an appropriate assay (e.g., SIB or SOB) that is less than the binding capacity of the preformed polymer for the competing anions (e.g., phosphate, citrate and/or taurocholate) in the same appropriate assay (e.g., SIB or SOB). In one embodiment the preformed amine polymer has a Swelling Ratio in the range of 3 to 8. In one such embodiment, the preformed amine polymer has a Swelling Ratio in the range of 4 to 6.

A further aspect of the present disclosure is a process for the preparation of a crosslinked amine polymer comprising two discrete crosslinking steps. In the first crosslinking step, a preformed amine polymer is formed, the preformed amine polymer having a chloride binding capacity of at least 10 mmol/g in Simulated Gastric Fluid ("SGP") and a Swelling Ratio in the range of 2 to 10 and an average particle size of at least 80 microns. The preformed amine polymer Is (at least partially) deprotonated with a base and, in the second step, the deprotonated preformed amine polymer is crosslinked with a crosslinker containing amine reactive moieties to form a post-polymerization crosslinked amine polymer. In one embodiment the preformed amine polymer has a Swelling Ratio in the range of 3 to 8. In one such embodiment, the preformed amine polymer has a Swelling Ratio in the range of 4 to 6.

A further aspect of the present disclosure is a process for the preparation of a crosslinked amine polymer comprising two discrete polymerization/crosslinking steps. In the first step, a preformed amine polymer having a chloride binding capacity of at least 10 mmol/g in Simulated Gastric Fluid ("SGF") and a Swelling Ratio in the range of 2 to 10 is formed. The preformed amine polymer is (at least partially) deprotonated with a base and contacted with a swelling agent to swell the deprotonated preformed amine polymer. In the second step, the swollen, deprotonated preformed amine polymer is crosslinked with a crosslinker containing amine reactive moieties to form a post-polymerization crosslinked amine polymer. In one embodiment the preformed amine polymer has a Swelling Ratio in the range of 3 to 8. In one such embodiment, the preformed amine polymer has a Swelling Ratio in the range of 4 to 6.

A further aspect of the present disclosure is a pharmaceutical composition comprising a crosslinked amine polymer and a pharmaceutically acceptable excipient. The crosslinked amine polymer, for example, may be prepared as set forth in certain paragraphs above. The crosslinked amine polymer, for example, may be prepared by crosslinking a preformed amine polymer in a reaction mixture containing the preformed amine polymer, a solvent, a crosslinking agent, and a swelling agent for the preformed amine polymer. The swelling agent is preferably immiscible with the solvent, the preformed amine polymer has an absorption capacity for the swelling agent, and the amount of swelling agent in the reaction mixture is less than the absorption capacity of the preformed amine polymer for the swelling agent. The crosslinked amine polymer, for example, may also be prepared by crosslinking a preformed amine polymer in a reaction mixture containing the preformed amine polymer, a solvent, and a crosslinking agent to form a crosslinked amine polymer. Prior to the crosslinking step, the preformed amine polymer binds a first amount of chloride and competing anions (e.g., phosphate, citrate and/or taurocholate) and after the crosslinking step, the crosslinked amine polymer binds a second (different) amount of chloride and competing anions (e.g., phosphate, citrate and/or taurocholate) in an appropriate assay (e.g., SIB or SOB). For example, in one such embodiment, the second amount of the competing anions (e.g., phosphate, citrate and/or taurocholate) bound is relatively less than the first amount of the competing anions. The crosslinked amine polymer, for example, may also be prepared by two discrete polymerization/crosslinking steps performed in accordance with one aspect of the present disclosure. In the first step, a preformed amine polymer is prepared. The preformed amine polymer is deprotonated and further crosslinked in a second polymerization/crosslinking step to form a post-polymerization crosslinked polymer. Advantageously, the primary crosslinking reaction is between carbon atoms (i.e., carbon-carbon crosslinking) in the first step, whereas crosslinking is primarily between amine moieties comprised by the preformed amine polymer in the second step. The crosslinked amine polymer, for example, may also be prepared by two discrete polymerization/crosslinking steps, where in the first step, a preformed amine polymer having a chloride binding capacity of at least 10 mmol/g in Simulated Gastric Fluid ("SGF") and a Swelling Ratio in the range of 2 to 10 is formed. In the second step, the preformed amine polymer is crosslinked with a crosslinker containing amine reactive moieties to form a post-polymerization crosslinked amine polymer. The resulting post-polymerization crosslinked amine polymer has a binding capacity for competing anions (e.g., phosphate, citrate and/or taurocholate) in an appropriate assay (e.g., SIB or SOB) that is less than the binding capacity of the preformed polymer for the competing anions (e.g., phosphate, citrate and/or taurocholate) in the same appropriate assay (e.g., SIB or SOB). In one embodiment the preformed amine polymer has a Swelling Ratio in the range of 3 to 8. In one such embodiment, the preformed amine polymer has a Swelling Ratio in the range of 4 to 6. The crosslinked amine polymer, for example, may also be prepared by two discrete crosslinking steps, where in the first crosslinking step, a preformed amine polymer is formed, the preformed amine polymer having a chloride binding capacity of at least 10 mmol/g in Simulated Gastric Fluid ("SGF") and a Swelling Ratio in the range of 2 to 10 and an average particle size of at least 80 microns. The preformed amine polymer is (at least partially) deprotonated with a base and, in the second step, the deprotonated preformed amine polymer is crosslinked with a crosslinker containing amine reactive moieties to form a post-polymerization crosslinked amine polymer. In one embodiment the preformed amine polymer has a Swelling Ratio in the range of 3 to 8. In one such embodiment, the preformed amine polymer has a Swelling Ratio in the range of 4 to 6. The crosslinked amine polymer, for example, may also be prepared by two discrete polymerization/crosslinking steps, where in the first step, a preformed amine polymer having a chloride binding capacity of at least 10 mmol/g in Simulated Gastric Fluid ("SGF") and a Swelling Ratio in the range of 2 to 10 is formed. The preformed amine polymer is (at least partially) deprotonated with a base and contacted with a swelling agent to swell the deprotonated preformed amine polymer. In the second step, the swollen, deprotonated preformed amine polymer is crosslinked with a crosslinker containing amine reactive moieties to form a post-polymerization crosslinked amine polymer. In one embodiment the preformed amine polymer has a Swelling Ratio in the range of 3 to 8. In one such embodiment, the preformed amine polymer has a Swelling Ratio in the range of 4 to 6.

A further aspect of the present disclosure is a pharmaceutical composition comprising a crosslinked amine polymer having a chloride ion binding capacity of at least 4 mmol/g in Simulated Small Intestine Inorganic Buffer ("SIB"). In one embodiment, the crosslinked amine polymer has a chloride ion binding capacity of at least 4.5, 5, 5.5, or even at least 6 mmol/g in Simulated Small Intestine Inorganic Buffer ("SIB").

A further aspect of the present disclosure is a pharmaceutical composition comprising a crosslinked amine polymer having a ratio of chloride ion binding capacity to phosphate ion binding capacity in Simulated Small Intestine Inorganic Buffer ("SIB") of at least 2.3:1, respectively. In one embodiment, the crosslinked amine polymer has a ratio of chloride ion binding capacity to phosphate ion binding capacity in Simulated Small Intestine Inorganic Buffer ("SIB") of at least 2.5:1, 3:1, 3.5:1, or even 4:1, respectively.

A further aspect of the present disclosure is a pharmaceutical composition comprising a crosslinked amine polymer having a chloride ion binding capacity of at least 1 mmol/g in Simulated Small Intestine Inorganic Buffer ("SIB"), a phosphate ion binding capacity of less than 0.4 mmol/g in SIB, and a chloride ion to phosphate ion binding ratio in SIB of at least 2.3:1, respectively. In one such embodiment, the crosslinked amine polymer has a chloride ion binding capacity of at least 1.5 mmol/g in Simulated Small Intestine Inorganic Buffer ("SIB"), a phosphate ion binding capacity of less than 0.6 mmol/g in SIB, and a chloride ion to phosphate ion binding ratio in SIB of at least 2.3:1, respectively. In another such embodiment, the crosslinked amine polymer has a chloride ion binding capacity of at least 2.0 mmol/g in Simulated Small Intestine Inorganic Buffer ("SIB"), a phosphate ion binding capacity of less than 0.8 mmol/g in SIB, and a chloride ion to phosphate ion binding ratio in SIB of at least 2.3:1, respectively. In one such embodiment, the crosslinked amine polymer has a chloride ion binding capacity of at least 2.5 mmol/g in Simulated Small Intestine Inorganic Buffer ("SIB"), a phosphate ion binding capacity of less than 1.0 mmol/g in SIB, and a chloride ion to phosphate ion binding ratio in SIB of at least 2.3:1, respectively. In one such embodiment, the crosslinked amine polymer has a chloride ion binding capacity of at least 3.0 mmol/g in Simulated Small Intestine Inorganic Buffer ("SIB"), a phosphate ion binding capacity of less than 1.3 mmol/g in SIB, and a chloride ion to phosphate ion binding ratio in SIB of at least 2.3:1, respectively. In one such embodiment, the crosslinked amine polymer has a chloride ion binding capacity of at least 3.5 mmol/g in Simulated Small Intestine Inorganic Buffer ("SIB"), a phosphate ion binding capacity of less than 1.5 mmol/g in SIB, and a chloride ion to phosphate ion binding ratio in SIB of at least 2.3:1, respectively. In one such embodiment, the crosslinked amine polymer has a chloride ion binding capacity of at least 4.0 mmol/g in Simulated Small Intestine Inorganic Buffer ("SIB"), a phosphate ion binding capacity of less than 1.7 mmol/g in SIB, and a chloride ion to phosphate ion binding ratio in SIB of at least 2.3:1, respectively. In one such embodiment, the crosslinked amine polymer has a chloride ion binding capacity of at least 4.5 mmol/g in Simulated Small Intestine Inorganic Buffer ("SIB"), a phosphate ion binding capacity of less than 1.9 mmol/g in SIB, and a chloride ion to phosphate ion binding ratio in SIB of at least 2.3:1, respectively. In one such embodiment, the crosslinked amine polymer has a chloride ion binding capacity of at least 5.0 mmol/g in Simulated Small Intestine Inorganic Buffer ("SIB"), a phosphate ion binding capacity of less than 2.1 mmol/g in SIB, and a chloride ion to phosphate ion binding ratio in SIB of at least 2.3:1, respectively. In each of the foregoing embodiments, the crosslinked amine polymer may have a chloride ion to phosphate ion binding ratio in SIB of at least 2.5, at least 3, at least 3.5 or even at least 4, respectively.

A further aspect of the present disclosure is a pharmaceutical composition comprising a crosslinked amine polymer having a ratio of chloride ion binding capacity to phosphate ion binding capacity in Simulated Small Intestine Inorganic Buffer ("SIB") of at least 2.3:1, respectively, and a Swelling Ratio of less than 5. For example, in one such embodiment, the crosslinked amine polymer may have a chloride ion to phosphate ion binding ratio in SIB of at least 2.3:1, at least 2.5, at least 3, at least 3.5 or even at least 4, respectively, and a Swelling Ratio of less than 5, less than 4, less than 3, less than 2, less than 1.5 or even less than 1.

A further aspect of the present disclosure is a pharmaceutical composition comprising a crosslinked amine polymer has a retained chloride content of at least 30% of the chloride that was initially bound in a GI Compartment Transit Assay ("GICTA") (i.e., bound during the SGF binding step). In one such embodiment, the crosslinked amine polymer has a retained chloride content of at least 30%, at least 40%, at least 50%, at least 60%, at least 70%, at least 80% or even at least 90% of the chloride that was initially bound in a GI Compartment Transit Assay.

A further aspect of the present disclosure is a pharmaceutical composition comprising a crosslinked amine polymer has a retained chloride content of at least 0.5 mmol chloride/g of polymer in a GI Compartment Transit Assay ("GICTA"). In one such embodiment, the crosslinked amine polymer has a retained chloride content of at least 0.5, at least 1, at least 1.5, at least 2, at least 2.5, at least 3, at least 3.5, at least 4, at least 4.5, or even at least 5 mmol chloride/g of polymer in a GI Compartment Transit Assay ("GICTA").

A further aspect of the present disclosure is a pharmaceutical composition comprising a crosslinked amine polymer has a retained chloride content of at least 0.5 mmol chloride/g of polymer in a GI Compartment Transit Assay ("GICTA") and a chloride retention at the end of the GICTA of at least 30% of the chloride that was initially bound in the GICTA (i.e., bound during the SGF binding step). In one such embodiment, the crosslinked amine polymer has a retained chloride content of at least 30%, at least 40%, at least 50%, at least 60%, at least 70%, at least 80% or even at least 90% of the chloride that was initially bound in a GI Compartment Transit Assay and a retained chloride content of at least 0.5, at least 1, at least 1.5, at least 2, at least 2.5, at least 3, at least 3.5, at least 4, at least 4.5, or even at least 5 mmol chloride/g of polymer in a GI Compartment Transit Assay ("GICTA").

A further aspect of the present disclosure is a pharmaceutical composition comprising a crosslinked amine polymer having a chloride ion binding capacity of at least 5 mmol/g in a 1-hour Simulated Gastric Fluid ("SGF") Assay and a chloride ion binding capacity of at least 8 mmol/g in a 24-hour Simulated Gastric Fluid ("SGF") Assay. In one such embodiment, the crosslinked amine polymer has a chloride ion binding capacity of at least 5 mmol/g in a 1-hour Simulated Gastric Fluid ("SGF") Assay and a chloride ion binding capacity of at least 8, at least 9, at least 10, at least 11, at least 12, at least 13, or even at least 14 mmol/g in a 24-hour Simulated Gastric Fluid ("SGF") Assay.

A further aspect of the present disclosure is a pharmaceutical composition comprising a crosslinked amine polymer having a chloride ion binding capacity in a 1-hour Simulated Gastric Fluid ("SGF") Assay that is at least 50% of its chloride ion binding capacity in a 24-hour Simulated Gastric Fluid ("SGF") Assay. In one such embodiment, the crosslinked amine polymer has a chloride ion binding capacity in a 1-hour Simulated Gastric Fluid ("SGF") Assay that is at least 50%, at least 60%, at least 70%, at least 80%, or even at least 90% of its chloride ion binding capacity in a 24-hour Simulated Gastric Fluid ("SGF") Assay.

A further aspect of the present disclosure is a pharmaceutical composition comprising a crosslinked amine polymer having a chloride ion binding capacity of at least 5 mmol/g in a 1-hour Simulated Gastric Fluid ("SGF") Assay, a chloride ion binding capacity of at least 8 mmol/g in a 24-hour Simulated Gastric Fluid ("SGF") Assay, and a chloride ion binding capacity in a 1-hour Simulated Gastric Fluid ("SGF") Assay that is at least 50% of its chloride ion binding capacity in a 24-hour Simulated Gastric Fluid ("SGF") Assay. In one such embodiment, the crosslinked amine polymer has a chloride ion binding capacity of at least 5 mmol/g in a 1-hour Simulated Gastric Fluid ("SGF") Assay and a chloride ion binding capacity of at least 8, at least 9, at least 10, at least 11, at least 12, at least 13, or even at least 14 mmol/g in a 24-hour Simulated Gastric Fluid ("SGF") Assay and the crosslinked amine polymer has a chloride ion binding capacity in a 1-hour Simulated Gastric Fluid ("SGF") Assay that is at least 50%, at least 60%, at least 70%, at least 80%, or even at least 90% of its chloride ion binding capacity in a 24-hour Simulated Gastric Fluid ("SGF") Assay.

A further aspect of the present disclosure is a pharmaceutical composition comprising a crosslinked amine polymer having a chloride ion binding capacity in a 24-hour Simulated Small Intestine Organic and Inorganic Buffer ("SOB") assay of at least 2.5 mmol chloride/g polymer. In one such embodiment, the crosslinked amine polymer has a chloride ion binding capacity in a 24-hour Simulated Small Intestine Organic and Inorganic Buffer ("SOB") assay of at least 2.5, at least 3, at least 3.5, at least 4, at least 4.5, or even at least 5 mmol chloride/g polymer.

A further aspect of the present disclosure is a pharmaceutical composition comprising a crosslinked amine polymer having a chloride ion binding capacity in a 2-hour Simulated Small Intestine Organic and Inorganic Buffer ("SOB") assay of at least 0.5 mmol chloride/g polymer and a 24-hour Simulated Small Intestine Organic and Inorganic Buffer ("SOB") assay of at least 2.5 mmol chloride/g polymer. In one such embodiment, the crosslinked amine polymer has a chloride ion binding capacity in a 2-hour Simulated Small Intestine Organic and Inorganic Buffer ("SOB") assay of at least 0.5, at least 1, at least 1.5, at least 2, at least 2.5, or even at least 3 mmol chloride/g polymer and a 24-hour Simulated Small Intestine Organic and Inorganic Buffer ("SOB") assay of at least 2.5, at least 3, at least 3.5, at least 4, at least 4.5, or even at least 5 mmol chloride/g polymer.

A further aspect of the present disclosure is a pharmaceutical composition comprising a crosslinked amine polymer having a chloride ion binding capacity of at least 2 mmol chloride/g polymer at 4 hours in Simulated Small Intestine Inorganic Buffer ("SIB"). In one such embodiment, the crosslinked amine polymer has a chloride ion binding capacity of at least 2, at least 2.5, at least 3, at least 3.5, or even at least 4 mmol chloride/g polymer at 4 hours in Simulated Small Intestine Inorganic Buffer ("SIB").

A further aspect of the present disclosure is a pharmaceutical composition comprising a crosslinked amine polymer having a chloride ion binding capacity of at least 2 mmol chloride/g polymer at 4 hours in Simulated Small Intestine Inorganic Buffer ("SIB") and a crosslinked amine polymer having a chloride ion binding capacity of at least 2 mmol chloride/g polymer at 24 hours in Simulated Small Intestine Inorganic Buffer ("SIB"). In one such embodiment, the crosslinked amine polymer has a chloride ion binding capacity of at least 2, at least 2.5, at least 3, at least 3.5, or even at least 4 mmol chloride/g polymer at 4 hours in Simulated Small Intestine Inorganic Buffer ("SIB") and a crosslinked amine polymer having a chloride ion binding capacity of at least 2, at least 2.5, at least 3, at least 3.5, or even at least 4 mmol chloride/g polymer at 24 hours in Simulated Small Intestine Inorganic Buffer ("SIB").

A further aspect of the present disclosure is a pharmaceutical composition comprising a crosslinked amine polymer having a chloride ion binding capacity in a 24-hour Simulated Small Intestine Organic and Inorganic Buffer ("SOB") assay of at least 5.5 mmol chloride/g polymer. In one such embodiment, the crosslinked amine polymer has a chloride ion binding capacity in a 24-hour Simulated Small Intestine Organic and Inorganic Buffer ("SOB") assay of at least 6 mmol chloride/g polymer.

A further aspect of the present disclosure is a pharmaceutical composition comprising a crosslinked amine polymer as described in certain paragraphs above wherein the crosslinked amine polymer has a pKa of at least 6 (at equilibrium, measured in 100 mM NaCl). In one such embodiment, the crosslinked amine polymer has a pKa of at least 6.5, at least 7, or even at least 7.5 (at equilibrium, measured in 100 mM NaCl). A further aspect of the present disclosure is a pharmaceutical composition comprising a crosslinked amine polymer, wherein the crosslinked amine polymer has a pKa of at least 6 (at equilibrium, measured in 100 mM NaCl), prepared by a process comprising two discrete polymerization/crosslinking steps, where in the first step, a preformed amine polymer having a chloride binding capacity of at least 10 mmol/g in Simulated Gastric Fluid ("SGF") and a Swelling Ratio in the range of 2 to 10 is formed. In the second step, the preformed amine polymer is crosslinked with a crosslinker containing amine reactive moieties to form a post-polymerization crosslinked amine polymer. The resulting post-polymerization crosslinked amine polymer has a binding capacity for competing anions (e.g., phosphate, citrate and/or taurocholate) in an appropriate assay (e.g., SIB or SOB) that is less than the binding capacity of the preformed polymer for the competing anions (e.g., phosphate, citrate and/or taurocholate) in the same appropriate assay (e.g., SIB or SOB). In one embodiment the preformed amine polymer has a Swelling Ratio in the range of 3 to 8. In one such embodiment, the preformed amine polymer has a Swelling Ratio in the range of 4 to 6. In one such embodiment, the crosslinked amine polymer has a pKa of at least 6.5, at least 7, or even at least 7.5 (at equilibrium, measured in 100 mM NaCl). A further aspect of the present disclosure is a pharmaceutical composition comprising a crosslinked amine polymer, wherein the crosslinked amine polymer has a pKa of at least 6 (at equilibrium, measured in 100 mM NaCl), prepared by a process comprising two discrete crosslinking steps, where in the first crosslinking step, a preformed amine polymer is formed, the preformed amine polymer having a chloride binding capacity of at least 10 mmol/g in Simulated Gastric Fluid ("SGF") and a Swelling Ratio in the range of 2 to 10 and an average particle size of at least 80 microns. The preformed amine polymer is (at least partially) deprotonated with a base and, in the second step, the deprotonated preformed amine polymer Is crosslinked with a crosslinker containing amine reactive moieties to form a post-polymerization crosslinked amine polymer. In one embodiment the preformed amine polymer has a Swelling Ratio in the range of 3 to 8. In one such embodiment, the preformed amine polymer has a Swelling Ratio in the range of 4 to 6. In one such embodiment, the crosslinked amine polymer has a pKa of at least 6.5, at least 7, or even at least 7.5 (at equilibrium, measured in 100 mM NaCl). A further aspect of the present disclosure is a pharmaceutical composition comprising a crosslinked amine polymer, wherein the crosslinked amine polymer has a pKa of at least 6 (at equilibrium, measured in 100 mM NaCl), prepared by a process comprising two discrete polymerization/crosslinking steps, where in the first step, a preformed amine polymer having a chloride binding capacity of at least 10 mmol/g in Simulated Gastric Fluid ("SGF") and a Swelling Ratio in the range of 2 to 10 is formed. The preformed amine polymer is (at least partially) deprotonated with a base and contacted with a swelling agent to swell the deprotonated preformed amine polymer. In the second step, the swollen, deprotonated preformed amine polymer is crosslinked with a crosslinker containing amine reactive moieties to form a post-polymerization crosslinked amine polymer. In one embodiment the preformed amine polymer has a Swelling Ratio in the range of 3 to 8. In one such embodiment, the preformed amine polymer has a Swelling Ratio in the range of 4 to 6. In one such embodiment, the crosslinked amine polymer has a pKa of at least 6.5, at least 7, or even at least 7.5 (at equilibrium, measured in 100 mM NaCl). A further aspect of the present disclosure is a pharmaceutical composition comprising a crosslinked amine polymer, wherein the crosslinked amine polymer has a pKa of at least 6 (at equilibrium, measured in 100 mM NaCl), and a pharmaceutically acceptable excipient. The crosslinked amine polymer, for example, may be prepared by crosslinking a preformed amine polymer in a reaction mixture containing the preformed amine polymer, a solvent, a crosslinking agent, and a swelling agent for the preformed amine polymer. The swelling agent is preferably immiscible with the solvent, the preformed amine polymer has an absorption capacity for the swelling agent, and the amount of swelling agent in the reaction mixture is less than the absorption capacity of the preformed amine polymer for the swelling agent. The crosslinked amine polymer, for example, may be prepared by crosslinking a preformed amine polymer in a reaction mixture containing the preformed amine polymer, a solvent, and a crosslinking agent to form a crosslinked amine polymer. Prior to the crosslinking step, the preformed amine polymer binds a first amount of chloride and competing anions (e.g., phosphate, citrate and/or taurocholate) and after the crosslinking step, the crosslinked amine polymer binds a second (different) amount of chloride and competing anions (e.g., phosphate, citrate and/or taurocholate) in an appropriate assay (e.g., SIB or SOB). For example, in one such embodiment, the second amount of the competing anions (e.g., phosphate, citrate and/or taurocholate) bound is relatively less than the first amount of the competing anions. The crosslinked amine polymer, for example, may be prepared by two discrete polymerization/crosslinking steps are performed in accordance with one aspect of the present disclosure, where in the first step, a preformed amine polymer is prepared. The preformed amine polymer is deprotonated and further crosslinked in a second polymerization/crosslinking step to form a post-polymerization crosslinked polymer. Advantageously, the primary crosslinking reaction is between carbon atoms (i.e., carbon-carbon crosslinking) in the first step, whereas crosslinking is primarily between amine moieties comprised by the preformed amine polymer in the second step. The crosslinked amine polymer, for example, may be prepared by discrete polymerization/crosslinking steps, where in the first step, a preformed amine polymer having a chloride binding capacity of at least 10 mmol/g in Simulated Gastric Fluid ("SGF") and a Swelling Ratio in the range of 2 to 10 is formed. In the second step, the preformed amine polymer is crosslinked with a crosslinker containing amine reactive moieties to form a post-polymerization crosslinked amine polymer. The resulting post-polymerization crosslinked amine polymer has a binding capacity for competing anions (e.g., phosphate, citrate and/or taurocholate) in an appropriate assay (e.g., SIB or SOB) that is less than the binding capacity of the preformed polymer for the competing anions (e.g., phosphate, citrate and/or taurocholate) in the same appropriate assay (e.g., SIB or SOB). In one embodiment the preformed amine polymer has a Swelling Ratio in the range of 3 to 8. In one such embodiment, the preformed amine polymer has a Swelling Ratio in the range of 4 to 6. The crosslinked amine polymer, for example, may be prepared by two discrete crosslinking steps, where in the first crosslinking step, a preformed amine polymer is formed, the preformed amine polymer having a chloride binding capacity of at least 10 mmol/g in Simulated Gastric Fluid ("SGF") and a Swelling Ratio in the range of 2 to 10 and an average particle size of at least 80 microns. The preformed amine polymer is (at least partially) deprotonated with a base and, in the second step, the deprotonated preformed amine polymer is crosslinked with a crosslinker containing amine reactive moieties to form a post-polymerization crosslinked amine polymer. In one embodiment the preformed amine polymer has a Swelling Ratio in the range of 3 to 8. In one such embodiment, the preformed amine polymer has a Swelling Ratio in the range of 4 to 6. The crosslinked amine polymer, for example, may be prepared by two discrete polymerization/crosslinking steps, where in the first step, a preformed amine polymer having a chloride binding capacity of at least 10 mmol/g in Simulated Gastric Fluid ("SGF") and a Swelling Ratio in the range of 2 to 10 is formed. The preformed amine polymer is (at least partially) deprotonated with a base and contacted with a swelling agent to swell the deprotonated preformed amine polymer. In the second step, the swollen, deprotonated preformed amine polymer is crosslinked with a crosslinker containing amine reactive moieties to form a post-polymerization crosslinked amine polymer. In one embodiment the preformed amine polymer has a Swelling Ratio in the range of 3 to 8. In one such embodiment, the preformed amine polymer has a Swelling Ratio in the range of 4 to 6. A further aspect of the present disclosure is a pharmaceutical composition comprising a crosslinked amine polymer, wherein the crosslinked amine polymer has a pKa of at least 6 (at equilibrium, measured in 100 mM NaCl), having a chloride ion binding capacity of at least 4 mmol/g in Simulated Small Intestine Inorganic Buffer ("SIB"). In one embodiment, the crosslinked amine polymer has a chloride ion binding capacity of at least 4.5, 5, 5.5, or even at least 6 mmol/g in Simulated Small Intestine Inorganic Buffer ("SIB"). In one such embodiment, the crosslinked amine polymer has a pKa of at least 6.5, at least 7, or even at least 7.5 (at equilibrium, measured in 100 mM NaCl). A further aspect of the present disclosure is a pharmaceutical composition comprising a crosslinked amine polymer, wherein the crosslinked amine polymer has a pKa of at least 6 (at equilibrium, measured in 100 mM NaCl), having a ratio of chloride ion binding capacity to phosphate ion binding capacity in Simulated Small Intestine Inorganic Buffer ("SIB") of at least 2.3:1, respectively. In one embodiment, the crosslinked amine polymer has a ratio of chloride ion binding capacity to phosphate Ion binding capacity In Simulated Small Intestine Inorganic Buffer ("SIB") of at least 2.5:1, 3:1, 3.5:1, or even 4:1, respectively. In one such embodiment, the crosslinked amine polymer has a pKa of at least 6.5, at least 7, or even at least 7.5 (at equilibrium, measured in 100 mM NaCl). A further aspect of the present disclosure is a pharmaceutical composition comprising a crosslinked amine polymer, wherein the crosslinked amine polymer has a pKa of at least 6 (at equilibrium, measured in 100 mM NaCl), having a chloride ion binding capacity of at least 1 mmol/g in Simulated Small Intestine Inorganic Buffer ("SIB"), a phosphate ion binding capacity of less than 0.4 mmol/g in SIB, and a chloride ion to phosphate ion binding ratio in SIB of at least 2.3:1, respectively. In one such embodiment, the crosslinked amine polymer has a chloride ion binding capacity of at least 1.5 mmol/g in Simulated Small Intestine Inorganic Buffer ("SIB"), a phosphate ion binding capacity of less than 0.6 mmol/g in SIB, and a chloride ion to phosphate ion binding ratio in SIB of at least 2.3:1, respectively. In another such embodiment, the crosslinked amine polymer has a chloride ion binding capacity of at least 2.0 mmol/g in Simulated Small Intestine Inorganic Buffer ("SIB"), a phosphate ion binding capacity of less than 0.8 mmol/g in SIB, and a chloride ion to phosphate ion binding ratio in SIB of at least 2.3:1, respectively. In one such embodiment, the crosslinked amine polymer has a chloride ion binding capacity of at least 2.5 mmol/g in Simulated Small Intestine Inorganic Buffer ("SIB"), a phosphate ion binding capacity of less than 1.0 mmol/g in SIB, and a chloride ion to phosphate ion binding ratio in SIB of at least 2.3:1, respectively. In one such embodiment, the crosslinked amine polymer has a chloride ion binding capacity of at least 3.0 mmol/g in Simulated Small Intestine Inorganic Buffer ("SIB"), a phosphate ion binding capacity of less than 1.3 mmol/g in SIB, and a chloride ion to phosphate ion binding ratio in SIB of at least 2.3:1, respectively. In one such embodiment, the crosslinked amine polymer has a chloride ion binding capacity of at least 3.5 mmol/g in Simulated Small Intestine Inorganic Buffer ("SIB"), a phosphate ion binding capacity of less than 1.5 mmol/g in SIB, and a chloride ion to phosphate ion binding ratio in SIB of at least 2.3:1, respectively. In one such embodiment, the crosslinked amine polymer has a chloride ion binding capacity of at least 4.0 mmol/g in Simulated Small Intestine Inorganic Buffer ("SIB"), a phosphate ion binding capacity of less than 1.7 mmol/g in SIB, and a chloride ion to phosphate ion binding ratio in SIB of at least 2.3:1, respectively. In one such embodiment, the crosslinked amine polymer has a chloride ion binding capacity of at least 4.5 mmol/g in Simulated Small Intestine Inorganic Buffer ("SIB"), a phosphate ion binding capacity of less than 1.9 mmol/g in SIB, and a chloride ion to phosphate ion binding ratio in SIB of at least 2.3:1, respectively. In one such embodiment, the crosslinked amine polymer has a chloride ion binding capacity of at least 5.0 mmol/g in Simulated Small Intestine Inorganic Buffer ("SIB"), a phosphate ion binding capacity of less than 2.1 mmol/g in SIB, and a chloride ion to phosphate ion binding ratio in SIB of at least 2.3:1, respectively. In one such embodiment, the crosslinked amine polymer has a pKa of at least 6.5, at least 7, or even at least 7.5 (at equilibrium, measured in 100 mM NaCl). In each of the foregoing embodiments, the crosslinked amine polymer may have a chloride ion to phosphate ion binding ratio in SIB of at least 2.5, at least 3, at least 3.5 or even at least 4, respectively. A further aspect of the present disclosure is a pharmaceutical composition comprising a crosslinked amine polymer, wherein the crosslinked amine polymer has a pKa of at least 6 (at equilibrium, measured in 100 mM NaCl), having a ratio of chloride ion binding capacity to phosphate ion binding capacity in Simulated Small Intestine Inorganic Buffer ("SIB") of at least 2.3:1, respectively, and a Swelling Ratio of less than 5. For example, in one such embodiment, the crosslinked amine polymer may have a chloride ion to phosphate ion binding ratio in SIB of at least 2.3:1, at least 2.5, at least 3, at least 3.5 or even at least 4, respectively, and a Swelling Ratio of less than 5, less than 4, less than 3, less than 2, less than 1.5 or even less than 1. In one such embodiment, the crosslinked amine polymer has a pKa of at least 6.5, at least 7, or even at least 7.5 (at equilibrium, measured in 100 mM NaCl). A further aspect of the present disclosure is a pharmaceutical composition comprising a crosslinked amine polymer, wherein the crosslinked amine polymer has a pKa of at least 6 (at equilibrium, measured in 100 mM NaCl), having a retained chloride content of at least 30% of the chloride that was initially bound in a GI Compartment Transit Assay ("GICTA") (i.e., bound during the SGF binding step). In one such embodiment, the crosslinked amine polymer has a retained chloride content of at least 30%, at least 40%, at least 50%, at least 60%, at least 70%, at least 80% or even at least 90% of the chloride that was initially bound in a GI Compartment Transit Assay. In one such embodiment, the crosslinked amine polymer has a pKa of at least 6.5, at least 7, or even at least 7.5 (at equilibrium, measured in 100 mM NaCl). A further aspect of the present disclosure is a pharmaceutical composition comprising a crosslinked amine polymer, wherein the crosslinked amine polymer has a pKa of at least 6 (at equilibrium, measured in 100 mM NaCl), having a retained chloride content of at least 0.5 mmol chloride/g of polymer in a GI Compartment Transit Assay ("GICTA"). In one such embodiment, the crosslinked amine polymer has a retained chloride content of at least 0.5, at least 1, at least 1.5, at least 2, at least 2.5, at least 3, at least 3.5, at least 4, at least 4.5, or even at least 5 mmol chloride/g of polymer in a GI Compartment Transit Assay ("GICTA"). In one such embodiment, the crosslinked amine polymer has a pKa of at least 6.5, at least 7, or even at least 7.5 (at equilibrium, measured in 100 mM NaCl). A further aspect of the present disclosure is a pharmaceutical composition comprising a crosslinked amine polymer, wherein the crosslinked amine polymer has a pKa of at least 6 (at equilibrium, measured in 100 mM NaCl), having a retained chloride content of at least 0.5 mmol chloride/g of polymer in a GI Compartment Transit Assay ("GICTA") and a chloride retention at the end of the GICTA of at least 30% of the chloride that was initially bound in the GICTA (i.e., bound during the SGF binding step). In one such embodiment, the crosslinked amine polymer has a retained chloride content of at least 30%, at least 40%, at least 50%, at least 60%, at least 70%, at least 80% or even at least 90% of the chloride that was initially bound in a GI Compartment Transit Assay and a retained chloride content of at least 0.5, at least 1, at least 1.5, at least 2, at least 2.5, at least 3, at least 3.5, at least 4, at least 4.5, or even at least 5 mmol chloride/g of polymer in a GI Compartment Transit Assay ("GICTA"). In one such embodiment, the crosslinked amine polymer has a pKa of at least 6.5, at least 7, or even at least 7.5 (at equilibrium, measured in 100 mM NaCl). A further aspect of the present disclosure is a pharmaceutical composition comprising a crosslinked amine polymer, wherein the crosslinked amine polymer has a pKa of at least 6 (at equilibrium, measured in 100 mM NaCl), having a chloride ion binding capacity of at least 5 mmol/g in a 1-hour Simulated Gastric Fluid ("SGF") Assay and a chloride ion binding capacity of at least 8 mmol/g in a 24-hour Simulated Gastric Fluid ("SGF") Assay. In one such embodiment, the crosslinked amine polymer has a chloride ion binding capacity of at least 5 mmol/g in a 1-hour Simulated Gastric Fluid ("SGF") Assay and a chloride ion binding capacity of at least 8, at least 9, at least 10, at least 11, at least 12, at least 13, or even at least 14 mmol/g in a 24-hour Simulated Gastric Fluid ("SGF") Assay. In one such embodiment, the crosslinked amine polymer has a pKa of at least 6.5, at least 7, or even at least 7.5 (at equilibrium, measured in 100 mM NaCl). A further aspect of the present disclosure is a pharmaceutical composition comprising a crosslinked amine polymer, wherein the crosslinked amine polymer has a pKa of at least 6 (at equilibrium, measured in 100 mM NaCl), having a chloride ion binding capacity in a 1-hour Simulated Gastric Fluid ("SGF") Assay that is at least 50% of its chloride ion binding capacity in a 24-hour Simulated Gastric Fluid ("SGF") Assay. In one such embodiment, the crosslinked amine polymer has a chloride ion binding capacity in a 1-hour Simulated Gastric Fluid ("SGF") Assay that is at least 50%, at least 60%, at least 70%, at least 80%, or even at least 90% of its chloride ion binding capacity in a 24-hour Simulated Gastric Fluid ("SGF") Assay. In one such embodiment, the crosslinked amine polymer has a pKa of at least 6.5, at least 7, or even at least 7.5 (at equilibrium, measured in 100 mM NaCl). A further aspect of the present disclosure is a pharmaceutical composition comprising a crosslinked amine polymer, wherein the crosslinked amine polymer has a pKa of at least 6 (at equilibrium, measured in 100 mM NaCl), having a chloride ion binding capacity of at least 5 mmol/g in a 1-hour Simulated Gastric Fluid ("SGF") Assay, a chloride ion binding capacity of at least 8 mmol/g in a 24-hour Simulated Gastric Fluid ("SGF") Assay, and a chloride ion binding capacity in a 1-hour Simulated Gastric Fluid ("SGF") Assay that is at least 50% of its chloride ion binding capacity in a 24-hour Simulated Gastric Fluid ("SGF") Assay. In one such embodiment, the crosslinked amine polymer has a chloride ion binding capacity of at least 5 mmol/g in a 1-hour Simulated Gastric Fluid ("SGF") Assay and a chloride ion binding capacity of at least 8, at least 9, at least 10, at least 11, at least 12, at least 13, or even at least 14 mmol/g in a 24-hour Simulated Gastric Fluid ("SGF") Assay and the crosslinked amine polymer has a chloride ion binding capacity in a 1-hour Simulated Gastric Fluid ("SGF") Assay that is at least 50%, at least 60%, at least 70%, at least 80%, or even at least 90% of its chloride ion binding capacity in a 24-hour Simulated Gastric Fluid ("SGF") Assay. In one such embodiment, the crosslinked amine polymer has a pKa of at least 6.5, at least 7, or even at least 7.5 (at equilibrium, measured in 100 mM NaCl). A further aspect of the present disclosure is a pharmaceutical composition comprising a crosslinked amine polymer, wherein the crosslinked amine polymer has a pKa of at least 6 (at equilibrium, measured in 100 mM NaCl), having a chloride ion binding capacity in a 24-hour Simulated Small Intestine Organic and Inorganic Buffer ("SOB") assay of at least 2.5 mmol chloride/g polymer. In one such embodiment, the crosslinked amine polymer has a chloride ion binding capacity in a 24-hour Simulated Small Intestine Organic and Inorganic Buffer ("SOB") assay of at least 2.5, at least 3, at least 3.5, at least 4, at least 4.5, or even at least 5 mmol chloride/g polymer. In one such embodiment, the crosslinked amine polymer has a pKa of at least 6.5, at least 7, or even at least 7.5 (at equilibrium, measured in 100 mM NaCl). A further aspect of the present disclosure is a pharmaceutical composition comprising a crosslinked amine polymer, wherein the crosslinked amine polymer has a pKa of at least 6 (at equilibrium, measured in 100 mM NaCl), having a chloride ion binding capacity in a 2-hour Simulated Small Intestine Organic and Inorganic Buffer ("SOB") assay of at least 0.5 mmol chloride/g polymer and a 24-hour Simulated Small Intestine Organic and Inorganic Buffer ("SOB") assay of at least 2.5 mmol chloride/g polymer. In one such embodiment, the crosslinked amine polymer has a chloride ion binding capacity in a 2-hour Simulated Small Intestine Organic and Inorganic Buffer ("SOB") assay of at least 0.5, at least 1, at least 1.5, at least 2, at least 2.5, or even at least 3 mmol chloride/g polymer and a 24-hour Simulated Small Intestine Organic and Inorganic Buffer ("SOB") assay of at least 2.5, at least 3, at least 3.5, at least 4, at least 4.5, or even at least 5 mmol chloride/g polymer. In one such embodiment, the crosslinked amine polymer has a pKa of at least 6.5, at least 7, or even at least 7.5 (at equilibrium, measured in 100 mM NaCl). A further aspect of the present disclosure is a pharmaceutical composition comprising a crosslinked amine polymer, wherein the crosslinked amine polymer has a pKa of at least 6 (at equilibrium, measured in 100 mM NaCl), having a chloride ion binding capacity of at least 2 mmol chloride/g polymer at 4 hours in Simulated Small Intestine inorganic Buffer ("SIB"). In one such embodiment, the crosslinked amine polymer has a chloride ion binding capacity of at least 2, at least 2.5, at least 3, at least 3.5, or even at least 4 mmol chloride/g polymer at 4 hours in Simulated Small Intestine Inorganic Buffer ("SIB"). In one such embodiment, the crosslinked amine polymer has a pKa of at least 6.5, at least 7, or even at least 7.5 (at equilibrium, measured in 100 mM NaCl). A further aspect of the present disclosure is a pharmaceutical composition comprising a crosslinked amine polymer, wherein the crosslinked amine polymer has a pKa of at least 6 (at equilibrium, measured in 100 mM NaCl), having a chloride ion binding capacity of at least 2 mmol chloride/g polymer at 4 hours in Simulated Small Intestine Inorganic Buffer ("SIB") and a crosslinked amine polymer having a chloride ion binding capacity of at least 2 mmol chloride/g polymer at 24 hours in Simulated Small intestine Inorganic Buffer ("SIB"). In one such embodiment, the crosslinked amine polymer has a chloride ion binding capacity of at least 2, at least 2.5, at least 3, at least 3.5, or even at least 4 mmol chloride/g polymer at 4 hours in Simulated Small Intestine Inorganic Buffer ("SIB") and a crosslinked amine polymer having a chloride ion binding capacity of at least 2, at least 2.5, at least 3, at least 3.5, or even at least 4 mmol chloride/g polymer at 24 hours in Simulated Small Intestine Inorganic Buffer ("SIB"). In one such embodiment, the crosslinked amine polymer has a pKa of at least 6.5, at least 7, or even at least 7.5 (at equilibrium, measured in 100 mM NaCl). A further aspect of the present disclosure is a pharmaceutical composition comprising a crosslinked amine polymer, wherein the crosslinked amine polymer has a pKa of at least 6 (at equilibrium, measured in 100 mM NaCl), having a chloride ion binding capacity in a 24-hour Simulated Small Intestine Organic and Inorganic Buffer ("SOB") assay of at least 5.5 mmol chloride/g polymer. In one such embodiment, the crosslinked amine polymer has a chloride ion binding capacity in a 24-hour Simulated Small Intestine Organic and Inorganic Buffer ("SOB") assay of at least 6 mmol chloride/g polymer. In one such embodiment, the crosslinked amine polymer has a pKa of at least 6.5, at least 7, or even at least 7.5 (at equilibrium, measured in 100 mM NaCl).

A further aspect of the present disclosure is a pharmaceutical composition comprising a crosslinked amine polymer having (i) a proton-binding capacity and a chloride binding capacity of at least 5 mmol/g in Simulated Gastric Fluid; and (ii) a chloride ion binding capacity of at least 4 mmol/g at 1 hour in Simulated Small Intestine inorganic Buffer ("SIB").

A further aspect of the present disclosure is a pharmaceutical composition comprising a crosslinked amine polymer having (i) a proton-binding capacity and a chloride binding capacity of at least 5 mmol/g in Simulated Gastric Fluid; and (ii) a chloride ion binding capacity of at least 4 mmol/g, and a phosphate ion binding capacity of less than 2 mmol/g in Simulated Small Intestine Inorganic Buffer ("SIB").

A further aspect of the present disclosure is a pharmaceutical composition comprising a crosslinked amine polymer having (i) a proton-binding capacity and a chloride binding capacity of at least 5 mmol/g in Simulated Gastric Fluid; and (ii) a chloride ion binding capacity at 1 hour in Simulated Small Intestine Inorganic Buffer ("SIB") of at least (i) 2 mmol/g, (ii) 2.5 mmol/g, or (iii) 3 mmol/g.

A further aspect of the present disclosure is a pharmaceutical composition comprising a crosslinked amine polymer having (i) a proton-binding capacity and a chloride binding capacity of at least 5 mmol/g in Simulated Gastric Fluid; and (ii) a chloride to phosphate ion binding ratio of at least 2.3:1, respectively, in Simulated Small Intestine Inorganic Buffer ("SIB").

A further aspect of the present disclosure is a pharmaceutical composition comprising a crosslinked amine polymer having (i) a proton-binding capacity and a chloride binding capacity of at least 5 mmol/g at one hour in Simulated Gastric Fluid and (ii) a proton-binding capacity and a chloride binding capacity in Simulated Gastric Fluid of at least (a) 8 mmol/g, (b) 10 mmol/g, (c) 12 mmol/g, or (d) 14 mmol/g.

A further aspect of the present disclosure is a pharmaceutical composition comprising a crosslinked amine polymer having a proton-binding capacity and a chloride binding capacity at one hour in Simulated Gastric Fluid that is at least X % of the proton-binding capacity and the chloride binding capacity, respectively, of the crosslinked amine polymer at 24 hours in Simulated Gastric Fluid wherein X % is at least (i) 50%, (ii) 60%, (iii) 70%, (iv) 80%, or even (v) 90%.

A further aspect of the present disclosure is a pharmaceutical composition comprising a crosslinked amine polymer having (I) a selectivity for chloride over citrate, phosphate and taurocholate in Simulated Small Intestine Organic and Inorganic Buffer ("SOB"), and (ii) a chloride binding capacity at 24 hours in SOB of at least 4 mmol/g.

A further aspect of the present disclosure is a pharmaceutical composition comprising a crosslinked amine polymer having a selectivity for chloride over citrate, phosphate and taurocholate in Simulated Small Intestine Organic and Inorganic Buffer ("SOB"), at (i) 1 hour, (ii) 4 hours, (iii) 12 hours, (iv) 18 hours, (v) 24 hours, (vi) 30 hours, (vii) 36 hours, or even (viii) 48 hours.

A further aspect of the present disclosure is a pharmaceutical composition comprising a crosslinked amine polymer having a chloride ion binding capacity of at least 4 mmol/g, and a phosphate ion binding capacity of less than 2 mmol/g in Simulated Small Intestine Inorganic Buffer ("SIB") at (i) 1 hour, (ii) 2 hours, (iii) 3 hours, (iv) 4 hours, and/or (v) greater than 4 hours.

Other aspects and features will be in part apparent and in part pointed out hereinafter.

ABBREVIATIONS AND DEFINITIONS

Figure 1A:
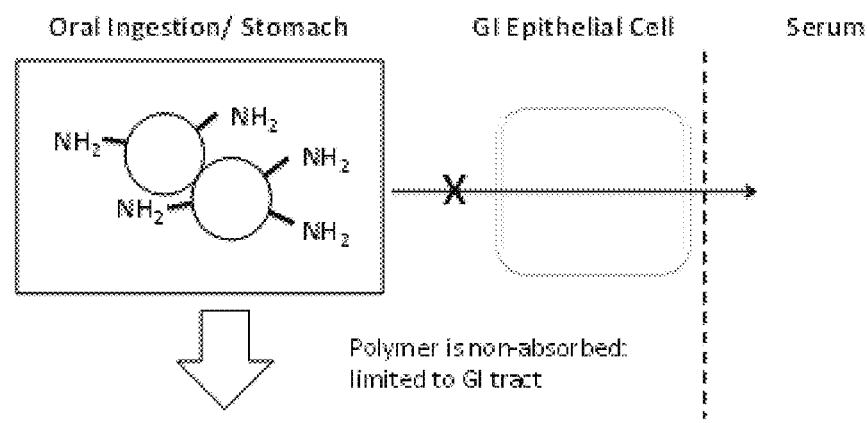
FIG. 1A-1C is a flow chart schematically depicting the mechanism of action of the polymer when passing through the gastrointestinal tract of an individual from oral ingestion/stomach (FIG. 1A), to the upper GI tract (FIG. 1B) to the lower GI tract/colon (FIG. 1C).

The following definitions and methods are provided to better define the present invention and to guide those of ordinary skill in the art in the practice of the present invention. Unless otherwise noted, terms are to be understood according to conventional usage by those of ordinary skill in the relevant art.

The term "absorption capacity" as used herein in connection with a polymer and a swelling agent (or in the case of a mixture of swelling agents, the mixture of swelling agents) is the amount of the swelling agent (or such mixture) absorbed during a period of at least 16 hours at room temperature by a given amount of a dry polymer (e.g., in the form of a dry bead) immersed in an excess amount of the swelling agent (or such mixture).

The term "acrylamide" denotes a moiety having the structural formula $H_2C\!\!=\!\!CH\!\!-\!\!C(O)NR\!\!-\!\!*$, where * denotes the point of attachment of the moiety to the remainder of the molecule and R is hydrogen, hydrocarbyl, or substituted hydrocarbyl.

The term "acrylic" denotes a moiety having the structural formula $H_2C\!\!=\!\!CH\!\!-\!\!C(O)O\!\!-\!\!*$, where * denotes the point of attachment of the moiety to the remainder of the molecule.

The term "alicyclic", "alicyclo" or "alicyclyl" means a saturated monocyclic group of 3 to 8 carbon atoms and includes cyclopentyl, cyclohexyl, cycloheptyl, and the like.

The term "aliphatic" denotes saturated and non-aromatic unsaturated hydrocarbyl moieties having, for example, one to about twenty carbon atoms or, in specific embodiments, one to about twelve carbon atoms, one to about ten carbon atoms, one to about eight carbon atoms, or even one to about four carbon atoms. The aliphatic groups include, for example, alkyl moieties such as methyl, ethyl, n-propyl, isopropyl, n-butyl, isobutyl, sec-butyl, tert-butyl, pentyl, iso-amyl, hexyl and the like, and alkenyl moieties of comparable chain length.

The term "alkanol" denotes an alkyl moiety that has been substituted with at least one hydroxyl group. In some embodiments, alkanol groups are "lower alkanol" groups comprising one to six carbon atoms, one of which is attached to an oxygen atom. In other embodiments, lower alkanol groups comprise one to three carbon atoms.

The term "alkenyl group" encompasses linear or branched carbon radicals having at least one carbon-carbon double bond. The term "alkenyl group" can encompass conjugated and non-conjugated carbon-carbon double bonds or combinations thereof. An alkenyl group, for example and without being limited thereto, can encompass two to about twenty carbon atoms or, in a particular embodiment, two to about twelve carbon atoms. In certain embodiments, alkenyl groups are "lower alkenyl" groups having two to about four carbon atoms. Examples of alkenyl groups include, but are not limited thereto, ethenyl, propenyl, allyl, vinyl, butenyl and 4-methylbutenyl. The terms "alkenyl group" and "lower alkenyl group", encompass groups having "cis" or "trans" orientations, or alternatively, "E" or "Z" orientations.

The term "alkyl group" as used, either alone or within other terms such as "haloalkyl group," "aminoalkyl group" and "alkylamino group", encompasses saturated linear or branched carbon radicals having, for example, one to about twenty carbon atoms or, in specific embodiments, one to about twelve carbon atoms. In other embodiments, alkyl groups are "lower alkyl" groups having one to about six carbon atoms. Examples of such groups include, but are not limited thereto, methyl, ethyl, n-propyl, isopropyl, n-butyl, isobutyl, sec-butyl, tert-butyl, pentyl, iso-amyl, hexyl and the like. In more specific embodiments, lower alkyl groups have one to four carbon atoms.

The term "alkylamino group" refers to amino groups directly attached to the remainder of the molecule via the nitrogen atom of the amino group and wherein the nitrogen atom of the alkylamino group is substituted by one or two alkyl groups. In some embodiments, alkylamino groups are "lower alkylamino" groups having one or two alkyl groups of one to six carbon atoms, attached to a nitrogen atom. In other embodiments, lower alkylamino groups have one to three carbon atoms. Suitable "alkylamino" groups may be mono or dialkylamino such as N-methylamino, N-ethylamino, N,N-dimethylamino, N,N-diethylamino, pentamethyleneamine and the like.

The term "allyl" denotes a moiety having the structural formula $H_2C=CH-CH_2-$*, where * denotes the point of attachment of the moiety to the remainder of the molecule and the point of attachment is to a heteroatom or an aromatic moiety.

The term "allylamine" denotes a moiety having the structural formula $H_2C=CH-CH_2N(X_8)(X_9)$, wherein $X_8$ and $X_9$ are independently hydrogen, hydrocarbyl, or substituted hydrocarbyl, or $X_8$ and $X_9$ taken together form a substituted or unsubstituted alicyclic, aryl, or heterocyclic moiety, each as defined in connection with such term, typically having from 3 to 8 atoms in the ring.

The term "amine" or "amino" as used alone or as part of another group, represents a group of formula $-N(X_8)(X_9)$, wherein $X_8$ and $X_9$ are independently hydrogen, hydrocarbyl, or substituted hydrocarbyl, heteroaryl, or heterocyclo, or $X_8$ and $X_9$ taken together form a substituted or unsubstituted alicyclic, aryl, or heterocyclic moiety, each as defined in connection with such term, typically having from 3 to 8 atoms in the ring.

The term "aminoalkyl group" encompasses linear or branched alkyl groups having one to about ten carbon atoms, any one of which may be substituted with one or more amino groups, directly attached to the remainder of the molecule via an atom other than a nitrogen atom of the amine group(s). In some embodiments, the aminoalkyl groups are "lower aminoalkyl" groups having one to six carbon atoms and one or more amino groups. Examples of such groups include aminomethyl, aminoethyl, aminopropyl, aminobutyl and aminohexyl.

The term "aromatic group" or "aryl group" means an aromatic group having one or more rings wherein such rings may be attached together in a pendent manner or may be fused. In particular embodiments, an aromatic group is one, two or three rings. Monocyclic aromatic groups may contain 5 to 10 carbon atoms, typically 5 to 7 carbon atoms, and more typically 5 to 6 carbon atoms in the ring. Typical polycyclic aromatic groups have two or three rings. Polycyclic aromatic groups having two rings typically have 8 to 12 carbon atoms, preferably 8 to 10 carbon atoms in the rings. Examples of aromatic groups include, but are not limited to, phenyl, naphthyl, tetrahydronaphthyl, indanyl, biphenyl, phenanthryl, anthryl or acenaphthyl.

The term "bead" is used to describe a crosslinked polymer that is substantially spherical in shape.

The term "binds" as used herein in connection with a polymer and one or more ions, that is, a cation (e.g. "proton-binding" polymer) and an anion, is an "ion-binding" polymer and/or when it associates with the ion, generally though not necessarily in a non-covalent manner, with sufficient association strength that at least a portion of the ion remains bound under the in vitro or in vivo conditions in which the polymer is used for sufficient time to effect a removal of the ion from solution or from the body.

The term "crosslinker" as used, either alone or within other terms, encompasses hydrocarbyl or substituted hydrocarbyl, linear or branched molecules capable of reacting with any of the described monomers, or the infinite polymer network, as described in Formula 1, more than one time. The reactive group in the crosslinker can include, but is not limited to alkyl halide, epoxide, phosgene, anhydride, carbamate, carbonate, isocyanate, thioisocyanate, esters, activated esters, carboxylic acids and derivatives, sulfonates and derivatives, acyl halides, aziridines, alpha,beta-unsaturated carbonyls, ketones, aldehydes, pentafluoroaryl groups, vinyl, allyl, acrylate, methacrylate, acrylamide, methacrylamide, styrenic, acrylonitriles and combinations thereof. In one exemplary embodiment, the crosslinker's reactive group will include alkyl halide, epoxide, anhydrides, isocyanates, allyl, vinyl, acrylamide, and combinations thereof. In one such embodiment, the crosslinker's reactive group will be alkyl halide, epoxide, or allyl.

The term "diallylamine" denotes an amino moiety having two allyl groups.

The terms "dry bead" and "dry polymer" refer to beads or polymers that contain no more than 5% by weight of a non-polymer swelling agent or solvent. Often the swelling agent/solvent is water remaining at the end of a purification. This is generally removed by lyophilization or oven drying before storage or further crosslinking of a preformed amine polymer. The amount of swelling agent/solvent can be measured by heating (e.g., heating to 100-200° C.) and measuring the resulting change in weight. This is referred to a "loss on drying" or "LOD."

The term "ethereal" denotes a moiety having an oxygen bound to two separate carbon atoms as depicted the structural formula $*-H_xC-O-CH_x-*$, where * denotes the point of attachment to the remainder of the moiety and x independently equals 0, 1, 2, or 3.

The term "gel" is used to describe a crosslinked polymer that has an irregular shape.

The term "GI Compartment Transit Assay" or "GICTA" denotes an assay where the free amine test polymers, including free amine sevelamer and bixalomer controls, are sequentially exposed to different buffers that simulate different conditions to which a polymer will be exposed while passing through human GI tract. Incubation times in these different conditions are selected to represent the approximate transit time of polymers through a particular section of GI tract. The first step in the "GICTA" is to perform a "simulated gastric fluid (SGF)" assay, in which, polymers are incubated in SGF buffer at a polymer concentration of 2.5 mg/ml. SGF composition reflects typical ionic concentration in a fasting stomach (and are described elsewhere). The polymers are incubated for 1 hour at 37° C., in solid phase extraction (SPE) tubes fitted with 20 micrometer pore-size frits. Blank SPE tubes that contain SGF buffer without polymer are included and processed in an identical manner throughout the "GICTA" screen. A 400 microliter sample is removed, filtered, diluted if necessary, and assayed for chloride content using ion chromatography. For each tested polymer, chloride binding is calculated using the following equation $$\frac{(Cl\ start - Cl\ eq) \times 4}{2.5}$$

Binding capacity expressed as mmol chloride/g polymer: where Cl start corresponds to the starting concentration of chloride in the SGF buffer (mM), Cl eq corresponds to the equilibrium value of chloride in the diluted measured filtrates after exposure to the test polymer for 1 hour (mM), 4 is the dilution factor and 2.5 is the polymer concentration in mg/ml. The SPE tubes are further rinsed with DI water twice and excess liquid is removed by applying negative pressure at the bottom. Simulated Small Intestine Organic and Inorganic Buffer (SOB) buffer is then added to the tubes to achieve polymer concentration of 2.5 mg/ml (assuming no loss of polymer while sampling supernatant for ion chromatography analysis in SGF binding step). The concentrations of potential competing anions in SOB buffer reflect typical composition of fluid present in small intestine (and are described elsewhere). The polymers are incubated in this buffer for 2 hours at 37° C. A 400 microliter sample is removed, filtered, diluted if necessary, and assayed for ions bound or released in this buffer using ion chromatography. For each tested polymer, and for each anion present in the SOB buffer binding is calculated as mmol of anion bound per gram of polymer.

$$\text{Ions bound/released (mmol/g)} = \frac{([\text{Ion}]_{start} - [\text{Ion}]_{final}) \times [\text{dilution factor}]}{2.5}$$

where $[\text{Ion}]_{start}$ corresponds to the starting concentration of an ion in the SOB buffer (mM), $[\text{Ion}]_{final}$ corresponds to the final value of that particular ion in the measured filtrates after exposure to the test polymer (mM), and 2.5 is the polymer concentration in mg/ml. Excess SOB buffer is then removed by applying negative pressure at the bottom of the tube and tubes are further rinsed with DI water twice and excess liquid is removed by applying negative pressure at the bottom. "Retention Buffer" is then added to the tubes to achieve polymer concentration of 2.5 mg/ml (assuming no loss of polymer while sampling supernatant for ion chromatography analysis in SGF and SOB binding steps). Retention Buffer comprises 50 mM N,N-bis(2-hydroxyethyl)-2-aminoethanesulfonic acid (BES), 100 mM sodium acetate, 2 mM sodium phosphate, 3 mM sodium sulphate, 17 mM sodium chloride and 30 mM sodium bicarbonate adjusted to pH 7. The anion composition in Retention Buffer represent typical late-colon lumen concentrations (Wrong, O et al. [1965] Clinical Science 28, 357-375). The SPE tubes are capped and sealed and incubated at 37° C. for approximately 40 hours, which is a typical transit time for the human large intestine (Metcalf, A M et al. Gastroenterology [1987] 92: 40-47). A 400 microliter sample is removed, filtered, diluted if necessary, and assayed for anion content as described above for SOB. For each tested polymer, ions bound or released from the polymer in retention matrix are calculated using the following calculation $$\text{Ions bound/released (mmol/g)} = \frac{([\text{Ion}]_{start} - [\text{Ion}]_{final}) \times [\text{dilution factor}]}{2.5}$$

where $[\text{Ion}]_{start}$ corresponds to the starting concentration of an ion in Retention Buffer (mM), $[\text{Ion}]_{final}$ corresponds to the final value of that particular ion in the measured filtrates after exposure to the test polymer for 40 hours (mM), and 2.5 is the polymer concentration in mg/ml. The excess retention matrix is removed by applying negative pressure to the bottom of the SPE tubes. The tubes are further rinsed with DI water twice and excess liquid is removed by applying negative pressure at the bottom. Ions that remain bound to the polymers are eluted by adding 0.2M NaOH to the SPE tubes to achieve a final polymer concentration of 2.5 mg/ml (assuming no loss of polymer in prior three binding steps) and incubating for 16-20 hours at 37° C. A 600 microliter sample is removed, filtered, diluted if necessary, and assayed for anion content as described above for SOB. For each tested polymer, ions released from the polymer in retention matrix is calculated using the following calculation $$\text{Ions released (mmol/g)} = \frac{([\text{Ion}]_{start} - [\text{Ion}]_{final}) \times [\text{dilution factor}]}{2.5}$$

where $[\text{Ion}]_{start}$ corresponds to the starting concentration of an ion in the elution solution (0.2 M NaOH) in mM, $[\text{Ion}]_{final}$ corresponds to the final value of that particular ion in the measured filtrates after exposure to the test polymer for 16-20 hours in 0.2 M NaOH (mM), and 2.5 is the polymer concentration in mg/ml.

The term "halo" means halogens such as fluorine, chlorine, bromine or iodine atoms.

The term "haloalkyl group" encompasses groups wherein any one or more of the alkyl carbon atoms is substituted with halo as defined above. Specifically encompassed are mono-haloalkyl, dihaloalkyl and polyhaloalkyl groups including perhaloalkyl. A monohaloalkyl group, for example, may have either an iodo, bromo, chloro or fluoro atom within the group. Dihalo and polyhaloalkyl groups may have two or more of the same halo atoms or a combination of different halo groups. "Lower haloalkyl group" encompasses groups having 1-6 carbon atoms. In some embodiments, lower haloalkyl groups have one to three carbon atoms. Examples of haloalkyl groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl.

The term "heteroaliphatic" describes a chain of 1 to 25 carbon atoms, typically 1 to 12 carbon atoms, more typically 1 to 10 carbon atoms, and most typically 1 to 8 carbon atoms, and in some embodiments 1 to 4 carbon atoms that can be saturated or unsaturated (but not aromatic), containing one or more heteroatoms, such as halogen, oxygen, nitrogen, sulfur, phosphorus, or boron. A heteroatom atom may be a part of a pendant (or side) group attached to a chain of atoms (e.g., —CH(OH)—CH(NH$_2$)— where the carbon atom is a member of a chain of atoms) or it may be one of the chain atoms (e.g., —ROR— or —RNHR— where each R is aliphatic). Heteroaliphatic encompasses heteroalkyl and heterocyclo but does not encompass heteroaryl.

The term "heteroalkyl" describes a fully saturated heteroaliphatic moiety.

The term "heteroaryl" means a monocyclic or bicyclic aromatic radical of 5 to 10 ring atoms, unless otherwise stated, where one or more, (in one embodiment, one, two, or three), ring atoms are heteroatom selected from N, O, or S, the remaining ring atoms being carbon. Representative examples include, but are not limited to, pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl, tetrazolyl, and the like. As defined herein, the terms "heteroaryl" and "aryl" are mutually exclusive. "Heteroarylene" means a divalent heteroaryl radical.

The term "heteroatom" means an atom other than carbon and hydrogen. Typically, but not exclusively, heteroatoms are selected from the group consisting of halogen, sulfur, phosphorous, nitrogen, boron and oxygen atoms. Groups containing more than one heteroatom may contain different heteroatoms.

The term "heterocyclo," "heterocyclic," or heterocyclyl" means a saturated or unsaturated group of 4 to 8 ring atoms in which one or two ring atoms are heteroatom such as N, O, B, P and $S(O)_n$, where n is an integer from 0 to 2, the remaining ring atoms being carbon. Additionally, one or two ring carbon atoms in the heterocyclyl ring can optionally be replaced by a —C(O)— group. More specifically the term heterocyclyl includes, but is not limited to, pyrrolidino, piperidino, homopiperidino, 2-oxopyrrolidinyl, 2-oxopiperidinyl, morpholino, piperazino, tetrahydro-pyranyl, thiomorpholino, and the like. When the heterocyclyl ring is unsaturated it can contain one or two ring double bonds provided that the ring is not aromatic. When the heterocyclyl group contains at least one nitrogen atom, it is also referred to herein as heterocycloamino and is a subset of the heterocyclyl group.

The term "hydrocarbon group" or "hydrocarbyl group" means a chain of 1 to 25 carbon atoms, typically 1 to 12 carbon atoms, more typically 1 to 10 carbon atoms, and most typically 1 to 8 carbon atoms. Hydrocarbon groups may have a linear or branched chain structure. Typical hydrocarbon groups have one or two branches, typically one branch. Typically, hydrocarbon groups are saturated. Unsaturated hydrocarbon groups may have one or more double bonds, one or more triple bonds, or combinations thereof. Typical unsaturated hydrocarbon groups have one or two double bonds or one triple bond; more typically unsaturated hydrocarbon groups have one double bond.

"Initiator" is a term used to describe a reagent that initiates a polymerization.

The term "molecular weight per nitrogen" or "MW/N" represents the calculated molecular weight in the polymer per nitrogen atom. It represents the average molecular weight to present one amine function within the crosslinked polymer. It is calculated by dividing the mass of a polymer sample by the moles of nitrogen present in the sample. "MW/N" is the inverse of theoretical capacity, and the calculations are based upon the feed ratio, assuming full reaction of crosslinker and monomer. The lower the molecular weight per nitrogen the higher the theoretical capacity of the crosslinked polymer.

"Optional" or "optionally" means that the subsequently described event or circumstance may but need not occur, and that the description includes instances where the event or circumstance occurs and instances in which it does not. For example, "heterocyclyl group optionally substituted with an alkyl group" means that the alkyl may but need not be present, and the description includes embodiments in which the heterocyclyl group is substituted with an alkyl group and embodiments in which the heterocyclyl group is not substituted with alkyl.

"Pharmaceutically acceptable" as used in connection with a carrier, diluent or excipient means a carrier, diluent or an excipient, respectively, that is useful in preparing a pharmaceutical composition that is generally safe, non-toxic and neither biologically nor otherwise undesirable for veterinary use and/or human pharmaceutical use.

"Simulated Gastric Fluid" or "SGF" Assay describes a test to determine total chloride binding capacity for a test polymer using a defined buffer that simulates the contents of gastric fluid as follows: Simulated gastric fluid (SGF) consists of 35 mM NaCl, 63 mM HCl, pH 1.2. To perform the assay, the free-amine polymer being tested is prepared at a concentration of 2.5 mg/ml (25 mg dry mass) in 10 mL of SGF buffer. The mixture is incubated at 37° C. overnight for ~12-16 hours with agitation on a rotisserie mixer. Unless another time period is otherwise stated, SGF binding data or binding capacities recited herein are determined in a time period of this duration. After incubation and mixing, the tubes containing the polymer are centrifuged for 2 minutes at 500-1000×g to pellet the test samples. Approximately 750 microliters of supernatant are removed and filtered using an appropriate filter, for example a 0.45 micrometer pore-size syringe filter or an 800 microliter, 1 micrometer pore-size, 96-well, glass filter plate that has been fitted over a 96-well 2 mL collection plate. With the latter arrangement multiple samples tested in SGF buffer can be prepared for analysis, including the standard controls of free amine sevelamer, free amine bixalomer and a control tube containing blank buffer that is processed through all of the assay steps. With the samples arrayed in the filter plate and the collection plate fitted on the bottom, the unit is centrifuged at 1000×g for 1 minute to filter the samples. In cases of small sample sets, a syringe filter may be used in lieu of the filter plate, to retrieve ~2-4 mL of filtrate into a 15 mL container. After filtration, the respective filtrates are diluted 4× with water and the chloride content of the filtrate is measured via ion chromatography (IC). The IC method (e.g. Dionex ICS-2100, Thermo Scientific) consists of an AS11 column and a 15 mM KOH mobile phase, an injection volume of 5 microliters, with a run time of 3 minutes, a washing/rinse volume of 1000 microliters, and flow rate of 1.25 mL/min. To determine the chloride bound to the polymer, the following calculation is completed:

$$\frac{(Cl\ \text{start} - Cl\ eq) \times 4}{2.5}.$$

Binding capacity expressed as mmol chloride/g polymer: where Cl start corresponds to the starting concentration of chloride in the SGF buffer, Cl eq corresponds to the equilibrium value of chloride in the diluted measured filtrates after exposure to the test polymer, 4 is the dilution factor and 2.5 is the polymer concentration in mg/ml.

"Simulated Small Intestine Inorganic Buffer" or "SIB" is a test to determine the chloride and phosphate binding capacity of free amine test polymers in a selective specific interfering buffer assay (SIB). The chloride and phosphate binding capacity of free amine test polymers, along with the chloride and phosphate binding capacity of free amine sevelamer and bixalomer control polymers, was determined using the selective specific interfering buffer assay (SIB) as follows: The buffer used for the SIB assay comprises 36 mM NaCl, 20 mM $NaH_2PO_4$, 50 mM 2-(N-morpholino)ethanesulfonic acid (MES) buffered to pH 5.5. The SIB buffer contains concentrations of chloride, phosphate and pH that are present in the human duodenum and upper gastrointestinal tract (Stevens T, Conwell D L, Zuccaro G, Van Lente F, Khandwala F, Purich E, et al. Electrolyte composition of endoscopically collected duodenal drainage fluid after synthetic porcine secretin stimulation in healthy subjects. Gastrointestinal endoscopy. 2004; 60(3):351-5, Fordtran J, Locklear T. Ionic constituents and osmolality of gastric and small-intestinal fluids after eating. Digest Dis Sci. 1966; 11(7):503-21) and is an effective measure of the selectivity of chloride binding compared to phosphate binding by a polymer. To perform the assay, the free amine polymer being tested is prepared at a concentration of 2.5 mg/ml (25 mg dry mass) in 10 mL of SIB buffer. The mixture is incubated at 37° C. for 1 hour with agitation on a rotisserie mixer. Unless another time period is otherwise stated, SIB binding data or binding capacities recited herein are determined in a time period of this duration. After incubation and mixing, the tubes containing the polymer are centrifuged for 2 minutes at 1000×g to pellet the test samples. 750 microliter of supernatant is removed and filtered using an 800 microliter, 1 micrometer pore-size, 96-well, glass filter plate that has been fitted over a 96-well 2 mL collection plate; with this arrangement multiple samples tested in SIB buffer can be prepared for analysis, including the standard controls of free amine sevelamer, free amine bixalomer and a control tube containing blank buffer that is processed through all of the assay steps. With the samples arrayed in the filter plate and the collection plate fitted on the bottom, the unit is centrifuged at 1000×g for 1 minute to filter the samples. In cases of small sample sets, a syringe filter (0.45 micrometer) may be used in lieu of the filter plate, to retrieve ~2-4 mL of filtrate into a 15 mL vial. After filtration into the collection plate, the respective filtrates are diluted before measuring for chloride or phosphate content. For the measurement of chloride and phosphate, the filtrates under analysis are diluted 4× with water. The chloride and phosphate content of the filtrate is measured via ion chromatography (IC). The IC method (e.g. Dionex ICS-2100, Thermo Scientific) consists of an AS24A column, a 45 mM KOH mobile phase, an injection volume of 5 microliters, with a run time of about 10 minutes, a washing/rinse volume of 1000 microliter, and flow rate of 0.3 mL/min. To determine the chloride bound to the polymer, the following calculation is completed:

Binding capacity expressed as mmol chloride/g polymer =
$$\frac{(Cl_{start} - Cl_{final}) \times 4}{2.5}$$

where $Cl_{start}$ corresponds to the starting concentration of chloride in the SIB buffer, $Cl_{final}$ corresponds to the final value of chloride in the measured diluted filtrates after exposure to the test polymer, 4 is the dilution factor and 2.5 is the polymer concentration in mg/ml. To determine the phosphate bound to the polymer, the following calculation is completed:

Binding capacity expressed as mmol phosphate/g polymer =
$$\frac{(P_{start} - P_{final}) \times 4}{2.5}$$

where $P_{start}$ corresponds to the starting concentration of phosphate in the SIB buffer, $P_{final}$ corresponds to the final value of phosphate in the measured diluted filtrates after exposure to the test polymer, 4 is the dilution factor and 2.5 is the polymer concentration in mg/ml.

"Simulated Small Intestine Organic and Inorganic Buffer" or "SOB" is a test to determine the chloride binding capacity, measured in the presence of specific organic and inorganic interferents commonly found in the gastrointestinal tract. The chloride binding capacity, as well as the binding capacity for other anions, of free amine test polymers and of free amine sevelamer and bixalomer control polymers, was measured in the presence of specific organic interferents commonly found in the gastrointestinal tract as follows: To mimic the conditions of the GI lumen, the SOB screen is used to determine the chloride binding capacity of free amine polymers when they are exposed to chloride in the presence of other potential competing anions such as bile acid, fatty acid, phosphate, acetate and citrate. The test buffer used for SOB assay comprises 50 mM 2-(N-morpholino)ethanesulfonic acid (MES), 50 mM sodium acetate, 36 mM sodium chloride, 7 mM sodium phosphate, 1.5 mM sodium citrate, 30 mM oleic acid and 5 mM Sodium taurocholate, buffered to pH 6.2. The concentrations of potential competing anions reflect typical gastrointestinal lumen concentrations found at various points of the GI tract and the pH is an average value representative of pH values encountered both the duodenum and the large intestine. The chloride concentration used is the same as that used in the SIB screen. To perform the assay, the free amine polymer to be tested is accurately weighed in a 16×100 mm glass tube with a liquid-tight screw cap. An appropriate amount of SOB buffer is added to the test tube to achieve a final polymer concentration of 2.5 mg/ml. The mixture is incubated at 37° C. for 2 hours (unless a different time is stated) with agitation on a rotisserie mixer. Unless another time period is otherwise stated, SOB binding data or binding capacities recited herein are determined in a time period of this duration. After incubation and mixing, 600 microliters of supernatant is removed and filtered using a 96-well glass filter plate. With the samples arrayed in the filter plate and the collection plate fitted on the bottom, the unit is centrifuged at 1000×g for 1 minute to filter the samples. In cases of small sample sets, a syringe filter may be used in lieu of the filter plate, to retrieve ~2-4 mL of filtrate into a 15 mL vial. After filtration into the collection plate, the respective filtrates are diluted appropriately before measuring for anion content. The IC method (e.g. Dionex ICS-2100, Thermo Scientific) consists of an AS24A column, a KOH gradient from 20 mM to 100 mM, an injection volume of 5 microliters, with a run time of about 30 minutes, a washing/rinse volume of 1000 microliters, and flow rate of 0.3 mL/min. This method is suitable for quantitating chloride, phosphate, and taurocholate. Other appropriate methods may be substituted. To determine the ions bound to the polymer, the following calculation is completed Binding capacity expressed as mmol of ion/g polymer =
$$\frac{([Ion]_{start} - [Ion]_{final}) \times [\text{dilution factor}]}{2.5}$$

where $[Ion]_{start}$ corresponds to the starting concentration of an ion in the SOB buffer, $[Ion]_{final}$ corresponds to the final value of that particular ion in the measured filtrates after exposure to the test polymer, dilution factor is the dilution factor and 2.5 is the polymer concentration in mg/ml.

The term "substituted hydrocarbyl," "substituted alkyl," "substituted alkenyl," "substituted aryl," "substituted heterocyclo," or "substituted heteroaryl" as used herein denotes hydrocarbyl, alkyl, alkenyl, aryl, heterocyclo, or heteroaryl moieties which are substituted with at least one atom other than carbon and hydrogen, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, keto, acyl, acyloxy, nitro, amino, amido, nitro, cyano, thiol, ketals, acetals, esters and ethers.

"Swelling Ratio" or simply "Swelling" describes the amount of water absorbed by a given amount of polymer divided by the weight of the polymer aliquot. The Swelling Ratio is expressed as: swelling=(g swollen polymer−g dry polymer)/g dry polymer. The method used to determine the Swelling Ratio for any given polymer comprised the following:

a. 50-100 mg of dry (less than 5 weight % water content) polymer is placed into an 11 mL sealable test tube (with screw cap) of known weight (weight of tube=Weight A).
b. Deionized water (10 mL) Is added to the tube containing the polymer. The tube is sealed and tumbled for 16 hours (overnight) at room temperature. After incubation, the tube is centrifuged at 3000×g for 3 minutes and the supernatant is carefully removed by vacuum suction. For polymers that form a very loose sediment, another step of centrifugation is performed.
c. After step (b), the weight of swollen polymer plus tube (Weight B) is recorded.
d. Freeze at −40° C. for 30 minutes. Lyophilize for 48 h. Weigh dried polymer and test tube (recorded as Weight C).
e. Calculate g water absorbed per g of polymer, defined as: [(Weight B−Weight A)−(Weight C−Weight A)]/(Weight C−Weight A).

A "target ion" is an ion to which the polymer binds, and usually refers to the major ions bound by the polymer, or the Ions whose binding to the polymer is thought to produce the therapeutic effect of the polymer (e.g. proton and chloride binding which leads to net removal of HCl).

The term "theoretical capacity" represents the calculated, expected binding of hydrochloric acid in an "SGF" assay, expressed in mmol/g. The theoretical capacity is based on the assumption that 100% of the amines from the monomer(s) and crosslinker(s) are incorporated in the cross-linked polymer based on their respective feed ratios. Theoretical capacity is thus equal to the concentration of amine functionalities in the polymer (mmol/g). The theoretical capacity assumes that each amine is available to bind the respective anions and cations and is not adjusted for the type of amine formed (e.g. it does not subtract capacity of quaternary amines that are not available to bind proton).

"Therapeutically effective amount" means the amount of a proton-binding crosslinked amine polymer that, when administered to a patient for treating a disease, is sufficient to effect such treatment for the disease. The amount constituting a "therapeutically effective amount" will vary depending on the polymer, the severity of the disease and the age, weight, etc., of the mammal to be treated.

"Treating" or "treatment" of a disease includes (i) inhibiting the disease, i.e., arresting or reducing the development of the disease or its clinical symptoms; or (ii) relieving the disease, i.e., causing regression of the disease or its clinical symptoms. Inhibiting the disease, for example, would include prophylaxis.

The term "triallylamine" denotes an amino moiety having three allyl groups.

The term "vinyl" denotes a moiety having the structural formula $R_xH_yC=CH—*$, where * denotes the point of attachment of the moiety to the remainder of the molecule wherein the point of attachment is a heteroatom or aryl, X and Y are independently 0, 1 or 2, such that X+Y=2, and R is hydrocarbyl or substituted hydrocarbyl.

The term "weight percent crosslinker" represents the calculated percentage, by mass, of a polymer sample that is derived from the crosslinker. Weight percent crosslinker is calculated using the feed ratio of the polymerization, and assumes full conversion of the monomer and crosslinker(s). The mass attributed to the crosslinker is equal to the expected increase of molecular weight in the infinite polymer network after reaction (e.g. 1,3-dichloropropane is 113 amu, but only 42 amu are added to a polymer network after crosslinking with DCP because the chlorine atoms, as leaving groups, are not incorporated into the polymer network).

When introducing elements of the present invention or the preferred embodiments(s) thereof, the articles "a", "an", "the" and "said" are intended to mean that there are one or more of the elements. The terms "comprising", "including" and "having" are intended to be inclusive and not exclusive (i.e., there may be other elements in addition to the recited elements).

EMBODIMENTS

As previously noted, among the various aspects of the present disclosure may be noted treatment methods using compositions comprising a nonabsorbed, crosslinked polymer containing free amine moieties. In one embodiment, the crosslinked amine polymers have the capacity to remove clinically significant quantities of protons and chloride ions from the gastrointestinal tract of an animal, including for example humans, upon administration of a therapeutically effective amount (i.e., an effective dose) of the crosslinked amine polymer to achieve a therapeutic or prophylactic benefit.

A therapeutically effective dose of the crosslinked amine polymers disclosed herein will depend, at least in part, on the disease being treated, the capacity of the crosslinked free amine polymer, and the intended effect. In one embodiment, the daily dose of the crosslinked free amine polymer is sufficient to retard the rate of reduction of serum bicarbonate levels over a prolonged period. In another embodiment, the daily dose of the crosslinked free amine polymer is sufficient to maintain serum bicarbonate levels over a prolonged period. In another embodiment, the daily dose of the crosslinked free amine polymer is sufficient to increase serum bicarbonate levels over a prolonged period. For example, in one embodiment, the daily dose is sufficient to achieve or maintain a serum bicarbonate level of at least about 20 mEq/L over a prolonged period. By way of further example, in one such embodiment, the daily dose is sufficient to achieve or maintain a serum bicarbonate level of at least about 21 mEq/L over a prolonged period. By way of further example, in one such embodiment, the daily dose is sufficient to achieve or maintain a serum bicarbonate level of at least about 22 mEq/L over a prolonged period. In yet another embodiment, the daily dose is sufficient to achieve or maintain a serum bicarbonate level of at least about 24 mEq/L over a prolonged period. In each of the foregoing embodiments, a prolonged period is a period of at least one month; for example, at least two months, at least three months, or even at least several months.

In general, the dosage levels of the crosslinked amine polymers for therapeutic and/or prophylactic uses may range from about 0.5 g/day to about 20 g/day. To facilitate patient compliance, it is generally preferred that the dose be in the range of about 1 g/day to about 10 g/day. For example, in one such embodiment, the dose will be about 2 g/day to about 7 g/day. By way of further example, in one such embodiment, the dose will be about 3 g/day to about 6 g/day. By way of further example, in one such embodiment, the dose will be about 4 g/day to about 5 g/day. Optionally, the daily dose may be administered as a single dose (i.e., one time a day), or divided into multiple doses (e.g., two, three or more doses) over the course of a day. In general the crosslinked amine polymers for therapeutic and/or prophylactic uses may be administered as a fixed daily dose or titrated based on the serum bicarbonate values of the patient in need of treatment or other indicators of acidosis. The titration may occur at the onset of treatment or throughout, as required, and starting and maintenance dosage levels may differ from patient to patient based on severity of the underlying disease.

Figure 1B:
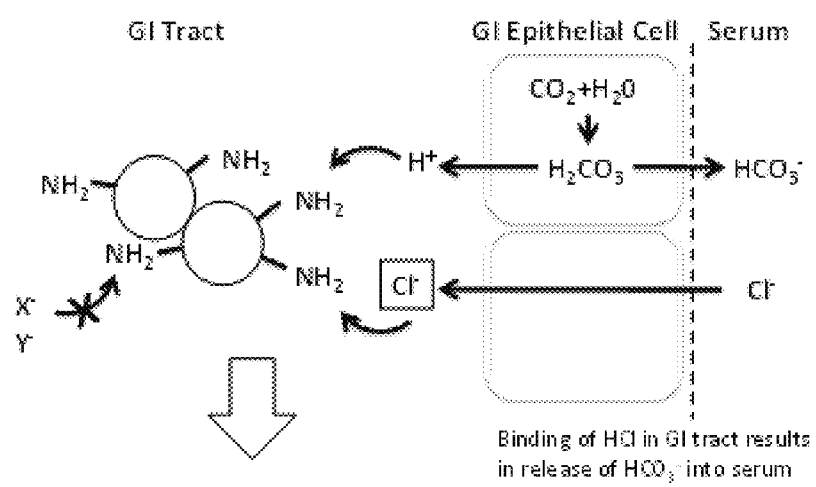
Figure 1C:
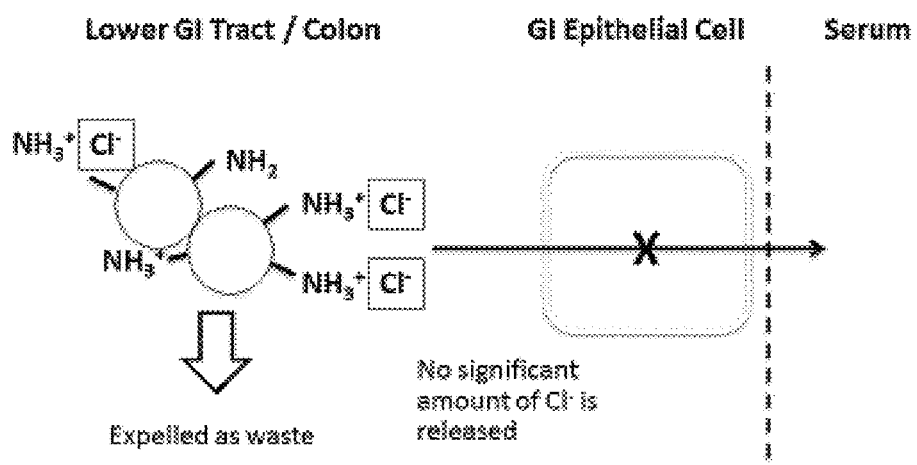

As schematically depicted in FIGS. 1A-1C and in accordance with one embodiment, a non-absorbed, free-amine polymer of the present disclosure is orally ingested and used to treat metabolic acidosis (including by increasing serum bicarbonate and normalizing blood pH) in a mammal by binding HCl in the gastrointestinal ("GI") tract and removing HCl through the feces. Free-amine polymer is taken orally (FIG. 1A) at compliance enhancing dose targeted to chronically bind sufficient amounts of HCl to enable clinically meaningful increase in serum bicarbonate of 3 mEq/l. In the stomach (FIG. 1B), free amine becomes protonated by binding $H^+$. Positive charge on polymer is then available to bind $Cl^-$; by controlling access of binding sites through crosslinking and hydrophilicity/hydrophobicity properties, other larger organic anions (e.g., acetate, propionate, butyrate, etc., depicted as $X^-$ and $Y^-$) are bound to a lesser degree, if at all. The net effect is therefore binding of HCl. In the lower GI tract/colon (FIG. 1C), $Cl^-$ is not fully released and HCl is removed from the body through regular bowel movement and fecal excretion, resulting in net alkalinization in the serum. $Cl^-$ bound in this fashion is not available for exchange via the $Cl^-/HCO_3^-$ antiporter system.

In one embodiment, the polymer is designed to simultaneously maximize efficacy (net HCl binding and excretion) and minimize GI side effects (through low swelling particle design and particle size distribution). Optimized HCl binding may be accomplished through a careful balance of capacity (number of amine binding sites), selectivity (preferred binding of chloride versus other anions, in particular organic anions in the colon) and retention (not releasing significant amounts of chloride in the lower GI tract to avoid the activity of the $Cl^-/HCO_3^-$ exchanger [antiporter] in the colon and intestine; if chloride is not tightly bound to the polymer the $Cl^-/HCO_3^-$ exchanger can mediate uptake of chloride ion from the intestinal lumen and reciprocal exchange for bicarbonate from the serum, thus effectively decreasing serum bicarbonate.

Competing anions that displace chloride lead to a decrease in net bicarbonate through the following mechanisms. First, displacement of chloride from the polymer in the GI lumen, particularly the colon lumen, provides for a facile exchange with bicarbonate in the serum. The colon has an anion exchanger (chloride/bicarbonate antiporter) that moves chloride from the luminal side in exchange for secreted bicarbonate. When free chloride is released from the polymer in the GI tract it will exchange for bicarbonate, which will then be lost in the stool and cause a reduction in total extracellular bicarbonate (Davis, 1983; D'Agostino, 1953). The binding of short chain fatty acids (SCFA) in exchange for bound chloride on the polymer, will result in the depletion of extracellular $HCO^{3-}$ stores. Short chain fatty acids are the product of bacterial metabolism of complex carbohydrates that are not catabolized by normal digestive processes (Chemlarova, 2007). Short chain fatty acids that reach the colon are absorbed and distributed to various tissues, with the common metabolic fate being the generation of $H_2O$ and $CO_2$, which is converted to bicarbonate equivalents. Thus, binding of SCFA to the polymer to neutralize the proton charge would be detrimental to overall bicarbonate stores and buffering capacity, necessitating the design of chemical and physical features in the polymer that limit SCFA exchange. Finally, phosphate binding to the polymer should be limited as well, since phosphate represents an additional source of buffering capacity in the situation where ammoniagenesis and/or hydrogen ion secretion is compromised in chronic renal disease.

For each binding of proton, an anion is preferably bound as the positive charge seeks to leave the human body as a neutral polymer. "Binding" of an ion, is more than minimal binding, i.e., at least about 0.2 mmol of ion/g of polymer, at least about 1 mmol of ion/g of polymer in some embodiments, at least about 1.5 mmol of ion/g of polymer in some embodiments, at least about 3 mmol of ion/g of polymer in some embodiments, at least about 5 mmol of ion/g of polymer in some embodiments, at least about 10 mmol of ion/g of polymer in some embodiments, at least about 12 mmol of ion/g of polymer in some embodiments, at least about 13 mmol of ion/g of polymer in some embodiments, or even at least about 14 mmol of ion/g of polymer in some embodiments. In one embodiment, the polymers are characterized by their high capacity of proton binding while at the same time providing selectivity for anions; selectivity for chloride is accomplished by reducing the binding of interfering anions that include but are not limited to phosphate, citrate, acetate, bile acids and fatty acids. For example, in some embodiments, polymers of the present disclosure bind phosphate with a binding capacity of less than about 5 mmol/g, less than about 4 mmol/g, less than about 3 mmol/g, less than about 2 mmol/g or even less than about 1 mmol/g. In some embodiments, polymers of the invention bind bile and fatty acids with a binding capacity of less than about less than about 5 mmol/g, less than about 4 mmol/g, less than about 3 mmol/g, less than about 2 mmol/g, less than about 1 mmol/g in some embodiments, less than about 0.5 mmol/g in some embodiments, less than about 0.3 mmol/g in some embodiments, and less than about 0.1 mmol/g in some embodiments.

The effectiveness of the polymer may be established in animal models, or in human volunteers and patients. In addition, in vitro, ex vivo and in vivo approaches are useful to establish HCl binding. In vitro binding solutions can be used to measure the binding capacity for proton, chloride and other ions at different pHs. Ex vivo extracts, such as the gastrointestinal lumen contents from human volunteers or from model animals can be used for similar purposes. The selectivity of binding and/or retaining certain ions preferentially over others can also be demonstrated in such in vitro and ex vivo solutions. In vivo models of metabolic acidosis can be used to test the effectiveness of the polymer in normalizing acid/base balance—for example 5/6 nephrectomized rats fed casein-containing chow (as described in Phisitkul S, Hacker C, Simoni J, Tran R M, Wesson D E. Dietary protein causes a decline in the glomerular filtration rate of the remnant kidney mediated by metabolic acidosis and endothelin receptors. Kidney international. 2008; 73(2):

192-9), or adenine-fed rats (Terai K, K Mizukami and M Okada. 2008. Comparison of chronic renal failure rats and modification of the preparation protocol as a hyperphosphatemia model. Nephrol. 13: 139-146).

In one embodiment, the polymers described in the current disclosure are provided to an animal, including a human, in once, twice or three times a day dosing most preferably not exceeding a daily dose of 5 g or less per day) to treat metabolic acidosis and achieve a clinically significant and sustained increase of serum bicarbonate of approximately 3 mEq/L at these daily doses. The amount of HCl binding achieved by oral administration of the polymer is determined by the polymer binding capacity, which is generally in the range of 5-25 mEq of HCl per 1 g of polymer. Additionally, the polymer is preferably selective in terms of the anion that is bound to counterbalance the proton binding, with chloride being the preferred anion. Anions other than chloride, bound to neutralize the proton positive charge, include phosphate, short chain fatty acids, long chain fatty acids, bile acids or other organic or inorganic anions. Binding of these anions, other than chloride, influences overall bicarbonate stores in the intracellular and extracellular compartments.

In one embodiment, the mechanism of action for the HCl polymeric binder comprises the following. In the stomach or elsewhere in the GI tract, the free amine polymer becomes protonated by binding proton ($H^+$). The positive charge formed as a result of this binding is then available for chloride anion binding. After exiting the stomach, the polymer sequentially encounters different GI tract environments in the order duodenum, jejunum, ileum and colon, each with a complement of distinct organic and inorganic anions. Physical and chemical properties of the polymer are designed to control access of protonated binding sites to this collection of anions. Physical barriers include crosslinking (size exclusion to prevent anion binding) and chemical moieties (to repel larger, organic ions such as acetate, propionate, butyrate or other short chain fatty acids commonly present in the colon), and combinations of the two properties to limit phosphate, bile acid and fatty acid binding. By tailoring the bead crosslinking and the chemical nature of the amine binding sites, chloride can be bound tightly so that exchange for other anions and release in the lower GI tract is reduced or eliminated. Without being bound by theory, anions with a larger ionic and/or hydration radius than chloride can be excluded, or their binding reduced, by incorporating these properties into the HCl binding polymer. For example, the ionic radius of chloride, either in the hydrated or unhydrated form is smaller than the corresponding values for phosphate and other anions commonly encountered in the GI tract lumen (Supramolecular Chemistry, Steed, J W (2009) John Wiley and Sons, page 226; Kielland, J (1937), J. Am. Chem. Soc. 59:1675-1678). To selectively bind smaller ions, polymers typically display high crosslinking densities in order to create preferential access to the polymer binding sites. High crosslinking density materials are, however, typically characterized by low Swelling Ratios. The Swelling Ratio, can be affected by the following composition and process variables: 1) the molar ratio of amine monomer (or polymer) and crosslinker, 2) the monomer+crosslinker to solvent ratio in the crosslinking reaction, 3) the net charge of the polymer (at the physiological pH and tonicity of the milieu in which it will be used), 4) the hydrophilic/hydrophobic balance of the backbone polymer and/or 5) post-crosslinking of an existing material.

In some embodiments, the theoretical chloride binding capacity of the polymers of the present disclosure may range from about 1 mmol/g to about 25 mmol/g. In one embodiment, the theoretical chloride binding capacity of the polymer is about 3 mmol/g to about 25 mmol/g. In another embodiment, the theoretical chloride binding capacity of the polymer is about 6 mmol/g to about 20 mmol/g. In another embodiment, the theoretical chloride binding capacity of the polymer about 9 mmol/g to about 17 mmol/g.

In one embodiment, a crosslinked polymer of the present disclosure is characterized by a chloride ion binding capacity of at least 2 mmol/g at 1 hour in Simulated Small Intestine Inorganic Buffer ("SIB"). For example, in one such embodiment a crosslinked polymer of the present disclosure is characterized by a chloride ion binding capacity of at least 2.5 mmol/g at 1 hour in SIB. By way of further example, in one such embodiment a crosslinked polymer of the present disclosure is characterized by a chloride ion binding capacity of at least 3 mmol/g at 1 hour in SIB. By way of further example, in one such embodiment a crosslinked polymer of the present disclosure is characterized by a chloride ion binding capacity of at least 3.5 mmol/g at 1 hour in SIB. By way of further example, in one such embodiment a crosslinked polymer of the present disclosure is characterized by a chloride ion binding capacity of at least 4 mmol/g at 1 hour in SIB. By way of further example, in one such embodiment a crosslinked polymer of the present disclosure is characterized by a chloride ion binding capacity of at least 4.5 mmol/g at 1 hour in SIB. By way of further example, in one such embodiment a crosslinked polymer of the present disclosure is characterized by a chloride ion binding capacity of at least 5 mmol/g at 1 hour in SIB. By way of further example, in one such embodiment a crosslinked polymer of the present disclosure is characterized by a chloride ion binding capacity of at least 5.5 mmol/g at 1 hour in SIB. By way of further example, in one such embodiment a crosslinked polymer of the present disclosure is characterized by a chloride ion binding capacity of at least 6 mmol/g at 1 hour in SIB. In one exemplary embodiment of each of the foregoing embodiments of this paragraph, the crosslinked amine polymer may have a Swelling Ratio not in excess of about 1.5.

In one embodiment, a crosslinked polymer of the present disclosure is characterized by a chloride ion binding capacity of at least 4 mmol/g, and a phosphate ion binding capacity of less than 2 mmol/g in Simulated Small Intestine Inorganic Buffer ("SIB"). For example, in one such embodiment the crosslinked amine polymer has a chloride ion binding capacity of at least 4 mmol/g, and a phosphate ion binding capacity of less than 2 mmol/g after 1 hour in SIB. By way of further example, in one such embodiment the crosslinked amine polymer has a chloride ion binding capacity of at least 4 mmol/g, and a phosphate ion binding capacity of less than 2 mmol/g after 2 hours in SIB. By way of further example, in one such embodiment the crosslinked amine polymer has a chloride ion binding capacity of at least 4 mmol/g, and a phosphate ion binding capacity of less than 2 mmol/g after 3 hours in SIB. By way of further example, in one such embodiment the crosslinked amine polymer has a chloride ion binding capacity of at least 4 mmol/g, and a phosphate ion binding capacity of less than 2 mmol/g after 4 hours in SIB. By way of further example, in one such embodiment the crosslinked amine polymer has a chloride to phosphate ion binding ratio of at least 2.5:1, respectively, in SIB. In one exemplary embodiment of each of the foregoing embodiments of this paragraph, the crosslinked amine polymer may have a Swelling Ratio not in excess of about 1.5.

In one embodiment, a crosslinked polymer of the present disclosure is characterized by a proton-binding capacity and a chloride binding capacity in Simulated Gastric Fluid of at least 8 mmol/g in Simulated Gastric Fluid ("SGF"). For example, in one such embodiment the crosslinked polymer of the present disclosure is characterized by a proton-binding capacity and a chloride binding capacity in Simulated Gastric Fluid of at least 10 mmol/g in SGF. By way of further example, in one such embodiment the crosslinked polymer of the present disclosure is characterized by a proton-binding capacity and a chloride binding capacity in SGF of at least 12 mmol/g in SGF. By way of further example, in one such embodiment the crosslinked polymer of the present disclosure is characterized by a proton-binding capacity and a chloride binding capacity in SGF of at least 14 mmol/g in SGF. By way of further example, in one such embodiment the crosslinked polymer of the present disclosure is characterized by a proton-binding capacity and a chloride binding capacity after 1 hour in SGF that is at least 50% of the proton-binding capacity and the chloride binding capacity, respectively, of the crosslinked amine polymer at 24 hours in SGF. By way of further example, in one such embodiment the crosslinked polymer of the present disclosure is characterized by a proton-binding capacity and a chloride binding capacity after 1 hour in SGF that is at least 60% of the proton-binding capacity and the chloride binding capacity, respectively, of the crosslinked amine polymer at 24 hours in SGF. By way of further example, in one such embodiment the crosslinked polymer of the present disclosure is characterized by a proton-binding capacity and a chloride binding capacity after 1 hour in SGF that is at least 70% of the proton-binding capacity and the chloride binding capacity, respectively, of the crosslinked amine polymer at 24 hours in SGF. By way of further example, in one such embodiment the crosslinked polymer of the present disclosure is characterized by a proton-binding capacity and a chloride binding capacity after 1 hour in SGF that is at least 80% of the proton-binding capacity and the chloride binding capacity, respectively, of the crosslinked amine polymer at 24 hours in SGF. By way of further example, in one such embodiment the crosslinked polymer of the present disclosure is characterized by a proton-binding capacity and a chloride binding capacity after 1 hour in SGF that is at least 90% of the proton-binding capacity and the chloride binding capacity, respectively, of the crosslinked amine polymer at 24 hours in SGF.

In one embodiment, a crosslinked polymer of the present disclosure is characterized by a selectivity for chloride over citrate, phosphate and taurocholate in Simulated Small Intestine Organic and Inorganic Buffer ("SOB"), or a chloride binding capacity at 24 hours in SOB of at least 4 mmol/g.

In one embodiment, a crosslinked polymer of the present disclosure is characterized by a selectivity for chloride over citrate, phosphate and taurocholate after 1 hour in Simulated Small Intestine Organic and Inorganic Buffer ("SOB"). For example, in one such embodiment the crosslinked polymer is characterized by a selectivity for chloride over citrate, phosphate and taurocholate after 4 hours in SOB. By way of further example, in one such embodiment at the crosslinked polymer is characterized by a selectivity for chloride over citrate, phosphate and taurocholate after 12 hours in SOB. By way of further example, in one such embodiment at the crosslinked polymer is characterized by a selectivity for chloride over citrate, phosphate and taurocholate after 18 hours in SOB. By way of further example, in one such embodiment at the crosslinked polymer is characterized by a selectivity for chloride over citrate, phosphate and taurocholate after 24 hours in SOB. By way of further example, in one such embodiment at the crosslinked polymer is characterized by a selectivity for chloride over citrate, phosphate and taurocholate after 30 hours in SOB. By way of further example, in one such embodiment at the crosslinked polymer is characterized by a selectivity for chloride over citrate, phosphate and taurocholate after 36 hours in SOB. By way of further example, in one such embodiment at the crosslinked polymer is characterized by a selectivity for chloride over citrate, phosphate and taurocholate after 42 hours in SOB. By way of further example, in one such embodiment at the crosslinked polymer is characterized by a selectivity for chloride over citrate, phosphate and taurocholate after 48 hours in SOB.

In general, it is preferred that a crosslinked polymer having the characteristics described above and elsewhere herein have a pKa of at least 6, at least 6.5, at least 7, at least 7.5, or at least in physiological ionic conditions, which are the upper end of the pH values encountered along the GI tract (Fallingborg, J Aliment. Pharmacol. Therap [1989] 3:05-613).

In some embodiments, the molecular weight per nitrogen of the polymers of the present disclosure may range from about 40 to about 1000 Daltons. In one embodiment, the molecular weight per nitrogen of the polymer is from about 40 to about 500 Daltons. In another embodiment, the molecular weight per nitrogen of the polymer is from about 50 to about 170 Daltons. In another embodiment, the molecular weight per nitrogen of the polymer is from about 60 to about 110 Daltons.

In some embodiments, the crosslinker weight % range will be about 10 to 90 weight % of the crosslinked amine polymer. For example, in some embodiments the crosslinker weight % range will be about 15 to 90 weight % of the crosslinked amine polymer or even about 25 to 90 weight % of the crosslinked amine polymer.

As previously noted, crosslinked amine polymers having a high capacity for chloride binding and high selectivity for chloride over other competing anions such as phosphate may be prepared in a two-step process in accordance with one embodiment of the present disclosure. In general, the selectivity of the polymer is a function of its crosslinking density and the capacity of the polymer is a function of the free amine density of the crosslinked amine polymer. Advantageously, the two step process disclosed herein provides both, high capacity for chloride binding, and high selectivity for chloride over other competing Ions by relying primarily upon carbon-carbon crosslinking in the first step, and nitrogen-nitrogen crosslinking in the second step.

In the first step, the crosslinking is preferably capacity-sparing, i.e., free amine sparing, crosslinking from carbon to carbon. In the second step, the crosslinking is amine-consuming and is directed towards tuning for selectivity. Based on the desired high capacity, the C—N ratio is preferably optimized to maximize amine functionalities for HCl binding, while still maintaining a spherical polymer particle of controlled particle size to ensure non absorption and acceptable mouth feel that is stable under GI conditions. The preferred extent of carbon-carbon crosslinking achieved after the first step is sufficient to permit the resulting bead to swell between 4× and 6× in water (i.e., a Swelling Ratio of 4 to 6).

In general, the crosslinked amine polymers may be crosslinked homopolymers or crosslinked copolymers comprising free amine moieties. The free amine moieties may be separated, for example, by the same or varying lengths of repeating linker (or intervening) units. In some embodiments, the polymers comprise repeat units containing an amine moiety and an intervening linker unit. In other embodiments, multiple amine-containing repeat units are separated by one or more linker units. Additionally, the polyfunctional crosslinkers may comprise HCl binding functional groups, e.g., amines, ("active crosslinkers") or may lack HCl binding functional groups such as amines ("passive crosslinkers").

In a preferred embodiment, the first polymerization (crosslinking) step yields preformed amine polymer beads having a target size and chloride binding capacity. For example, in one such embodiment the beads having a chloride binding capacity of at least 10 mmol/g in Simulated Gastric Fluid ("SGF") and a Swelling Ratio in the range of 4 to 6. The resulting preformed amine polymer is then preferably (at least partially) deprotonated with a base and combined with a non-protonating swelling agent to swell the free amine polymer without protonating the amine functions. Furthermore, the amount of the non-protonating swelling agent is selected to tune the subsequent degree of crosslinking effectively forming a template that is then locked into place via the amine consuming crosslinking step. In the second crosslinking step, the swollen, deprotonated preformed amine polymer is crosslinked with a crosslinker containing amine reactive moieties to form a post-polymerization crosslinked amine polymer.

In general, selectivity for chloride over other competing ions is achieved with highly crosslinked amine polymers. For example, relatively high chloride binding capacity maybe be attained by reading a preformed amine polymer bead with neat crosslinker in the presence of a swelling agent (water). While this "non-dispersed" reaction provides access to high selectivity for chloride over competing ions in the SIB and SOB assays, it also results in macroscopically (and microscopically) aggregated polymer beads. Accordingly, it is advantageous to include a solvent (e.g., heptane) in the second crosslinking step to disperse the preformed crosslinked polymer beads so as to avoid inter-bead reactions and resulting aggregation. The use of too much solvent (dispersant), however, can dilute the reaction solution to the point where the resulting bead is not sufficiently crosslinked to have the desired selectivity for chloride over other competing anions (see Table 12). By using a crosslinking agent that also functions as a solvent (dispersant), however, sufficient solvent (dispersant) may be included in the reaction mixture to avoid inter-bead reactions and aggregation without diluting the mixture to the point where the degree of amine-consuming crosslinking is insufficient. For example, in an effort to utilize the dispersing properties of a solvent (to avoid aggregation during the reaction) while maintaining reactivity, DCE and DCP were used neat, thus performing a dual purpose role, as both solvent (dispersant) and crosslinker. Interestingly, DCE was discovered to have excellent dispersal properties as a solvent, when compared to similar reactions with DCP and/or heptane. Additionally, less aggregation was observed when the beads were first dispersed in DCE and then in a second operation, the water is added to swell the beads. If water is added to the preformed amine polymer before the bead is dispersed in the DCE, aggregation may occur.

The use of 1,2-dichloroethane ("DCE") as the crosslinking solvent also generates HCl molecules during the second step. These HCl molecules protonate some of the free amine sites which block the reaction sites for the crosslinking reaction and thereby limit the number of binding sites available for crosslinking. Consequently, the use of DCE creates a self-limiting effect on the secondary crosslinking.

In each of the foregoing embodiments, the reaction mixture may contain a wide range of amounts of crosslinking agents. For example, in one embodiment the crosslinker may be used in large excess relative to the amount of preformed amine polymer in the reaction mixtures. Stated differently, in such embodiments the crosslinking agent is a crosslinking solvent, i.e., it is both a solvent for the reaction mixture and a crosslinking agent for the preformed amine polymer. In such embodiments, other solvents may optionally be included in the reaction mixture but are not required. Alternatively, the preformed amine polymer, swelling agent and crosslinker may be dispersed in a solvent that is miscible with the crosslinker and immiscible with the swelling agent. For example, in some embodiments the swelling agent may be a polar solvent; in some such embodiments, for example, the swelling agent may comprise water, methanol, ethanol, n-propanol, isopropanol, formic acid, acetic acid, acetonitrile, N,N-dimethylformamide, dimethylsulfoxide, nitromethane, or a combination thereof. By way of further example, when the swelling agent comprises a polar solvent, the solvent system for the reaction mixture will typically comprise a non-polar solvent such as pentane, cyclopentane, hexane, cyclohexane, benzene, toluene, 1,4-dioxane, chloroform, diethyl ether, dichloromethane, dichloroethane, dichloropropane, dichlorobutane, or a combination thereof. In certain embodiments, the crosslinker and the solvent may be the same; i.e., the solvent is a crosslinking solvent such as 1,2-dichloroethane, 1,3-dichloropropane, 1,4-dichlorobutane or a combination thereof.

In one embodiment, the preformed amine polymer is dispersed in a reaction mixture comprising a crosslinking agent, a swelling agent for the preformed amine polymer, and a (dispersing) solvent. In one such embodiment, for example, the ratio of (dispersing) solvent to preformed amine polymer in the reaction mixture is at least 2:1 (milliliters of solvent:grams of preformed amine polymer). By way of further example, in one such embodiment the ratio of (dispersing) solvent to preformed amine polymer in the reaction mixture is at least 3:1 (milliliters of solvent:grams of preformed amine polymer). By way of further example, in one such embodiment the ratio of (dispersing) solvent to preformed amine polymer in the reaction mixture Is at least 4:1 (milliliters of solvent:grams of preformed amine polymer). By way of further example, in one such embodiment the ratio of (dispersing) solvent to preformed amine polymer in the reaction mixture is at least 5:1 (milliliters of solvent: grams of preformed amine polymer). By way of further example, in one such embodiment the ratio of (dispersing) solvent to preformed amine polymer in the reaction mixture is at least 7.5:1 (milliliters of solvent:grams of preformed amine polymer). By way of further example, in one such embodiment the ratio of (dispersing) solvent to preformed amine polymer in the reaction mixture is at least 10:1 (milliliters of solvent:grams of preformed amine polymer). In each of the foregoing embodiments, the (dispersing) solvent may comprise a combination of an inert solvent (relative to the preformed amine polymer) such as one of the previously identified non-polar solvents and a crosslinking solvent or the (dispersing) solvent may exclusively comprise a crosslinking solvent (e.g., DCE or DCP).

It is notable that in a crosslinking solvent (e.g., a OCE-dispersed reaction), there is a large excess of crosslinker regardless of the amount of crosslinking solvent (e.g., DCE) used to disperse the bead (e.g., both 1 g:3 mL::bead:DCE and 1 g:10 mL::bead:DCE are a large excess of crosslinker, most of which is not consumed during the reaction). Despite this, the relative degree of crosslinking, and the performance in SIB and SOB assays, are unaffected by changes in the ratio of reactive crosslinker to polymer bead (see Table 6). This is possible because the reaction is limited by the acid-neutralizing capacity of the polymer bead, rather than the amount of crosslinker (e.g., DCE).

To more efficiently react with DCE or other crosslinker, the amines of the preformed polymer bead preferably have a free electron pair (neutral, deprotonated). As the free amines of the preformed polymer bead react with the crosslinker (e.g., DCE), HCl is produced and the amines become protonated, thus limiting the reaction. For this reason, the preformed amine polymer beads preferably start as the free amine in the second crosslinking step. If the preformed amine polymer bead is protonated after the first step of carbon-carbon crosslinking, amine-consuming crosslinking in the second step will be limited, thus reducing the desired selectivity for chloride over other competing ions. This has been demonstrated by adding known quantities of HCl to preformed amine polymer beads immediately before second step crosslinking with DCE (TABLE 7). When less than 3 mol % HCl (to amine in preformed polymer amine bead) is added prior to second step crosslinking, total chloride capacity (SGF) and chloride selectivity in SIB and SOB are similar to beads not treated with HCl in the second step. When greater than 5 mol % HCl (to amine in preformed polymer amine bead) is added prior to second step crosslinking, total chloride capacity (SGF) increases and chloride selectivity in SIB and SOB decreases, indicating lower incorporation of crosslinker.

The benefits of deprotonated preformed polymer beads in the second step crosslinking highlights the advantages of using two steps to achieve the final product. In the first step, to form the amine polymer bead, all monomers (e.g., allylamine and DAPDA) are protonated to remain in the aqueous phase and to avoid the radical transfer reactions that severely limit the polymerization of non-protonated allylamine (and derivatives). Once the bead is formed through carbon-carbon crosslinks, the bead can then be deprotonated and further crosslinked with an amine reactive crosslinker in a second step.

Given the large excess of dual crosslinker/solvent, mono-incorporation of this reagent can occur leading to alkyl chloride functional groups on the crosslinked polymer bead that are hydrophobic in nature and can increase non-specific interactions with undesirable solutes other than HCl that are more hydrophobic in nature. Washing with ammonium hydroxide solution converts the alkyl-chloride to alkyl-amine functions that are hydrophilic and minimize non-specific interactions with undesirable solutes. Other modifications that yield more hydrophilic groups than alkyl chloride such as —OH are suitable to quench mono-incorporated crosslinker/solvent.

Any of a range of polymerization chemistries may be employed in the first reaction step, provided that the crosslinking mechanism is primarily carbon-carbon crosslinking. Thus, in one exemplary embodiment, the first reaction step comprises radical polymerization. In such reactions, the amine monomer will typically be a mono-functional vinyl, allyl, or acrylamide (e.g., allylamine) and crosslinkers will have two or more vinyl, allyl or acrylamide functionalities (e.g., diallylamine). Concurrent polymerization and crosslinking occurs through radically initiated polymerization of a mixture of the mono- and multifunctional allylamines. The resulting polymer network is thusly crosslinked through the carbon backbone. Each crosslinking reaction forms a carbon-carbon bond (as opposed to substitution reactions in which a carbon-heteroatom bond is formed during crosslinking). During the concurrent polymerization and crosslinking, the amine functionalities of the monomers do not undergo crosslinking reactions and are preserved in the final polymer (i.e., primary amines remain primary, secondary amines remain secondary, and tertiary amines remain tertiary).

In those embodiments in which the first reaction step comprises radical polymerization, a wide range of initiators may be used including cationic and radical initiators. Some examples of suitable initiators that may be used include: the free radical peroxy and azo type compounds, such as azo-diisobutyronitrile, azodiisovaleronitrile, dimethylazodi-isobutyrate, 2,2'azo bis(isobutyronitrile), 2,2'-azobis(N,N'-dimethyl-eneisobutyramidine)dihydrochloride, 2,2'-azobis(2-amidinopropane)dihydrochloride, 2,2'-azobis(N,N'-dimethyleneisobutyramidine), 1,1'-azo bis(1-cyclohexanecarbo-nitrile), 4,4'-azobis(4-cyanopentanoic acid), 2,2'-azobis(isobutyramide)dihydrate, 2,2'-azobis(2-methylpropane), 2,2'-azobis(2-methylbutyronitrile), VAZO 67, cyanopentanoic acid, the peroxypivalates, dodecylbenzene peroxide, benzoyl peroxide, di-t-butyl hydroperoxide, t-butyl peracetate, acetyl peroxide, dicumyl peroxide, cumylhydroperoxide, dimethyl bis(butylperoxy)hexane.

In some embodiments, the preformed amine polymer comprises the residue of an amine corresponding to Formula 1:

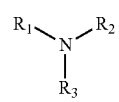

Formula 1 wherein $R_1$, $R_2$ and $R_3$ are independently hydrogen, hydrocarbyl, substituted hydrocarbyl provided, however, at least one of $R_1$, $R_2$ and $R_3$ is other than hydrogen. Stated differently, at least one of $R_1$, $R_2$ and $R_3$ is hydrocarbyl or substituted hydrocarbyl, and the others of $R_1$, $R_2$ and $R_3$ are independently hydrogen, hydrocarbyl, or substituted hydrocarbyl. In one embodiment, for example, $R_1$, $R_2$ and $R_3$ are independently hydrogen, aryl, aliphatic, heteroaryl, or heteroaliphatic provided, however, each of $R_1$, $R_2$ and $R_3$ are not hydrogen. By way of further example, in one such embodiment $R_1$, $R_2$ and $R_3$ are independently hydrogen, saturated hydrocarbons, unsaturated aliphatic, unsaturated heteroaliphatic, heteroalkyl, heterocyclic, aryl or heteroaryl, provided, however, each of $R_1$, $R_2$ and $R_3$ are not hydrogen. By way of further example, in one such embodiment $R_1$, $R_2$ and $R_3$ are independently hydrogen, alkyl, alkenyl, allyl, vinyl, aryl, aminoalkyl, alkanol, haloalkyl, hydroxyalkyl, ethereal, heteroaryl or heterocyclic provided, however, each of $R_1$, $R_2$ and $R_3$ are not hydrogen. By way of further example, in one such embodiment $R_1$, $R_2$ and $R_3$ are independently hydrogen, alkyl, aminoalkyl, alkanol, aryl, haloalkyl, hydroxyalkyl, ethereal, heteroaryl or heterocyclic provided, however, each of $R_1$, $R_2$ and $R_3$ are not hydrogen. By way of further example, in one such embodiment $R_1$ and $R_2$ (in combination with the nitrogen atom to which they are attached) together constitute part of a ring structure, so that the monomer as described by Formula 1 is a nitrogen-containing heterocycle (e.g., piperidine) and $R_3$ is hydrogen, or heteroaliphatic. By way of further example, in one embodiment $R_1$, $R_2$ and $R_3$ are independently hydrogen, aliphatic or heteroaliphatic provided, however, at least one of $R_1$, $R_2$ and $R_3$ is other than hydrogen. By way of further example, in one embodiment $R_1$, $R_2$ and $R_3$ are independently hydrogen, allyl, or aminoalkyl.

In one embodiment, the preformed amine polymer comprises the residue of an amine corresponding to Formula 1 wherein $R_1$, $R_2$, and $R_3$ are independently hydrogen, heteroaryl, aryl, aliphatic or heteroaliphatic provided, however, at least one of $R_1$, $R_2$, and $R_3$ is aryl or heteroaryl. For example, in this embodiment $R_1$ and $R_2$, in combination with the nitrogen atom to which they are attached, may form a saturated or unsaturated nitrogen-containing heterocyclic ring. By way of further example, $R_1$ and $R_2$, in combination with the nitrogen atom to which they are attached may constitute part of a pyrrolidino, pyrrole, pyrazolidine, pyrazole, imidazolidine, imidazole, piperidine, pyridine, piperazine, diazine, or triazine ring structure. By way of further example, $R_1$ and $R_2$, in combination with the nitrogen atom to which they are attached may constitute part of a piperidine ring structure.

In one embodiment, the preformed amine polymer comprises the residue of an amine corresponding to Formula 1 wherein $R_1$, $R_2$, and $R_3$ are independently hydrogen, aliphatic, or heteroaliphatic provided, however, at least one of $R_1$, $R_2$, and $R_3$ is other than hydrogen. For example, in this embodiment $R_1$, $R_2$, and $R_3$ may independently be hydrogen, alkyl, alkenyl, allyl, vinyl, aminoalkyl, alkanol, haloalkyl, hydroxyalkyl, ethereal, or heterocyclic provided, however, at least one of $R_1$, $R_2$, and $R_3$ is other than hydrogen. By way of further example, in one such embodiment $R_1$ and $R_2$, in combination with the nitrogen atom to which they are attached, may form a saturated or unsaturated nitrogen-containing heterocyclic ring. By way of further example, in one such embodiment $R_1$ and $R_2$, in combination with the nitrogen atom to which they are attached may constitute part of a pyrrolidino, pyrole, pyrazolidine, pyrazole, imidazolidine, imidazole, piperidine, piperazine, or diazine ring structure. By way of further example, in one such embodiment $R_1$ and $R_2$, in combination with the nitrogen atom to which they are attached may constitute part of a piperidine ring structure. By way of further example, in one such embodiment the amine corresponding to Formula 1 is acyclic and at least one of $R_1$, $R_2$, and $R_3$ is aliphatic or heteroaliphatic. By way of further example, in one such embodiment $R_1$, $R_2$, and $R_3$ are independently hydrogen, alkyl, allyl, vinyl, alicyclic, aminoalkyl, alkanol, or heterocyclic, provided at least one of $R_1$, $R_2$, and $R_3$ is other than hydrogen.

In some embodiments, an amine-containing monomer is polymerized and the polymer is concurrently crosslinked in a substitution polymerization reaction in the first reaction step. The amine reactant (monomer) in the concurrent polymerization and crosslinking reaction can react more than one time for the substitution polymerization. In one such embodiment, the amine monomer is a linear amine possessing at least two reactive amine moieties to participate in the substitution polymerization reaction. In another embodiment, the amine monomer is a branched amine possessing at least two reactive amine moieties to participate in the substitution polymerization reaction. Crosslinkers for the concurrent substitution polymerization and crosslinking typically have at least two amine-reactive moieties such as alkyl-chlorides, and alkyl-epoxides. In order to be incorporated into the polymer, primary amines react at least once and potentially may react up to three times with the crosslinker, secondary amines can react up to twice with the crosslinkers, and tertiary amines can only react once with the crosslinker. In general, however, the formation of a significant number of quaternary nitrogens/amines is generally not preferred because quaternary amines cannot bind protons.

Exemplary amines that may be used in substitution polymerization reactions described herein include 1,3-Bis[bis(2-aminoethyl)amino]propane, 3-Amino-1-{[2-(bis{2-[bis(3-aminopropyl)amino]ethyl}amino)ethyl](3-aminopropyl)amino}propane, 2-[Bis(2-aminoethyl)amino]ethanamine, Tris(3-aminopropyl)amine, 1,4-Bis[bis(3-aminopropyl)amino]butane, 1,2-Ethanediamine, 2-Amino-1-(2-aminoethylamino)ethane, 1,2-Bis(2-aminoethylamino)ethane, 1,3-Propanediamine, 3,3'-Diaminodipropylamine, 2,2-dimethyl-1,3-propanediamine, 2-methyl-1,3-propanediamine, N,N'-dimethyl-1,3-propanediamine, N-methyl-1,3-diaminopropane, 3,3'-diamino-N-methyldipropylamine, 1,3-diaminopentane, 1,2-diamino-2-methylpropane, 2-methyl-1,5-diaminopentane, 1,2-diaminopropane, 1,10-diaminodecane, 1,8-diaminooctane, 1,9-diaminooctane, 1,7-diaminoheptane, 1,6-diaminohexane, 1,5-diaminopentane, 3-bromopropylamine hydrobromide, N,2-dimethyl-1,3-propanediamine, N-isopropyl-1,3-diaminopropane, N,N'-bis(2-aminoethyl)-1,3-propanediamine, N,N'-bis(3-aminopropyl)ethylenediamine, N,N'-bis(3-aminopropyl)-1,4-butanediamine tetrahydrochloride, 1,3-diamino-2-propanol, N-ethylethylenediamine, 2,2'-diamino-N-methyldiethylamine, N,N'-diethylethylenediamine, N-isopropylethylenediamine, N-methylethylenediamine, N,N'-di-tert-butylethylenediamine, N,N'-diisopropylethylenediamine, N,N'-dimethylethylenediamine, N-butylethylenediamine, 2-(2-aminoethylamino)ethanol, 1,4,7,10,13,16-hexaazacyclooctadecane, 1,4,7,10-tetraazacyclododecane, 1,4,7-triazacyclononane, N,N'-bis(2-hydroxyethyl)ethylenediamine, piperazine, bis(hexamethylene)triamine, N-(3-hydroxypropyl)ethylenediamine, N-(2-Aminoethyl)piperazine, 2-Methylpiperazine, Homopiperazine, 1,4,8,11-Tetraazacyclotetradecane, 1,4,8,12-Tetraazacyclopentadecane, 2-(Aminomethyl)piperidine, 3-(Methylamino)pyrrolidine Exemplary crosslinking agents that may be used in substitution polymerization reactions and post-polymerization crosslinking reactions include, but are not limited to, one or more multifunctional crosslinking agents such as: dihaloalkanes, haloalkyloxiranes, alkyloxirane sulfonates, di(haloalkyl)amines, tri(haloalkyl) amines, diepoxides, triepoxides, tetraepoxides, bis (halomethyl)benzenes, tri(halomethyl) benzenes, tetra(halomethyl)benzenes, epihalohydrins such as epichlorohydrin and epibromohydrin poly(epichlorohydrin), (iodomethyl)oxirane, glycidyl tosylate, glycidyl 3-nitrobenzenesulfonate, 4-tosyloxy-1,2-epoxybutane, bromo-1,2-epoxybutane, 1,2-dibromoethane, 1,3-dichloropropane, 1,2-dichloroethane, 1-bromo-2-chloroethane, 1,3-dibromopropane, bis(2-chloroethyl)amine, tris(2-chloroethyl)amine, and bis(2-chloroethyl)methylamine, 1,3-butadiene diepoxide, 1,5-hexadiene diepoxide, diglycidyl ether, 1,2,7,8-diepoxyoctane, 1,2,9,10-diepoxydecane, ethylene glycol diglycidyl ether, propylene glycol diglycidyl ether, 1,4-butanediol diglycidyl ether, 1,2 ethanedioldiglycidyl ether, glycerol diglycidyl ether, 1,3-diglycidyl glyceryl ether, N,N-diglycidylaniline, neopentyl glycol diglycidyl ether, diethylene glycol diglycidyl ether, 1,4-bis(glycidyloxy)benzene, resorcinol digylcidyl ether, 1,6-hexanediol diglycidyl ether, trimethylolpropane diglycidyl ether, 1,4-cyclohexanedimethanol diglycidyl ether, 1,3-bis-(2,3-epoxypropyloxy)-2-(2,3-dihydroxypropy loxy)propane, 1,2-cyclohexanedicarboxylic acid diglycidyl ester, 2,2'-bis(glycidyloxy) diphenylmethane, bisphenol F diglycidyl ether, 1,4-bis(2', 3'epoxypropyl)perfluoro-n-butane, 2,6-di(oxiran-2-ylmethyl)-1,2,3,5,6,7-hexahydropyrrolo[3,4-f]isoindol-1,3,5,7- tetraone, bisphenol A diglycidyl ether, ethyl 5-hydroxy-6,8-di(oxiran-2-ylmethyl)-4-oxo-4-h-chromene-2-carboxylate, bis[4-(2,3-epoxy-propylthio)phenyl]-sulfide, 1,3-bis(3-glycidoxypropyl) tetramethyldisiloxane, 9,9-bis[4-(glycidyloxy)phenyl]fluorine, triepoxyisocyanurate, glycerol triglycidyl ether, N,N-diglycidyl-4-glycidyloxyaniline, isocyanuric acid (S,S,S)-triglycidyl ester, isocyanuric acid (R,R,R)-triglycidyl ester, triglycidyl isocyanurate, trimethylolpropane triglycidyl ether, glycerol propoxylate triglycidyl ether, triphenylolmethane triglycidyl ether, 3,7,14-tris[[3-(epoxypropoxy)propyl]dimethylsilyloxy]-1,3,5,7,9,11,14-heptacyclopentyltricyclo [7,3,3,15,11]heptasiloxane, 4,4'methylenebis(N,N-diglycidylaniline), bis(halomethyl)benzene, bis(halomethyl)biphenyl and bis(halomethyl)naphthalene, toluene diisocyanate, acrylol chloride, methyl acrylate, ethylene bisacrylamide, pyrometallic dianhydride, succinyl dichloride, dimethylsuccinate, 3-chloro-1-(3-chloropropylamino-2-propanol, 1,2-bis(3-chloropropylamino)ethane, Bis(3-chloropropyl)amine, 1,3-Dichloro-2-propanol, 1,3-Dichloropropane, 1-chloro-2,3-epoxypropane, tris[(2-oxiranyl)methyl]amine.

In some embodiments, the preformed amine polymer is a crosslinked amine polymer comprising the residue of an amine corresponding to Formula 1a and the crosslinked amine polymer is prepared by radical polymerization of an amine corresponding to Formula 1a:

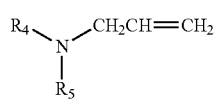

Formula 1a wherein $R_4$ and $R_5$ are independently hydrogen, hydrocarbyl, or substituted hydrocarbyl. In one embodiment, for example, $R_4$ and $R_5$ are independently hydrogen, saturated hydrocarbon, unsaturated aliphatic, aryl, heteroaryl, unsaturated heteroaliphatic, heterocyclic, or heteroalkyl. By way of further example, in one such embodiment $R_4$ and $R_5$ are independently hydrogen, aliphatic, heteroaliphatic, aryl, or heteroaryl. By way of further example, in one such embodiment $R_4$ and $R_5$ are independently hydrogen, alkyl, alkenyl, allyl, vinyl, aryl, aminoalkyl, alkanol, haloalkyl, hydroxyalkyl, ethereal, heteroaryl or heterocyclic. By way of further example, in one such embodiment $R_4$ and $R_5$ are independently hydrogen, alkyl, allyl, aminoalkyl, alkanol, aryl, haloalkyl, hydroxyalkyl, ethereal, or heterocyclic. By way of further example, in one such embodiment $R_4$ and $R_5$ (in combination with the nitrogen atom to which they are attached) together constitute part of a ring structure, so that the monomer as described by Formula 1a is a nitrogen-containing heterocycle (e.g., piperidine). By way of further example, in one such embodiment $R_4$ and $R_5$ are independently hydrogen, aliphatic or heteroaliphatic. By way of further example, in one embodiment $R_4$ and $R_5$ are independently hydrogen, allyl, or aminoalkyl.

In some embodiments, the preformed amine polymer is a crosslinked amine polymer comprising the residue of an amine corresponding to Formula 1 b and the crosslinked amine polymer is prepared by substitution polymerization of the amine corresponding to Formula 1b with a polyfunctional crosslinker (optionally also comprising amine moieties):

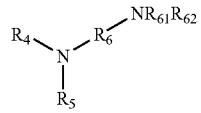

Formula 1b wherein $R_4$ and $R_5$ are independently hydrogen, hydrocarbyl, or substituted hydrocarbyl, $R_6$ is aliphatic and $R_{61}$ and $R_{62}$ are independently hydrogen, aliphatic, or heteroaliphatic. In one embodiment, for example, $R_4$ and $R_5$ are independently hydrogen, saturated hydrocarbon, unsaturated aliphatic, aryl, heteroaryl, heteroalkyl, or unsaturated heteroaliphatic. By way of further example, in one such embodiment $R_4$ and $R_5$ are independently hydrogen, aliphatic, heteroaliphatic, aryl, or heteroaryl. By way of further example, in one such embodiment $R_4$ and $R_5$ are independently hydrogen, alkyl, alkenyl, allyl, vinyl, aryl, aminoalkyl, alkanol, haloalkyl, hydroxyalkyl, ethereal, heteroaryl or heterocyclic. By way of further example, in one such embodiment $R_4$ and $R_5$ are independently hydrogen, alkyl, alkenyl, aminoalkyl, alkanol, aryl, haloalkyl, hydroxyalkyl, ethereal, heteroaryl or heterocyclic. By way of further example, in one such embodiment $R_4$ and $R_5$ (in combination with the nitrogen atom to which they are attached) together constitute part of a ring structure, so that the monomer as described by Formula 1a is a nitrogen-containing heterocycle (e.g., piperidine). By way of further example, in one embodiment $R_4$ and $R_5$ are independently hydrogen, aliphatic or heteroaliphatic. By way of further example, in one embodiment $R_4$ and $R_5$ are independently hydrogen, allyl, or aminoalkyl. By way of further example, in each of the embodiments recited in this paragraph, $R_e$ may be methylene, ethylene or propylene, and $R_{61}$ and $R_{62}$ may independently be hydrogen, allyl or aminoalkyl.

In some embodiments, the preformed amine polymer is a crosslinked amine polymer comprising the residue of an amine corresponding to Formula 1c:

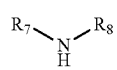

Formula 1c wherein $R_7$ is hydrogen, aliphatic or heteroaliphatic and $R_8$ is aliphatic or heteroaliphatic. For example, in one such embodiment, for example, $R_7$ is hydrogen and $R_8$ is aliphatic or heteroaliphatic. By way of further example, in one such embodiment $R_7$ and $R_8$ are independently aliphatic or heteroaliphatic. By way of further example, in one such embodiment at least one of $R_7$ and $R_8$ comprises an allyl moiety. By way of further example, in one such embodiment at least one of $R_7$ and $R_8$ comprises an aminoalkyl moiety. By way of further example, in one such embodiment $R_7$ and $R_8$ each comprise an allyl moiety. By way of further example, in one such embodiment $R_7$ and $R_8$ each comprise an aminoalkyl moiety. By way of further example, in one such embodiment $R_7$ comprises an allyl moiety and $R_8$ comprises an aminoalkyl moiety.

In some embodiments, the preformed amine polymer is a crosslinked amine polymer comprising the residue of an amine corresponding to Formula 2:

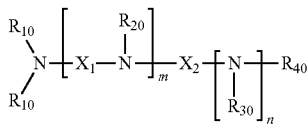

Formula 2 wherein m and n are independently non-negative integers;

$R_{10}$, $R_{20}$, $R_{30}$, and $R_{40}$ are independently hydrogen, hydrocarbyl, or substituted hydrocarbyl;

$X_1$ is

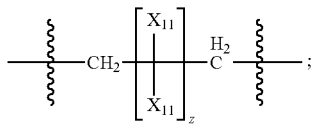

$X_2$ is hydrocarbyl or substituted hydrocarbyl;

each $X_{11}$ is independently hydrogen, hydrocarbyl, substituted hydrocarbyl, hydroxyl, amino, boronic acid, or halo; and z is a non-negative number.

In one embodiment, the preformed amine polymer is a crosslinked amine polymer comprising the residue of an amine corresponding to Formula 2, the crosslinked amine polymer is prepared by (i) substitution polymerization of the amine corresponding to Formula 2 with a polyfunctional crosslinker (optionally also comprising amine moieties) or (2) radical polymerization of an amine corresponding to Formula 2, and m and n are independently 0, 1, 2 or 3 and n is 0 or 1.

In one embodiment, the preformed amine polymer is a crosslinked amine polymer comprising the residue of an amine corresponding to Formula 2, the crosslinked amine polymer is prepared by (i) substitution polymerization of the amine corresponding to Formula 2 with a polyfunctional crosslinker (optionally also comprising amine moieties) or (2) radical polymerization of an amine corresponding to Formula 2, and $R_{10}$, $R_{20}$, $R_{30}$, and $R_{40}$ are independently hydrogen, aliphatic, aryl, heteroaliphatic, or heteroaryl. By way of further example, in one such embodiment $R_{10}$, $R_{20}$, $R_{30}$, and $R_{40}$ are independently hydrogen, aliphatic, or heteroaliphatic. By way of further example, in one such embodiment $R_{10}$, $R_{20}$, $R_{30}$, and $R_{40}$ are independently hydrogen, alkyl, allyl, vinyl, or aminoalkyl. By way of further example, in one such embodiment $R_{10}$, $R_{20}$, $R_{30}$, and $R_{40}$ are independently hydrogen, alkyl, allyl, vinyl, $-(CH_2)_d NH_2$, $-(CH_2)_d N[(CH_2)_e NH_2]_2$ where d and e are independently 2-4. In each of the foregoing exemplary embodiments of this paragraph, m and z may independently be 0, 1, 2 or 3 and n is 0 or 1.

In one embodiment, the preformed amine polymer is a crosslinked amine polymer comprising the residue of an amine corresponding to Formula 2, the crosslinked amine polymer is prepared by (i) substitution polymerization of the amine corresponding to Formula 2 with a polyfunctional crosslinker (optionally also comprising amine moieties) or (2) radical polymerization of an amine corresponding to Formula 2, and $X_2$ is aliphatic or heteroaliphatic. For example, in one such embodiment $X_2$ is aliphatic or heteroaliphatic and $R_{10}$, $R_{20}$, $R_{30}$, and $R_{40}$ are independently hydrogen, aliphatic, heteroaliphatic. By way of further example, in one such embodiment $X_2$ is alkyl or aminoalkyl and $R_{10}$, $R_{20}$, $R_{30}$, and $R_{40}$ are independently hydrogen, aliphatic, or heteroaliphatic. By way of further example, in one such embodiment $X_2$ is alkyl or aminoalkyl and $R_{10}$, $R_{20}$, $R_{30}$, and $R_{40}$ are independently hydrogen, alkyl, allyl, vinyl, or aminoalkyl. In each of the foregoing exemplary embodiments of this paragraph, m and z may independently be 0, 1, 2 or 3 and n is 0 or 1.

In one embodiment, the preformed amine polymer is a crosslinked amine polymer comprising the residue of an amine corresponding to Formula 2, the crosslinked amine polymer is prepared by (i) substitution polymerization of the amine corresponding to Formula 2 with a polyfunctional crosslinker (optionally also comprising amine moieties) or (2) radical polymerization of an amine corresponding to Formula 2, and m is a positive integer. For example, in one such embodiment m is a positive integer, z is zero and $R_{20}$ is hydrogen, aliphatic or heteroaliphatic. By way of further example, in one such embodiment m is a positive integer (e.g., 1 to 3), z is a positive integer (e.g., 1 to 2), $X_{11}$ is hydrogen, aliphatic or heteroaliphatic, and $R_{20}$ is hydrogen, aliphatic or heteroaliphatic. By way of further example, in one such embodiment m is a positive integer, z is zero, one or two, $X_{11}$ is hydrogen alkyl, alkenyl, or aminoalkyl, and $R_{20}$ is hydrogen, alkyl, alkenyl, or aminoalkyl.

In one embodiment, the preformed amine polymer is a crosslinked amine polymer comprising the residue of an amine corresponding to Formula 2, the crosslinked amine polymer is prepared by (i) substitution polymerization of the amine corresponding to Formula 2 with a polyfunctional crosslinker (optionally also comprising amine moieties) or (2) radical polymerization of an amine corresponding to Formula 2, and n is a positive integer and $R_{30}$ is hydrogen, aliphatic or heteroaliphatic. By way of further example, in one such embodiment n is 0 or 1, and $R_{30}$ is hydrogen, alkyl, alkenyl, or aminoalkyl.

In one embodiment, the preformed amine polymer is a crosslinked amine polymer comprising the residue of an amine corresponding to Formula 2, the crosslinked amine polymer is prepared by (i) substitution polymerization of the amine corresponding to Formula 2 with a polyfunctional crosslinker (optionally also comprising amine moieties) or (2) radical polymerization of an amine corresponding to Formula 2, and m and n are independently non-negative integers and $X_2$ is aliphatic or heteroaliphatic. For example, in one such embodiment m is 0 to 2, n is 0 or 1, $X_2$ is aliphatic or heteroaliphatic, and $R_{10}$, $R_{20}$, $R_{30}$, and $R_{40}$ are independently hydrogen, aliphatic, or heteroaliphatic. By way of further example, in one such embodiment m is 0 to 2, n is 0 or 1, $X_2$ is alkyl or aminoalkyl, and $R_{10}$, $R_{20}$, $R_{30}$, and $R_{40}$ are independently hydrogen, aliphatic, or heteroaliphatic. By way of further example, in one such embodiment m is 0 to 2, n is 0 or 1, $X_2$ is alkyl or aminoalkyl, and $R_{10}$, $R_{20}$, $R_{30}$, and $R_{40}$ are independently hydrogen, alkyl, alkenyl, or aminoalkyl.

In some embodiments, the preformed amine polymer is a crosslinked amine polymer comprising the residue of an amine corresponding to Formula 2a and the crosslinked amine polymer is prepared by substitution polymerization of the amine corresponding to Formula 2a with a polyfunctional crosslinker (optionally also comprising amine moieties):

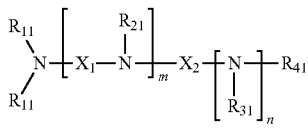

Formula 2a wherein m and n are independently non-negative integers;

each $R_{11}$ is independently hydrogen, hydrocarbyl, heteroaliphatic, or heteroaryl;

$R_{21}$ and $R_{31}$, are independently hydrogen or heteroaliphatic;

$R_{41}$ is hydrogen, substituted hydrocarbyl, or hydrocarbyl; $X_1$ is

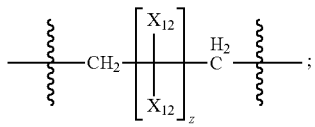

$X_2$ is alkyl or substituted hydrocarbyl;

each $X_{12}$ is independently hydrogen, hydroxy, amino, aminoalkyl, boronic acid or halo; and z is a non-negative number.

In one embodiment, the preformed amine polymer is a crosslinked amine polymer comprising the residue of an amine corresponding to Formula 2a, the crosslinked amine polymer is prepared by substitution polymerization of the amine corresponding to Formula 1 with a polyfunctional crosslinker (optionally also comprising amine moieties). For example, in one such embodiment, m and z are independently 0, 1, 2 or 3, and n is 0 or 1.

In one embodiment, the preformed amine polymer is a crosslinked amine polymer comprising the residue of an amine corresponding to Formula 2a, the crosslinked amine polymer is prepared by substitution polymerization of the amine corresponding to Formula 2a with a polyfunctional crosslinker (optionally also comprising amine moieties), and each $R_{11}$ is independently hydrogen, aliphatic, aminoalkyl, haloalkyl, or heteroaryl, $R_{21}$ and $R_{31}$ are independently hydrogen or heteroaliphatic and $R_{41}$ is hydrogen, aliphatic, aryl, heteroaliphatic, or heteroaryl. For example, in one such embodiment each Rn is hydrogen, aliphatic, aminoalkyl, or haloalkyl, $R_{21}$ and $R_{31}$ are independently hydrogen or heteroaliphatic and $R_{41}$ is hydrogen, alkylamino, aminoalkyl, aliphatic, or heteroaliphatic. By way of further example, in one such embodiment each $R_{11}$ is hydrogen, aliphatic, aminoalkyl, or haloalkyl, $R_2$, and $R_{31}$ are hydrogen or aminoalkyl, and $R_{41}$ is hydrogen, aliphatic, or heteroaliphatic. By way of further example, in one such embodiment each $R_{11}$ and $R_{41}$ is independently hydrogen, alkyl, or aminoalkyl, and $R_{21}$ and $R_{31}$ are independently hydrogen or heteroaliphatic. By way of further example, in one such example, each $R_{11}$ and $R_{41}$ is independently hydrogen, alkyl, $-(CH_2)_d NH_2$, $-(CH_2)_d N[(CH_2)_e NH_2)]_2$ where d and e are independently 2-4, and $R_{21}$ and $R_{31}$ are independently hydrogen or heteroaliphatic. In each of the foregoing exemplary embodiments of this paragraph, m and z may independently be 0, 1, 2 or 3, and n is 0 or 1.

Exemplary amines for the synthesis of polymers comprising repeat units corresponding to Formula 2a include, but are not limited to, amines appearing in Table A.

TABLE A

| Abbreviation | IUPAC name | Other names | | MW (g/mol) |
|---|---|---|---|---|
| C2A3BTA | 1,3-Bis[bis(2-aminoethyl)amino]propane | | | 288.48 |
| C2A3G2 | 3-Amino-1-{[2-(bis{2-[bis(3-aminopropyl)amino]ethyl}amino)ethyl](3-aminopropyl)amino}propane | | | 488.81 |

TABLE A-continued

| Abbreviation | IUPAC name | Other names | Structure | MW (g/mol) |
|---|---|---|---|---|
| C2PW | 2-[Bis(2-aminoethyl)amino]ethanamine | 2,2',2''-Triaminotriethylamine or 2,2',2''-Nitrilotriethylamine | | 146.24 |
| C3PW | Tris(3-aminopropyl)amine | | | 188.32 |
| C4A3BTA | 1,4-Bis[bis(3-aminopropyl)amino]butane | | | 316.54 |
| EDA1 | 1,2-Ethanediamine | | | 60.1 |
| EDA2 | 2-Amino-1-(2-aminoethylamino)ethane | Bis(2-aminoethyl)amine or 2,2'-Diaminodiethylamine | | 103.17 |
| EDA3 | 1,2-Bis(2-aminoethylamino)ethane | N,N'-Bis(2-aminoethyl)ethane-1,2-diamine | | 146.24 |
| PDA1 | 1,3-Propanediamine | | | 74.3 |
| PDA2 | 3,3'-Diaminodipropylamine | | | 131.22 |

Exemplary crosslinkers for the synthesis of polymers comprising the residue of amines corresponding to Formula 2a include but are not limited to crosslinkers appearing in Table B.

TABLE B

| Abbreviation | Common name | IUPAC name | | MW (g/mol) |
|---|---|---|---|---|
| BCPA | Bis(3-chloropropyl)amine | Bis(3-chloropropyl)amine · HCl | Cl~~~N(H)~~~Cl · HCl | 206.54 |
| DC2OH | 1,3-dichloroisopropanol | 1,3-Dichloro-2-propanol | Cl~~~CH(OH)~~~Cl | 128.98 |
| DCE | dichloroethane | 1,2-dichloroethane | Cl~~~Cl | 98.96 |
| DCP | Dichloropropane | 1,3-Dichloropropane | Cl~~~Cl | 112.98 |
| ECH | Epichlorohydrin | 1-chloro-2,3-epoxypropane | epoxide-CH2-Cl | 92.52 |
| TGA | Triglycidyl amine | Tris[(2-oxiranyl)methyl]amine | N(CH2-epoxide)3 | 185.22 |
| BCPOH | Bis(3-chloropropyl)amine-OH | 3-Chloro-1-(3-chloropropylamino)-2-propanol | Cl~~~N(H)~~~CH(OH)~~~Cl | 186.08 |
| BCPEDA | Bis(chloropropyl)ethylenediamine | 1,2-Bis(3-chloropropylamino)ethane | Cl~~~N(H)~~~N(H)~~~Cl | 213.15 |

In some embodiments, the preformed amine polymer is a crosslinked amine polymer comprising the residue of an amine corresponding to Formula 2b and the crosslinked amine polymer is prepared by radical polymerization of an amine corresponding to Formula 2b:

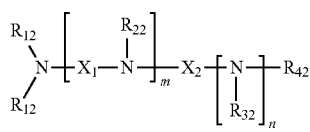

Formula 2b wherein m and n are independently non-negative integers;

each $R_{12}$ is independently hydrogen, substituted hydrocarbyl, or hydrocarbyl;

$R_{22}$ and $R_{32}$ are independently hydrogen substituted hydrocarbyl, or hydrocarbyl;

$R_{42}$ is hydrogen, hydrocarbyl or substituted hydrocarbyl;

$X_1$ is

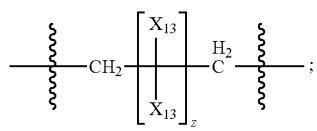

$X_2$ is alkyl, aminoalkyl, or alkanol;

each $X_{13}$ is independently hydrogen, hydroxy, alicyclic, amino, aminoalkyl, halogen, alkyl, heteroaryl, boronic acid or aryl;

z is a non-negative number, and the amine corresponding to Formula 2b comprises at least one allyl group.

In one embodiment, the preformed amine polymer is a crosslinked amine polymer comprising the residue of an amine corresponding to Formula 2b, the crosslinked amine polymer is prepared by radical polymerization of an amine corresponding to Formula 2b, and m and z are independently 0, 1, 2 or 3, and n is 0 or 1.

In one embodiment, the preformed amine polymer is a crosslinked amine polymer comprising the residue of an amine corresponding to Formula 2b, the crosslinked amine polymer is prepared by radical polymerization of an amine corresponding to Formula 1, and (i) $R_{12}$ or $R_{42}$ independently comprise at least one allyl or vinyl moiety, (ii) m is a positive integer and $R_n$ comprises at least one allyl or vinyl moiety, and/or (iii) n is a positive integer and $R_{32}$ comprises at least one allyl moiety. For example, in one such embodiment, m and z are independently 0, 1, 2 or 3 and n is 0 or 1. For example, in one such embodiment $R_{12}$ or $R_{42}$, in combination comprise at least two allyl or vinyl moieties. By way of further example, in one such embodiment, m is a positive integer and $R_{12}$, $R_{22}$ and $R_{42}$, in combination comprise at least two allyl or vinyl moieties. By way of further example, in one such embodiment, n is a positive integer and $R_{12}$, $R_{32}$ and $R_{42}$, in combination comprise at least two allyl or vinyl moieties. By way of further example, in one such embodiment, m is a positive integer, n is a positive integer and $R_{12}$, $R_{22}$, $R_{32}$ and $R_{42}$, in combination, comprise at least two allyl or vinyl moieties.

In one embodiment, the preformed amine polymer is a crosslinked amine polymer comprising the residue of an amine corresponding to Formula 2b, the crosslinked amine polymer is prepared by radical polymerization of an amine corresponding to Formula 2b, and each $R_{12}$ is independently hydrogen, aminoalkyl, allyl, or vinyl, $R_{22}$ and $R_{32}$ are independently hydrogen, alkyl, aminoalkyl, haloalkyl, alkenyl, alkanol, heteroaryl, alicyclic heterocyclic, or aryl, and $R_{42}$ is hydrogen or substituted hydrocarbyl. For example, in one such embodiment each $R_{12}$ is aminoalkyl, allyl or vinyl, $R_{22}$ and $R_{32}$ are independently hydrogen, alkyl, aminoalkyl, haloalkyl, alkenyl, or alkanol, and $R_{42}$ is hydrogen or substituted hydrocarbyl. By way of further example, in one such embodiment each $R_{12}$ and $R_{42}$ is independently hydrogen, alkyl, allyl, vinyl, —$(CH_2)_d NH_2$ or —$(CH_2)_d N[(CH_2)_e NH_2]_2$ where d and e are independently 2-4, and $R_{22}$ and $R_{32}$ are independently hydrogen or heteroaliphatic.

Exemplary amines and crosslinkers (or the salts thereof, for example the hydrochloric acid, phosphoric acid, sulfuric acid, or hydrobromic acid salts thereof) for the synthesis of polymers described by Formula 2b include but are not limited to the ones in Table C.

In some embodiments, the preformed amine polymer is a crosslinked amine polymer derived from a reaction of the resulting preformed polymers that utilize monomers described in any of Formulae 1, 1a, 1b, 1c, 2, 2a and 2b or a linear polymer comprised of a repeat unit described by Formula 3 with external crosslinkers or pre-existing polymer functionality that can serve as crosslinking sites. Formula 3 can be a repeat unit of a preformed copolymer or terpolymer where $X_{15}$ is either a random, alternating, or block copolymer. The repeating unit in Formula 3 can also represent the repeating unit of a preformed polymer that is branched, or hyperbranched, wherein the primary branch point can be from any atom in the main chain of the polymer:

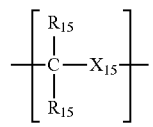

Formula 3

TABLE C

| Abbreviation | Common name | IUPAC name | | MW (g/mol) |
|---|---|---|---|---|
| DABDA1 | Diallylbutyldiamine | 1,4-Bis(allylamino)butane | | 241.2 |
| DAEDA1 | Diallylethyldiamine | 1,2-Bis(allylamino)ethane | | 213.15 |
| DAEDA2 | Diallyldiethylenetriamine | 2-(Allylamino)-1-[2-(allylamino)ethylamino]ethane | | 292.67 |
| DAPDA | Diallylpropyldiamine | 1,3-Bis(allylamino)propane | | 227.17 |
| POHDA | Diallylamineisopropanol | 1,3-Bis(allylamino)-2-propanol | | 243.17 |
| AAH | Allylamine | 2-Propen-1-ylamine | | 93.5 |
| AEAAH | Aminoethylallylamine | 1-(Allylamino)-2-aminoethane | | 173.08 |
| BAEAAH | Bis(2-aminoethyl)allylamine | 1-[N-Allyl(2-aminoethyl)amino]-2-aminoethane | | 252.61 |
| TAA | Triallylamine | N,N,N-triallylamine | | 137.22 | wherein $R_{15}$, $R_{16}$ and $R_{17}$ are independently hydrogen, hydrocarbyl, substituted hydrocarbyl, hydroxyl, amino, boronic acid or halo;

$X_{15}$ is

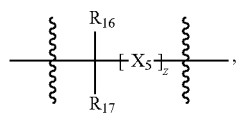

$X_5$ is hydrocarbyl, substituted hydrocarbyl, oxo (—O—), or amino and z is a non-negative number.

In one embodiment, $R_{15}$, $R_{16}$ and $R_{17}$ are independently hydrogen, aryl, or heteroaryl, $X_5$ is hydrocarbyl, substituted hydrocarbyl, oxo or amino, and m and z are non-negative integers. In another embodiment, $R_{15}$, $R_{16}$ and $R_{17}$ are independently aliphatic or heteroaliphatic, $X_5$ is hydrocarbyl, substituted hydrocarbyl, oxo (—O—) or amino, and m and z are non-negative integers. In another embodiment, $R_{15}$, $R_{16}$ and $R_{17}$ are independently unsaturated aliphatic or unsaturated heteroaliphatic, $X_5$ is hydrocarbyl, substituted hydrocarbyl, oxo, or amino, and z is a non-negative integer. In another embodiment, $R_{15}$, $R_{16}$ and $R_{17}$ are independently alkyl or heteroalkyl, $X_5$ is hydrocarbyl, substituted hydrocarbyl, oxo, or amino, and z is a non-negative integer. In another embodiment, $R_{15}$, $R_{16}$ and $R_{17}$ are independently alkylamino, aminoalkyl, hydroxyl, amino, boronic acid, halo, haloalkyl, alkanol, or ethereal, $X_5$ is hydrocarbyl, substituted hydrocarbyl, oxo, or amino, and z is a non-negative integer. In another embodiment, $R_{15}$, $R_{16}$ and $R_{17}$ are independently hydrogen, hydrocarbyl, substituted hydrocarbyl, hydroxyl, amino, boronic acid or halo, $X_5$ is oxo, amino, alkylamino, ethereal, alkanol, or haloalkyl, and z is a non-negative integer.

Exemplary crosslinking agents that may be used in radical polymerization reactions include, but are not limited to, one or more multifunctional crosslinking agents such as: 1,4-bis(allylamino)butane, 1,2-bis(allylamino)ethane, 2-(allylamino)-1-[2-(allylamino)ethylamino]ethane, 1,3-bis(allylamino)propane, 1,3-bis(allylamino)-2-propanol, triallylamine, diallylamine, divinylbenzene, 1,7-octadiene, 1,6-heptadiene, 1,8-nonadiene, 1,9-decadiene, 1,4-divinyloxybutane, 1,6-hexamethylenebisacrylamide, ethylene bisacrylamide, N,N'-bis(vinylsulfonylacetyl)ethylene diamine, 1,3-bis(vinylsulfonyl) 2-propanol, vinylsulfone, N,N'-methylenebisacrylamide polyvinyl ether, polyallylether, divinylbenzene, 1,4-divinyloxybutane, and combinations thereof.

Crosslinked polymers derived from the monomers and polymers in formulas 1 through 3 may be synthesized either in solution or bulk or in dispersed media. Examples of solvents that are suitable for the synthesis of polymers of the present disclosure include, but are not limited to water, low boiling alcohols (methanol, ethanol, propanol, butanol), dimethylformamide, dimethylsulfoxide, heptane, chlorobenzene, toluene.

As previously noted, the product of the first polymerization step is preferably in the form of beads whose diameter is controlled in the 5 to 1000 microns range, preferably 10 to 500 microns and most preferred 40-180 microns.

The product of the first polymerization step is preferably in the form of beads whose Swelling Ratio in water is between 2 and 10, more preferably about 3 to about 8, and most preferably about 4 to about 6.

Additionally, if the crosslinked polymer beads resulting from the first polymerization step are protonated, this may reduce the amount of nitrogen-nitrogen crosslinking in the second crosslinking step. Accordingly, in certain embodiments the preformed amine polymer is at least partially deprotonated by treatment with a base, preferably a strong base such as a hydroxide base. For example, in one embodiment the base may be NaOH, KOH, $NH_4OH$, $NaHCO_3$, $Na_2CO_3$, $K_2CO_3$, LiOH, $Li_2CO_3$, CsOH or other metal hydroxides. If the charges are removed from the preformed crosslinked amine polymer bead by deprotonation, the bead will tend to collapse and the crosslinking agent used in the second step may not be able to access binding sites on the polymer unless the bead is prevented from collapsing. One means of preventing the crosslinked polymer bead from collapsing is the use of a swelling agent such as water to swell the bead, thereby allowing the second-step crosslinker to access binding sites.

The preformed polymer may be crosslinked to form the post-polymerization crosslinked polymer using any of a range of crosslinking compounds containing at least two amine-reactive functional groups. In one such embodiment, the crosslinker is a compound containing at least two amine-reactive groups selected from the group consisting of halides, epoxides, phosgene, anhydrides, carbamates, carbonates, isocyanates, thioisocyanates, esters, activated esters, carboxylic acids and derivatives thereof, sulfonates and derivatives thereof, acyl halides, aziridines, α,β-unsaturated carbonyls, ketones, aldehydes, and pentafluoroaryl groups. The crosslinker may be, for example, any of the crosslinkers disclosed herein, including a crosslinker selected from Table B. By way of further example, in one such embodiment the crosslinker is a dihalide such as a dichloroalkane.

As noted above, in certain embodiments a swelling agent for the preformed amine polymer may be included in the reaction mixture for the second polymerization step along with the crosslinking agent. In general, the swelling agent and the crosslinking agent may be miscible or immiscible and the swelling agent may be any composition or combination of compositions that have the capacity to swell the preformed amine polymer. Exemplary swelling agents include polar solvents such as water, methanol, ethanol, n-propanol, isopropanol, n-butanol, formic acid, acetic acid, acetonitrile, dimethylformamide, dimethylsulfoxide, nitromethane, propylene carbonate, or a combination thereof. Additionally, the amount of swelling agent included in the reaction mixture will typically be less than absorption capacity of the preformed amine polymer for the swelling agent. For example, it is generally preferred that the weight ratio of swelling agent to preformed polymer in the reaction mixture be less than 4:1. By way of further example, in some embodiments the weight ratio of swelling agent to preformed polymer in the reaction mixture will be less than 3:1. By way of further example, in some embodiments the weight ratio of swelling agent to preformed polymer in the reaction mixture will be less than 2:1. By way of further example, in some embodiments the weight ratio of swelling agent to preformed polymer in the reaction mixture will be less than 1:1. By way of further example, in some embodiments the weight ratio of swelling agent to preformed polymer in the reaction mixture will be less than 0.5:1. By way of further example, in some embodiments the weight ratio of swelling agent to preformed polymer in the reaction mixture will be less than 0.4:1. By way of further example, in some embodiments the weight ratio of swelling agent to preformed polymer in the reaction mixture will be less than 0.3:1. In general, however, the weight ratio of swelling agent to preformed polymer in the reaction mixture will typically be at least 0.05:1, respectively.

When the swelling agent comprises water, the weight ratio of water to preformed amine polymer in the reaction mixture will typically be less than about 4:1 (water to polymer). For example, in one such embodiment the reaction mixture comprises water as a swelling agent and the weight ratio of water to preformed amine polymer in the reaction mixture will typically be less than about 3.5:1. By way of further example, in one such embodiment the reaction mixture comprises water as a swelling agent and the weight ratio of water to preformed amine polymer in the reaction mixture will typically be less than about 3:1. By way of further example, in one such embodiment the reaction mixture comprises water as a swelling agent and the weight ratio of water to preformed amine polymer in the reaction mixture will typically be less than about 2.5:1. By way of further example, in one such embodiment the reaction mixture comprises water as a swelling agent and the weight ratio of water to preformed amine polymer in the reaction mixture will typically be less than about 2:1. By way of further example, in one such embodiment the reaction mixture comprises water as a swelling agent and the weight ratio of water to preformed amine polymer in the reaction mixture will typically be less than about 1.5:1. By way of further example, in one such embodiment the reaction mixture comprises water as a swelling agent and the weight ratio of water to preformed amine polymer in the reaction mixture will typically be less than about 1:1. By way of further example, in one such embodiment the reaction mixture comprises water as a swelling agent and the weight ratio of water to preformed amine polymer in the reaction mixture will typically be less than about 0.75:1. By way of further example, in one such embodiment the reaction mixture comprises water as a swelling agent and the weight ratio of water to preformed amine polymer in the reaction mixture will typically be less than about 0.5:1. By way of further example, in one such embodiment the reaction mixture comprises water as a swelling agent and the weight ratio of water to preformed amine polymer in the reaction mixture will typically be less than about 0.25:1. In general, however, when water is employed as a swelling agent the weight ratio of water to preformed amine polymer in the reaction mixture will typically be at least about 0.15:1 (water to polymer) but less than the water absorption capacity of the preformed amine polymer. By way of further example, in one embodiment the weight ratio of water to preformed amine polymer in the reaction mixture will typically be at least about 0.2:1 but less than the water absorption capacity of the preformed amine polymer. By way of further example, in one embodiment the weight ratio of water to preformed amine polymer in the reaction mixture will typically be at least about 0.25:1 but less than the water absorption capacity of the preformed amine polymer. By way of further example, in one embodiment the weight ratio of water to preformed amine polymer in the reaction mixture will typically be at least about 0.5:1 but less than the water absorption capacity of the preformed amine polymer. By way of further example, in one embodiment the weight ratio of water to preformed amine polymer in the reaction mixture will typically be at least about 0.75:1 but less than the water absorption capacity of the preformed amine polymer. By way of further example, in one embodiment the weight ratio of water to preformed amine polymer in the reaction mixture will typically be at least about 1:1 but less than the water absorption capacity of the preformed amine polymer. By way of further example, in one embodiment the weight ratio of water to preformed amine polymer in the reaction mixture will typically be at least about 1.5:1 but less than the water absorption capacity of the preformed amine polymer. By way of further example, in one embodiment the weight ratio of water to preformed amine polymer in the reaction mixture will typically be at least about 2:1 but less than the water absorption capacity of the preformed amine polymer. By way of further example, in one embodiment the weight ratio of water to preformed amine polymer in the reaction mixture will typically be at least about 2.5:1 but less than the water absorption capacity of the preformed amine polymer. By way of further example, in one embodiment the weight ratio of water to preformed amine polymer in the reaction mixture will typically be at least about 3:1 but less than the water absorption capacity of the preformed amine polymer. By way of further example, in one embodiment the weight ratio of water to preformed amine polymer in the reaction mixture will typically be at least about 3.5:1 but less than the water absorption capacity of the preformed amine polymer. Thus, in certain embodiments the weight ratio of water to preformed amine polymer will be in the range of about 0.15:1 to about 4:1. By way of further example, in certain embodiments the weight ratio of water to preformed amine polymer will be in the range of about 0.2:1 to about 3.5:1. By way of further example, in certain embodiments the weight ratio of water to preformed amine polymer will be in the range of about 0.2:1 to about 3:1.

In each of the foregoing embodiments, the reaction mixture may contain a wide range of amounts of crosslinking agents. For example, in one embodiment the crosslinker may be used in large excess relative to the amount of preformed amine polymer in the reaction mixtures. Stated differently, in such embodiments the crosslinking agent is a crosslinking solvent, i.e., it is both a solvent for the reaction mixture and a crosslinking agent for the preformed amine polymer. In such embodiments, other solvents may optionally be included in the reaction mixture but are not required. Alternatively, the preformed amine polymer, swelling agent and crosslinker may be dispersed in a solvent that is miscible with the crosslinker and immiscible with the swelling agent. For example, in some embodiments the swelling agent may be a polar solvent; in some such embodiments, for example, the swelling agent may comprise water, methanol, ethanol, n-propanol, isopropanol, formic acid, acetic acid, acetonitrile, dimethylformamide, dimethylsulfoxide, nitromethane, or a combination thereof. By way of further example, when the swelling agent comprises a polar solvent, the solvent system for the reaction mixture will typically comprise a non-polar solvent such as pentane, cyclopentane, hexane, cyclohexane, benzene, toluene, 1,4-dioxane, chloroform, diethyl ether, dichloromethane, dichloroethane, dichloropropane, dichlorobutane, or a combination thereof. In certain embodiments, the crosslinker and the solvent may be the same; i.e., the solvent is a crosslinking solvent such as 1,2-dichloroethane, 1,3-dichloropropane, 1,4-dichlorobutane or a combination thereof.

In those embodiments in which the reaction mixture comprises a swelling agent, it is sometimes preferred to combine the preformed amine polymer with the solvent (sometimes alternatively referred to as a dispersant) before the preformed amine polymer is combined with the swelling agent in the reaction mixture. In certain embodiments, the resulting crosslinked polymer tends to be less aggregated when the preformed amine polymer is combined with a solvent (dispersant) that is immiscible with the swelling agent before the preformed amine polymer is combined with the swelling agent. Thus, in certain embodiments less than 25% of the particles in a representative sample of a population of post polymerization crosslinked amine particles are aggregated into agglomerates. For example, in some embodiments less than 20% of the particles in a representative sample of a population of post polymerization crosslinked amine particles are aggregated into agglomerates. By way of further example, in some embodiments less than 15% of the particles in a representative sample of a population of post polymerization crosslinked amine particles are aggregated into agglomerates. By way of further example, in some embodiments less than 10% of the particles in a representative sample of a population of post polymerization crosslinked amine particles are aggregated into agglomerates. By way of further example, in some embodiments less than 5% of the particles in a representative sample of a population of post polymerization crosslinked amine particles are aggregated into agglomerates. By way of further example, in some embodiments less than 1% of the particles in a representative sample of a population of post polymerization crosslinked amine particles are aggregated into agglomerates. Aggregation can be evaluated using microscopy or other means of measuring particle size distribution. Lack of aggregation can be defined as generally separated, free-flowing beads lacking macroscopic and/or microscopic clumps. Particle size distribution (as defined elsewhere) can indicate that aggregation has occurred, for example if the average size (d(50)) and/or d(90) of the post-polymerization crosslinked amine polymer increases after the crosslinking step relative to the preformed amine polymer breads as previously described.

In one embodiment, a preformed amine polymer is formed in a first step and the preformed amine polymer is crosslinked in a second step to for the post-polymerization crosslinked polymer without isolating the preformed amine polymer between the first and second steps (sometimes referred to as a "one-pot synthesis"). For example, in one such embodiment a preformed amine polymer is formed in a first reaction mixture (as previously described herein) and, without isolating the preformed amine polymer formed in the first reaction mixture, the preformed amine polymer is then crosslinked using any of the crosslinkers disclosed herein (including, e.g., a crosslinker selected from Table B). By way of further example, in one such embodiment the preformed polymer may be dispersed in any of the non-polar solvents disclosed herein (including for example, a cross-linking solvent) to form a reaction mixture and a swelling agent is added to the reaction mixture. In one such exemplary embodiment, the crosslinker is selected from Table B, the solvent is a crosslinking water-immiscible solvent such as 1,2-dichloroethane ("DCE") or 1,3-dichloropropane ("DCP"), and the swelling agent comprises water. In each of the foregoing embodiments, the preformed polymer may be an amine-containing polymer containing a residue of a monomer described in any of Formulae 1, 1a, 1b, 1c, 2, 2a and 2b or a linear polymer comprised of a repeat unit described by Formula 3; for example, in each of the foregoing embodiments, the preformed polymer may contain the residue of two or more small molecule amines and crosslinkers disclosed in Table C.

In one exemplary embodiment, a preformed polyamine polymer is crosslinked under, for example suspension conditions to generate a particle of targeted particle size and morphology. The crosslinker can be either water miscible or water miscible. When a water immiscible crosslinker (e.g., DCE or DCP) is used as the dispersant, high chloride binding selectivities are achieved, as demonstrated, for example, in SIB and/or SOB.

In one embodiment an amine polymer can be formed and then further crosslinked in the same reaction flask and in one reaction series. A crosslinked amine polymer can be prepared under, for example, suspension conditions to generate a particle of targeted particle size and morphology. In the same reaction flask, and without isolation, the water content in the beads can be lowered by Dean Stark methods or other similar evaporative techniques. The water is adjusted to the targeted amount such that a second crosslinking reaction can be conducted to produce a final polymer with the desired properties and characteristics.

In one embodiment, the crosslinked amine polymer is treated to reduce the concentration of any residual amine-reactive groups (e.g., amine-reactive functional groups) introduced to the crosslinked polymer by a crosslinker. For example, in one such embodiment the crosslinked polymer (e.g., a post-polymerization crosslinked polymer as previously described) is treated with a quenching agent such as a base, washed, heated, or otherwise treated to remove or quench the amine-reactive groups. For example, in one embodiment the crosslinked polymer is treated with ammonium hydroxide. The ammonium hydroxide treatment can occur immediately after the reaction, during the washing steps, or after the polymer has been washed and dried, in which case the polymer can be processed through another series of washing steps. In another embodiment, the crosslinked polymer is heated in a conventional or in a vacuum oven at a temperature above room temperature for a period of time, for example 60° C. for greater than 36 hours. The oven incubation may occur under an inert atmosphere (e.g., nitrogen or argon) to reduce the possibility of oxidation.

In one embodiment, a preformed amine polymer characterized by a first selectivity for chloride relative to citrate, phosphate and/or taurocholate in SGF, SIB and/or SOB is crosslinked in a post-polymerization crosslinking reaction to provide a crosslinked polymer (i.e., the post-polymerization crosslinked polymer) having a second (different) selectivity for chloride relative to citrate, phosphate and/or taurocholate in SGF, SIB and/or SOB. In one such embodiment, the preformed amine polymer is the reaction product of a substitution polymerization of polyfunctional reagents at least one of which comprises amine moieties. In another such embodiment, the preformed polymer is the reaction product of a radical polymerization of a monomer comprising at least one amine moiety or nitrogen containing moiety. In a second crosslinking step (which may optionally be carried out after the preformed polymer is isolated or as a second step in a one-pot reaction), the preformed amine polymer is crosslinked with a polyfunctional crosslinker, optionally containing amine moieties.

In one exemplary embodiment the post-polymerization crosslinked polymer has an increased binding capacity for chloride and a decreased binding capacity for phosphate in SIB relative to the preformed amine polymer. For example, in one such embodiment the post-polymerization crosslinked polymer has an increased binding capacity for chloride and a decreased binding capacity for phosphate in SIB relative to the preformed polymer. By way of further example, in one such embodiment the post-polymerization crosslinked polymer has a capacity for chloride in SIB that is at least 10% greater than the binding capacity of the preformed polymer for chloride in SIB. By way of further example, in one such embodiment the post-polymerization crosslinked polymer has a capacity for chloride in SIB that is at least 25% greater than the binding capacity of the preformed polymer for chloride in SIB. By way of further example, in one such embodiment the post-polymerization crosslinked polymer has a capacity for chloride in SIB that is at least 50% greater than the binding capacity of the preformed polymer for chloride in SIB. By way of further example, in one such embodiment the post-polymerization crosslinked polymer has a capacity for chloride in SIB that is at least 75% greater than the binding capacity of the preformed polymer for chloride in SIB. By way of further example, in one such embodiment the post-polymerization crosslinked polymer has a capacity for chloride in SIB that is at least 100% greater than the binding capacity of the preformed polymer for chloride in SIB. By way of further example, in one such embodiment the post-polymerization crosslinked polymer has a capacity for chloride in SIB that is at least 125% greater than the binding capacity of the preformed polymer for chloride in SIB. By way of further example, in one such embodiment the post-polymerization crosslinked polymer has a capacity for chloride in SIB that is at least 150% greater than the binding capacity of the preformed polymer for chloride in SIB. By way of further example, in one such embodiment the post-polymerization crosslinked polymer has a capacity for chloride in SIB that is at least 200% greater than the binding capacity of the preformed polymer for chloride in SIB. By way of further example, in one such embodiment the post-polymerization crosslinked polymer has a capacity for phosphate in SIB that is at least 10% less than the binding capacity of the preformed polymer for phosphate in SIB. By way of further example, in one such embodiment the post-polymerization crosslinked polymer has a capacity for phosphate in SIB that is at least 20% less than the binding capacity of the preformed polymer for phosphate in SIB. By way of further example, in one such embodiment the post-polymerization crosslinked polymer has a capacity for phosphate in SIB that is at least 30% less than the binding capacity of the preformed polymer for phosphate in SIB. By way of further example, in one such embodiment the post-polymerization crosslinked polymer has a capacity for phosphate in SIB that is at least 40% less than the binding capacity of the preformed polymer for phosphate in SIB. By way of further example, in one such embodiment the post-polymerization crosslinked polymer has a capacity for phosphate in SIB that is at least 50% less than the binding capacity of the preformed polymer for phosphate in SIB. By way of further example, in one such embodiment the post-polymerization crosslinked polymer has a capacity for phosphate in SIB that is at least 60% less than the binding capacity of the preformed polymer for phosphate in SIB. By way of further example, in one such embodiment the post-polymerization crosslinked polymer has a capacity for phosphate in SIB that is at least 70% less than the binding capacity of the preformed polymer for phosphate in SIB. By way of further example, in one such embodiment the post-polymerization crosslinked polymer has a capacity for phosphate in SIB that is at least 80% less than the binding capacity of the preformed polymer for phosphate in SIB. By way of further example, in one such embodiment the post-polymerization crosslinked polymer has a capacity for phosphate in SIB that is at least 90% less than the binding capacity of the preformed polymer for phosphate in SIB. By way of further example, in one such embodiment the post-polymerization crosslinked polymer has a capacity for phosphate in SIB that is at least 95% less than the binding capacity of the preformed polymer for phosphate in SIB. By way of further example, in one such embodiment the post-polymerization crosslinked polymer has (i) an increased binding capacity for chloride (the percentage increase being at least 10%, 25%, 50%, 75%, 100%, 125%, 150%, 175%, or even at least 200%) and a decreased binding capacity for phosphate in SIB (the percentage decrease being at least 10%, 20%, 30%, 40%, 50%, 60%, 70%, 80%, 90% or even at least 95%) relative to the preformed amine polymer and (ii) a decreased binding capacity for chloride in SGF relative to the preformed amine polymer.

In one exemplary embodiment the post-polymerization crosslinked polymer has an increased binding capacity for chloride and a decreased binding capacity for phosphate, citrate or taurocholate in SOB relative to the preformed amine polymer. For example, in one such embodiment the post-polymerization crosslinked polymer has an increased binding capacity for chloride and a decreased binding capacity for phosphate in SOB relative to the preformed polymer. By way of further example, in one such embodiment the post-polymerization crosslinked polymer has an increased binding capacity for chloride and a decreased binding capacity for citrate in SOB relative to the preformed amine polymer. By way of further example, in one such embodiment the post-polymerization crosslinked polymer has an increased binding capacity for chloride and a decreased binding capacity for taurocholate in SOB relative to the preformed amine polymer. By way of further example, in one such embodiment the post-polymerization crosslinked polymer has an increased binding capacity for chloride and a decreased binding capacity for phosphate, citrate and taurocholate, combined, in SOB relative to the preformed amine polymer.

By way of further example, in one such embodiment the post-polymerization crosslinked polymer has a capacity for chloride in SOB that is at least 10% greater than the binding capacity of the preformed polymer for chloride in SOB. By way of further example, in one such embodiment the post-polymerization crosslinked polymer has a capacity for chloride in SOB that is at least 25% greater than the binding capacity of the preformed polymer for chloride in SOB. By way of further example, in one such embodiment the post-polymerization crosslinked polymer has a capacity for chloride in SOB that is at least 50% greater than the binding capacity of the preformed polymer for chloride in SOB. By way of further example, in one such embodiment the post-polymerization crosslinked polymer has a capacity for chloride in SOB that is at least 75% greater than the binding capacity of the preformed polymer for chloride in SOB. By way of further example, in one such embodiment the post-polymerization crosslinked polymer has a capacity for chloride in SOB that is at least 100% greater than the binding capacity of the preformed polymer for chloride in SOB. By way of further example, in one such embodiment the post-polymerization crosslinked polymer has a capacity for chloride in SOB that is at least 125% greater than the binding capacity of the preformed polymer for chloride in SOB. By way of further example, in one such embodiment the post-polymerization crosslinked polymer has a capacity for chloride in SOB that is at least 150% greater than the binding capacity of the preformed polymer for chloride in SOB. By way of further example, in one such embodiment the post-polymerization crosslinked polymer has a capacity for chloride in SOB that is at least 200% greater than the binding capacity of the preformed polymer for chloride in SOB. By way of further example, in one such embodiment the post-polymerization crosslinked polymer has a capacity for phosphate, citrate and taurocholate in SOB that is at least 10% less than the binding capacity of the preformed polymer for phosphate, citrate and taurocholate in SOB. By way of further example, in one such embodiment the post-polymerization crosslinked polymer has a capacity for phosphate, citrate and taurocholate in SOB that is at least 20% less than the binding capacity of the preformed polymer for phosphate, citrate and taurocholate in SOB. By way of further example, in one such embodiment the post-polymerization crosslinked polymer has a capacity for phosphate, citrate and taurocholate in SOB that is at least 30% less than the binding capacity of the preformed polymer for phosphate, citrate and taurocholate in SOB. By way of further example, in one such embodiment the post-polymerization crosslinked polymer has a capacity for phosphate, citrate and taurocholate in SOB that is at least 40% less than the binding capacity of the preformed polymer for phosphate, citrate and taurocholate in SOB. By way of further example, in one such embodiment the post-polymerization crosslinked polymer has a capacity for phosphate, citrate and taurocholate in SOB that is at least 50% less than the binding capacity of the preformed polymer for phosphate, citrate and taurocholate in SOB. By way of further example, in one such embodiment the post-polymerization crosslinked polymer has a capacity for phosphate, citrate and taurocholate in SOB that is at least 60% less than the binding capacity of the preformed polymer for phosphate, citrate and taurocholate in SOB. By way of further example, in one such embodiment the post-polymerization crosslinked polymer has a capacity for phosphate, citrate and taurocholate in SOB that is at least 70% less than the binding capacity of the preformed polymer for phosphate, citrate and taurocholate in SOB. By way of further example, in one such embodiment the post-polymerization crosslinked polymer has a capacity for phosphate, citrate and taurocholate in SOB that is at least 80% less than the binding capacity of the preformed polymer for phosphate, citrate and taurocholate in SOB. By way of further example, in one such embodiment the post-polymerization crosslinked polymer has a capacity for phosphate, citrate and taurocholate in SOB that is at least 90% less than the binding capacity of the preformed polymer for phosphate, citrate and taurocholate in SOB. By way of further example, in one such embodiment the post-polymerization crosslinked polymer has a capacity for phosphate, citrate and taurocholate in SOB that is at least 95% less than the binding capacity of the preformed polymer for phosphate, citrate and taurocholate in SOB. By way of further example, in one such embodiment the post-polymerization crosslinked polymer has (i) an increased binding capacity for chloride (the percentage increase being at least 10%, 25%, 50%, 75%, 100%, 125%, 150%, 175%, or even at least 200%) and a decreased binding capacity for phosphate, citrate and taurocholate in SOB (the percentage decrease being at least 10%, 20%, 30%, 40%, 50%, 60%, 70%, 80%, 90% or even at least 95%) relative to the preformed amine polymer and (ii) a decreased binding capacity in SGF relative to the preformed amine polymer.

The starting molecules described in formulas 1 through 3 may be copolymerized with one or more other monomers of the invention, oligomers or other polymerizable groups. Such copolymer architectures can include, but are not limited to, block or block-like polymers, graft copolymers, and random copolymers. Incorporation of monomers described by formulas 1 through 3 can range from 1% to 99%. In some embodiments, the incorporation of comonomer is between 20% and 80%.

Non-limiting examples of comonomers which may be used alone or in combination include: styrene, allylamine hydrochloride, substituted allylamine hydrochloride, substituted styrene, alkyl acrylate, substituted alkyl acrylate, alkyl methacrylate, substituted alkyl methacrylate, acrylonitrile, methacrylonitrile, acrylamide, methacrylamide, N-alkylacrylamide, N-alkylmethacrylamide, N,N-dialkylacrylamide, N,N-dialkylmethacrylamide, isoprene, butadiene, ethylene, vinyl acetate, N-vinyl amide, maleic acid derivatives, vinyl ether, allyle, methallyl monomers and combinations thereof. Functionalized versions of these monomers may also be used. Additional specific monomers or comonomers that may be used in this invention include, but are not limited to, 2-propen-1-ylamine, 1-(allylamino)-2-aminoethane, 1-[N-allyl(2-aminoethyl)amino]-2-aminoethane, methyl methacrylate, ethyl methacrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, amethylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-tert-butylmethacrylamide, N—N-butylmethacrylamide, N-methylolmethacrylamide, N-ethylolmethacrylamide, N-tert-butylacryl amide, N-Nbutylacrylamide, N-methylolacrylamide, N-ethylolacrylamide, 4-acryloylmorpholine, vinyl benzoic acid (all isomers), diethylaminostyrene (all isomers), a-methylvinyl benzoic acid (all isomers), diethylamino a-methylstyrene (all isomers), p-vinylbenzene sulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropyl methacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysilylpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, maleic anhydride, N-phenylmaleimide, N-butylmaleimide, N-vinylformamide, N-vinyl acetamide, allylamine, methallylamine, allylalcohol, methyl-vinylether, ethylvinylether, butylvinyltether, butadiene, isoprene, chloroprene, ethylene, vinyl acetate, and combinations thereof.

Additional modification to the preformed crosslinked polymer can be achieved through the addition of modifiers, including but not limited to amine monomers, additional crosslinkers, and polymers. Modification can be accomplished through covalent or non-covalent methods. These modifications can be evenly or unevenly dispersed throughout the preformed polymer material, including modifications biased to the surface of the preformed crosslinked polymer. Furthermore, modifications can be made to change the physical properties of the preformed crosslinked polymer, including but not limited to reactions that occur with remaining reactive groups such as haloalkyl groups and allyl groups in the preformed polymer. Reactions and modifications to the preformed crosslinked polymer can include but are not limited to acid-base reactions, nucleophilic substitution reactions, Michael reactions, non-covalent electrostatic interactions, hydrophobic interactions, physical interactions (crosslinking) and radical reactions.

In one embodiment, the post-polymerization crosslinked amine polymer is a crosslinked amine polymer comprising a structure corresponding to Formula 4:

Formula 4

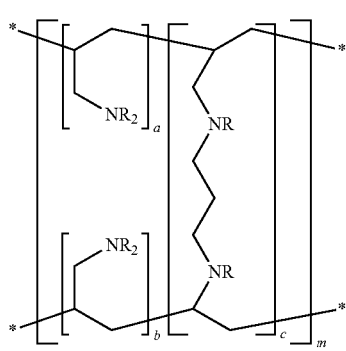

wherein each R is indendently hydrogen or an ethylene crosslink between two nitrogen atoms of the crosslinked amine polymer

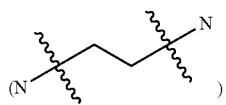

and a, b, c, and m are integers.

Typically, m is a large integer indicating an extended polymer network. In one such embodiment, a ratio of the sum of a and b to c (i.e., a+b:c) is in the range of about 1:1 to 5:1. For example, in one such embodiment a ratio of the sum of a and b to c (i.e., a+b:c) is in the range of about 1.5:1 to 4:1. By way of further example, in one such embodiment a ratio of the sum of a and b to c (i.e., a+b:c) is in the range of about 1.75:1 to 3:1. For example, in one such embodiment a ratio of the sum of a and b is 57, c is 24 and m is large integer indicating an extended polymer network. In each of the foregoing embodiments R may be to c (i.e., a+b:c) is in the range of about 2:1 to 2.5:1. As noted in each of the foregoing embodiments, each R may independently be hydrogen or an ethylene crosslink between two nitrogen atoms. Typically, however, 50-95% of the R substituents will be hydrogen and 5-50% will be an ethylene crosslink

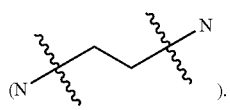

For example, in one such embodiment, 55-90% of the R substituents are hydrogen and 10-45% are an ethylene crosslink

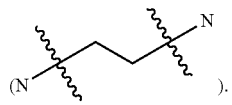

By way of further example, in one such embodiment, 60-90% of the R substituents are hydrogen and 10-40% are an ethylene crosslink. By way of further example, in one such embodiment, 65-90% of the R substituents are hydrogen and 10-35% are an ethylene crosslink.

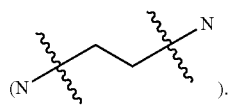

By way of further example, in one such embodiment, 70-90% of the R substituents are hydrogen and 10-30% are an ethylene crosslink. By way of further example, in one such embodiment, 75-85% of the R substituents are hydrogen and 15-25% are an ethylene crosslink. By way of further example, in one such embodiment, 80-85% of the R substituents are hydrogen and 15-20% are an ethylene crosslink. By way of further example, in one such embodiment, about 81% of the R substituents are hydrogen and about 19% are an ethylene crosslink.

As described in greater detail in the Examples, polymers in which crosslinking and/or entanglement were increased were found to have lower swelling than those with lower crosslinking and/or entanglement, yet also had a binding capacity for target ion (e.g., chloride) that was as great as or greater than the lower crosslinking and/or entanglement polymers while binding of interfering ions such as phosphate were significantly reduced. The selectivity effect was Introduced in two different manners: 1) Overall capacity was sacrificed for chloride specificity. Crosslinkers that don't include chloride binding sites (e.g. epichlorohydrin) allow for increased crosslinking while overall capacity is decreased proportional to the amount of crosslinker incorporated into the polymer. 2) Overall capacity is preserved for chloride specificity: Crosslinkers that include chloride binding sites (e.g. diallylamines) allow for increased crosslinking while overall capacity is staying the same or is reduced by only a small amount.

The polymers described herein exhibit ion binding properties, generally proton binding to form the positive charge followed by anion-binding. In preferred embodiments, the polymers exhibit chloride binding properties. Ion (e.g., chloride) binding capacity is a measure of the amount of a particular ion an ion binder can bind in a given solution. For example, binding capacities of ion-binding polymers can be measured in vitro, e.g., in water or in saline solution or in solutions/matrices containing cations and anions representative of gastrointestinal lumen conditions, or in vivo, e.g., from ion (e.g., bicarbonate or citrate) urinary excretion, or ex vivo, for example using aspirate liquids, e.g., chime/gastrointestinal lumen contents obtained from lab animals, patients or volunteers. Measurements can be made in a solution containing only the target ion, or at least no other competing solutes that compete with target ions for binding to the polymer. In these cases, a non-interfering buffer would be used (e.g. a solution of hydrochloric acid, with or without additional sodium chloride). Alternatively, measurements can be made in an interfering buffer that contains other competing solutes, e.g., other ions or metabolites that compete with target ions for binding to the resin.

In some embodiments the polymer binds hydrochloric acid. For in vivo use, e.g., in treating metabolic acidosis, it is desirable that the polymer have a high proton and chloride binding capacity. In vitro measurements of binding capacity do not necessarily translate into in vivo binding capacities. Hence, it is useful to define binding capacity in terms of both in vitro and in vivo capacity.

The in vitro chloride binding capacity of the polymers of the invention in HCl can be greater than about 5, 6, 7, 8, 9, 10, 11, 12, 13, 14 or 15 mmol/g. In some embodiments, the in vitro chloride binding capacity of the polymers of the invention for target ion is greater than about 5.0 mmol/g, preferably greater than about 7.0 mmol/g, even more preferably greater than about 9.0 mmol/g, and yet even more preferably greater than about 10.0 mmol/g. In some embodiments, the chloride binding capacity can range from about 5.0 mmol/g to about 25 mmol/g, preferably from about 7.5 mmol/g to about 20 mmol/g, and even more preferably from about 10 mmol/g to about 15 mmol/g. Several techniques are known in the art to determine the chloride binding capacity.

The in vivo maximum binding capacity (i.e. the maximum amount of [proton and] chloride bound in conditions likely to be encountered in the GI tract of a human) can be evaluated by 12-16 h chloride binding in the Simulated Gastric Fluid assay ("SGF") and is a structural measure for how well the monomers and crosslinkers were incorporated. The SGF values represent an experimental confirmation of the theoretical maximum binding capacity of the polymers and fall in the same range as the calculated capacity based on the stoichiometry of the starting materials.

In order to counterbalance the proton binding, chloride is the anion of choice to be bound as its removal has no negative impact on serum bicarbonate. Anions other than chloride, bound to neutralize the proton positive charge, include phosphate, short chain fatty acids, long chain fatty acids, bile acids or other organic or inorganic anions. Binding of these anions, other than chloride, influences overall bicarbonate stores in the intracellular and extracellular compartments.

The selectivity of the polymer for binding chloride can be evaluated in vitro using conditions that mimic various conditions, anions and anion concentrations encountered in the GI lumen. The chloride binding can be compared versus phosphate alone (e.g. SIB [Simulated Intestinal Buffer]; or versus a range of anions found in the GI tract (e.g., SOB).

In some embodiments, the chloride binding in the SIB assay after one hours exposure of the polymer to the test buffer at 37° C. is greater than about 2.0 mmol per gram of polymer, preferably greater than about 2.5 mmol/g of polymer, more preferably greater than about 3.0 mmol/g of polymer, even more preferably greater than about 3.5 mmol/g of polymer and most preferably greater than about 4.0 mmol/g of polymer.

In some embodiments, the chloride binding in the SOB assay after two hours exposure of the polymer to the test buffer at 37° C. is greater than about 1.0 mmol per gram of polymer, preferably greater than about 2.0 mmol/g of polymer, more preferably greater than about 3.0 mmol/g of polymer, even more preferably greater than about 3.5 mmol/g of polymer and most preferably greater than about 4.0 mmol/g of polymer.

In some embodiments, the chloride binding in this SOB assay after twenty-four hours exposure of the polymer to the test buffer at 37° C. is greater than about 0.5 mmol per gram of polymer, preferably greater than about 1 mmol/g of polymer, more preferably greater than about 1.5 mmol/g of polymer, even more preferably greater than about 2.0 mmol/g of, even more preferably greater than about 2.5 mmol/g of polymer and most preferably greater than about 3.0 mmol/g of polymer. The chloride binding in SOB after 24 hours exposure at 37° C. is one measure of the ability of a polymer to retain chloride as it passes through the GI tract.

Another way of measuring (proton and) chloride retention is to first expose the polymer to SGF, to isolate the polymer, then expose the polymer to SOB, to isolate the polymer again and then to expose the polymer to conditions that are typical of the colon lumen, for example using the "GI Compartment Transit Assay" (GICTA) buffer. In some embodiments, the amount of chloride remaining bound to the polymer after one hour exposure to SGF, then two hours exposure to SOB at 37° C. and then 48 hours exposure to GICTA at 37° C. is greater than about 0.5 mmol per gram of polymer, preferably greater than about 0.5 mmol/g of polymer, more preferably greater than about 1.0 mmol/g of polymer, even more preferably greater than about 2.0 mmol/g of polymer and most preferably greater than about 3.0 mmol/g of polymer. In one embodiment, the polymer has a retained chloride content of at least 30% of the chloride that was initially bound in a GI Compartment Transit Assay ("GICTA") (i.e., bound during the SGF binding step). In one such embodiment, the crosslinked amine polymer has a retained chloride content of at least 30%, at least 40%, at least 50%, at least 60%, at least 70%, at least 80% or even at least 90% of the chloride that was initially bound in a GI Compartment Transit Assay. In one embodiment, the polymer has a retained chloride content of at least 0.5, at least 1, at least 1.5, at least 2, at least 2.5, at least 3, at least 3.5, at least 4, at least 4.5, or even at least 5 mmol chloride/g of polymer in a GI Compartment Transit Assay ("GICTA"). In one embodiment, the crosslinked amine polymer has a retained chloride content of at least 30%, at least 40%, at least 50%, at least 60%, at least 70%, at least 80% or even at least 90% of the chloride that was initially bound in a GI Compartment Transit Assay and a retained chloride content of at least 0.5, at least 1, at least 1.5, at least 2, at least 2.5, at least 3, at least 3.5, at least 4, at least 4.5, or even at least 5 mmol chloride/g of polymer in a GI Compartment Transit Assay ("GICTA").

In some embodiments, the in vivo binding performance of polymers of the present disclosure can be evaluated by measuring the change in urine acid levels after administration to an animal, including a human, with normal renal function. The removal of additional HCl (or HCl equivalent) from the body by the action of the administered polymer, given enough time to reach metabolic equilibrium, is reflected in changes in urine bicarbonate, titratable acid, citrate or other indicators of urinary acid excretion.

In order to bind protons, the amine constituents of the polymers can be primary, secondary or tertiary amines, but not quaternary amines. Quaternary amines remain substantially charged at all physiological conditions and therefore do not bind a proton before an anion is bound. The percentage of quaternary amines can be measured in a number of ways, including titration and back titration approaches. Another simple but accurate method is to compare anion (e.g. chloride) binding at low and high pH. While chloride binding at low pH (e.g. the SGF buffer conditions; pH 1.2) does not distinguish quaternary amines from other amines, chloride binding assay at high pH (e.g. QAA buffer conditions; pH 11.5) does. At this high pH, primary, secondary and tertiary amines are not substantially protonated and do not contribute to chloride binding. Therefore any binding observed under these conditions can be attributed to the presence of permanently charged quaternary amines. A comparison of chloride binding at low pH (e.g. SGF conditions) versus high pH (e.g. QAA conditions) is a measure of the degree of quaternization and by extension is a measure of the amount of proton bound along with the chloride. The polymers of the current disclosure contain no more than 40%, 30%, 20%, 10%, most preferably 5% quaternary amines.

The Swelling Ratio of the polymers of the present disclosure represent an experimental confirmation of the degree of crosslinking and by extension the relative pore sizes of the polymers and accessibility to anions larger than (or with a hydration ratio larger than) chloride. In some embodiments the swelling is measured in deionized water and is expressed in terms of grams of water per gram of dry polymer. The polymers of the current disclosure have a Swelling Ratio in deionized water of $\leq 5$ g/g, $\leq 4$ g/g, $\leq 3$ g/g, $\leq 2$ g/g or $\leq 1$ g/g.

The ability of polymer to retain chloride (and not release it, allowing exchange with other anions) as it passes through different conditions experienced in the GI lumen is an important characteristic that is likely to be a predictor of relative in vivo efficacy. The GI Compartment transit assay (GICTA) can be used to evaluate chloride retention. A SGF and then a SOB (Simulated Intestinal Organic/Inorganic Buffer) screen are first performed to allow chloride and other anions to bind to the polymers, the polymers are isolated and exposed to conditions mimicking the colon lumen (e.g. GICTA retention assay matrix) for 40 hours. The polymers are again isolated and the anions remaining bound to the polymer are eluted in sodium hydroxide and measured. The polymers of the current disclosure retain more than 30%, 40%, 50%, 60%, 70%, 80% or most preferably more than 90% of chloride bound in SGF after being submitted to the chloride retention assay as described.

Using heterogeneous polymerization processes, polymer particles are obtained as spherical beads, whose diameter is controlled in the 5 to 1000 microns range, preferably 10 to 500 microns and most preferred 40-180 microns.

In general, a pharmaceutical composition of the present disclosure comprises a proton-binding, crosslinked amine polymer described herein. Preferably, the pharmaceutical composition comprising the crosslinked amine polymer is formulated for oral administration. The form of the pharmaceutical in which the polymer is administered includes powders, tablets, pills, lozenges, sachets, cachets, elixirs, suspensions, syrups, soft or hard gelatin capsules, and the like. In one embodiment, the pharmaceutical composition comprises only the crosslinked amine polymer. Alternatively, the pharmaceutical composition may comprise a carrier, a diluent, or excipient in addition to the crosslinked amine polymer. Examples of carriers, excipients, and diluents that may be used in these formulations as well as others, include foods, drinks, lactose, dextrose, sucrose, sorbitol, mannitol, starches, gum acacia, alginates, tragacanth, gelatin, calcium silicate, microcrystalline cellulose, polyvinylpyrrolidone, cellulose, methyl cellulose, methylhydroxybenzoates, propylhydroxybenzoates, propylhydroxybenzoates, and talc. Pharmaceutical excipients useful in the pharmaceutical compositions further include a binder, such as microcrystalline cellulose, colloidal silica and combinations thereof (Prosolv 90), carbopol, providone and xanthan gum; a flavoring agent, such as sucrose, mannitol, xylitol, maltodextrin, fructose, or sorbitol; a lubricant, such as magnesium stearate, stearic acid, sodium stearyl fumurate and vegetable based fatty acids; and, optionally, a disintegrant, such as croscarmellose sodium, gellan gum, low-substituted hydroxypropyl ether of cellulose, sodium starch glycolate. Other additives may include plasticizers, pigments, talc, and the like. Such additives and other suitable ingredients are well-known in the art; see, e.g., Gennaro A R (ed), Remington's Pharmaceutical Sciences, 20th Edition.

In one embodiment, pharmaceutical compositions comprising a crosslinked amine polymer of the present disclosure contain relatively low amounts of sodium. For example, in one such embodiment the pharmaceutical composition comprises less than 1 g of sodium per dose. By way of further example, in one such embodiment the pharmaceutical composition comprises less than 0.5 g sodium per dose. By way of further example, in one such embodiment the pharmaceutical composition comprises less than 0.1 g sodium per dose. By way of further example, in one such embodiment the pharmaceutical composition is sodium-free.

In one embodiment, the daily dose of the new chronic metabolic acidosis treatment is compliance enhancing (approximately 5 g or less per day) and achieves a clinically significant and sustained increase of serum bicarbonate of approximately 3 mEq/L at these daily doses. The non-absorbed nature of the polymer and the lack of sodium load and/or introduction of other deleterious ions for such an oral drug enable for the first time a safe, chronic treatment of metabolic acidosis without worsening blood pressure/hypertension and/or without causing increased fluid retention and fluid overload. Another benefit is further slowing of the progression of kidney disease and time to onset of lifelong renal replacement therapy (End Stage Renal Disease "ESRD" including 3 times a week dialysis) or need for kidney transplants. Both are associated with significant mortality, low quality of life and significant burden to healthcare systems around the world. In the United States alone, approximately 20% of the 400,000 ESRD patients die and 100,000 new patients start dialysis every year.

In one embodiment, the pharmaceutical composition comprises a sodium-free, non-absorbed, cross-linked, amine polymer for treatment of metabolic acidosis that increases serum bicarbonate and normalizes blood pH in a mammal by binding HCl. One preferred embodiment includes the polymer binding $H^+$ in the stomach/upper GI tract followed by binding $Cl^-$ in sufficient amounts to cause a clinically meaningful increase of serum bicarbonate of at least 1.6 mEq/L, more preferred of at least 2 mEq/L and most preferred of equal or greater 3 mEq/L. The amount of HCl binding is determined by the polymer's capacity (targeted range of HCl binding capacity of 5-20 mEq of HCl per 1 g of polymer) and selectivity. In the stomach, free amine becomes protonated by binding $H^+$. The positive charge formed in situ on the polymer is then available to bind $Cl^-$; by controlling access of binding sites through crosslinking (size exclusion, mesh size) and chemical moieties (to repel larger, organic ions (such as acetate, propionate and butyrate or other short chain fatty acids commonly present in the colon), phosphate, bile and fatty acids through tailored hydrophilicity/hydrophobicity), anions other than chloride are bound to a lesser degree if at all. By tailoring the bead crosslinking and the chemical nature of the amine binding sites, chloride can be bound tightly to ensure that it is not released in the lower GI tract. HCl is removed from the body through regular bowel movement/feces, resulting in net HCl binding. In another embodiment, the polymer comes preformed with some quaternized/protonated amine groups and chloride binding is achieved through ion exchange with citrate or carbonate where up to 90% of cationic binding sites on the polymer come pre-loaded with citrate and/or carbonate as the counter-ion.

In one embodiment, a key feature of the sodium-free, non-absorbed, amine polymer for treatment of metabolic acidosis that increases serum bicarbonate and normalizes blood pH in a mammal is that it does not increase blood pressure or worsen hypertension which is of particular concern in diabetic kidney disease patients. An additional benefit of not introducing sodium is the lack of related increase in fluid retention causing fluid overload which is of particular concern in heart failure patients. The polymer's ability to safely and efficaciously treat metabolic acidosis without introducing deleterious counter-ions allows for slowing of progression of kidney disease which is of particular concern in chronic kidney disease patients who are not on dialysis yet. The onset of dialysis could be delayed by at least 3, 6, 9 or 12 months.

In yet another embodiment of the sodium-free, non-absorbed, amine polymer for treatment of metabolic acidosis, the polymer is a crosslinked bead with a preferred particle size range that is (i) large enough to avoid passive or active absorption through the GI tract and (ii) small enough to not cause grittiness or unpleasant mouth feel when ingested as a powder, sachet and/or chewable tablet/dosage form with an average particle size of 40-180 microns. Preferably, the desired particle size morphology is accomplished through a heterogeneous polymerization reaction such as a suspension or emulsion polymerization. To minimize GI side effects in patients that are often related to a large volume polymer gel moving through the GI tract, a low Swelling Ratio of the polymer is preferred (0.5-5 times its own weight in water). In yet another embodiment, the polymer carries a molecular entity permanently/covalently and/or temporarily attached to a polymer or on its own that blocks the $Cl^-/HCO_3^-$ exchanger (antiporter) in the colon and intestine. The net effect of blocking the antiporter is to reduce uptake of $Cl^-$ from the intestinal lumen and related exchange for bicarbonate from the serum, thus effectively increasing serum bicarbonate.

In one embodiment, the crosslinked amine polymer may be co-administered with other active pharmaceutical agents depending on the condition being treated. This co-administration may include simultaneous administration of the two agents in the same dosage form, simultaneous administration in separate dosage forms, and separate administration. For example, for the treatment of metabolic acidosis, the crosslinked amine polymer may be co-administered with common treatments that are required to treat underlying co-morbidities including but not limited to hypertension, diabetes, obesity, heart failure and complications of Chronic Kidney Disease. These medications and the crosslinked amine polymer can be formulated together in the same dosage form and administered simultaneously as long as they do not display any clinically significant drug-drug-interactions. Alternatively, these treatments and the crosslinked amine polymer may be separately and sequentially administered with the administration of one being followed by the administration of the other.

The present disclosure further includes the following enumerated embodiments.

Embodiment 1. A process for the preparation of a crosslinked amine polymer comprising crosslinking a preformed amine polymer in a reaction mixture to form a crosslinked amine polymer, the reaction mixture comprising the preformed amine polymer, a solvent, a crosslinking agent, and a swelling agent for the preformed amine polymer, wherein the preformed amine polymer has an absorption capacity for the swelling agent, and the amount of swelling agent in the reaction mixture is less than the absorption capacity of the preformed amine polymer for the swelling agent.

Embodiment 2. A process for the preparation of a particulate crosslinked amine polymer, the process comprising (i) polymerizing an amine-containing monomer to form a particulate preformed amine polymer, (ii) deprotonating the preformed amine polymer with a base, (iii) swelling the deprotonated preformed amine polymer with a swelling agent, and (iv) crosslinking the preformed amine polymer with a crosslinking agent comprising amine-reactive moieties in a reaction mixture, wherein carbon-carbon crosslinks are primarily formed in the polymerization step and nitrogen-nitrogen crosslinks are primarily formed in the crosslinking step.

Embodiment 3. A process for the preparation of a particulate crosslinked amine polymer, the process comprising forming the particulate crosslinked amine polymer in at least two polymerization/crosslinking steps, the first step comprising polymerizing an amine-containing monomer to form a preformed amine polymer having a chloride binding capacity of at least 10 mmol/g in Simulated Gastric Fluid ("SGF") and a Swelling Ratio in the range of 2 to 10, the second step comprising crosslinking the preformed amine polymer with a crosslinking agent in a reaction mixture to produce nitrogen-nitrogen crosslinks within the preformed amine polymer.

Embodiment 4. A process for the preparation of a particulate crosslinked amine polymer, the process comprising two discrete polymerization/crosslinking steps, the first step comprising forming a preformed amine polymer having a chloride binding capacity of at least 10 mmol/g in Simulated Gastric Fluid ("SGF") and a Swelling Ratio in the range of 2 to 10, the second step comprising crosslinking the preformed amine polymer with a crosslinking agent containing amine reactive moieties to form a post-polymerization crosslinked amine polymer in a reaction mixture, the resulting post-polymerization crosslinked amine polymer having a binding capacity for phosphate, citrate and/or taurocholate in SIB or SOB that is less than the binding capacity of the preformed amine polymer for phosphate, citrate and/or taurocholate in that same assay.

Embodiment 5. A process for the preparation of a particulate crosslinked amine polymer, the process comprising (i) forming a preformed amine polymer having a chloride binding capacity of at least 10 mmol/g in Simulated Gastric Fluid ("SGF"), a Swelling Ratio in the range of 2 to 10 and an average particle size of at least 80 microns, (ii) at least partially deprotonating the preformed amine polymer with a base and (iii) crosslinking the deprotonated preformed amine polymer in a reaction mixture with a crosslinking agent containing amine reactive moieties to form a post-polymerization crosslinked amine polymer.

Embodiment 6. A process for the preparation of a particulate crosslinked amine polymer, the process comprising (i) forming a preformed amine polymer having a chloride binding capacity of at least 10 mmol/g in Simulated Gastric Fluid ("SGF") and a Swelling Ratio in the range of 2 to 10, (ii) at least partially deprotonating the preformed amine polymer with a base, (iii) contacting the preformed amine polymer with a swelling agent to swell the deprotonated preformed amine polymer, and (iv) in a reaction mixture crosslinking the swollen, deprotonated preformed amine polymer with a crosslinking agent containing amine reactive moieties to form a post-polymerization crosslinked amine polymer.

Embodiment 7. The process of any preceding enumerated Embodiment wherein the swelling agent is a polar solvent.

Embodiment 8. The process of any preceding enumerated Embodiments wherein the swelling agent is water, methanol, ethanol, n-propanol, isopropanol, n-butanol, formic acid, acetic acid, acetonitrile, dimethylformamide, dimethylsulfoxide, nitromethane, propylene carbonate, or a combination thereof.

Embodiment 9. The process of any preceding enumerated Embodiment wherein the weight ratio of swelling agent to preformed amine polymer in the reaction mixture is less than 4:1.

Embodiment 10. The process of any preceding enumerated Embodiment wherein the weight ratio of swelling agent to preformed amine polymer in the reaction mixture is less than 3:1.

Embodiment 11. The process of any preceding enumerated Embodiment wherein the weight ratio of swelling agent to preformed amine polymer in the reaction mixture is less than 2:1.

Embodiment 12. The process of any preceding enumerated Embodiment wherein the weight ratio of swelling agent to preformed amine polymer in the reaction mixture is less than 1:1.

Embodiment 13. The process of any preceding enumerated Embodiment wherein the weight ratio of swelling agent to preformed amine polymer in the reaction mixture is less than 0.5:1.

Embodiment 14. The process of any preceding enumerated Embodiment wherein the weight ratio of swelling agent to preformed amine polymer in the reaction mixture is less than 0.4:1.

Embodiment 15. The process of any preceding enumerated Embodiment wherein the weight ratio of swelling agent to preformed amine polymer in the reaction mixture is less than 0.3:1.

Embodiment 16. The process of any preceding enumerated Embodiment wherein the weight ratio of swelling agent to preformed amine polymer in the reaction mixture is at least 0.15:1.

Embodiment 17. The process of any preceding enumerated Embodiment wherein the crosslinking agent comprises at least two amine-reactive functional groups.

Embodiment 18. The process of any preceding enumerated Embodiment wherein the crosslinking agent is a compound containing at least two amine-reactive groups selected from the group consisting of alkyl halides, epoxides, phosgene, anhydrides, carbamates, carbonates, isocyanates, thioisocyanates, esters, activated esters, carboxylic acids and derivatives thereof, sulfonates and derivatives thereof, acyl halides, aziridines, $\alpha,\beta$-unsaturated carbonyls, ketones, aldehydes, and pentafluoroaryl groups.

Embodiment 19. The process of any preceding enumerated Embodiment wherein the crosslinking agent is a crosslinking agent selected from Table B.

Embodiment 20. The process of any preceding enumerated Embodiment wherein the crosslinking agent is a dichloroalkane.

Embodiment 21. The process of any preceding enumerated Embodiment wherein the crosslinking agent is dichloroethane or dichloropropane.

Embodiment 22. The process of any preceding enumerated Embodiment wherein the reaction mixture comprises a non-polar solvent.

Embodiment 23. The process of any preceding enumerated Embodiment wherein the reaction mixture comprises a crosslinking solvent.

Embodiment 24. The process of any preceding enumerated Embodiment wherein the swelling agent and the solvent are immiscible.

Embodiment 25. The process of any preceding enumerated Embodiment wherein the swelling agent and the crosslinking agent are immiscible.

Embodiment 26. The process of any preceding enumerated Embodiment wherein the preformed polymer is combined with the crosslinking agent and solvent before the polymer is combined with the swelling agent.

Embodiment 27. The process of any preceding enumerated Embodiment wherein the process additionally comprises forming the preformed amine polymer in a solvent system and the crosslinked amine polymer is formed without isolation of the preformed amine polymer from the solvent system.

Embodiment 28. The process of any preceding enumerated Embodiment wherein the preformed amine polymer comprises the residue of an amine selected from Table C.

Embodiment 29. The process of any preceding enumerated Embodiment wherein the preformed amine polymer comprises the residue of an amine corresponding to Formula 1:

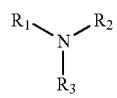

Formula 1 wherein $R_1$, $R_2$ and $R_3$ are independently hydrogen, hydrocarbyl, substituted hydrocarbyl provided, however, at least one of $R_1$, $R_2$ and $R_3$ is other than hydrogen.

Embodiment 30. The process of any preceding enumerated Embodiment wherein the preformed amine polymer is characterized by a first selectivity for chloride relative to citrate, phosphate and/or taurocholate in SIB and/or SOB and the crosslinked polymer is characterized by a second selectivity for chloride relative to citrate, phosphate and/or taurocholate in SIB and/or SOB wherein:

(i) the crosslinked polymer has an increased binding capacity for chloride and a decreased binding capacity for phosphate in SIB relative to the preformed amine polymer, (ii) the crosslinked polymer has an increased binding capacity for chloride and a decreased binding capacity for phosphate in SOB relative to the preformed amine polymer, (iii) the crosslinked polymer has an increased binding capacity for chloride and a decreased binding capacity for citrate in SOB relative to the preformed amine polymer, or (iv) the crosslinked polymer has an increased binding capacity for chloride and a decreased binding capacity for taurocholate in SOB relative to the preformed amine polymer.

Embodiment 31. The process of Embodiment 30 wherein the crosslinked polymer has a decreased binding capacity for chloride in SGF relative to the preformed amine polymer.

Embodiment 32. The process of Embodiment 30 wherein relative to the preformed amine polymer the post-polymerization crosslinked polymer has (i) an increased binding capacity for chloride and a decreased binding capacity for phosphate in SIB and (ii) a decreased binding capacity in SGF.

Embodiment 33. The process of Embodiment 30 wherein relative to the preformed amine polymer the post-polymerization crosslinked polymer has (i) an increased binding capacity for chloride and a decreased binding capacity for phosphate, citrate and/or taurocholate, in combination, in SOB and (ii) a decreased binding capacity in SGF.

Embodiment 34. A process for the preparation of a crosslinked amine polymer comprising crosslinking a preformed amine polymer in a reaction mixture to form a crosslinked amine polymer, the reaction mixture comprising the preformed amine polymer, a solvent, and a crosslinking agent, wherein the preformed amine polymer is characterized by a first selectivity for chloride relative to citrate, phosphate and/or taurocholate in SIB and/or SOB and the crosslinked polymer is characterized by a second selectivity for chloride relative to citrate, phosphate and/or taurocholate in SIB and/or SOB wherein:

(i) the crosslinked polymer has an increased binding capacity for chloride and a decreased binding capacity for phosphate in SIB relative to the preformed amine polymer, (ii) the crosslinked polymer has an increased binding capacity for chloride and a decreased binding capacity for citrate in SIB relative to the preformed amine polymer, (iii) the crosslinked polymer has an increased binding capacity for chloride and a decreased binding capacity for citrate in SOB relative to the preformed amine polymer, or (iv) the crosslinked polymer has an increased binding capacity for chloride and a decreased binding capacity for taurocholate in SOB relative to the preformed amine polymer.

Embodiment 35. The process of Embodiment 34 wherein the crosslinked polymer has a decreased binding capacity for chloride in SGF relative to the preformed amine polymer.

Embodiment 36. The process of Embodiment 34 wherein relative to the preformed amine polymer the post-polymerization crosslinked polymer has (i) an increased binding capacity for chloride and a decreased binding capacity for phosphate in SIB and (ii) a decreased binding capacity in SGF.

Embodiment 37. The process of Embodiment 34 wherein relative to the preformed amine polymer the post-polymerization crosslinked polymer has (i) an increased binding capacity for chloride and a decreased binding capacity for phosphate, citrate and/or taurocholate, in combination, in SOB and (ii) a decreased binding capacity in SGF.

Embodiment 38. A pharmaceutical composition comprising a crosslinked amine polymer characterized by a binding capacity for chloride and/or a selectivity for chloride relative to citrate, phosphate and/or taurocholate in SGF, SIB and/or SOB as described in certain paragraphs above. A pharmaceutical composition comprising a crosslinked amine polymer characterized by a binding capacity for chloride and/or a selectivity for chloride relative to citrate, phosphate and/or taurocholate in SGF, SIB and/or SOB having a chloride ion binding capacity of at least 4 mmol/g in Simulated Small Intestine Inorganic Buffer ("SIB"). In one embodiment, the crosslinked amine polymer has a chloride ion binding capacity of at least 4.5, 5, 5.5, or even at least 6 mmol/g in Simulated Small Intestine Inorganic Buffer ("SIB"). A pharmaceutical composition comprising a crosslinked amine polymer characterized by a binding capacity for chloride and/or a selectivity for chloride relative to citrate, phosphate and/or taurocholate in SGF, SIB and/or SOB having a ratio of chloride ion binding capacity to phosphate ion binding capacity in Simulated Small Intestine Inorganic Buffer ("SIB") of at least 2.3:1, respectively. In one embodiment, the crosslinked amine polymer has a ratio of chloride ion binding capacity to phosphate ion binding capacity in Simulated Small Intestine Inorganic Buffer ("SIB") of at least 2.5:1, 3:1, 3.5:1, or even 4:1, respectively. A pharmaceutical composition comprising a crosslinked amine polymer characterized by a binding capacity for chloride and/or a selectivity for chloride relative to citrate, phosphate and/or taurocholate in SGF, SIB and/or SOB having a chloride ion binding capacity of at least 1 mmol/g in Simulated Small Intestine Inorganic Buffer ("SIB"), a phosphate ion binding capacity of less than 0.4 mmol/g in SIB, and a chloride ion to phosphate ion binding ratio in SIB of at least 2.3:1, respectively. In one such embodiment, the crosslinked amine polymer has a chloride ion binding capacity of at least 1.5 mmol/g in Simulated Small Intestine Inorganic Buffer ("SIB"), a phosphate ion binding capacity of less than 0.6 mmol/g in SIB, and a chloride ion to phosphate ion binding ratio in SIB of at least 2.3:1, respectively. In another such embodiment, the crosslinked amine polymer has a chloride ion binding capacity of at least 2.0 mmol/g in Simulated Small Intestine Inorganic Buffer ("SIB"), a phosphate ion binding capacity of less than 0.8 mmol/g in SIB, and a chloride ion to phosphate ion binding ratio in SIB of at least 2.3:1, respectively. In one such embodiment, the crosslinked amine polymer has a chloride ion binding capacity of at least 2.5 mmol/g in Simulated Small Intestine Inorganic Buffer ("SIB"), a phosphate ion binding capacity of less than 1.0 mmol/g in SIB, and a chloride ion to phosphate ion binding ratio in SIB of at least 2.3:1, respectively. In one such embodiment, the crosslinked amine polymer has a chloride ion binding capacity of at least 3.0 mmol/g in Simulated Small Intestine Inorganic Buffer ("SIB"), a phosphate ion binding capacity of less than 1.3 mmol/g in SIB, and a chloride ion to phosphate ion binding ratio in SIB of at least 2.3:1, respectively. In one such embodiment, the crosslinked amine polymer has a chloride ion binding capacity of at least 3.5 mmol/g in Simulated Small Intestine Inorganic Buffer ("SIB"), a phosphate ion binding capacity of less than 1.5 mmol/g in SIB, and a chloride ion to phosphate ion binding ratio in SIB of at least 2.3:1, respectively. In one such embodiment, the crosslinked amine polymer has a chloride ion binding capacity of at least 4.0 mmol/g in Simulated Small Intestine Inorganic Buffer ("SIB"), a phosphate ion binding capacity of less than 1.7 mmol/g in SIB, and a chloride ion to phosphate ion binding ratio in SIB of at least 2.3:1, respectively. In one such embodiment, the crosslinked amine polymer has a chloride ion binding capacity of at least 4.5 mmol/g in Simulated Small intestine Inorganic Buffer ("SIB"), a phosphate ion binding capacity of less than 1.9 mmol/g in SIB, and a chloride ion to phosphate ion binding ratio in SIB of at least 2.3:1, respectively. In one such embodiment, the crosslinked amine polymer has a chloride ion binding capacity of at least 5.0 mmol/g in Simulated Small Intestine Inorganic Buffer ("SIB"), a phosphate ion binding capacity of less than 2.1 mmol/g in SIB, and a chloride ion to phosphate ion binding ratio in SIB of at least 2.3:1, respectively. In each of the foregoing embodiments, the crosslinked amine polymer may have a chloride ion to phosphate ion binding ratio in SIB of at least 2.5, at least 3, at least 3.5 or even at least 4, respectively. A pharmaceutical composition comprising a crosslinked amine polymer characterized by a binding capacity for chloride and/or a selectivity for chloride relative to citrate, phosphate and/or taurocholate in SGF, SIB and/or SOB having a ratio of chloride ion binding capacity to phosphate ion binding capacity in Simulated Small Intestine Inorganic Buffer ("SIB") of at least 2.3:1, respectively, and a Swelling Ratio of less than 5. For example, in one such embodiment, the crosslinked amine polymer may have a chloride ion to phosphate ion binding ratio in SIB of at least 2.3:1, at least 2.5, at least 3, at least 3.5 or even at least 4, respectively, and a Swelling Ratio of less than 5, less than 4, less than 3, less than 2, less than 1.5 or even less than 1. A pharmaceutical composition comprising a crosslinked amine polymer characterized by a binding capacity for chloride and/or a selectivity for chloride relative to citrate, phosphate and/or taurocholate in SGF, SIB and/or SOB having a retained chloride content of at least 30% of the chloride that was initially bound in a GI Compartment Transit Assay ("GICTA") (i.e., bound during the SGF binding step). In one such embodiment, the crosslinked amine polymer has a retained chloride content of at least 30%, at least 40%, at least 50%, at least 60%, at least 70%, at least 80% or even at least 90% of the chloride that was initially bound in a GI Compartment Transit Assay. A pharmaceutical composition comprising a crosslinked amine polymer characterized by a binding capacity for chloride and/or a selectivity for chloride relative to citrate, phosphate and/or taurocholate in SGF, SIB and/or SOB having a retained chloride content of at least 0.5 mmol chloride/g of polymer in a GI Compartment Transit Assay ("GICTA"). In one such embodiment, the crosslinked amine polymer has a retained chloride content of at least 0.5, at least 1, at least 1.5, at least 2, at least 2.5, at least 3, at least 3.5, at least 4, at least 4.5, or even at least 5 mmol chloride/g of polymer in a GI Compartment Transit Assay ("GICTA"). A pharmaceutical composition comprising a crosslinked amine polymer characterized by a binding capacity for chloride and/or a selectivity for chloride relative to citrate, phosphate and/or taurocholate in SGF, SIB and/or SOB having a retained chloride content of at least 0.5 mmol chloride/g of polymer in a GI Compartment Transit Assay ("GICTA") and a chloride retention at the end of the GICTA of at least 30% of the chloride that was initially bound in the GICTA (i.e., bound during the SGF binding step). In one such embodiment, the crosslinked amine polymer has a retained chloride content of at least 30%, at least 40%, at least 50%, at least 60%, at least 70%, at least 80% or even at least 90% of the chloride that was initially bound in a GI Compartment Transit Assay and a retained chloride content of at least 0.5, at least 1, at least 1.5, at least 2, at least 2.5, at least 3, at least 3.5, at least 4, at least 4.5, or even at least 5 mmol chloride/g of polymer in a GI Compartment Transit Assay ("GICTA"). A pharmaceutical composition comprising a crosslinked amine polymer characterized by a binding capacity for chloride and/or a selectivity for chloride relative to citrate, phosphate and/or taurocholate in SGF, SIB and/or SOB having a chloride ion binding capacity of at least 5 mmol/g in a 1-hour Simulated Gastric Fluid ("SGF") Assay and a chloride ion binding capacity of at least 8 mmol/g in a 24-hour Simulated Gastric Fluid ("SGF") Assay. In one such embodiment, the crosslinked amine polymer has a chloride ion binding capacity of at least 5 mmol/g in a 1-hour Simulated Gastric Fluid ("SGF") Assay and a chloride ion binding capacity of at least 8, at least 9, at least 10, at least 11, at least 12, at least 13, or even at least 14 mmol/g in a 24-hour Simulated Gastric Fluid ("SGF") Assay. A pharmaceutical composition comprising a crosslinked amine polymer characterized by a binding capacity for chloride and/or a selectivity for chloride relative to citrate, phosphate and/or taurocholate in SGF, SIB and/or SOB having a chloride ion binding capacity in a 1-hour Simulated Gastric Fluid ("SGF") Assay that is at least 50% of its chloride ion binding capacity in a 24-hour Simulated Gastric Fluid ("SGF") Assay. In one such embodiment, the crosslinked amine polymer has a chloride ion binding capacity in a 1-hour Simulated Gastric Fluid ("SGF") Assay that is at least 50%, at least 60%, at least 70%, at least 80%, or even at least 90% of its chloride ion binding capacity in a 24-hour Simulated Gastric Fluid ("SGF") Assay. A pharmaceutical composition comprising a crosslinked amine polymer characterized by a binding capacity for chloride and/or a selectivity for chloride relative to citrate, phosphate and/or taurocholate in SGF, SIB and/or SOB having a chloride ion binding capacity of at least 5 mmol/g in a 1-hour Simulated Gastric Fluid ("SGF") Assay, a chloride ion binding capacity of at least 8 mmol/g in a 24-hour Simulated Gastric Fluid ("SGF") Assay, and a chloride ion binding capacity in a 1-hour Simulated Gastric Fluid ("SGF") Assay that is at least 50% of its chloride ion binding capacity in a 24-hour Simulated Gastric Fluid ("SGF") Assay. In one such embodiment, the crosslinked amine polymer has a chloride ion binding capacity of at least 5 mmol/g in a 1-hour Simulated Gastric Fluid ("SGF") Assay and a chloride ion binding capacity of at least 8, at least 9, at least 10, at least 11, at least 12, at least 13, or even at least 14 mmol/g in a 24-hour Simulated Gastric Fluid ("SGF") Assay and the crosslinked amine polymer has a chloride ion binding capacity in a 1-hour Simulated Gastric Fluid ("SGF") Assay that is at least 50%, at least 60%, at least 70%, at least 80%, or even at least 90% of its chloride ion binding capacity in a 24-hour Simulated Gastric Fluid ("SGF") Assay. A pharmaceutical composition comprising a crosslinked amine polymer characterized by a binding capacity for chloride and/or a selectivity for chloride relative to citrate, phosphate and/or taurocholate in SGF, SIB and/or SOB having a chloride ion binding capacity in a 24-hour Simulated Small Intestine Organic and Inorganic Buffer ("SOB") assay of at least 2.5 mmol chloride/g polymer. In one such embodiment, the crosslinked amine polymer has a chloride ion binding capacity in a 24-hour Simulated Small intestine Organic and Inorganic Buffer ("SOB") assay of at least 2.5, at least 3, at least 3.5, at least 4, at least 4.5, or even at least 5 mmol chloride/g polymer. A pharmaceutical composition comprising a crosslinked amine polymer characterized by a binding capacity for chloride and/or a selectivity for chloride relative to citrate, phosphate and/or taurocholate in SGF, SIB and/or SOB having a chloride ion binding capacity in a 2-hour Simulated Small Intestine Organic and Inorganic Buffer ("SOB") assay of at least 0.5 mmol chloride/g polymer and a 24-hour Simulated Small Intestine Organic and Inorganic Buffer ("SOB") assay of at least 2.5 mmol chloride/g polymer. In one such embodiment, the crosslinked amine polymer has a chloride ion binding capacity in a 2-hour Simulated Small Intestine Organic and Inorganic Buffer ("SOB") assay of at least 0.5, at least 1, at least 1.5, at least 2, at least 2.5, or even at least 3 mmol chloride/g polymer and a 24-hour Simulated Small Intestine Organic and Inorganic Buffer ("SOB") assay of at least 2.5, at least 3, at least 3.5, at least 4, at least 4.5, or even at least 5 mmol chloride/g polymer. A pharmaceutical composition comprising a crosslinked amine polymer characterized by a binding capacity for chloride and/or a selectivity for chloride relative to citrate, phosphate and/or taurocholate in SGF, SIB and/or SOB having a chloride ion binding capacity of at least 2 mmol chloride/g polymer at 4 hours in Simulated Small Intestine Inorganic Buffer ("SIB"). In one such embodiment, the crosslinked amine polymer has a chloride ion binding capacity of at least 2, at least 2.5, at least 3, at least 3.5, or even at least 4 mmol chloride/g polymer at 4 hours in Simulated Small Intestine Inorganic Buffer ("SIB"). A pharmaceutical composition comprising a crosslinked amine polymer characterized by a binding capacity for chloride and/or a selectivity for chloride relative to citrate, phosphate and/or taurocholate in SGF, SIB and/or SOB having a chloride ion binding capacity of at least 2 mmol chloride/g polymer at 4 hours in Simulated Small Intestine Inorganic Buffer ("SIB") and a crosslinked amine polymer having a chloride ion binding capacity of at least 2 mmol chloride/g polymer at 24 hours in Simulated Small Intestine Inorganic Buffer ("SIB"). In one such embodiment, the crosslinked amine polymer has a chloride ion binding capacity of at least 2, at least 2.5, at least 3, at least 3.5, or even at least 4 mmol chloride/g polymer at 4 hours in Simulated Small Intestine Inorganic Buffer ("SIB") and a crosslinked amine polymer having a chloride ion binding capacity of at least 2, at least 2.5, at least 3, at least 3.5, or even at least 4 mmol chloride/g polymer at 24 hours in Simulated Small Intestine Inorganic Buffer ("SIB"). A pharmaceutical composition comprising a crosslinked amine polymer characterized by a binding capacity for chloride and/or a selectivity for chloride relative to citrate, phosphate and/or taurocholate in SGF, SIB and/or SOB having a chloride ion binding capacity in a 24-hour Simulated Small Intestine Organic and Inorganic Buffer ("SOB") assay of at least 5.5 mmol chloride/g polymer. In one such embodiment, the crosslinked amine polymer has a chloride ion binding capacity in a 24-hour Simulated Small Intestine Organic and Inorganic Buffer ("SOB") assay of at least 6 mmol chloride/g polymer. A pharmaceutical composition comprising a crosslinked amine polymer characterized by a binding capacity for chloride and/or a selectivity for chloride relative to citrate, phosphate and/or taurocholate in SGF, SIB and/or SOB wherein the crosslinked amine polymer has a pKa of at least 6 (at equilibrium, measured in 100 mM NaCl). In one such embodiment, the crosslinked amine polymer has a pKa of at least 6.5, at least 7, or even at least 7.5 (at equilibrium, measured in 100 mM NaCl). A pharmaceutical composition comprising a crosslinked amine polymer characterized by a binding capacity for chloride and/or a selectivity for chloride relative to citrate, phosphate and/or taurocholate in SGF, SIB and/or SOB having (i) a proton-binding capacity and a chloride binding capacity of at least 5 mmol/g in Simulated Gastric Fluid; and (ii) a chloride ion binding capacity of at least 4 mmol/g at 1 hour in Simulated Small Intestine Inorganic Buffer ("SIB"). A pharmaceutical composition comprising a crosslinked amine polymer characterized by a binding capacity for chloride and/or a selectivity for chloride relative to citrate, phosphate and/or taurocholate in SGF, SIB and/or SOB having (i) a proton-binding capacity and a chloride binding capacity of at least 5 mmol/g in Simulated Gastric Fluid; and (ii) a chloride ion binding capacity of at least 4 mmol/g, and a phosphate ion binding capacity of less than 2 mmol/g in Simulated Small Intestine Inorganic Buffer ("SIB"). A pharmaceutical composition comprising a crosslinked amine polymer characterized by a binding capacity for chloride and/or a selectivity for chloride relative to citrate, phosphate and/or taurocholate in SGF, SIB and/or SOB having (i) a proton-binding capacity and a chloride binding capacity of at least 5 mmol/g in Simulated Gastric Fluid; and (ii) a chloride ion binding capacity at 1 hour in Simulated Small Intestine Inorganic Buffer ("SIB") of at least (i) 2 mmol/g, (ii) 2.5 mmol/g, or (iii) 3 mmol/g. A pharmaceutical composition comprising a crosslinked amine polymer characterized by a binding capacity for chloride and/or a selectivity for chloride relative to citrate, phosphate and/or taurocholate in SGF, SIB and/or SOB having (i) a proton-binding capacity and a chloride binding capacity of at least 5 mmol/g in Simulated Gastric Fluid; and (ii) a chloride to phosphate ion binding ratio of at least 2.3:1, respectively, in Simulated Small Intestine Inorganic Buffer ("SIB"). A pharmaceutical composition comprising a crosslinked amine polymer characterized by a binding capacity for chloride and/or a selectivity for chloride relative to citrate, phosphate and/or taurocholate in SGF, SIB and/or SOB having (i) a proton-binding capacity and a chloride binding capacity of at least 5 mmol/g at one hour in Simulated Gastric Fluid and (ii) a proton-binding capacity and a chloride binding capacity in Simulated Gastric Fluid of at least (a) 8 mmol/g, (b) 10 mmol/g, (c) 12 mmol/g, or (d) 14 mmol/g. A pharmaceutical composition comprising a crosslinked amine polymer characterized by a binding capacity for chloride and/or a selectivity for chloride relative to citrate, phosphate and/or taurocholate in SGF, SIB and/or SOB having a proton-binding capacity and a chloride binding capacity at one hour in Simulated Gastric Fluid that is at least X % of the proton-binding capacity and the chloride binding capacity, respectively, of the crosslinked amine polymer at 24 hours in Simulated Gastric Fluid wherein X % is at least (i) 50%, (ii) 60%, (iii) 70%, (iv) 80%, or even (v) 90%. A pharmaceutical composition comprising a crosslinked amine polymer characterized by a binding capacity for chloride and/or a selectivity for chloride relative to citrate, phosphate and/or taurocholate in SGF, SIB and/or SOB having (i) a selectivity for chloride over citrate, phosphate and taurocholate in Simulated Small Intestine Organic and Inorganic Buffer ("SOB"), and (ii) a chloride binding capacity at 24 hours in SOB of at least 4 mmol/g. A pharmaceutical composition comprising a crosslinked amine polymer characterized by a binding capacity for chloride and/or a selectivity for chloride relative to citrate, phosphate and/or taurocholate in SGF, SIB and/or SOB having a selectivity for chloride over citrate, phosphate and taurocholate in Simulated Small Intestine Organic and Inorganic Buffer ("SOB"), at (i) 1 hour, (ii) 4 hours, (iii) 12 hours, (iv) 18 hours, (v) 24 hours, (vi) 30 hours, (vii) 36 hours, or even (viii) 48 hours. A pharmaceutical composition comprising a crosslinked amine polymer characterized by a binding capacity for chloride and/or a selectivity for chloride relative to citrate, phosphate and/or taurocholate in SGF, SIB and/or SOB having a chloride ion binding capacity of at least 4 mmol/g, and a phosphate ion binding capacity of less than 2 mmol/g in Simulated Small Intestine Inorganic Buffer ("SIB") at (i) 1 hour, (ii) 2 hours, (iii) 3 hours, (iv) 4 hours, and/or (v) greater than 4 hours.

Embodiment 39. A method of treating and acid/base disorder in an animal including a human by removing HCl through oral administration of a pharmaceutical composition of Embodiment 38.

Embodiment 40. A method of treating and acid/base disorder in an animal including a human by removing HCl through oral administration of a pharmaceutical composition comprising a crosslinked amine polymer prepared by the process of any of Embodiments 1 to 37.

Embodiment 41. A process for the preparation of a crosslinked amine polymer, the process comprising (i) swelling a preformed amine polymer with a swelling agent, (ii) dispersing the preformed amine polymer in a reaction mixture comprising a dispersing solvent, a crosslinking agent, and the swelling agent, and (iii) crosslinking the preformed amine polymer in the reaction mixture to form the crosslinked amine polymer, wherein the preformed amine polymer is crosslinked and has an absorption capacity for the swelling agent, and the amount of swelling agent in the reaction mixture is less than the absorption capacity of the preformed amine polymer for the swelling agent.

Embodiment 42. The process of Embodiment 41 wherein the process further comprises deprotonating the preformed amine polymer with a base before it is swollen with the swelling agent.

Embodiment 43. The process of Embodiment 41 or 42 wherein the crosslinks in the preformed amine polymer are primarily carbon-carbon crosslinks and nitrogen-nitrogen crosslinks are primarily formed in the crosslinking step.

Embodiment 44. The process of any of Embodiments 41 to 43 wherein the preformed amine polymer has a chloride binding capacity of at least 10 mmol/g in Simulated Gastric Fluid ("SGF") and a Swelling Ratio in the range of 2 to 10, and the crosslinked amine polymer has a binding capacity for phosphate, citrate and/or taurocholate in SIB or SOB that Is less than the binding capacity of the preformed amine polymer for phosphate, citrate and/or taurocholate in that same assay.

Embodiment 45. The process of any of Embodiments 41 to 44 wherein the dispersing solvent comprises a non-polar solvent.

Embodiment 46. The process of any of Embodiments 41 to 45 wherein the dispersing solvent comprises a solvent that is chemically inert to the preformed amine polymer.

Embodiment 47. The process of any of Embodiments 41 to 46 wherein the dispersing solvent comprises a crosslinking solvent.

Embodiment 48. The process of any of claims 41 to 44 wherein the crosslinking agent is the dispersing solvent.

Embodiment 49. The process of any of Embodiments 41 to 48 wherein the swelling agent and the dispersing solvent are immiscible.

Embodiment 50. The process of any of Embodiments 41 to 49 wherein the weight ratio of the swelling agent to preformed amine polymer in the reaction mixture is less than 4:1.

Embodiment 51. The process of any of Embodiments 41 to 50 wherein the weight ratio of the swelling agent to preformed amine polymer in the reaction mixture is less than 3:1.

Embodiment 52. The process of any of Embodiments 41 to 51 wherein the weight ratio of the swelling agent to preformed amine polymer in the reaction mixture is less than 2:1.

Embodiment 53. The process of any of Embodiments 41 to 52 wherein the weight ratio of the swelling agent to preformed amine polymer in the reaction mixture is less than 1:1.

Embodiment 54. A process for the preparation of a crosslinked amine polymer, the process comprising (i) swelling a preformed amine polymer with a swelling agent, and (ii) crosslinking the preformed amine polymer to form the crosslinked amine polymer in a reaction mixture comprising a crosslinking agent and the swelling agent, wherein the preformed amine polymer is crosslinked and has an absorption capacity for the swelling agent, the amount of swelling agent in the reaction mixture is less than the absorption capacity of the preformed amine polymer for the swelling agent, and the weight ratio of swelling agent to the preformed amine polymer in the reaction mixture is less than 1:1.

Embodiment 55. The process of any of Embodiments 41 to 54 wherein the swelling agent is a polar solvent.

Embodiment 56. The process of any of Embodiments 41 to 55 wherein the swelling agent is water, methanol, ethanol, n-propanol, isopropanol, n-butanol, formic acid, acetic acid, acetonitrile, dimethylformamide, dimethylsulfoxide, nitromethane, propylene carbonate, or a combination thereof.

Embodiment 57. The process of any of Embodiments 41 to 56 wherein the swelling agent is water.

Embodiment 58. The process of any of Embodiments 41 to 57 wherein the weight ratio of the swelling agent to preformed amine polymer in the reaction mixture is less than 0.5:1.

Embodiment 59. The process of any of Embodiments 41 to 58 wherein the weight ratio of the swelling agent to preformed amine polymer in the reaction mixture is less than 0.4:1.

Embodiment 60. The process of any of Embodiments 41 to 59 wherein the weight ratio of the swelling agent to preformed amine polymer in the reaction mixture is less than 0.3:1.

Embodiment 61. The process of any of Embodiments 41 to 60 wherein the weight ratio of the swelling agent to preformed amine polymer in the reaction mixture is at least 0.15:1.

Embodiment 62. The process of any of Embodiments 41 to 61 wherein the crosslinking agent comprises at least two amine-reactive functional groups.

Embodiment 63. The process of any of Embodiments 41 to 62 wherein the crosslinking agent is a compound containing at least two amine-reactive groups selected from the group consisting of alkyl halides, epoxides, phosgene, anhydrides, carbamates, carbonates, isocyanates, thioisocyanates, esters, activated esters, carboxylic acids and derivatives thereof, sulfonates and derivatives thereof, acyl halides, aziridines, $\alpha,\beta$-unsaturated carbonyls, ketones, aldehydes, and pentafluoroaryl groups.

Embodiment 64. The process of any of Embodiments 41 to 63 wherein the crosslinking agent is a crosslinking agent selected from Table B.

Embodiment 65. The process of any of Embodiments 41 to 64 wherein the crosslinking agent is a dichloroalkane.

Embodiment 66. The process of any of Embodiments 41 to 65 wherein the crosslinking agent is dichloroethane or dichloropropane.

Embodiment 67. The process of any of Embodiments 41 to 66 wherein the swelling agent and the crosslinking agent are immiscible.

Embodiment 68. The process of any of Embodiments 41 to 67 wherein the preformed polymer is combined with the crosslinking agent and the dispersing solvent before the polymer is swollen with the swelling agent.

Embodiment 69. The process of any of Embodiments 41 to 68 wherein the process additionally comprises forming the preformed amine polymer in a solvent system and the crosslinked amine polymer is formed without isolation of the preformed amine polymer from the solvent system.

Embodiment 70. The process of any of Embodiments 41 to 69 wherein the preformed amine polymer comprises the residue of an amine corresponding to Formula 1:

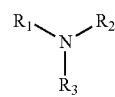

Formula 1

Embodiment 71. The process of any of Embodiments 41 to 69 wherein the preformed amine polymer comprises the residue of an amine corresponding to Formula 1a

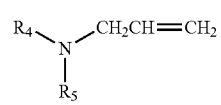

Formula 1a wherein R₄ and R₅ are independently hydrogen, hydrocarbyl, or substituted hydrocarbyl.

Embodiment 72. The process of claim 71 wherein R₄ and R₅ are independently hydrogen, aliphatic or heteroaliphatic.

Embodiment 73. The process of claim 71 wherein R₄ and R₅ are independently hydrogen, allyl, or aminoalkyl.

Embodiment 74. The process of any of Embodiments 41 to 73 wherein the preformed amine polymer comprises the residue of an amine of Table C.

Embodiment 75. The process of any of Embodiments 41 to 74 wherein the preformed amine polymer comprises the residue of allylamine.

Embodiment 76. The process of any of Embodiments 41 to 75 wherein the preformed amine polymer comprises the residue of diallylpropyldiamine.

Embodiment 77. The process of any of Embodiments 41 to 76 wherein the preformed amine polymer is a copolymer comprising the residues of allylamine and diallylpropyldiamine.

Embodiment 78. The process of any of Embodiments 41 to 77 wherein the preformed amine polymer is characterized by a first selectivity for chloride relative to citrate, phosphate and/or taurocholate in SIB and/or SOB and the crosslinked polymer is characterized by a second selectivity for chloride relative to citrate, phosphate and/or taurocholate in SIB and/or SOB wherein:

(i) the crosslinked polymer has an increased binding capacity for chloride and a decreased binding capacity for phosphate in SIB relative to the preformed amine polymer, (ii) the crosslinked polymer has an increased binding capacity for chloride and a decreased binding capacity for phosphate in SOB relative to the preformed amine polymer, (iii) the crosslinked polymer has an increased binding capacity for chloride and a decreased binding capacity for citrate in SOB relative to the preformed amine polymer, or (iv) the crosslinked polymer has an increased binding capacity for chloride and a decreased binding capacity for taurocholate in SOB relative to the preformed amine polymer.

Embodiment 79. The process of Embodiment 78 wherein the crosslinked polymer has a decreased binding capacity for chloride in SGF relative to the preformed amine polymer Embodiment 80. The process of Embodiment 78 wherein relative to the preformed amine polymer the post-polymerization crosslinked polymer has (i) an increased binding capacity for chloride and a decreased binding capacity for phosphate in SIB and (ii) a decreased binding capacity in SGF.

Embodiment 81. The process of Embodiment 78 wherein relative to the preformed amine polymer the post-polymerization crosslinked polymer has (i) an increased binding capacity for chloride and a decreased binding capacity for phosphate, citrate and/or taurocholate, in combination, in SOB and (ii) a decreased binding capacity in SGF.

Embodiment 82. A process for the preparation of a crosslinked amine polymer, the process comprising crosslinking a preformed amine polymer in a reaction mixture to form the crosslinked amine polymer, the reaction mixture comprising the preformed amine polymer, a swelling agent that swells the preformed amine polymer and dichloroethane.

Embodiment 83. The process of Embodiment 82 wherein the reaction mixture comprises a dispersing solvent.

Embodiment 84. The process of Embodiment 82 or 83 wherein the reaction mixture comprises a dispersing solvent dispersing solvent that is chemically inert to the preformed amine polymer.

Embodiment 85. The process of Embodiment 82 or 83 wherein the reaction mixture comprises a dispersing solvent and the dispersing solvent is dichloroethane.

Embodiment 86. The process of any of Embodiments 82 to 85 wherein the swelling agent and dichloroethane are immiscible.

Embodiment 87. The process of any of Embodiments 82 to 86 wherein the weight ratio of the swelling agent to preformed amine polymer in the reaction mixture is less than 4:1.

Embodiment 88. The process of any Embodiments 82 to 86 wherein the weight ratio of the swelling agent to preformed amine polymer in the reaction mixture is less than 3:1.

Embodiment 89. The process of any of Embodiments 82 to 86 wherein the weight ratio of the swelling agent to preformed amine polymer in the reaction mixture is less than 2:1.

Embodiment 90. The process of any of Embodiments 82 to 86 wherein the weight ratio of the swelling agent to preformed amine polymer in the reaction mixture is less than 1:1.

Embodiment 91. The process of any of Embodiments 82 to 86 wherein the weight ratio of the swelling agent to preformed amine polymer in the reaction mixture is less than 0.5:1.

Embodiment 92. The process of any of Embodiments 82 to 86 wherein the weight ratio of the swelling agent to preformed amine polymer in the reaction mixture is less than 0.4:1.

Embodiment 93. The process of any of Embodiments 82 to 86 wherein the weight ratio of the swelling agent to preformed amine polymer in the reaction mixture is less than 0.3:1.

Embodiment 94. The process of any of Embodiments 82 to 86 wherein the weight ratio of the swelling agent to preformed amine polymer in the reaction mixture is at least 0.15:1.

Embodiment 95. The process of any of Embodiments 82 to 94 wherein the preformed amine polymer is deprotonated with a base before it is crosslinked in the reaction mixture.

Embodiment 96. The process of any of Embodiments 82 to 95 wherein the preformed amine polymer is crosslinked and the crosslinks are primarily carbon-carbon crosslinks.

Embodiment 97. The process of any of Embodiments 82 to 96 wherein the swelling agent is a polar solvent.

Embodiment 98. The process of any of Embodiments 82 to 96 wherein the swelling agent is water, methanol, ethanol, n-propanol, isopropanol, n-butanol, formic acid, acetic acid, acetonitrile, dimethylformamide, dimethylsulfoxide, nitromethane, propylene carbonate, or a combination thereof.

Embodiment 99. The process of any of Embodiments 82 to 96 wherein the swelling agent is water.

Embodiment 100. The process of any of Embodiments 82 to 99 wherein the preformed amine polymer comprises the residue of an amine corresponding to Formula 1:

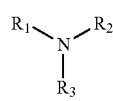

Formula 1

Embodiment 101. The process of any of Embodiments 82 to 99 wherein the preformed amine polymer comprises the residue of an amine corresponding to Formula 1a

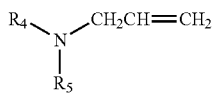

Formula 1a wherein $R_4$ and $R_5$ are independently hydrogen, hydrocarbyl, or substituted hydrocarbyl.

Embodiment 102. The process of Embodiment 101 wherein $R_4$ and $R_5$ are independently hydrogen, aliphatic or heteroaliphatic.

Embodiment 103. The process of Embodiment 101 wherein $R_4$ and $R_5$ are independently hydrogen, allyl, or aminoalkyl.

Embodiment 104. The process of any of Embodiments 82 to 99 wherein the preformed amine polymer comprises the residue of an amine of Table C.

Embodiment 105. The process of any of Embodiments 82 to 99 wherein the preformed amine polymer comprises the residue of allylamine.

Embodiment 106. The process of any of Embodiments 82 to 99 wherein the preformed amine polymer comprises the residue of diallylpropyldiamine.

Embodiment 107. The process of any of Embodiments 82 to 99 wherein the preformed amine polymer is a copolymer comprising the residues of allylamine and diallylpropyldiamine.

Embodiment 108. The process of any of Embodiments 82 to 107 wherein the preformed amine polymer is characterized by a first selectivity for chloride relative to citrate, phosphate and/or taurocholate in SIB and/or SOB and the crosslinked polymer is characterized by a second selectivity for chloride relative to citrate, phosphate and/or taurocholate in SIB and/or SOB wherein:
(i) the crosslinked polymer has an increased binding capacity for chloride and a decreased binding capacity for phosphate in SIB relative to the preformed amine polymer,
(ii) the crosslinked polymer has an increased binding capacity for chloride and a decreased binding capacity for phosphate in SOB relative to the preformed amine polymer,
(iii) the crosslinked polymer has an increased binding capacity for chloride and a decreased binding capacity for citrate in SOB relative to the preformed amine polymer, or
(iv) the crosslinked polymer has an increased binding capacity for chloride and a decreased binding capacity for taurocholate in SOB relative to the preformed amine polymer.

Embodiment 109. The process of Embodiment 108 wherein the crosslinked polymer has a decreased binding capacity for chloride in SGF relative to the preformed amine polymer.

Embodiment 110. The process of Embodiment 108 wherein relative to the preformed amine polymer the post-polymerization crosslinked polymer has (i) an increased binding capacity for chloride and a decreased binding capacity for phosphate in SIB and (ii) a decreased binding capacity in SGF.

Embodiment 111. The process of Embodiment 108 wherein relative to the preformed amine polymer the post-polymerization crosslinked polymer has (i) an increased binding capacity for chloride and a decreased binding capacity for phosphate, citrate and/or taurocholate, in combination, in SOB and (ii) a decreased binding capacity in SGF.

Embodiment 112. A pharmaceutical composition comprising a crosslinked amine polymer having a chloride ion binding capacity of at least 4 mmol/g in Simulated Small Intestine Inorganic Buffer ("SIB").

Embodiment 113. A pharmaceutical composition comprising a crosslinked amine polymer having a ratio of chloride ion binding capacity to phosphate ion binding capacity in Simulated Small Intestine Inorganic Buffer ("SIB") of at least 2.3:1, respectively.

Embodiment 114. A pharmaceutical composition comprising a crosslinked amine polymer having a chloride ion binding capacity of at least 1 mmol/g in Simulated Small Intestine Inorganic Buffer ("SIB"), a phosphate ion binding capacity of less than 0.4 mmol/g in SIB, and a chloride ion to phosphate ion binding ratio in SIB of at least 2.3:1, respectively.

Embodiment 115. A pharmaceutical composition comprising a crosslinked amine polymer having a ratio of chloride ion binding capacity to phosphate ion binding capacity in Simulated Small Intestine Inorganic Buffer ("SIB") of at least 2.3:1, respectively, and a Swelling Ratio of less than 5.

Embodiment 116. A pharmaceutical composition comprising a crosslinked amine polymer having a retained chloride content of at least 30% of the chloride that was initially bound in a GI Compartment Transit Assay ("GICTA").

Embodiment 117. A pharmaceutical composition comprising a crosslinked amine polymer having a retained chloride content of at least 0.5 mmol chloride/g of polymer in a GI Compartment Transit Assay ("GICTA").

Embodiment 118. A pharmaceutical composition comprising a crosslinked amine polymer having a retained chloride content of at least 0.5 mmol chloride/g of polymer in a GI Compartment Transit Assay ("GICTA") and a chloride retention at the end of the GICTA of at least 30% of the chloride that was initially bound in the GICTA.

Embodiment 119. A pharmaceutical composition comprising a crosslinked amine polymer having a chloride ion binding capacity of at least 5 mmol/g in a 1-hour Simulated Gastric Fluid ("SGF") Assay and a chloride ion binding capacity of at least 8 mmol/g in a 24-hour Simulated Gastric Fluid ("SGF") Assay.

Embodiment 120. A pharmaceutical composition comprising a crosslinked amine polymer having a chloride ion binding capacity in a 1-hour Simulated Gastric Fluid ("SGF") Assay that is at least 50% of its chloride ion binding capacity in a 24-hour Simulated Gastric Fluid ("SGF") Assay.

Embodiment 121. A pharmaceutical composition comprising a crosslinked amine polymer having a chloride ion binding capacity of at least 5 mmol/g in a 1-hour Simulated Gastric Fluid ("SGF") Assay, a chloride ion binding capacity of at least 8 mmol/g in a 24-hour Simulated Gastric Fluid ("SGF") Assay, and a chloride ion binding capacity in a 1-hour Simulated Gastric Fluid ("SGF") Assay that is at least 50% of its chloride ion binding capacity in a 24-hour Simulated Gastric Fluid ("SGF") Assay.

Embodiment 122. A pharmaceutical composition comprising a crosslinked amine polymer having a chloride ion binding capacity in a 24-hour Simulated Small Intestine Organic and Inorganic Buffer ("SOB") assay of at least 2.5 mmol chloride/g polymer.

Embodiment 123. A pharmaceutical composition comprising a crosslinked amine polymer having a chloride ion binding capacity in a 2-hour Simulated Small Intestine Organic and Inorganic Buffer ("SOB") assay of at least 0.5 mmol chloride/g polymer and a 24-hour Simulated Small Intestine Organic and Inorganic Buffer ("SOB") assay of at least 2.5 mmol chloride/g polymer.

Embodiment 124. A pharmaceutical composition comprising a crosslinked amine polymer having a chloride ion binding capacity of at least 2 mmol chloride/g polymer at 4 hours in Simulated Small Intestine Inorganic Buffer ("SIB").

Embodiment 125. A pharmaceutical composition comprising a crosslinked amine polymer having a chloride ion binding capacity of at least 2 mmol chloride/g polymer at 4 hours in Simulated Small Intestine Inorganic Buffer ("SIB") and a crosslinked amine polymer having a chloride ion binding capacity of at least 2 mmol chloride/g polymer at 24 hours in Simulated Small Intestine Inorganic Buffer ("SIB").

Embodiment 126. A pharmaceutical composition comprising a crosslinked amine polymer having a chloride ion binding capacity in a 24-hour Simulated Small Intestine Organic and Inorganic Buffer ("SOB") assay of at least 5.5 mmol chloride/g polymer.

Embodiment 127. A pharmaceutical composition comprising a crosslinked amine polymer as described in certain paragraphs above wherein the crosslinked amine polymer has a pKa of at least 6 (at equilibrium, measured in 100 mM NaCl). A pharmaceutical composition comprising a crosslinked amine polymer wherein the crosslinked amine polymer has a pKa of at least 6 (at equilibrium, measured in 100 mM NaCl) prepared by a process comprising two discrete polymerization/crosslinking steps. In the first step, a preformed amine polymer having a chloride binding capacity of at least 10 mmol/g in Simulated Gastric Fluid ("SGF") and a Swelling Ratio in the range of 2 to 10 is formed. In the second step, the preformed amine polymer is crosslinked with a crosslinker containing amine reactive moieties to form a post-polymerization crosslinked amine polymer. The resulting post-polymerization crosslinked amine polymer has a binding capacity for competing anions (e.g., phosphate, citrate and/or taurocholate) in an appropriate assay (e.g., SIB or SOB) that is less than the binding capacity of the preformed polymer for the competing anions (e.g., phosphate, citrate and/or taurocholate) in the same appropriate assay (e.g., SIB or SOB). In one embodiment the preformed amine polymer has a Swelling Ratio in the range of 3 to 8. In one such embodiment, the preformed amine polymer has a Swelling Ratio in the range of 4 to 6. A pharmaceutical composition comprising a crosslinked amine polymer wherein the crosslinked amine polymer has a pKa of at least 6 (at equilibrium, measured in 100 mM NaCl) prepared by a process comprising two discrete crosslinking steps. In the first crosslinking step, a preformed amine polymer is formed, the preformed amine polymer having a chloride binding capacity of at least 10 mmol/g in Simulated Gastric Fluid ("SGF") and a Swelling Ratio in the range of 2 to 10 and an average particle size of at least 80 microns. The preformed amine polymer is (at least partially) deprotonated with a base and, in the second step, the deprotonated preformed amine polymer is crosslinked with a crosslinker containing amine reactive moieties to form a post-polymerization crosslinked amine polymer. In one embodiment the preformed amine polymer has a Swelling Ratio in the range of 3 to 8. In one such embodiment, the preformed amine polymer has a Swelling Ratio in the range of 4 to 6. A pharmaceutical composition comprising a crosslinked amine polymer wherein the crosslinked amine polymer has a pKa of at least 6 (at equilibrium, measured in 100 mM NaCl) prepared by a process comprising two discrete polymerization/crosslinking steps. In the first step, a preformed amine polymer having a chloride binding capacity of at least 10 mmol/g in Simulated Gastric Fluid ("SGF") and a Swelling Ratio in the range of 2 to 10 is formed. The preformed amine polymer is (at least partially) deprotonated with a base and contacted with a swelling agent to swell the deprotonated preformed amine polymer. In the second step, the swollen, deprotonated preformed amine polymer is crosslinked with a crosslinker containing amine reactive moieties to form a post-polymerization crosslinked amine polymer. In one embodiment the preformed amine polymer has a Swelling Ratio in the range of 3 to 8. In one such embodiment, the preformed amine polymer has a Swelling Ratio in the range of 4 to 6. A pharmaceutical composition comprising a crosslinked amine polymer wherein the crosslinked amine polymer has a pKa of at least 6 (at equilibrium, measured in 100 mM NaCl) and a pharmaceutically acceptable excipient. The crosslinked amine polymer, for example, may be prepared by a process comprising crosslinking a preformed amine polymer in a reaction mixture containing the preformed amine polymer, a solvent, a crosslinking agent, and a swelling agent for the preformed amine polymer. The swelling agent is preferably immiscible with the solvent, the preformed amine polymer has an absorption capacity for the swelling agent, and the amount of swelling agent in the reaction mixture is less than the absorption capacity of the preformed amine polymer for the swelling agent. The crosslinked amine polymer, for example, may be prepared by a process comprising crosslinking a preformed amine polymer in a reaction mixture containing the preformed amine polymer, a solvent, and a crosslinking agent to form a crosslinked amine polymer. Prior to the crosslinking step, the preformed amine polymer binds a first amount of chloride and competing anions (e.g., phosphate, citrate and/or taurocholate) and after the crosslinking step, the crosslinked amine polymer binds a second (different) amount of chloride and competing anions (e.g., phosphate, citrate and/or taurocholate) in an appropriate assay (e.g., SIB or SOB). For example, in one such embodiment, the second amount of the competing anions (e.g., phosphate, citrate and/or taurocholate) bound is relatively less than the first amount of the competing anions. The crosslinked amine polymer, for example, may be prepared by a process comprising two discrete polymerization/crosslinking steps are performed in accordance with one aspect of the present disclosure. In the first step, a preformed amine polymer is prepared. The preformed amine polymer is deprotonated and further crosslinked in a second polymerization/crosslinking step to form a post-polymerization crosslinked polymer. Advantageously, the primary crosslinking reaction is between carbon atoms (i.e., carbon-carbon crosslinking) in the first step, whereas crosslinking is primarily between amine moieties comprised by the preformed amine polymer in the second step. The crosslinked amine polymer, for example, may be prepared by a process comprising two discrete polymerization/crosslinking steps. In the first step, a preformed amine polymer having a chloride binding capacity of at least 10 mmol/g in Simulated Gastric Fluid ("SGF") and a Swelling Ratio in the range of 2 to 10 is formed. In the second step, the preformed amine polymer is crosslinked with a crosslinker containing amine reactive moieties to form a post-polymerization crosslinked amine polymer. The resulting post-polymerization crosslinked amine polymer has a binding capacity for competing anions (e.g., phosphate, citrate and/or taurocholate) in an appropriate assay (e.g., SIB or SOB) that is less than the binding capacity of the preformed polymer for the competing anions (e.g., phosphate, citrate and/or taurocholate) in the same appropriate assay (e.g., SIB or SOB). In one embodiment the preformed amine polymer has a Swelling Ratio in the range of 3 to 8. In one such embodiment, the preformed amine polymer has a Swelling Ratio in the range of 4 to 6. The crosslinked amine polymer, for example, may be prepared by a process comprising two discrete crosslinking steps. In the first crosslinking step, a preformed amine polymer is formed, the preformed amine polymer having a chloride binding capacity of at least 10 mmol/g in Simulated Gastric Fluid ("SGF") and a Swelling Ratio in the range of 2 to 10 and an average particle size of at least 80 microns. The preformed amine polymer is (at least partially) deprotonated with a base and, in the second step, the deprotonated preformed amine polymer is crosslinked with a crosslinker containing amine reactive moieties to form a post-polymerization crosslinked amine polymer. In one embodiment the preformed amine polymer has a Swelling Ratio in the range of 3 to 8. In one such embodiment, the preformed amine polymer has a Swelling Ratio in the range of 4 to 6. The crosslinked amine polymer, for example, may be prepared by a process comprising two discrete polymerization/crosslinking steps. In the first step, a preformed amine polymer having a chloride binding capacity of at least 10 mmol/g in Simulated Gastric Fluid ("SGF") and a Swelling Ratio in the range of 2 to 10 is formed. The preformed amine polymer is (at least partially) deprotonated with a base and contacted with a swelling agent to swell the deprotonated preformed amine polymer. In the second step, the swollen, deprotonated preformed amine polymer is crosslinked with a crosslinker containing amine reactive moieties to form a post-polymerization crosslinked amine polymer. In one embodiment the preformed amine polymer has a Swelling Ratio in the range of 3 to 8. In one such embodiment, the preformed amine polymer has a Swelling Ratio in the range of 4 to 6. A pharmaceutical composition comprising a crosslinked amine polymer wherein the crosslinked amine polymer has a pKa of at least 6 (at equilibrium, measured in 100 mM NaCl) having a chloride ion binding capacity of at least 4 mmol/g in Simulated Small Intestine Inorganic Buffer ("SIB"). In one embodiment, the crosslinked amine polymer has a chloride ion binding capacity of at least 4.5, 5, 5.5, or even at least 6 mmol/g in Simulated Small Intestine Inorganic Buffer ("SIB"). A pharmaceutical composition comprising a crosslinked amine polymer wherein the crosslinked amine polymer has a pKa of at least 6 (at equilibrium, measured in 100 mM NaCl) having a ratio of chloride ion binding capacity to phosphate ion binding capacity in Simulated Small Intestine Inorganic Buffer ("SIB") of at least 2.3:1, respectively. In one embodiment, the crosslinked amine polymer has a ratio of chloride ion binding capacity to phosphate ion binding capacity in Simulated Small Intestine Inorganic Buffer ("SIB") of at least 2.5:1, 3:1, 3.5:1, or even 4:1, respectively. A pharmaceutical composition comprising a crosslinked amine polymer wherein the crosslinked amine polymer has a pKa of at least 6 (at equilibrium, measured in 100 mM NaCl) having a chloride ion binding capacity of at least 1 mmol/g in Simulated Small Intestine Inorganic Buffer ("SIB"), a phosphate ion binding capacity of less than 0.4 mmol/g in SIB, and a chloride ion to phosphate ion binding ratio in SIB of at least 2.3:1, respectively. In one embodiment, the crosslinked amine polymer has a chloride ion binding capacity of at least 1.5 mmol/g in Simulated Small Intestine Inorganic Buffer ("SIB"), a phosphate ion binding capacity of less than 0.6 mmol/g in SIB, and a chloride ion to phosphate ion binding ratio in SIB of at least 2.3:1, respectively. In another such embodiment, the crosslinked amine polymer has a chloride ion binding capacity of at least 2.0 mmol/g in Simulated Small Intestine Inorganic Buffer ("SIB"), a phosphate ion binding capacity of less than 0.8 mmol/g in SIB, and a chloride ion to phosphate ion binding ratio in SIB of at least 2.3:1, respectively. In one such embodiment, the crosslinked amine polymer has a chloride ion binding capacity of at least 2.5 mmol/g in Simulated Small Intestine Inorganic Buffer ("SIB"), a phosphate ion binding capacity of less than 1.0 mmol/g in SIB, and a chloride ion to phosphate ion binding ratio in SIB of at least 2.3:1, respectively. In one such embodiment, the crosslinked amine polymer has a chloride ion binding capacity of at least 3.0 mmol/g in Simulated Small Intestine Inorganic Buffer ("SIB"), a phosphate ion binding capacity of less than 1.3 mmol/g in SIB, and a chloride ion to phosphate ion binding ratio in SIB of at least 2.3:1, respectively. In one such embodiment, the crosslinked amine polymer has a chloride ion binding capacity of at least 3.5 mmol/g in Simulated Small Intestine Inorganic Buffer ("SIB"), a phosphate ion binding capacity of less than 1.5 mmol/g in SIB, and a chloride ion to phosphate ion binding ratio in SIB of at least 2.3:1, respectively. In one such embodiment, the crosslinked amine polymer has a chloride ion binding capacity of at least 4.0 mmol/g in Simulated Small Intestine Inorganic Buffer ("SIB"), a phosphate ion binding capacity of less than 1.7 mmol/g in SIB, and a chloride ion to phosphate ion binding ratio in SIB of at least 2.3:1, respectively. In one such embodiment, the crosslinked amine polymer has a chloride ion binding capacity of at least 4.5 mmol/g in Simulated Small Intestine Inorganic Buffer ("SIB"), a phosphate ion binding capacity of less than 1.9 mmol/g in SIB, and a chloride ion to phosphate ion binding ratio in SIB of at least 2.3:1, respectively. In one such embodiment, the crosslinked amine polymer has a chloride ion binding capacity of at least 5.0 mmol/g in Simulated Small Intestine Inorganic Buffer ("SIB"), a phosphate ion binding capacity of less than 2.1 mmol/g in SIB, and a chloride ion to phosphate ion binding ratio in SIB of at least 2.3:1, respectively. In each of the foregoing embodiments, the crosslinked amine polymer may have a chloride ion to phosphate ion binding ratio in SIB of at least 2.5, at least 3, at least 3.5 or even at least 4, respectively. A pharmaceutical composition comprising a crosslinked amine polymer wherein the crosslinked amine polymer has a pKa of at least 6 (at equilibrium, measured in 100 mM NaCl) having a ratio of chloride ion binding capacity to phosphate ion binding capacity in Simulated Small Intestine Inorganic Buffer ("SIB") of at least 2.3:1, respectively, and a Swelling Ratio of less than 5. For example, in one such embodiment, the crosslinked amine polymer may have a chloride ion to phosphate ion binding ratio in SIB of at least 2.3:1, at least 2.5, at least 3, at least 3.5 or even at least 4, respectively, and a Swelling Ratio of less than 5, less than 4, less than 3, less than 2, less than 1.5 or even less than 1. A pharmaceutical composition comprising a crosslinked amine polymer wherein the crosslinked amine polymer has a pKa of at least 6 (at equilibrium, measured in 100 mM NaCl) having a retained chloride content of at least 30% of the chloride that was initially bound in a GI Compartment Transit Assay ("GICTA") (i.e., bound during the SGF binding step). In one such embodiment, the crosslinked amine polymer has a retained chloride content of at least 30%, at least 40%, at least 50%, at least 60%, at least 70%, at least 80% or even at least 90% of the chloride that was initially bound in a GI Compartment Transit Assay. A pharmaceutical composition comprising a crosslinked amine polymer wherein the crosslinked amine polymer has a pKa of at least 6 (at equilibrium, measured in 100 mM NaCl) having a retained chloride content of at least 0.5 mmol chloride/g of polymer in a GI Compartment Transit Assay ("GICTA"). In one such embodiment, the crosslinked amine polymer has a retained chloride content of at least 0.5, at least 1, at least 1.5, at least 2, at least 2.5, at least 3, at least 3.5, at least 4, at least 4.5, or even at least 5 mmol chloride/g of polymer in a GI Compartment Transit Assay ("GICTA"). A pharmaceutical composition comprising a crosslinked amine polymer wherein the crosslinked amine polymer has a pKa of at least 6 (at equilibrium, measured in 100 mM NaCl) having a retained chloride content of at least 0.5 mmol chloride/g of polymer in a GI Compartment Transit Assay ("GICTA") and a chloride retention at the end of the GICTA of at least 30% of the chloride that was initially bound in the GICTA (i.e., bound during the SGF binding step). In one such embodiment, the crosslinked amine polymer has a retained chloride content of at least 30%, at least 40%, at least 50%, at least 60%, at least 70%, at least 80% or even at least 90% of the chloride that was initially bound in a GI Compartment Transit Assay and a retained chloride content of at least 0.5, at least 1, at least 1.5, at least 2, at least 2.5, at least 3, at least 3.5, at least 4, at least 4.5, or even at least 5 mmol chloride/g of polymer in a GI Compartment Transit Assay ("GICTA"). A pharmaceutical composition comprising a crosslinked amine polymer wherein the crosslinked amine polymer has a pKa of at least 6 (at equilibrium, measured in 100 mM NaCl) having a chloride ion binding capacity of at least 5 mmol/g in a 1-hour Simulated Gastric Fluid ("SGF") Assay and a chloride ion binding capacity of at least 8 mmol/g in a 24-hour Simulated Gastric Fluid ("SGF") Assay. In one such embodiment, the crosslinked amine polymer has a chloride ion binding capacity of at least 5 mmol/g in a 1-hour Simulated Gastric Fluid ("SGF") Assay and a chloride ion binding capacity of at least 8, at least 9, at least 10, at least 11, at least 12, at least 13, or even at least 14 mmol/g in a 24-hour Simulated Gastric Fluid ("SGF") Assay. A pharmaceutical composition comprising a crosslinked amine polymer wherein the crosslinked amine polymer has a pKa of at least 6 (at equilibrium, measured in 100 mM NaCl) having a chloride ion binding capacity in a 1-hour Simulated Gastric Fluid ("SGF") Assay that is at least 50% of its chloride ion binding capacity in a 24-hour Simulated Gastric Fluid ("SGF") Assay. In one such embodiment, the crosslinked amine polymer has a chloride ion binding capacity in a 1-hour Simulated Gastric Fluid ("SOF") Assay that is at least 50%, at least 60%, at least 70%, at least 80%, or even at least 90% of its chloride ion binding capacity in a 24-hour Simulated Gastric Fluid ("SGF") Assay. A pharmaceutical composition comprising a crosslinked amine polymer wherein the crosslinked amine polymer has a pKa of at least 6 (at equilibrium, measured in 100 mM NaCl) having a chloride ion binding capacity of at least 5 mmol/g in a 1-hour Simulated Gastric Fluid ("SGF") Assay, a chloride ion binding capacity of at least 8 mmol/g in a 24-hour Simulated Gastric Fluid ("SGF") Assay, and a chloride ion binding capacity in a 1-hour Simulated Gastric Fluid ("SGF") Assay that is at least 50% of its chloride ion binding capacity in a 24-hour Simulated Gastric Fluid ("SGF") Assay. In one such embodiment, the crosslinked amine polymer has a chloride ion binding capacity of at least 5 mmol/g in a 1-hour Simulated Gastric Fluid ("SGF") Assay and a chloride ion binding capacity of at least 8, at least 9, at least 10, at least 11, at least 12, at least 13, or even at least 14 mmol/g in a 24-hour Simulated Gastric Fluid ("SGF") Assay and the crosslinked amine polymer has a chloride ion binding capacity in a 1-hour Simulated Gastric Fluid ("SGF") Assay that is at least 50%, at least 60%, at least 70%, at least 80%, or even at least 90% of its chloride ion binding capacity in a 24-hour Simulated Gastric Fluid ("SGF") Assay. A pharmaceutical composition comprising a crosslinked amine polymer wherein the crosslinked amine polymer has a pKa of at least 6 (at equilibrium, measured in 100 mM NaCl) having a chloride ion binding capacity in a 24-hour Simulated Small Intestine Organic and Inorganic Buffer ("SOB") assay of at least 2.5 mmol chloride/g polymer. In one such embodiment, the crosslinked amine polymer has a chloride ion binding capacity in a 24-hour Simulated Small Intestine Organic and Inorganic Buffer ("SOB") assay of at least 2.5, at least 3, at least 3.5, at least 4, at least 4.5, or even at least 5 mmol chloride/g polymer. A pharmaceutical composition comprising a crosslinked amine polymer wherein the crosslinked amine polymer has a pKa of at least 6 (at equilibrium, measured in 100 mM NaCl) having a chloride ion binding capacity in a 2-hour Simulated Small Intestine Organic and Inorganic Buffer ("SOB") assay of at least 0.5 mmol chloride/g polymer and a 24-hour Simulated Small Intestine Organic and Inorganic Buffer ("SOB") assay of at least 2.5 mmol chloride/g polymer. In one such embodiment, the crosslinked amine polymer has a chloride ion binding capacity in a 2-hour Simulated Small Intestine Organic and Inorganic Buffer ("SOB") assay of at least 0.5, at least 1, at least 1.5, at least 2, at least 2.5, or even at least 3 mmol chloride/g polymer and a 24-hour Simulated Small Intestine Organic and Inorganic Buffer ("SOB") assay of at least 2.5, at least 3, at least 3.5, at least 4, at least 4.5, or even at least 5 mmol chloride/g polymer. A pharmaceutical composition comprising a crosslinked amine polymer wherein the crosslinked amine polymer has a pKa of at least 6 (at equilibrium, measured in 100 mM NaCl) having a chloride ion binding capacity of at least 2 mmol chloride/g polymer at 4 hours in Simulated Small Intestine Inorganic Buffer ("SIB"). In one such embodiment, the crosslinked amine polymer has a chloride ion binding capacity of at least 2, at least 2.5, at least 3, at least 3.5, or even at least 4 mmol chloride/g polymer at 4 hours in Simulated Small Intestine Inorganic Buffer ("SIB"). A pharmaceutical composition comprising a crosslinked amine polymer wherein the crosslinked amine polymer has a pKa of at least 6 (at equilibrium, measured in 100 mM NaCl) having a chloride ion binding capacity of at least 2 mmol chloride/g polymer at 4 hours in Simulated Small Intestine Inorganic Buffer ("SIB") and a crosslinked amine polymer having a chloride ion binding capacity of at least 2 mmol chloride/g polymer at 24 hours in Simulated Small Intestine Inorganic Buffer ("SIB"). In one such embodiment, the crosslinked amine polymer has a chloride ion binding capacity of at least 2, at least 2.5, at least 3, at least 3.5, or even at least 4 mmol chloride/g polymer at 4 hours in Simulated Small Intestine Inorganic Buffer ("SIB") and a crosslinked amine polymer having a chloride ion binding capacity of at least 2, at least 2.5, at least 3, at least 3.5, or even at least 4 mmol chloride/g polymer at 24 hours in Simulated Small Intestine Inorganic Buffer ("SIB"). A pharmaceutical composition comprising a crosslinked amine polymer wherein the crosslinked amine polymer has a pKa of at least 6 (at equilibrium, measured in 100 mM NaCl) having a chloride ion binding capacity in a 24-hour Simulated Small Intestine Organic and Inorganic Buffer ("SOB") assay of at least 5.5 mmol chloride/g polymer. In one such embodiment, the crosslinked amine polymer has a chloride ion binding capacity in a 24-hour Simulated Small Intestine Organic and Inorganic Buffer ("SOB") assay of at least 6 mmol chloride/g polymer.

Embodiment 128. A pharmaceutical composition comprising a crosslinked amine polymer having (i) a proton-binding capacity and a chloride binding capacity of at least 5 mmol/g in Simulated Gastric Fluid; and (ii) a chloride ion binding capacity of at least 4 mmol/g at 1 hour in Simulated Small Intestine Inorganic Buffer ("SIB").

Embodiment 129. A pharmaceutical composition comprising a crosslinked amine polymer having (i) a proton-binding capacity and a chloride binding capacity of at least 5 mmol/g in Simulated Gastric Fluid; and (ii) a chloride ion binding capacity of at least 4 mmol/g, and a phosphate ion binding capacity of less than 2 mmol/g in Simulated Small Intestine Inorganic Buffer ("SIB").

Embodiment 130. A pharmaceutical composition comprising a crosslinked amine polymer having (i) a proton-binding capacity and a chloride binding capacity of at least 5 mmol/g in Simulated Gastric Fluid; and (ii) a chloride ion binding capacity at 1 hour in Simulated Small Intestine Inorganic Buffer ("SIB") of at least 2 mmol/g.

Embodiment 131. A pharmaceutical composition comprising a crosslinked amine polymer having (i) a proton-binding capacity and a chloride binding capacity of at least 5 mmol/g in Simulated Gastric Fluid; and (ii) a chloride to phosphate ion binding ratio of at least 2.3:1, respectively, in Simulated Small Intestine Inorganic Buffer ("SIB").

Embodiment 132. A pharmaceutical composition comprising a crosslinked amine polymer having (i) a proton-binding capacity and a chloride binding capacity of at least 5 mmol/g at one hour in Simulated Gastric Fluid and (ii) a proton-binding capacity and a chloride binding capacity in Simulated Gastric Fluid of at least 8 mmol/g.

Embodiment 133. A pharmaceutical composition comprising a crosslinked amine polymer having a proton-binding capacity and a chloride binding capacity at one hour in Simulated Gastric Fluid that is at least X % of the proton-binding capacity and the chloride binding capacity, respectively, of the crosslinked amine polymer at 24 hours in Simulated Gastric Fluid wherein X % is at least 50%.

Embodiment 134. A pharmaceutical composition comprising a crosslinked amine polymer having (i) a selectivity for chloride over citrate, phosphate and taurocholate in Simulated Small Intestine Organic and Inorganic Buffer ("SOB"), and (ii) a chloride binding capacity at 24 hours in SOB of at least 4 mmol/g.

Embodiment 135. A pharmaceutical composition comprising a crosslinked amine polymer having a selectivity for chloride over citrate, phosphate and taurocholate in Simulated Small Intestine Organic and Inorganic Buffer ("SOB"), at (i) 1 hour, (ii) 4 hours, (iii) 12 hours, (iv) 18 hours, (v) 24 hours, (vi) 30 hours, (vii) 36 hours, or even (viii) 48 hours.

Embodiment 136. A pharmaceutical composition comprising a crosslinked amine polymer having a chloride ion binding capacity of at least 4 mmol/g, and a phosphate ion binding capacity of less than 2 mmol/g in Simulated Small Intestine Inorganic Buffer ("SIB") at (i) 1 hour, (ii) 2 hours, (iii) 3 hours, (iv) 4 hours, and/or (v) greater than 4 hours.

Embodiment 137. A method of treating an acid/base disorder in an animal including a human by removing HCl through oral administration of a pharmaceutical composition of any of Embodiments 122 to 136.

Embodiment 138. A method of treating an acid/base disorder in an animal including a human by removing HCl through oral administration of a pharmaceutical composition comprising a crosslinked amine polymer prepared by the process of any of Embodiments 41 to 111.

Embodiment 139. A polymer comprising a structure corresponding to Formula 4:

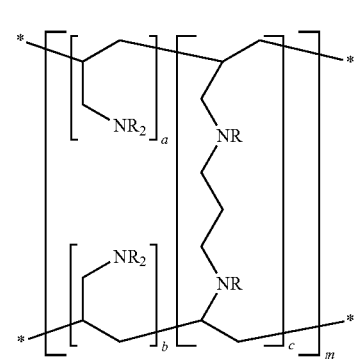

Formula 4 wherein each R is indendently hydrogen or an ethylene crosslink between two nitrogen atoms of the crosslinked amine polymer

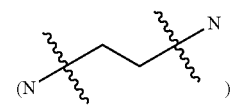

and a, b, c, and m are integers.

Embodiment 140. The polymer of Embodiment 139 wherein m is a large integer indicating an extended polymer network.

Embodiment 141. The polymer of Embodiment 139 or 140 wherein a ratio of the sum of a and b to c (i.e., a+b:c) is in the range of about 1:1 to 5:1.

Embodiment 142. The polymer of Embodiment 139 or 140 wherein a ratio of the sum of a and b to c (i.e., a+b:c) is in the range of about 1.5:1 to 4:1.

Embodiment 143. The polymer of Embodiment 139 or 140 wherein a ratio of the sum of a and b to c (i.e., a+b:c) is in the range of about 1.75:1 to 3:1.

Embodiment 144. The polymer of Embodiment 139 or 140 wherein a ratio of the sum of a and b to c (i.e., a+b:c) is in the range of about 2:1 to 2.5:1.

Embodiment 145. The polymer of Embodiment 139 or 140 wherein the sum of a and b is 57 and c is 24.

Embodiment 146. The polymer of any of Embodiments 139 to 145 wherein 50-95% of the R substituents are hydrogen and 5-50% are an ethylene crosslink between two nitrogens of the crosslinked amine polymer.

Embodiment 147. The polymer of any of Embodiments 139 to 145 wherein 55-90% of the R substituents are hydrogen and 10-45% are an ethylene crosslink between two nitrogens of the crosslinked amine polymer.

Embodiment 148. The polymer of any of Embodiments 139 to 145 wherein 60-90% of the R substituents are hydrogen and 10-40% are an ethylene crosslink between two nitrogens of the crosslinked amine polymer.

Embodiment 149. The polymer of any of Embodiments 139 to 145 wherein 65-90% of the R substituents are hydrogen and 10-35% are an ethylene crosslink between two nitrogens of the crosslinked amine polymer.

Embodiment 150. The polymer of any of Embodiments 139 to 145 wherein 70-90% of the R substituents are hydrogen and 10-30% are an ethylene crosslink between two nitrogens of the crosslinked amine polymer.

Embodiment 151. The polymer of any of Embodiments 139 to 145 wherein 75-85% of the R substituents are hydrogen and 15-25% are an ethylene crosslink between two nitrogens of the crosslinked amine polymer.

Embodiment 152. The polymer of any of Embodiments 139 to 145 wherein 80-85% of the R substituents are hydrogen and 15-205% are an ethylene crosslink between two nitrogens of the crosslinked amine polymer.

Embodiment 153. The polymer of any of Embodiments 139 to 145 wherein about 81% of the R substituents are hydrogen and about 19% are an ethylene crosslink.

Embodiment 154. A pharmaceutical composition comprising a pharmaceutically acceptable excipient and a crosslinked amine polymer of any of Embodiments 139 to 153.

Embodiment 155. A method of treating an acid/base disorder in an animal including a human by removing HCl through oral administration of a pharmaceutical composition of Embodiment 154.

Having described the invention in detail, it will be apparent that modifications and variations are possible without departing the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

General Procedure for DCE-Dispersed Crosslinking

Dry preformed amine polymer beads were added to a reactor vessel equipped with a stir paddle and nitrogen gas inlet. To the beads was added 1,2-dichloroethane (DCE). The beads were dispersed in the DCE using mechanical agitation. Water was added directly to the dispersion, and stirring was continued for 30 minutes. After 30 minutes, the flask was immersed into an oil bath held at a chosen temperature. The reaction was held in the oil bath and agitated using mechanical stirring under a nitrogen atmosphere for a chosen amount of time. Methanol was added to the reaction and, solvent was removed by decanting. The beads were then filtered, and then purified by washing (MeOH two times, $H_2O$ once, 1N HCl two times, $H_2O$ once, 1N NaOH three times, and then $H_2O$ until the pH of solution after washing was 7). The purified beads were then dried by lyophilization for 48 hours.

Specific Example Procedure for DCE-Dispersed Crosslinking

Unless otherwise noted, the example procedure below is the standard recipe for all of the examples in this section. Specifically, this denotes a 1:6 bead to DCE (g/mL) ratio, 0.25:1 water to bead mass ratio, 70° C. jacket (oil bath) temperature, and 16 hours reaction time.

Dry preformed amine polymer beads (15.00 g) were added to a 250 mL round bottom flask equipped with a stir paddle and nitrogen gas inlet. To the beads was added 1,2-dichloroethane (DCE) (90 mL, resulting in a 1:6 bead to DCE (g/mL) ratio). The beads were dispersed in the DCE using mechanical agitation (~150 rpm stirring). Water (3.75 mL, resulting in a 0.25:1 water to bead mass ratio) was added directly to the dispersion, and stirring was continued for 30 minutes. After 30 minutes, the flask was immersed into an oil bath held at 70° C. The reaction was held in the oil bath and agitated using mechanical stirring under a nitrogen atmosphere for 16 hours. Methanol (100 mL) was added to the reaction and, solvent was removed by decanting. The beads were then filtered, and then purified by washing (MeOH two times, $H_2O$ once, 1N HCl two times, $H_2O$ once, 1N NaOH three times, and then $H_2O$ until the pH of solution after washing was 7). The purified beads were then dried by lyophilization for 48 hours.

Effect of Water on DCE-Dispersed Crosslinking Reaction

The effect of the amount of water added to an example reaction mixture was explored (Table 1). Under these conditions, chloride binding in SIB and SOB increased while phosphate, citrate and taurocholate binding decreased relative to that of the preformed amine polymer (sample 019069-A1). The particle sizes decreased after second step crosslinking. The water content that yielded the highest selectivity and highest total chloride binding as measured in SIB was found to be in the range of 0.25-0.35 water to bead ratio.

The preformed amine polymer beads that were the source dry beads for the DCE-dispersed crosslinking reaction were prepared as follows. Two aqueous stock solutions of monomer (50% w/w) were prepared by independently dissolving 43.83 g allylamine hydrochloride and 45.60 g DAPDA in water. A 3-neck, 2 L round bottom flask with four side baffles equipped with an overhead stirrer (stirring at 180 rpm), Dean-Stark apparatus and condenser, and nitrogen inlet, was charged with 12 g surfactant (Stepan Sulfonic 100) dissolved in 1,200 g of a heptane/chlorobenzene solution (26/74 v/v), followed by the aqueous stock solutions, and an additional portion of water (59.14 g). In a separate vessel, a 15 wt % solution of initiator V-50 (9.08 g) in water was prepared. The two mixtures were independently sparged with nitrogen while the reaction vessel was brought to 67° C. in an oil bath (approximately 30 min). Under inert atmosphere, the initiator solution was added to the reaction mixture, and subsequently heated at 67° C. for 16 hours. A second aliquot of initiator solution (equal to the first) and the reaction mixture, were sparged with nitrogen for 30 minutes and combined before increasing the temperature to 115° C. for a final dehydration step (Dean-Stark). The reaction was held at 115° C. until water stopped collecting in the Dean-Stark trap (6 h, 235 mL removed, >90% of total water, $T_{internal}$>99° C.). The reaction was allowed to cool to room temperature, and the stirring stopped to allow the beads to settle. The organic phase was removed from the bead cake by decanting. The beads were purified by washing (MeOH two times, $H_2O$ once, 1N HCl two times, $H_2O$ once, 1N NaOH three times, and then $H_2O$ until the pH of solution after washing was 7) and dried by lyophilization.

TABLE 1

Water content gradient for DCE-dispersed second step crosslinking.

| | | | Particle Size (microns) | | | | | | Binding (mmol/g) | | | |
| | | | | | | | | | SOB-Cl | SOB-P | SOB-Cl | SOB-P |
| Unique ID | Water:Bead | Swelling | D10 | D50 | D90 | SGF | SIB-Cl | SIB-P | (2 h) | (2 h) | (24 h) | (24 h) |
|---|---|---|---|---|---|---|---|---|---|---|---|---|
| Averaged from 019069-A1 FA pooled batch* | — | 5.0 | 79 | 129 | 209 | 13.9 | 2.0 | 6.0 | 0.4 | 1.3 | 0.5 | 1.2 |
| 030008-A1 FA | 0.00 | 1.9 | NM | NM | NM | 11.8 | 2.4 | 4.0 | NM | NM | NM | NM |
| 019070-A1 FA | 0.05 | 1.5 | 64 | 99 | 155 | 11.1 | 2.4 | 3.5 | 2.0 | 0.0 | 3.2 | 0.1 |
| 019070-A2 FA | 0.15 | 1.1 | 64 | 97 | 147 | 11.0 | 3.3 | 2.5 | 1.0 | 0.0 | 2.5 | 0.1 |
| 019070-A3 FA | 0.25 | 1.2 | 63 | 102 | 168 | 10.4 | 4.4 | 1.4 | 0.8 | 0.0 | 2.8 | 0.1 |
| 019070-A4 FA | 0.35 | 0.7 | 59 | 91 | 140 | 10.7 | 4.5 | 1.3 | 0.9 | 0.0 | 3.0 | 0.1 |
| 019070-A5 FA | 0.45 | 1.6 | 63 | 105 | 184 | 11.1 | 3.7 | 2.5 | 1.0 | 0.0 | 3.2 | 0.1 |

*Averaged data from 4 batches of preformed polyamine bead;
NM: not measured

Effect of Time and Temperature

The effect of temperature on the reaction was studied by following the reaction progress as a function of time. In these experiments, it was found that the desired performance could be attained at all of the temperatures studied between 55° C. and 70° C., though the reaction progress is slower at lower temperatures (Table 2, Table 3, Table 4 and Table 5).

TABLE 2

Time course for DCE dispersed second step crosslinking at 70° C. The example procedure was used with the following changes: 20 g of dry beads were used for the reaction, using the ratios as described, and 1 g samples were removed at the time intervals indicated in the table.

| | Time | | Particle Size (microns) | | | | | | Binding (mmol/g) | | | |
| | | | | | | | | | SOB-Cl | SOB-P | SOB-Cl | SOB-P |
| Unique ID | (h) | Swelling | D10 | D50 | D90 | SGF | SIB-Cl | SIB-P | (2 h) | (2 h) | (24 h) | (24 h) |
|---|---|---|---|---|---|---|---|---|---|---|---|---|
| 019076-A7 FA | 2 | 1.2 | NM | NM | NM | 12.1 | 2.9 | 3.9 | 1.2 | 0.1 | 3.3 | 0.1 |
| 019074-A1 FA | 3 | 1.2 | 64 | 102 | 163 | 11.8 | 3.6 | 3.1 | 0.9 | 0.1 | 3.1 | 0.1 |
| 019074-A2 FA | 6 | 1.1 | 65 | 102 | 162 | 11.5 | 4.5 | 2.0 | 0.8 | 0.1 | 2.2 | 0.1 |
| 019074-A3 FA | 9 | 1.1 | 61 | 100 | 168 | 11.2 | 4.4 | 1.8 | 0.9 | 0.1 | 3.0 | 0.1 |
| 019074-A4 FA | 12 | 1.0 | 65 | 102 | 161 | 11.0 | 4.8 | 1.2 | 1.0 | 0.1 | 3.3 | 0.1 |
| 018082-A6 FA | 24 | 1.0 | NM | NM | NM | 10.1 | 4.6 | 0.8 | 2.2 | 0.0 | 4.3 | 0.2 |

NM: Not measured

TABLE 3

Time course for DCE dispersed second step crosslinking at 65° C. The example procedure was used with the following changes: 20 g of dry beads were used for the reaction, using the ratios as described, and 1 g samples were removed at the time intervals indicated in the table.

| | Time | | Particle Size (microns) | | | | | | Binding (mmol/g) | | | |
| | | | | | | | | | SOB-Cl | SOB-P | SOB-Cl | SOB-P |
| Unique ID | (h) | Swelling | D10 | D50 | D90 | SGF | SIB-Cl | SIB-P | (2 h) | (2 h) | (24 h) | (24 h) |
|---|---|---|---|---|---|---|---|---|---|---|---|---|
| 019079-A1 FA | 2 | 1.4 | NM | NM | NM | 12.7 | 2.5 | 4.8 | 0.7 | 0.0 | 3.2 | 0.1 |
| 019079-A2 FA | 4 | 1.4 | NM | NM | NM | 12.2 | 3.3 | 3.8 | 0.6 | 0.0 | 2.8 | 0.1 |
| 019079-A3 FA | 6 | 1.1 | NM | NM | NM | 12.3 | 3.9 | 2.9 | 0.7 | 0.0 | 3.4 | 0.1 |
| 019079-A4 FA | 8 | 1.2 | NM | NM | NM | 12.0 | 4.4 | 2.5 | 0.7 | 0.0 | 3.3 | 0.1 |
| 019079-A5 FA | 10 | 1.5 | NM | NM | NM | 11.8 | 4.7 | 2.1 | 0.6 | 0.0 | 2.7 | 0.1 |
| 019079-A6 FA | 12 | 1.4 | NM | NM | NM | 11.8 | 4.8 | 1.9 | 0.6 | 0.0 | 2.9 | 0.1 |
| 019079-A7 FA | 24 | 1.2 | NM | NM | NM | 11.4 | 5.1 | 1.4 | 0.8 | 0.0 | 2.7 | 0.1 |

NM: Not measured

TABLE 4

Time course for DCE dispersed second step crosslinking at 60° C. The example procedure was used with the following changes: 20 g of dry beads were used for the reaction, using the ratios as described, and 1 g samples were removed at the time intervals indicated in the table.

| Unique ID | Time (h) | Swelling | Particle Size (microns) | | | SGF | SIB-Cl | SIB-P | Binding (mmol/g) | | | |
|---|---|---|---|---|---|---|---|---|---|---|---|---|
| | | | D10 | D50 | D90 | | | | SOB-Cl (2 h) | SOB-P (2 h) | SOB-Cl (24 h) | SOB-P (24 h) |
| 025002-A1 FA | 2 | 1.6 | NM | NM | NM | 12.7 | 2.0 | 5.2 | 1.2 | 0.0 | 3.3 | 0.1 |
| 025002-A2 FA | 4 | 1.4 | NM | NM | NM | 12.4 | 2.7 | 4.2 | 0.7 | 0.0 | 3.3 | 0.1 |
| 025002-A3 FA | 6 | 1.4 | NM | NM | NM | 12.3 | 3.4 | 3.4 | 0.9 | 0.0 | 3.7 | 0.1 |
| 025002-A4 FA | 8 | 1.3 | NM | NM | NM | 11.9 | 3.9 | 2.8 | 0.7 | 0.0 | 2.7 | 0.1 |
| 025002-A5 FA | 10 | 1.8 | NM | NM | NM | 11.9 | 4.3 | 2.4 | 1.0 | 0.0 | 4.1 | 0.1 |
| 025002-A6 FA | 12 | 1.0 | NM | NM | NM | 11.8 | 4.6 | 2.1 | 0.6 | 0.0 | 2.8 | 0.0 |
| 025002-A7 FA | 24 | 1.2 | NM | NM | NM | 11.2 | 5.0 | 1.2 | 0.6 | 0.0 | 2.3 | 0.0 |

NM: Not measured

TABLE 5

Time course for DCE dispersed second step crosslinking at 55° C. The example procedure was used with the following changes: 20 g of dry beads were used for the reaction, using the ratios as described, and 1 g samples were removed at the time intervals indicated in the table.

| Unique ID | Time (h) | Swelling | Particle Size (microns) | | | SGF | SIB-Cl | SIB-P | Binding (mmol/g) | | | |
|---|---|---|---|---|---|---|---|---|---|---|---|---|
| | | | D10 | D50 | D90 | | | | SOB-Cl (2 h) | SOB-P (2 h) | SOB-Cl (24 h) | SOB-P (24 h) |
| 025002-C1 FA | 2 | 1.6 | NM | NM | NM | 13.1 | 1.9 | 5.5 | 3.9 | 0.2 | 4.7 | 0.4 |
| 025002-C2 FA | 4 | 1.6 | NM | NM | NM | 12.7 | 2.3 | 4.9 | 0.8 | 0.0 | 3.2 | 0.2 |
| 025002-C3 FA | 6 | 1.7 | NM | NM | NM | 12.3 | 2.9 | 4.4 | 0.6 | 0.0 | 3.1 | 0.1 |
| 025002-C4 FA | 8 | 1.4 | NM | NM | NM | 12.2 | 3.5 | 3.9 | 0.6 | 0.0 | 3.5 | 0.1 |
| 025002-C5 FA | 10 | 1.4 | NM | NM | NM | 12.1 | 3.6 | 3.2 | 0.6 | 0.0 | 3.3 | 0.1 |
| 025002-C6 FA | 12 | 1.5 | NM | NM | NM | 12.3 | 3.9 | 2.8 | 0.8 | 0.0 | 3.7 | 0.1 |
| 025002-C7 FA | 24 | 1.1 | NM | NM | NM | 12.0 | 4.7 | 1.5 | 0.6 | 0.0 | 3.3 | 0.1 |

NM: Not measured

Effect of DCE to Preformed Amine Polymer Ratio on Second Step Crosslinking

The effect of the amount of DCE added to the reaction mixture to disperse the beads was explored (Table 6). Under these conditions, it was found that the ratio of DCE to bead (preformed amine polymer) does not substantially change the chloride binding or selectivity in SIB or SOB. Note that 3:1 ratio is approximately minimum to have enough DCE for dispersing the beads.

Effect of HCl in Preformed Amine Polymer on Second Step Crosslinking

The effect of residual hydrochloric acid in preformed amine polymer (e.g. due to an insufficient washing) on the second step crosslinking was studied (Table 7). In these experiments, it was found that the chloride selectivity and binding capacity were unaffected if less than 3% of the amines in the pre-formed amine polymer are protonated.

TABLE 6

Series examining the effect of the DCE to bead ratio. The example procedure was used for the 6:1 DCE to bead ratio, which used 90 mL of DCE in a 250 mL flask. For each of the other ratios, 90 mL of DCE was kept constant, and the amount of beads used were adjusted to satisfy the DCE to bead ratio. The water was adjusted accordingly (e.g. the 10:1 DCE to bead ratio used 9 g of beads, and 2.25 g of water)

| Unique ID | DCE:Bead | Swelling | Particle Size (microns) | | | SGF | SIB-Cl | SIB-P | Binding (mmol/g) | | | |
|---|---|---|---|---|---|---|---|---|---|---|---|---|
| | | | D10 | D50 | D90 | | | | SOB-Cl (2 h) | SOB-P (2 h) | SOB-Cl (24 h) | SOB-P (24 h) |
| 018082-A1 FA | 3 | 1.1 | 68 | 109 | 185 | 10.9 | 4.7 | 1.3 | 1.2 | 0.0 | 3.2 | 0.1 |
| 018082-A2 FA | 4 | 1.2 | 62 | 94 | 150 | 11.2 | 4.9 | 1.3 | 1.2 | 0.0 | 3.8 | 0.1 |
| 018082-A3 FA | 5 | 1.1 | 58 | 93 | 147 | 11.0 | 4.8 | 1.3 | 1.2 | 0.0 | 3.8 | 0.1 |
| 019070-A3 FA | 6 | 1.2 | 63 | 102 | 168 | 10.4 | 4.4 | 1.4 | 0.8 | 0.0 | 2.8 | 0.1 |
| 018082-A5 FA | 10 | 1.0 | 61 | 97 | 160 | 10.9 | 4.8 | 1.1 | 0.9 | 0.0 | 3.0 | 0.1 |

TABLE 7

Effect of residual hydrochloric acid in preformed amine polymer on second step crosslinking reaction.
(100 mL vessel, 3 g beads, 6:1 DCE to heptane ratio, 0.5:1 water to bead ratio, 70° C., 16 hours,
no Dean-Stark). Hydrochloric acid was added to the bead in the water used in the reaction.

| | mol % | | Particle Size (microns) | | | | | | Binding (mmol/g) | | | |
| | HCl:Amine | | | | | | | | SOB-Cl | SOB-P | SOB-Cl | SOB-P |
| Unique ID | bead | Swelling | D10 | D50 | D90 | SGF | SIB-Cl | SIB-P | (2 h) | (2 h) | (24 h) | (24 h) |
|---|---|---|---|---|---|---|---|---|---|---|---|---|
| 015046-A1 FA | 0 | 1.0 | NM | NM | NM | 11.6 | 5.2 | 1.4 | 1.7 | 0.0 | 4.5 | 0.1 |
| 015046-A2 FA | 0.1 | 1.1 | NM | NM | NM | 11.4 | 5.0 | 1.5 | NM | NM | NM | NM |
| 015046-A3 FA | 1 | 1.1 | 91 | 162 | 281 | 11.6 | 4.9 | 1.5 | NM | NM | NM | NM |
| 015046-A4 FA | 1.9 | 1.4 | NM | NM | NM | 11.5 | 5.0 | 1.5 | NM | NM | NM | NM |
| 015046-A5 FA | 2.9 | 1.3 | NM | NM | NM | 11.6 | 4.8 | 1.8 | NM | NM | NM | NM |
| 015050-A2 FA | 5 | 0.9 | NM | NM | NM | 11.8 | 4.3 | 2.1 | 1.4 | 0.0 | 5.0 | 0.1 |
| 015050-A3 FA | 10 | 1.6 | NM | NM | NM | 11.8 | 3.8 | 2.6 | 1.1 | 0.0 | 4.4 | 0.1 |
| 015050-A4 FA | 25 | 2.8 | 61 | 105 | 173 | 12.5 | 3.4 | 3.6 | 2.9 | 0.1 | 5.3 | 0.4 |

NM: Not measured

2) General Procedure for Solvent-Dispersed Crosslinking—DCE

Dry preformed amine polymer beads were added to a reaction vessel equipped with a stir paddle and nitrogen gas inlet. To the beads was added an inert (i.e. not a crosslinker) dispersing solvent. The beads were dispersed in the solvent using mechanical agitation. Water was added directly to the dispersion, and stirring was continued for 30 minutes. Neat dichloroethane was added to the flask, which was then immersed into an oil bath heated to a chosen temperature. The reaction was heated using mechanical stirring under a nitrogen atmosphere for 16 hours. Methanol was added to the reaction and, solvent was removed by decanting. The beads were then filtered, and then purified by washing (MeOH two times, H₂O once, 1N HCl two times, H₂O once, 1N NaOH three times, and then H₂O until the pH of solution after washing was 7). The purified beads were then dried by lyophilization for 48 hours.

Specific Example Procedure for Solvent-Dispersed Crosslinking—DCE Crosslinker

Unless otherwise noted, the example procedure below is the standard recipe for all of the examples in this section.

Specifically, this denotes a 1:6 bead to dispersing solvent (g/mL) ratio, 1:1 water to bead mass ratio, 70° C. Jacket temperature, and 16 hours reaction time.

Dry beads (3.00 g) were added to a 250 mL round bottom flask equipped with a stir paddle and nitrogen gas inlet. To the beads was added heptane (18 mL, resulting in a 1:6 bead to DCE g/mL ratio). The beads were dispersed in the heptane using mechanical agitation (~100 rpm stirring). Water (3 mL, resulting in a 1:1 water to bead ratio) was added directly to the dispersion, and stirring was continued for 20 minutes. Neat dichloroethane (3.57 g, 35.9 mmol) was added to the flask, which was then heated to 70° C. The reaction was heated using mechanical stirring under a nitrogen atmosphere for 16 hours. Methanol (100 mL) was added to the reaction and, solvent was removed by decanting. The beads were then filtered, and then purified by washing (MeOH two times, H₂O once, 1N HCl two times, H₂O once, 1N NaOH three times, and then H₂O until the pH of solution after washing was 7). The purified beads were then dried by lyophilization for 48 hours.

Effect of DCE Crosslinker Amount on Heptane Dispersed Reaction

The effect of DCE amount added to an inert solvent-dispersed second step crosslinking was explored (Table 8). In these experiments, 2 equivalents of DCE (relative to nitrogen in preformed amine polymer) yielded the material with best combination of high selectivity and high chloride binding as measured in SIB and SOB.

TABLE 8

Effect of DCE amount (expressed as molar equivalent) in heptane dispersed reaction on chloride selectivity

| | DCE | | Particle Size (microns) | | | | | | Binding (mmol/g) | | | |
| | | | | | | | | | SOB-Cl | SOB-P | SOB-Cl | SOB-P |
| Unique ID | mol eq | Swelling | D10 | D50 | D90 | SGF | SIB-Cl | SIB-P | (2 h) | (2 h) | (24 h) | (24 h) |
|---|---|---|---|---|---|---|---|---|---|---|---|---|
| 019048-A1 FA | 0.33 | 1.2 | NM | NM | NM | 13.2 | 2.2 | 5.4 | 2.7 | 0.2 | 4.6 | 0.5 |
| 019048-A2 FA | 0.66 | 1.2 | NM | NM | NM | 12.4 | 2.4 | 4.9 | 1.8 | 0.1 | 3.9 | 0.3 |
| 019048-A3 FA | 1 | 1.1 | NM | NM | NM | 12.6 | 2.4 | 4.9 | 1.5 | 0.0 | 3.7 | 0.2 |
| 019048-A4 FA | 1.33 | 1.2 | NM | NM | NM | 12.4 | 2.4 | 4.8 | 1.5 | 0.0 | 3.8 | 0.2 |
| 019048-A5 FA | 1.66 | 1.2 | NM | NM | NM | 11.9 | 2.5 | 4.7 | 1.2 | 0.0 | 3.9 | 0.2 |
| 019048-A6 FA | 2 | 1.3 | 48 | 102 | 218 | 12.0 | 3.1 | 3.9 | 1.1 | 0.0 | 4.1 | 0.2 |
| 019048-A7 FA | 2.33 | 1.4 | NM | NM | NM | 12.5 | 2.6 | 4.6 | 1.4 | 0.0 | 4.3 | 0.2 |
| 019048-A8 FA | 2.66 | 1.2 | NM | NM | NM | 12.3 | 2.4 | 4.7 | 1.0 | 0.0 | 3.9 | 0.2 |
| 019048-A9 FA | 3 | 0.9 | NM | NM | NM | 12.4 | 2.5 | 4.6 | 0.9 | 0.0 | 3.8 | 0.2 |

NM: Not measured

Effect of Dispersing Solvents—DCE Crosslinker

The effect of using different inert dispersing solvents was explored (Table 9). It was found that dimethylformamide (DMF, water miscible) provided materials with high chloride binding in SOB, but relatively low chloride selectivity and chloride binding in SIB. The addition of water to DMF reaction mixtures did not affect SIB performance, but significantly decreased chloride selectivity and binding in SOB.

Dry preformed amine polymer beads (3.00 g) were added to a 100 mL round bottom flask equipped with a stir paddle

TABLE 9

Second step crosslinking using DCE as crosslinker in DMF and chlorobenzene (PhCl) as dispersing solvent.

| Unique ID | Solvent | Water:Bead | DCE eq | Swelling | Particle Size (microns) | | | SGF | SIB-Cl | SIB-P | Binding (mmol/g) | | | |
|---|---|---|---|---|---|---|---|---|---|---|---|---|---|---|
| | | | | | D10 | D50 | D90 | | | | SOB-Cl (2 h) | SOB-P (2 h) | SOB-Cl (24 h) | SOB-P (24 h) |
| 019052-A1 FA | DMF | 0 | 0.66 | 1.8 | NM | NM | NM | 12.5 | 2.3 | 4.8 | 4.4 | 0.4 | 4.1 | 0.6 |
| 019052-A2 FA | DMF | 0 | 1.33 | 1.8 | NM | NM | NM | 12.0 | 2.3 | 4.4 | 3.9 | 0.1 | 4.3 | 0.3 |
| 019052-A3 FA | DMF | 0 | 2 | 1.4 | NM | NM | NM | 11.9 | 2.5 | 4.3 | 3.6 | 0.1 | 4.2 | 0.2 |
| 019054-C1 FA | DMF | 1 | 1.33 | 2.1 | NM | NM | NM | 12.0 | 2.3 | 4.5 | 3.2 | 0.8 | 3.1 | 1.0 |
| 019054-C2 FA | DMF | 2 | 1.33 | 2.5 | NM | NM | NM | 11.8 | 2.3 | 4.5 | 2.1 | 1.1 | 2.1 | 1.2 |
| 019054-C3 FA | DMF | 4 | 1.33 | 3.3 | NM | NM | NM | 12.2 | 2.2 | 4.6 | 1.4 | 1.2 | 1.4 | 1.2 |
| 019050-A1 FA | PhCl | 1 | 0.66 | 1.5 | 51 | 114 | 245 | 12.8 | 2.2 | 5.3 | 1.9 | 0.1 | 4.8 | 0.4 |
| 019050-A2 FA | PhCl | 1 | 1.33 | 1.2 | NM | NM | NM | 12.7 | 2.4 | 4.8 | 1.2 | 0.0 | 4.0 | 0.2 |
| 019050-A3 FA | PhCl | 1 | 2 | 1.2 | NM | NM | NM | 12.3 | 2.7 | 4.2 | 1.2 | 0.0 | 4.4 | 0.2 |

NM: Not measured

3) General Procedure for Solvent-Dispersed Crosslinking: DCE/DCP Mixed Crosslinker System Dry preformed amine polymer beads were added to a reactor vessel equipped with a stir paddle and nitrogen gas inlet. To the beads were sequentially added 1,3-dichloropropane (DCP) and 1,2-dichloroethane (DCE). The beads were dispersed in the DCE/DCP solution using mechanical agitation. Water was added directly to the dispersion, and stirring was continued for 30 minutes. After 30 minutes, the flask was immersed into an oil bath held at a chosen temperature. The reaction was held in the oil bath and agitated using mechanical stirring under a nitrogen atmosphere for a chosen amount of time. Methanol was added to the reaction and, solvent was removed by decanting. The beads were then filtered, and then purified by washing (MeOH two times, $H_2O$ once, 1N HCl two times, $H_2O$ once, 1N NaOH three times, and then $H_2O$ until the pH of solution after washing was 7). The purified beads were then dried by lyophilization for 48 hours.

and nitrogen gas inlet. To the beads was added DCP (4.30 mL) and DCE (13.70 mL), resulting in a 1:6 bead to DCE mass/volume ratio). The beads were dispersed in the DCE using mechanical agitation (~150 rpm stirring). Water (3.00 mL, resulting in a 1:1 water to bead mass ratio) was added directly to the dispersion, and stirring was continued for 30 minutes. After 30 minutes, the flask was immersed into an oil bath held at 70° C. The reaction was held in the oil bath and agitated using mechanical stirring under a nitrogen atmosphere for 16 hours. Methanol (60 mL) was added to the reaction and, solvent was removed by decanting. The beads were then filtered, and then purified by washing (MeOH two times, $H_2O$ once, 1N HCl two times, $H_2O$ once, 1N NaOH three times, and then $H_2O$ until the pH of solution after washing was 7). The purified beads were then dried by lyophilization for 48.

DCE/DCP-Dispersed Crosslinking—Effect of DCE Amount

The effect of using different ratios in a mixed crosslinker system wherein the crosslinker(s) is also the dispersing solvent was explored (Table 10). It was found that increasing amounts of DCP led to a decreased selectivity for chloride over phosphate in SIB.

TABLE 10

Effect of using different ratios of DCE and DCP in second step crosslinking. The non-DCE portion of the solution is DCP (i.e. for 84 volume % DCE, the remaining 16 volume % is DCP).

| Unique ID | Vol % DCE | Swelling | Particle Size (microns) | | | SGF | SIB-Cl | SIB-P | Binding (mmol/g) | | | |
|---|---|---|---|---|---|---|---|---|---|---|---|---|
| | | | D10 | D50 | D90 | | | | SOB-Cl (2 h) | SOB-P (2 h) | SOB-Cl (24 h) | SOB-P (24 h) |
| 019031-B1 FA | 100 | 1.1 | NM | NM | NM | 11.3 | 5.2 | 1.3 | 1.5 | 0.0 | 3.7 | 0.1 |
| 019031-B2 FA | 92 | 1.0 | NM | NM | NM | 11.2 | 5.2 | 1.4 | 3.2 | 0.0 | 4.8 | 0.3 |
| 019031-B3 FA | 84 | 0.9 | NM | NM | NM | 11.3 | 4.9 | 1.7 | 2.9 | 0.1 | 4.8 | 0.3 |
| 019031-B4 FA | 76 | 1.0 | NM | NM | NM | 11.3 | 4.8 | 1.8 | 1.9 | 0.0 | 4.6 | 0.1 |
| 019031-B5 FA | 68 | 1.0 | NM | NM | NM | 11.4 | 4.6 | 1.9 | 2.4 | 0.0 | 4.8 | 0.2 |
| 019031-B6 FA | 0 | 1.1 | NM | NM | NM | 11.2 | 3.1 | 3.5 | 3.1 | 0.1 | 4.4 | 0.3 |

NM: Not measured

Specific Example Procedure for Solvent-Dispersed Crosslinking: DCE/DCP Mixed Crosslinker System Unless otherwise noted, the example procedure below is the standard recipe for all of the examples in this section. Specifically, this denotes a 1:6 bead to crosslinker (g/mL) ratio, 1:1 water to bead mass ratio, 70° C. jacket (oil bath) temperature, and 16 hours reaction time.

DCE/DCP-Dispersed Crosslinking—Effect of Water Amount

The effect of water content added to a mixed crosslinker second step crosslinking was studied (Table 11). Under these conditions, the ideal water content was found to be 0.5-1.0 g water/g preformed amine polymer.

TABLE 11

Effect of water content in a mixed crosslinker second step crosslinker reaction.
The example procedure was used, but with 1 g of preformed amine polymer.

| | | | Particle Size (microns) | | | | | | Binding (mmol/g) | |
| | | | | | | | | | SOB-Cl | SOB-P |
| Unique ID | Water:Bead | Swelling | D10 | D50 | D90 | SGF | SIB-Cl | SIB-P | (2 h) | (2 h) |
| --- | --- | --- | --- | --- | --- | --- | --- | --- | --- | --- |
| 019022-A1 FA | 0 | 1.4 | NM | NM | NM | 11.0 | 2.2 | 3.7 | 3.0 | 0.1 |
| 019022-A2 FA | 0.5 | 1.5 | NM | NM | NM | 12.0 | 4.0 | 2.7 | 4.3 | 0.1 |
| 019022-A3 FA | 1 | 1.3 | NM | NM | NM | 11.8 | 3.9 | 2.7 | 5.2 | 0.3 |
| 019022-A4 FA | 1.5 | 1.3 | NM | NM | NM | 11.5 | 3.3 | 3.2 | 4.4 | 0.1 |
| 019022-A5 FA | 2 | 1.0 | NM | NM | NM | 11.2 | 2.8 | 3.5 | 4.3 | 0.1 |
| 019022-A6 FA | 2.5 | 1.3 | NM | NM | NM | 11.4 | 2.4 | 3.9 | 3.8 | 0.1 |

NM: Not measured

Effect of Heptane Amount on Mixed Crosslinker System DCE/DCP

The effect of diluting a mixed DCE/DCP crosslinker system with heptane was explored (Table 12). As the amount of heptane increases (e.g. 80% heptane), the reaction mixture much more closely resembles a crosslinking reaction where the dispersing solvent is an inert solvent (i.e. not a crosslinker). Under these conditions, both selectivity for chloride and total chloride binding in SIB as more heptane was added. Alternatively, neither selectivity nor total chloride binding as measured by SOB were substantially affected up to 40 volume % heptane.

TABLE 12

The effect of diluting a mixed crosslinker system with heptane was studied. The
example procedure was used, but on a 1 g scale of preformed polymer amine, where
the described percentage of the crosslinker was replaced with heptane.

| | Vol % Heptane in | | | | | | | | Binding (mmol/g) | |
| | Dispersing | | Particle Size (microns) | | | | | | SOB-Cl | SOB-P |
| Unique ID | Solvent Mixture | Swelling | D10 | D50 | D90 | SGF | SIB-Cl | SIB-P | (2 h) | (2 h) |
| --- | --- | --- | --- | --- | --- | --- | --- | --- | --- | --- |
| 019026-A1 FA | 0 | 1.1 | NM | NM | NM | 11.6 | 3.8 | 2.7 | 4.2 | 0.1 |
| 019026-A2 FA | 20 | 1.8 | NM | NM | NM | 11.6 | 3.4 | 3.2 | 4.4 | 0.1 |
| 019026-A3 FA | 40 | 1.2 | NM | NM | NM | 12.1 | 3.1 | 3.7 | 4.5 | 0.2 |
| 019026-A4 FA | 60 | 1.5 | NM | NM | NM | 11.8 | 2.9 | 3.8 | 3.6 | 0.1 |
| 019026-A5 FA | 80 | 1.7 | NM | NM | NM | 12.4 | 2.1 | 5.0 | 3.7 | 0.2 |
| 019026-A6 FA | 100 | 3.5 | NM | NM | NM | 13.8 | 1.7 | 6.2 | 0.8 | 1.4 |

NM: Not measured

4) General Procedure for "Non-Dispersed" Reaction Crosslinking—DCP Crosslinker

Dry preformed amine polymer beads were added to a reaction vessel. To the beads was added water. The beads were then stirred gently with a spatula to insure even wetting of the beads by the water. The beads were allowed to equilibrate for 20 minutes. Neat dichloropropane was added to the vial, and the beads were again stirred with a spatula. The vial was heated to 70° C. for 16 hours. Methanol was added to the reaction. The beads were filtered, and then purified by washing (MeOH two times, H₂O once, 1N HCl two times, H₂O once, 1N NaOH three times, and then H₂O until the pH of solution after washing was 7). The purified beads were then dried by lyophilization for 48 hours.

Specific Example Procedure for "Non-Dispersed" Reaction Crosslinking—DCP Crosslinker Unless otherwise noted, the example procedure below is the standard recipe for all of the examples in this section. Specifically, this denotes a 0.68 mol eq DCP (molar ratio of DCP to total nitrogen in preformed amine polymer) ratio, 0.25:1 water to bead mass ratio, 70° C. jacket (heating mantle) temperature, and 16 hours reaction time.

Dry preformed amine polymer beads (0.40 g) were added to a 20 mL scintillation vial. To the beads was added water (0.10 g, resulting in a 0.25:1 water to bead mass ratio). The beads were then stirred gently with a spatula to insure even wetting of the beads by the water. The beads were allowed to equilibrate for 20 minutes. Neat 1,3-dichloropropane (0.46 g, 4.1 mmol, 0.68 mol eq DCP per 1 mol nitrogen in the preformed amine polymer) was added to the vial, and the beads were again stirred with a spatula. The vial was heated to 70° C. for 16 hours. Methanol (10 mL) was added to the reaction. The beads were filtered, and then purified by washing (MeOH two times, H₂O once, 1N HCl two times, H₂O once, 1N NaOH three times, and then H₂O until the pH of solution after washing was 7). The purified beads were then dried by lyophilization for 48 hours.

Effect of Water Amount in Non-Dispersed Crosslinking Reaction

The effect of water added to non-dispersed crosslinking reactions was studied (Table 13). In these experiments, it was found that the water content that yielded the highest selectivity and highest chloride binding as measured in SIB was found to be less than 0.5:1 water to bead ratio.

TABLE 13

Effect of water content in non-dispersed crosslinking reaction

| | | | Particle Size (microns) | | | | | | Binding (mmol/g) | | | |
| | | | | | | | | | SOB-Cl | SOB-P | SOB-Cl | SOB-P |
| Unique ID | Water:Bead | Swelling | D10 | D50 | D90 | SGF | SIB-Cl | SIB-P | (2 h) | (2 h) | (24 h) | (24 h) |
| --- | --- | --- | --- | --- | --- | --- | --- | --- | --- | --- | --- | --- |
| 012020-A1 FA | 0.25 | 0.9 | NM | NM | NM | 11.3 | 3.9 | 1.7 | 3.7 | 0.1 | NM | NM |
| 012020-A2 FA | 0.5 | 0.8 | 67 | 108 | 171 | 11.9 | 3.9 | 2.1 | 4.8 | 0.2 | NM | NM |
| 012020-A3 FA | 0.75 | 1.2 | NM | NM | NM | 11.8 | 3.6 | 2.3 | 4.1 | 0.2 | NM | NM |
| 012020-A4 FA | 1 | 1.1 | NM | NM | NM | 11.3 | 2.9 | 3.2 | 4.1 | 0.1 | NM | NM |
| 012020-A5 FA | 1.25 | 1.3 | NM | NM | NM | 11.9 | 2.6 | 3.7 | 3.8 | 0.1 | NM | NM |
| 012020-A6 FA | 1.5 | 1.4 | NM | NM | NM | 11.3 | 2.4 | 4.0 | 3.6 | 0.3 | NM | NM |

NM: Not measured

Effect of Molar Equivalents of DCP Crosslinker on "Non-Dispersed" Reaction Crosslinking The effect of the amount of DCP added to non-dispersed crosslinking reaction was explored (Table 14). Under these conditions, it was found that the molar equivalents of DCP that yielded the highest selectivity and highest total chloride binding as measured in SIB was found to be less than 0.5:1 water to bead weight ratio.

Dry preformed amine polymer beads (3.00 g) were added to 100 mL round bottom flask with a stir paddle and nitrogen gas inlet. To the beads was added an inert (i.e. not a crosslinker) dispersing solvent (18 mL, resulting in a 1:6 bead to solvent (g/mL) ratio). The beads were dispersed in the solvent using mechanical agitation. Water (3 mL, resulting in a 1:1 water to bead mass ratio) was added directly to the dispersion, and stirring was continued for 30 minutes.

TABLE 14

Effect of molar equivalents of DCP on non-dispersed second step crosslinking.

| | DCP | | Particle Size (microns) | | | | | | Binding (mmol/g) | | | |
| | | | | | | | | | SOB-Cl | SOB-P | SOB-Cl | SOB-P |
| Unique ID | eq | Swelling | D10 | D50 | D90 | SGF | SIB-Cl | SIB-P | (2 h) | (2 h) | (24 h) | (24 h) |
| --- | --- | --- | --- | --- | --- | --- | --- | --- | --- | --- | --- | --- |
| 011053-A1 FA | 0.28 | 1.5 | NM | NM | NM | 12.7 | 2.2 | 5.0 | 1.3 | 1.5 | NM | NM |
| 011053-A2 FA | 0.38 | 1.7 | NM | NM | NM | 12.1 | 2.9 | 3.8 | 5.3 | 0.4 | NM | NM |
| 011053-A3 FA | 0.48 | 1.8 | NM | NM | NM | 12.6 | 2.6 | 4.4 | 5.1 | 0.3 | NM | NM |
| 011053-A4 FA | 0.58 | 1.6 | NM | NM | NM | 11.9 | 3.2 | 4.1 | 5.3 | 0.4 | NM | NM |
| 011053-A5 FA | 0.68 | 1.5 | NM | NM | NM | 12.0 | 3.1 | 3.0 | 5.3 | 0.4 | NM | NM |
| 011053-A6 FA | 0.78 | 1.5 | NM | NM | NM | 11.9 | 2.9 | 2.5 | 5.2 | 0.4 | NM | NM |
| 011053-A8 FA | 0.98 | 1.5 | NM | NM | NM | 11.7 | 2.7 | 2.3 | 4.9 | 0.3 | NM | NM |
| 011053-A9 FA | 1.08 | 1.5 | NM | NM | NM | 11.6 | 3.0 | 2.1 | 4.7 | 0.3 | NM | NM |
| 011053-A10 FA | 1.18 | 1.3 | NM | NM | NM | 11.8 | 3.0 | 2.9 | 4.7 | 0.3 | NM | NM |

NM: Not measured

5) General Procedure for Solvent-Dispersed Crosslinking—DCP Crosslinker

Dry preformed amine polymer beads were added to a reaction vessel equipped with a stir paddle and nitrogen gas inlet. To the beads was added an inert (i.e. not a crosslinker) dispersing solvent. The beads were dispersed in the solvent using mechanical agitation. Water was added directly to the dispersion, and stirring was continued for 30 minutes. Neat 1,3-dichloropropane (DCP) was added to the flask, which was then immersed into an oil bath heated to 70° C. The reaction was heated using mechanical stirring under a nitrogen atmosphere for 16 hours. Methanol was added to the reaction and, solvent was removed by decanting. The beads were then filtered, and then purified by washing (MeOH two times, H$_2$O once, 1N HCl two times, H$_2$O once, 1N NaOH three times, and then H$_2$O until the pH of solution after washing was 7). The purified beads were then dried by lyophilization for 48 hours.

Specific Example Procedure for Solvent-Dispersed Crosslinking—DCP Crosslinker

Unless otherwise noted, the example procedure below is the standard recipe for all of the examples in this section. Specifically, this denotes a 1:6 bead to dispersing solvent (g/mL) ratio, 1:1 water to bead mass ratio, 1 molar equivalent of DCP to nitrogen in preformed amine polymer, 70° C. jacket (heating mantle) temperature, and 16 hours reaction time.

Neat 1,3-dichloropropane (DCP) (5.22 g, 46.2 mmol) was added to the flask, which was then immersed into an oil bath heated to 70° C. The reaction was heated using mechanical stirring under a nitrogen atmosphere for 16 hours. Methanol (100 mL) was added to the reaction and, solvent was removed by decanting. The beads were then filtered, and then purified by washing (MeOH two times, H$_2$O once, 1N HCl two times, H$_2$O once, 1N NaOH three times, and then H$_2$O until the pH of solution after washing was 7). The purified beads were then dried by lyophilization for 48 hours.

Effect of Molar Equivalents Crosslinker on Heptane Dispersed Reaction—DCP Crosslinker The effect of the equivalents of DCP added to an inert solvent-dispersed second step crosslinking was explored (Table 15). In these experiments, 1.0-1.2 molar equivalents of DCP to nitrogen in preformed amine polymer yielded the material with best combination of high selectivity and high total chloride binding as measured in SIB and SOB (Table 15). Effect of water content in DCP—heptane reaction on chloride selectivity. (100 mL vessel, 1 g beads, 1:3 bead to heptane (g/mL) ratio, 1:1 water to bead mass ratio, 70° C., 16 hours, no Dean Stark). The above example procedure was used, but with a 1:3::bead to heptane (g/mL) ratio.

TABLE 15

| Unique ID | DCP mol eq | Swelling | Particle Size (microns) D10 | D50 | D90 | SGF | SIB-Cl | SIB-P | Binding (mmol/g) SOB-Cl (2 h) | SOB-P (2 h) | SOB-Cl (24 h) | SOB-P (24 h) |
|---|---|---|---|---|---|---|---|---|---|---|---|---|
| 011088-A1 FA | 0.2 | 1.4 | NM | NM | NM | 13.5 | 2.3 | 5.9 | 4.2 | 0.3 | NM | NM |
| 011088-A2 FA | 0.4 | 1.7 | NM | NM | NM | 13.2 | 2.4 | 5.8 | 4.7 | 0.2 | NM | NM |
| 011088-A3 FA | 0.6 | 1.3 | NM | NM | NM | 13.0 | 2.5 | 5.3 | 4.7 | 0.2 | NM | NM |
| 011088-A4 FA | 0.8 | 1.7 | NM | NM | NM | 13.0 | 2.5 | 5.3 | 4.7 | 0.3 | NM | NM |
| 011088-A5 FA | 1 | 1.5 | NM | NM | NM | 12.7 | 2.6 | 5.3 | 5.4 | 0.2 | NM | NM |
| 011088-A6 FA | 1.2 | 1.6 | NM | NM | NM | 13.0 | 2.7 | 5.1 | 5.3 | 0.3 | NM | NM |
| 019006-A3 FA | 1.4 | 1.3 | NM | NM | NM | 12.5 | 2.5 | 4.9 | 4.7 | 0.1 | NM | NM |
| 019006-A4 FA | 1.6 | 1.4 | 45 | 71 | 129 | 12.5 | 2.4 | 5.1 | 4.2 | 0.2 | NM | NM |
| 019006-A5 FA | 1.8 | 1.9 | NM | NM | NM | 12.7 | 2.3 | 5.1 | 4.7 | 0.2 | NM | NM |

NM: Not measured

Effect of Water on Heptane Dispersed Reaction—DCP Crosslinker

The effect of the amount of water added to an inert solvent-dispersed second step crosslinking was explored (Table 16). Under these conditions, a water content of less than 0.5:1 water to bead ratio yielded the material with best combination of high selectivity and high total chloride binding as measured in SIB and SOB.

TABLE 16

Effect of water content in DCP-heptane reaction on chloride selectivity. The above example procedure was used, but with one gram of preformed amine polymer, and a 1:3 bead to heptane (g/mL) ratio.

| Unique ID | Water: Bead | Swelling | Particle Size (microns) D10 | D50 | D90 | SGF | SIB-Cl | SIB-P | Binding (mmol/g) SOB-Cl (2 h) | SOB-P (2 h) |
|---|---|---|---|---|---|---|---|---|---|---|
| 011073-A1 FA | 0.25 | 1.2 | NM | NM | NM | 13.9 | 3.5 | 4.1 | 4.8 | 0.2 |
| 011073-A2 FA | 0.5 | 1.2 | 79 | 112 | 165 | 12.4 | 3.7 | 3.7 | 5.3 | 0.2 |
| 011073-A3 FA | 1 | 0.8 | NM | NM | NM | 12.0 | 3.6 | 3.3 | 3.9 | 0.2 |
| 011073-A4 FA | 2 | 1.8 | NM | NM | NM | 12.1 | 2.7 | 4.6 | 3.0 | 0.8 |
| 011073-A5 FA | 3 | 2.2 | NM | NM | NM | 12.1 | 2.7 | 4.3 | 3.3 | 0.5 |
| 011073-A6 FA | 4 | 2.7 | NM | NM | NM | 12.2 | 2.4 | 4.7 | 2.1 | 0.9 |

NM: Not measured

Effect of Dispersing Solvents—DCP Crosslinker

Examples of second step crosslinking of preformed amine polymer using different non-polar dispersing solvents are summarized in Table 17. Reactions with 1-octanol and 2-MeTHF were performed on a 0.4 g of preformed amine polymer in 20 mL scintillation vial with a 1:10 bead to solvent (g/mL) ratio, and 0.68 molar equivalents of DCP relative to 1 mol of nitrogen in preformed amine polymer. Cyclohexane used the example procedure on a 1 g scale using a 1:3 bead to solvent (g/mL) ratio. Chlorobenzene reactions used the example procedure.

TABLE 17

Second step crosslinking using various nonpolar dispersing solvents.

| Unique ID | Solvent | Water: Bead | DCP eq | Swelling | Particle Size (microns) D10 | D50 | D90 | SGF | SIB-Cl | SIB-P | Binding (mmol/g) SOB-Cl (2 h) | SOB-P (2 h) | SOB-Cl (24 h) | SOB-P (24 h) |
|---|---|---|---|---|---|---|---|---|---|---|---|---|---|---|
| 011039-C1 FA | 1-octanol | 1 | 0.68 | 2.7 | NM | NM | NM | 11.1 | 2.0 | 4.4 | 2.8 | 0.7 | NM | NM |
| 011039-C2 FA | 1-octanol | 0.50 | 0.68 | 2.7 | NM | NM | NM | 11.5 | 1.9 | 4.7 | 2.3 | 1.0 | NM | NM |
| 011039-C3 FA | 1-octanol | 0.25 | 0.68 | 3.4 | NM | NM | NM | 11.6 | 1.8 | 4.9 | 1.2 | 1.1 | NM | NM |
| 011039-B1 FA | 2-MeTHF | 1 | 0.68 | 1.3 | NM | NM | NM | 12.1 | 1.9 | 5.1 | 4.6 | 0.3 | NM | NM |

TABLE 17-continued

Second step crosslinking using various nonpolar dispersing solvents.

| | | | | | Particle Size (microns) | | | | | | Binding (mmol/g) | | | |
|---|---|---|---|---|---|---|---|---|---|---|---|---|---|---|
| Unique ID | Solvent | Water: Bead | DCP eq | Swelling | D10 | D50 | D90 | SGF | SIB-Cl | SIB-P | SOB-Cl (2 h) | SOB-P (2 h) | SOB-Cl (24 h) | SOB-P (24 h) |
| 011039-B2 FA | 2-MeTHF | 0.50 | 0.68 | 1.8 | NM | NM | NM | 12.5 | 1.8 | 5.4 | 1.7 | 1.9 | NM | NM |
| 011039-B3 FA | 2-MeTHF | 0.25 | 0.68 | 3.7 | NM | NM | NM | 12.7 | 1.8 | 5.5 | 1.0 | 1.3 | NM | NM |
| 011072-A4 FA | Cyclohexane | 0.25 | 1.36 | 1.2 | 53 | 86 | 146 | 12.8 | 2.6 | 5.0 | 4.4 | 0.2 | NM | NM |
| 011043-A3 FA | Cyclohexane | 1.00 | 1.00 | 5.0 | NM | NM | NM | 13.9 | 2.0 | 6.2 | 1.3 | 2.1 | NM | NM |
| 019050-C1 FA | PhCl | 1.00 | 0.66 | 1.5 | NM | NM | NM | 12.5 | 1.5 | 5.0 | 1.6 | 0.0 | 0.5 | 1.3 |
| 019050-C2 FA | PhCl | 1.00 | 1.33 | 1.6 | NM | NM | NM | 12.0 | 2.5 | 4.7 | 2.7 | 0.0 | 0.5 | 1.3 |
| 019050-C3 FA | PhCl | 1.00 | 2.00 | 1.5 | NM | NM | NM | 11.9 | 2.6 | 4.5 | 2.1 | 0.0 | 0.5 | 1.2 |

NM: Not measured

Water Miscible Dispersing Solvents—DCP Crosslinker

Examples of second step crosslinking of preformed amine polymer using different water-miscible dispersing solvents are summarized in the above example procedure was used, but on a 0.5 g of preformed amine polymer in a scintillation vial, and no water was added to any of the reactions.

TABLE 18

Second step crosslinking with DCP using methanol (MeOH) and ispropanol (IPA) as dispersing solvents.

| | | | | | Particle Size (microns) | | | | | | Binding (mmol/g) | | | |
|---|---|---|---|---|---|---|---|---|---|---|---|---|---|---|
| Unique ID | Solvent | Solvent: Bead (vol) | DCP eq | Swelling | D10 | D50 | D90 | SGF | SIB-Cl | SIB-P | SOB-Cl (2 h) | SOB-P (2 h) | SOB-Cl (24 h) | SOB-P (24 h) |
| 002082-B1 FA | MeOH | 7.0 | 0.01 | 4.6 | NM | NM | NM | 14.1 | 1.8 | 6.0 | 0.6 | 1.2 | NM | NM |
| 002082-B2 FA | MeOH | 7.0 | 0.27 | 3.2 | NM | NM | NM | 13.7 | 1.9 | 5.3 | 1.0 | 1.1 | NM | NM |
| 002082-B3 FA | MeOH | 7.0 | 0.54 | 3.2 | NM | NM | NM | 13.0 | 2.1 | 4.9 | 1.2 | 0.9 | NM | NM |
| 002082-B4 FA | MeOH | 7.0 | 0.68 | 3.2 | NM | NM | NM | 10.8 | 2.2 | 4.7 | 1.4 | 0.8 | NM | NM |
| 012010-A1 FA | MeOH | 1.0 | 0.68 | 1.3 | NM | NM | NM | 11.1 | 2.2 | 3.8 | 3.5 | 0.2 | NM | NM |
| 012010-A2 FA | MeOH | 2.0 | 0.68 | 1.8 | NM | NM | NM | 11.5 | 2.2 | 4.1 | 2.6 | 0.5 | NM | NM |
| 012010-A3 FA | MeOH | 3.0 | 0.68 | 2.7 | NM | NM | NM | 11.8 | 2.1 | 4.3 | 2.0 | 0.6 | NM | NM |
| 012010-A4 FA | MeOH | 4.0 | 0.68 | 2.6 | NM | NM | NM | 11.9 | 2.1 | 4.3 | 1.8 | 0.6 | NM | NM |
| 012010-C3 FA | IPA | 3.0 | 0.68 | 1.9 | NM | NM | NM | 11.7 | 2.2 | 4.0 | 2.7 | 0.5 | NM | NM |

NM: Not measured

Alternative Swelling Agents

In most of the examples in Table 17 (DMF is the exception), water is added to swell the bead and is immiscible with dispersing solvent being used. The effect of using alternative, non-miscible, non-aqueous swelling agents was summarized in Table 19. Reactions using methanol were performed on a 0.5 g of preformed amine polymer in 20 mL scintillation vial. Reactions using DMF followed the above example procedure. All of the conditions tested yielded materials with lower selectivity and total chloride binding than analogous reactions wherein water was the swelling agent of choice.

TABLE 19

Effect of using non-aqueous swelling agents in second step crosslinking.

| | | | | | | | | | | Binding (mmol/g) | | | |
|---|---|---|---|---|---|---|---|---|---|---|---|---|---|
| Unique ID | Dispersal Solvent | Swelling Solvent | Swelling solvent/Bead (v/m) | Xlinker | Xlinker eq | Swelling | SGF | SIB-Cl | SIB-P | SOB-Cl (2 h) | SOB-P (2 h) | SOB-Cl (24 h) | SOB-P (24 h) |
| 012010-B1 FA | Heptane | MeOH | 2.1 | DCP | 0.01 | 1.7 | 11.9 | 2.2 | 4.3 | 2.8 | 0.5 | NM | NM |

TABLE 19-continued

Effect of using non-aqueous swelling agents in second step crosslinking.

| Unique ID | Dispersal Solvent | Swelling Solvent | Swelling solvent/Bead (v/m) | Xlinker | Xlinker eq | Swelling | SGF | Binding (mmol/g) SIB-Cl | SIB-P | SOB-Cl (2 h) | SOB-P (2 h) | SOB-Cl (24 h) | SOB-P (24 h) |
|---|---|---|---|---|---|---|---|---|---|---|---|---|---|
| 012010-B2 FA | Heptane | MeOH | 1.6 | DCP | 0.27 | 1.4 | 11.9 | 2.2 | 4.2 | 3.4 | 0.4 | NM | NM |
| 012010-B3 FA | Heptane | MeOH | 1.4 | DCP | 0.54 | 1.2 | 11.7 | 2.2 | 4.2 | 3.8 | 0.2 | NM | NM |
| 012010-B4 FA | Heptane | MeOH | 1.1 | DCP | 0.68 | 1.1 | 11.9 | 2.3 | 4.2 | 3.5 | 0.1 | NM | NM |
| 015036-A1* FA | Heptane | DMF | 0.1 | DCE | 0.68 | 3.0 | 15.6 | 2.6 | 6.0 | 1.7 | 0.3 | 3.7 | 0.5 |
| 015036-A2* FA | Heptane | DMF | 0.2 | DCE | 0.68 | 2.2 | 15.5 | 2.9 | 6.0 | 1.3 | 0.2 | 2.7 | 0.3 |
| 015036-A3* FA | Heptane | DMF | 0.3 | DCE | 0.68 | 2.2 | 15.5 | 3.0 | 5.7 | 1.4 | 0.2 | 3.1 | 0.3 |

NM: Not measured;
*Source beads made from PAH/DCE as described in the example "SPECIFIC EXAMPLE FOR PREPARATION OF POLYALLYAMINE/DCE PREFORMED AMINE POLYMER"

6) General Procedure for Ammonium Hydroxide Treatment after Postcrosslinking

The general procedure can be performed with beads that have been purified by washing and dried by lyophilization, or with beads that have been partially purified by washing. In the latter case, treatment with ammonium hydroxide is typically performed after the three methanol washes, and normal purification by washing is resumed by washing with 1N HCl.

To post-crosslinked beads (dry or in the process of washing) was added an aqueous $NH_4OH$ solution that had been pre-heated to the desired reaction temperature. The beads were dispersed in the solution using mechanical stirring, and heated in the ammonium hydroxide solution for a chosen amount of time. After completion of the treatment, the beads were filtered, and then purified by washing (1N HCl two times, $H_2O$ once, 1N NaOH three times, and then $H_2O$ until the pH of solution after washing was 7). The purified beads were then dried by lyophilization for 48 hours.

Specific Example Procedure for Ammonium Hydroxide Treatment after Postcrosslinking A secondary crosslinking was performed by reacting preformed amine polymer (100 g dry beads) with DCE in the presence of water as a swelling agent. The beads were filtered after reaction, and washed three times with methanol. The wet beads were transferred to a 2000 mL round-bottomed flask, equipped with a nitrogen inlet and overhead stirrer. To the beads was added to 1000 mL (10:1::1N $NH_4OH$:dry beads (ml/g)) of a 1N $NH_4OH$ solution pre-heated to 70° C. The round-bottomed flask was immersed into an oil bath heated to 75° C., and the beads were stirred under a nitrogen atmosphere for four hours. The beads were filtered, and then purified by washing (1N HCl two times, $H_2O$ once, 1N NaOH three times, and then $H_2O$ until the pH of solution after washing was 7). The purified beads were then dried by lyophilization for 48 hours.

Ammonia Treatment as Part of Washing Protocol

Ammonia treatment of postcrosslinked polymer was performed according to the above example procedure, but with 10 g of beads where 0.5 g samples were taken, and the jacket temperature was 75° C. Ammonia treatment was performed as part of the washing, after the methanol washes, and before 1N HCl wash. The treatment time was varied between 0 and 24 hours and data are summarized in Table 20.

TABLE 20

| Unique ID | Time (h) | Swelling | Particle Size (microns) D10 | D50 | D90 | SGF | Binding (mmol/g) SIB-Cl | SIB-P | SOB-Cl (2 h) | SOB-P (2 h) | SOB-Cl (24 h) | SOB-P (24 h) |
|---|---|---|---|---|---|---|---|---|---|---|---|---|
| 030015-A1 FA | 0 | 1.4 | NM | NM | NM | 10.9 | 4.7 | 1.9 | 0.4 | 0.0 | 2.7 | 0.0 |
| 030015-A2 FA | 1 | 1.3 | NM | NM | NM | 11.4 | 4.7 | 2.0 | 0.7 | 0.0 | 3.9 | 0.1 |
| 030015-A3 FA | 2 | 1.3 | NM | NM | NM | 11.0 | 4.6 | 1.9 | 0.7 | 0.0 | 3.7 | 0.0 |
| 030015-A4 FA | 3 | 1.4 | NM | NM | NM | 11.1 | 4.7 | 2.0 | 0.8 | 0.0 | 4.1 | 0.1 |
| 030015-A5 FA | 4 | 1.2 | NM | NM | NM | 11.3 | 4.6 | 1.9 | 1.1 | 0.0 | 4.5 | 0.1 |
| 030015-A6 FA | 6 | 1.2 | NM | NM | NM | 11.1 | 4.7 | 2.0 | 1.1 | 0.0 | 4.5 | 0.1 |
| 030015-A7 FA | 24 | 1.2 | NM | NM | NM | 11.4 | 4.8 | 1.8 | 1.5 | 0.0 | 4.8 | 0.2 |

NM: Not measured

Ammonia Treatment of Postcrosslinked Purified and Dried Beads

Ammonia treatment of postcrosslinked polymer was performed according to the above example procedure except for treatment performed after the postcrosslinked polymer is purified and dried (Table 21).

TABLE 21

| | | Particle Size (microns) | | | | Binding (mmol/g) | | | | | |
|---|---|---|---|---|---|---|---|---|---|---|---|
| Unique ID | Swelling | D10 | D50 | D90 | SGF | SIB-Cl | SIB-P | SOB-Cl (2 h) | SOB-P (2 h) | SOB-Cl (24 h) | SOB-P (24 h) |
| 019092-A1 FA (untreated) | 1.4 | 44 | 72 | 112 | 11.4 | 4.6 | 1.9 | 0.5 | 0.0 | 2.5 | 0.0 |
| 019092-A2 FA (treated) | 1.3 | NM | NM | NM | 11.2 | 4.5 | 2.1 | 1.0 | 0.0 | 4.2 | 0.1 |

NM: Not measured

7) Example of Effect of Heating of Postcrosslinked Polymer During the Drying Step on Chloride Selectivity in SOB Preformed amine polymer beads were prepared as follows. Two aqueous stock solutions of monomer (50% w/w) were prepared by independently dissolving allylamine hydrochloride (93.9 g) and DAPDA (97.7) in water. The 3 L Ace Glass jacketed reactor, equipped with an overhead stirrer (stirring at 180 rpm), addition funnel, temperature probe, and nitrogen inlet, was charged with Stepan Sulf-100 (25.7 g) dissolved in a heptane/chlorobenzene solution (26/74 v/v, 2571.4 g), followed by the aqueous stock solutions, and additional water (126.7 g). In a separate vessel, a 15 wt % solution of V-50 (19.4 g) in water was prepared and added to the addition funnel. The two mixtures were independently sparged with nitrogen while the reaction vessel was brought to 67° C. (~1 h, $T_{internal}$>60° C.). Under inert atmosphere, the initiator solution was added to the reaction mixture, and subsequently heated at 67° C. for 16 h. A second aliquot of initiator solution (equal to the first) and the reaction mixture, were sparged with nitrogen for 30 minutes and combined before increasing the temperature to 115° C. for a final dehydration step (Dean-Stark). The reaction was held at 115° C. until water stopped collecting in the Dean-Stark trap (6 h, >90% of total water removed, $T_{internal}$>99° C.). The reaction was allowed to cool to room temperature, and the stirring stopped to allow the beads to settle. The organic phase was siphoned from the bead cake and methanol was added (1 L) to re-suspend the beads (with stirring, 150 rpm). The organic solvent removal step was repeated twice. The beads were allowed to drain into a 2 L media bottle and the reactor was rinsed with methanol (500 mL). The beads were purified by washing (MeOH two times, H2O once, 1N HCl two times, H2O once, 1N NaOH three times, and then H2O until the pH of solution after washing was 7), and were dried by lyophilization.

The preformed amine polymer beads were subjected to a second step of crosslinking according to the general procedure for solvent-dispersed crosslinking: DCE, using the specific example procedure described above scaled to 10 g of preformed amine polymer beads. At the end of the washing steps, the resulting polymers were again either dried in a lyophilizer, or in a conventional oven at 60° C. for 40 hours. The oven dried polymer had similar binding in SIB, but improved chloride binding in SOB, compared to the lyophilized polymer (Table 22).

TABLE 22

| | | Particle Size (microns) | | | | | Binding (mmol/g) | | | | | |
|---|---|---|---|---|---|---|---|---|---|---|---|---|
| Unique ID | Description | D10 | D50 | D90 | Swelling | SGF | SIB-Cl | SIB-P | SOB-Cl (2 h) | SOB-P (2 h) | SOB-Cl (24 h) | SOB-P (24 h) |
| 026001-A1 | Preformed amine polymer | 67 | 110 | 173 | 4.9 | 13.7 | 2.2 | 6.2 | 1.1 | 1.4 | 0.6 | 1.3 |
| 027076-A1 | Post-crosslinked polymer, dried by lyophilization | 48 | 74 | 109 | 1.3 | 10.6 | 5.0 | 1.1 | 1.1 | 0.1 | 4.1 | 0.1 |
| 027076-A2 | Post-crosslinked polymer, dried in oven | 51 | 77 | 112 | 0.8 | 10.3 | 4.8 | 1.1 | 2.4 | 0.1 | 4.3 | 0.3 |

8) Binding Kinetics Examples

Selected polymers were evaluated in SGF, SIB and SOB assays (described elsewhere), with samples taken at multiple time points (1, 2, 4, and 24 hours of incubation) to evaluate anion binding kinetics under these assay conditions. The results are shown in Tables 23, 24 and 25, below, which represent three sets of experiments. These polymers were synthesized by subjecting a preformed amine polymer, prepared using the general method for preparing preformed amine polymer described above, to a second step of crosslinking according to the "general procedure for solvent-dispersed crosslinking: DCE" described above.

TABLE 23

SGF Binding Kinetics

| Polymer ID | Composite description | Cross-linker | Dispersant | Water/bead ratio | Cl binding (mmol/g) 1 h | 2 h | 4 h | 24 h | Cl saturation at 1 h (% of 24 h value) |
|---|---|---|---|---|---|---|---|---|---|
| Sevelamer | Polyallylamine/ECH | ECH | n/a | n/a | 15.3 | 15.4 | 15.5 | 15.6 | 98 |
| Bix-30 | C4B3BTA/ECH | ECH | n/a | n/a | 13.7 | 13.7 | 13.8 | 14.0 | 98 |
| 019070-A1 | AAH/30% DAPDA/DCE | DCE | DCE | 0.05 | 11.0 | 11.3 | 11.2 | 11.5 | 95 |
| 019070-A2 | AAH/30% DAPDA/DCE | DCE | DCE | 0.15 | 7.8 | 9.1 | 10.2 | 11.3 | 69 |
| 019070-A3 | AAH/30% DAPDA/DCE | DCE | DCE | 0.25 | 8.1 | 9.0 | 9.6 | 11.2 | 72 |
| 019070-A4 | AAH/30% DAPDA/DCE | DCE | DCE | 0.35 | 8.0 | 8.9 | 9.6 | 11.1 | 72 |
| 019070-A5 | AAH/30% DAPDA/DCE | DCE | DCE | 0.45 | 9.5 | 10.2 | 10.7 | 11.6 | 82 |
| 019068-A1 | AAH/30% DAPDA/DCE | DCE | DCE | 0.5 | 10.4 | 11.0 | 11.4 | 12.0 | 87 |
| 019063-A2 | AAH/30% DAPDA/DCE | DCE | DCE | 1 | 12.1 | 12.1 | 12.1 | 12.3 | 98 | n/a: not applicable

TABLE 24

SIB Binding Kinetics

| Polymer ID | Composite description | Cross-linker | Dispersant | Water/bead ratio | Anion binding (mmol/g) | 1 h | 2 h | 4 h | 24 h |
|---|---|---|---|---|---|---|---|---|---|
| Sevelamer | Polyallylamine/ECH | ECH | n/a | n/a | Cl | 1.6 | 1.6 | 1.7 | 1.8 |
|  |  |  |  |  | PO4 | 6.8 | 6.9 | 6.9 | 7.1 |
| Bix-30 | C4B3BTA/ECH | ECH | n/a | n/a | Cl | 1.7 | 1.7 | 1.7 | 1.9 |
|  |  |  |  |  | PO4 | 5.2 | 5.2 | 5.3 | 5.4 |
| 019070-A1 | AAH/30% DAPDA/DCE | DCE | DCE | 0.05 | Cl | 2.4 | 2.6 | 2.4 | 2.5 |
|  |  |  |  |  | PO4 | 3.5 | 3.7 | 3.7 | 3.8 |
| 019070-A2 | AAH/30% DAPDA/DCE | DCE | DCE | 0.15 | Cl | 3.3 | 3.0 | 2.3 | 2.3 |
|  |  |  |  |  | PO4 | 2.2 | 3.2 | 3.6 | 3.8 |
| 019070-A3 | AAH/30% DAPDA/DCE | DCE | DCE | 0.25 | Cl | 4.4 | 4.2 | 3.1 | 2.2 |
|  |  |  |  |  | PO4 | 1.3 | 2.2 | 2.9 | 4.1 |
| 019070-A4 | AAH/30% DAPDA/DCE | DCE | DCE | 0.35 | Cl | 4.6 | 4.5 | 3.4 | 2.3 |
|  |  |  |  |  | PO4 | 1.0 | 1.9 | 2.5 | 4.0 |
| 019070-A5 | AAH/30% DAPDA/DCE | DCE | DCE | 0.45 | Cl | 3.9 | 3.2 | 2.5 | 2.3 |
|  |  |  |  |  | PO4 | 2.3 | 3.2 | 3.8 | 4.2 |
| 019068-A1* | AAH/30% DAPDA/DCE | DCE | DCE | 0.5 | Cl | 3.5 | 2.8 | 2.5 | 2.6 |
|  |  |  |  |  | PO4 | 2.9 | 3.7 | 4.0 | 4.2 |
| 019063-A2 | AAH/30% DAPDA/DCE | DCE | DCE | 1 | Cl | 2.2 | 2.2 | 2.2 | 2.4 |
|  |  |  |  |  | PO4 | 4.4 | 4.5 | 4.5 | 4.7 | n/a: not applicable

TABLE 25

SOB Binding Kinetics

| Polymer ID | Composite description | Cross-linker | Dispersant | Water/bead ratio | Anion binding (mmol/g) | 1 h | 2 h | 4 h | 24 h |
|---|---|---|---|---|---|---|---|---|---|
| Sevelamer | Polyallylamine/ECH | ECH | n/a | n/a | Cl | 0.5 | 0.4 | 0.3 | 0.4 |
|  |  |  |  |  | PO4 | 1.4 | 1.2 | 1.2 | 1.1 |
|  |  |  |  |  | Citrate | 0.5 | 0.5 | 0.4 | 0.4 |
|  |  |  |  |  | Taurocholate | 1.7 | 1.7 | 1.7 | 1.7 |
| Bix-30 | C4B3BTA/ECH | ECH | n/a | n/a | Cl | 0.8 | 0.6 | 0.6 | 0.5 |
|  |  |  |  |  | PO4 | 1.3 | 1.2 | 1.2 | 1.1 |
|  |  |  |  |  | Citrate | 0.5 | 0.5 | 0.5 | 0.5 |
|  |  |  |  |  | Taurocholate | 0.6 | 0.7 | 0.8 | 1.0 |
| 019070-A1 | AAH/30% DAPDA/DCE | DCE | DCE | 0.05 | Cl | 1.2 | 1.7 | 2.0 | 3.1 |
|  |  |  |  |  | PO4 | 0.0 | 0.1 | 0.1 | 0.1 |
|  |  |  |  |  | Citrate | 0.0 | 0.0 | 0.0 | 0.0 |
|  |  |  |  |  | Taurocholate | 0.0 | 0.0 | 0.0 | 0.1 |
| 019070-A2 | AAH/30% DAPDA/DCE | DCE | DCE | 0.15 | Cl | 0.6 | 0.7 | 0.9 | 1.7 |
|  |  |  |  |  | PO4 | 0.1 | 0.0 | 0.0 | 0.1 |
|  |  |  |  |  | Citrate | 0.0 | 0.0 | 0.0 | 0.0 |
|  |  |  |  |  | Taurocholate | 0.0 | 0.0 | 0.0 | 0.0 |

TABLE 25-continued

SOB Binding Kinetics

| Polymer ID | Composite description | Cross-linker | Dispersant | Water/bead ratio | Anion binding (mmol/g) | 1 h | 2 h | 4 h | 24 h |
|---|---|---|---|---|---|---|---|---|---|
| 019070-A3 | AAH/30% DAPDA/DCE | DCE | DCE | 0.25 | Cl | 0.7 | 0.6 | 0.8 | 2.2 |
| | | | | | PO4 | 0.1 | 0.0 | 0.0 | 0.1 |
| | | | | | Acetate | 2.4 | 1.9 | 1.9 | 1.2 |
| | | | | | Citrate | 0.0 | 0.0 | 0.0 | 0.0 |
| | | | | | Taurocholate | 0.0 | 0.0 | 0.0 | 0.0 |
| 019070-A4 | AAH/30% DAPDA/DCE | DCE | DCE | 0.35 | Cl | 0.8 | 0.8 | 1.1 | 2.7 |
| | | | | | PO4 | 0.1 | 0.0 | 0.0 | 0.1 |
| | | | | | Citrate | 0.0 | 0.0 | 0.0 | 0.0 |
| | | | | | Taurocholate | 0.0 | 0.0 | 0.0 | 0.0 |
| 019070-A5 | AAH/30% DAPDA/DCE | DCE | DCE | 0.45 | Cl | 0.9 | 0.9 | 1.1 | 3.0 |
| | | | | | PO4 | 0.1 | 0.0 | 0.0 | 0.1 |
| | | | | | Citrate | 0.0 | 0.0 | 0.0 | 0.0 |
| | | | | | Taurocholate | 0.0 | 0.0 | 0.0 | 0.0 |
| 019068-A1* | AAH/30% DAPDA/DCE | DCE | DCE | 0.5 | Cl | 0.9 | 1.2 | 2.0 | 4.6 |
| | | | | | PO4 | 0.0 | 0.0 | 0.0 | 0.1 |
| | | | | | Citrate | 0.0 | 0.0 | 0.0 | 0.0 |
| | | | | | Taurocholate | 0.0 | 0.0 | 0.0 | 0.0 |
| 019063-A2 | AAH/30% DAPDA/DCE | DCE | DCE | 1 | Cl | 2.6 | 2.7 | 3.1 | 3.9 |
| | | | | | PO4 | 0.1 | 0.1 | 0.1 | 0.2 |
| | | | | | Citrate | 0.0 | 0.0 | 0.0 | 0.0 |
| | | | | | Taurocholate | 0.0 | 0.0 | 0.0 | 0.0 | n/a: not applicable

Equilibrium Chloride Binding Measurement of Amine Polymers

The pH dependent equilibrium chloride binding of selected polymers was measured using an autotitrator. Polymers at a starting concentration of 4 mg/ml were incubated in a solution containing 100 mM sodium chloride for 16 hours at room temperature. The samples were continuously stirred and were maintained at a set pH during the entire length of incubation via slow addition of 0.1 N HCl solution by the autotitrator. After incubation, 400 microliters of the sample was removed, filtered, diluted if needed and then assayed for chloride content using ion chromatography. For each tested polymer, chloride binding is calculated using the following equation:

$$\frac{\{[Cl]_{start} + [Cl]_{HCl}\} - [Cl]_{final}}{\text{Concentration (mg/ml)}} \times \text{Dilution factor}$$

Where, $[Cl]_{start}$ is the starting chloride concentration in the incubation solution (mM), $[Cl]_{start}$ is the chloride added via autotitration using 0.1 N HCl (mM), and concentration (mg/ml) is the final concentration of the polymer in solution (after accounting for the volume of 0.1N HCl added).

Figure 2:
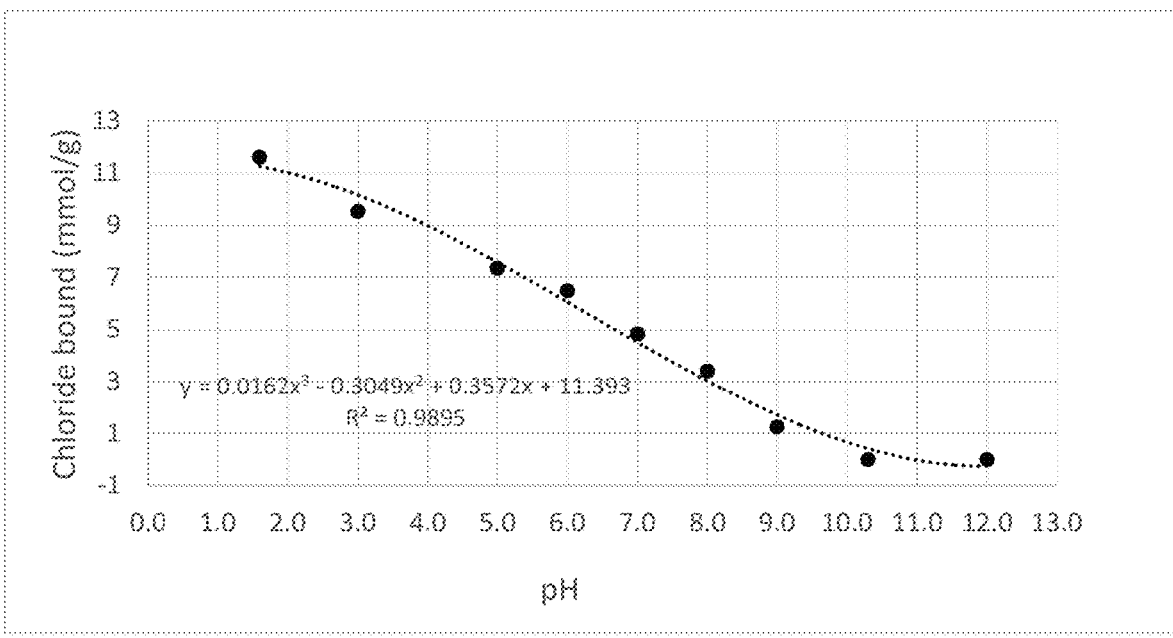
FIG. 2 is a plot of equilibrium chloride binding by (example 019067-A2) at different pH levels as described more fully in the Examples.
Figure 3:
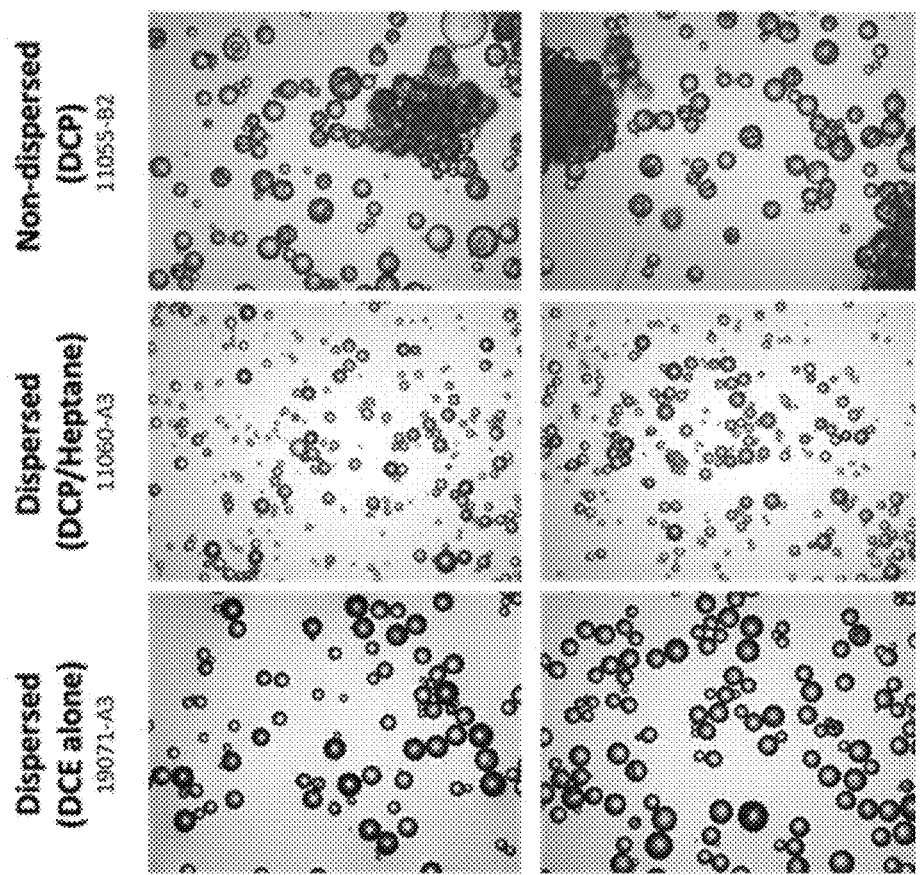
FIG. 3 is a series of photographs of particulate amine polymers demonstrating a lack of aggregation in solvent-dispersed Step 2 reactions compared to aggregation in a non-dispersed Step 2 reaction as described more fully in the Examples.
Figure 4:
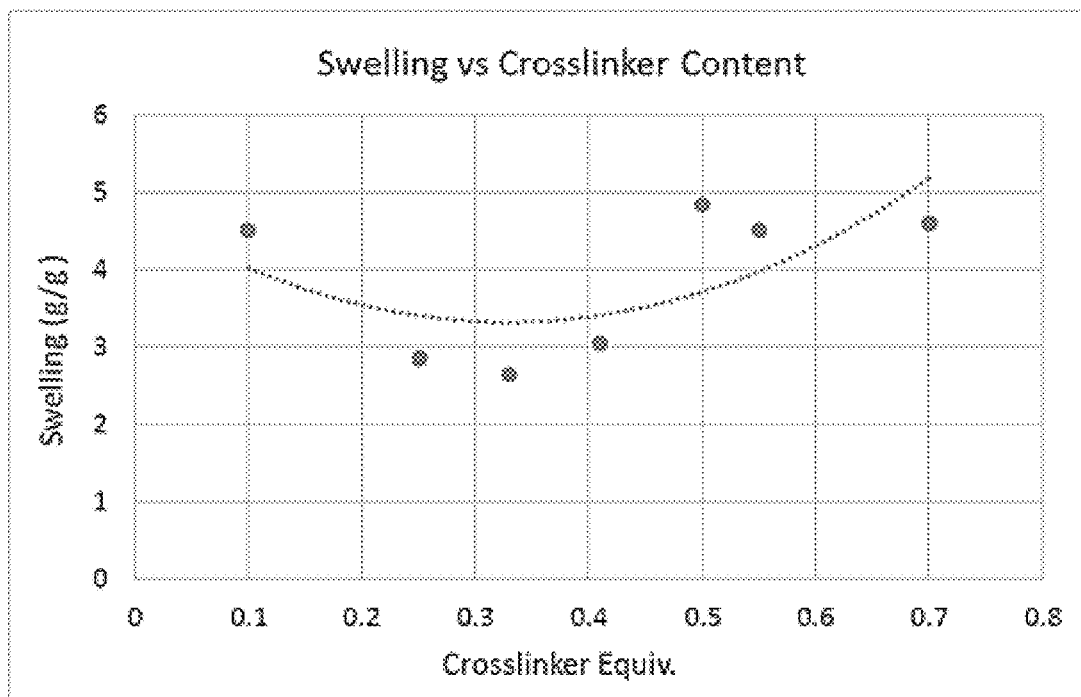
FIG. 4 is a plot of swelling of preformed amine polymer against amount of crosslinker used in the first polymerization/crosslinking step in accordance with one embodiment of the present disclosure.

Equilibrium chloride binding was measure using the above described method at pH ranging from 1.5 to 12. A plot of chloride binding vs pH allows the construction of a titration curve and determination of average pKa of a given polymer (FIG. 3). The example below shows equilibrium chloride binding (Table 26) and a plot of chloride binding vs pH for example 019067-A2 in the free amine form, measured using above described procedure (see FIG. 2).

The average pKa of this example was determined to be 6.15. Data was fitted using a fourth degree polynomial fit. Equilibrium chloride binding at various pH values were calculated from the equation obtained by the curve fitting and the pH value at which half of the maximum binding was observed was considered as the average pKa of the polymers.

TABLE 26

Measured equilibrium chloride binding at different pH

Sample: 019067-A2

| pH | 1.6 | 3.0 | 5.0 | 6.0 | 7.0 | 8.0 | 9.0 | 10.3 | 12.0 |
|---|---|---|---|---|---|---|---|---|---|
| Equilibrium chloride bound (mmol/g) | 11.6 | 9.53 | 7.35 | 6.49 | 4.83 | 3.4 | 1.25 | 0 | 0 |

9) GICTA Data Example

Polymers described in the table below were synthesized by subjecting a preformed amine polymer, prepared using the general method for preparing preformed amine polymer described above, to a second step of crosslinking according to the "general procedure for solvent-dispersed crosslinking—DCE" or "general procedure for solvent-dispersed crosslinking DCE/DCP Mixed Crosslinker System" described above. For 019067-A2, water removal was, carried out by applying addition dean-stark step after the reaction. The resulting polymers were evaluated using the GICTA assay. The results are described in Table 27.

TABLE 27

| Sample ID | Monomer | Cross-linker | Equivalents Crosslinker | Water/Bead ratio | Dispersant | Scale | GICTA assay data SGF 1 hr-Cl (mmol/g) | SOB Cl- (mmol/g) | Ret-Cl (mmol/g) | NaOH elution-Cl (mmol/g) | Cl retention (%) NaOH elution/SGF |
|---|---|---|---|---|---|---|---|---|---|---|---|
| 014003-A1 | Sevelamer FA | | | | | | 15.5 | 3.9 | 2.5 | 0.0 | 8 |
| 010080-A1 | C4A3BTA | ECH | 2.3 | NA | NA | NA | 13.4 | 5.5 | 1.4 | 0.2 | 6 |
| 019001-A1 | AAH/30% DAPDA Bead | DCE | 3 | 1 | DCE | 1 | 9.9 | 8.1 | 5.7 | 4.3 | 51 |
| 019033-A4 | AAH/30% DAPDA Bead | DCP/DCE | 1/3.9 | 0.5 | DCE/DCP | 3 | 9.4 | 7.4 | 6.1 | 4.5 | 56 |
| 019014-A2 | AAH/30% DAPDA Bead | DCP/DCE | 0.5/4.5 | 1 | DCP/DCE | 1 | 9.7 | 8.2 | 6.6 | 4.9 | 59 |
| 019036-A1 | AAH/30% DAPDA Bead | DCP/DCE | 1/3.9 | 1 | DCE/DCP | 3 | 11.8 | 8.1 | 6.0 | 4.3 | 43 |
| 019063-C1 | AAH/30% DAPDA Bead | DCE | 5.2 | 1 | DCE | 1 | 10.0 | 7.4 | 4.0 | 2.6 | 33 |
| 019064-C2 | AAH/30% DAPDA Bead | DCE | 5.2 | 1 | DCE | 1 | 10.0 | 7.8 | 3.6 | 2.5 | 30 |
| 019067-A2 | AAH/30% DAPDA Bead | DCE | 5.2 | 0.25 | DCE | 10 | 9.3 | 7.7 | 5.4 | 3.8 | 49 |
| 019070-A4 | AAH/30% DAPDA Bead | DCE | 5.2 | 0.35 | DCE | 15 | 8.4 | 7.2 | 4.5 | 3.2 | 46 |

NA: Not Applicable

10) Examples of Preparation of Polymers from Polyallylamine

Specific Example for Preparation of Polyallyamine/DCE Preformed Amine Polymer

To a 500 mL round bottom flask, polyallylamine (14 g, 15 kDa), and water (28 mL) were added. The solution was purged with nitrogen and stirred overhead at 220 rpm for 1 hour to completely dissolve the polymer. Next, 30 wt % aqueous NaOH (7 mL) was added and stirred for 5 minutes. A premade solution of DCE (175 mL), n-heptane (105 mL), and Span 80 (2.8 g) was added to the aqueous solution. The solution was heated to 70° C. and stirred for 16 hours. The Dean-Stark step was initiated by adding cyclohexane (100 mL) and heating the reaction to 95° C. to remove the water (>90%) from the beads (Table 28).

Specific Example for Polyallyamine/DCP Preformed Amine Polymer

To a 100 mL round bottom flask, DCP (31 mL), n-heptane (19 mL), and Span 80 (0.5 g) were added. A separate aqueous stock solution of polyallylamine (2.3 g, 900 kDa), Aq NaOH (1 mL, 30 wt %), and water (4 mL) was prepared. The aqueous stock solution was added to the organic solution in the round bottom flask. The solution was purged with nitrogen for 15 minutes, heated to 70° C., and stirred for 16 hours. Methanol (30 mL) was added to the reaction mixture and the organic solvent removed by decanting. The resulting beads were purified and isolated by washing the beads using, MeOH, HCl, aqueous sodium hydroxide, and water. The beads were dried using lyophilization techniques (Table 28).

Specific Example for Polyallyamine/Dichloro-2-Propanol Preformed Amine Polymer

Polyallylamine 15 kDa (3.0 g) and water (9.05 g) were dissolved in a conical flask. Sodium hydroxide (0.71 g) was added to the solution and the mixture was stirred for 30 minutes. To a 100 mL round bottom flask, equipped side arm and overhead stirrer was added 0.38 g of sorbitan sesquioleate and 37.9 g of toluene. The overhead stirrer was switched on to provide agitation to the reaction solution. Dichloropropanol (0.41 g) was added directly to the polyallylamine solution while stirring. The resulting aqueous polyallylamine solution was added to the toluene solution in the 100 mL flask. The reaction was heated to 50° C. for 16 hours. After this time the reaction was heated to 80° C. for hour and then cooled to room temperature. The resulting beads were purified and isolated by washing the beads using, MeOH, HCl, aqueous sodium hydroxide, and water. The beads were dried using lyophilization techniques (Table 28).

Specific Example for Polyallyamine/Epichlorohydrin Preformed Amine Polymer

Polyallylamine 15 kDa (3.1 g) and water (9.35 g) were dissolved in a conical flask. Sodium hydroxide (0.73 g) was added to the solution and the mixture was stirred for 30 minutes. To a 100 mL round bottom flask, equipped side arm and overhead stirrer was added 0.31 g of sorbitan trioleate and 39.25 g of toluene. The overhead stirrer was switched on to provide agitation to the reaction solution. The aqueous polyallylamine solution was added to the toluene solution in the 100 mL flask. Epichlorohydrin (0.30 g) was added directly to the reaction mixture using a syringe. The reaction was heated to 50° C. for 16 hours. After this time the reaction was heated to 80° C. for 1 hour and then cooled to room temperature. The resulting beads were purified and isolated by washing the beads using, MeOH, HCl, aqueous sodium hydroxide, and water. The beads were dried using lyophilization techniques.

Preformed amine polymer beads can be formed by the reaction of a soluble (un-crosslinked) polymer with a crosslinker. In this experiment, the soluble polymer was linear polyallylamine and was crosslinked with bifunctional crosslinkers. Aqueous-soluble crosslinkers may selected for these polymerizations, as the crosslinking reaction occurs in the aqueous phase. However, there are aqueous-immiscible crosslinkers (e.g. DCE and DCP) that can yield higher capacity polyamine beads due to their smaller molecular weight. In order to sufficiently crosslink linear polyallylamine, aqueous-immiscible crosslinkers were used as a crosslinking cosolvent during bead formation. The polyamine beads formed with aqueous-immiscible crosslinkers yielded higher total chloride binding capacity (as described by SGF) than those made with aqueous-miscible crosslinkers (Table 28).

Example of Postcrosslinking of a Preformed Amine Polymer without Isolation of the Preformed Amine Polymer Polyallylamine hydrochloride is dissolved in water. Sodium hydroxide is added to partially deprotonate the polyallylamine hydrochloride (preferably 50 mol %). The

TABLE 28

| Unique ID | Cross linker | Swelling | SGF | SIB-Cl | SIB-P | SOB-Cl (2 h) | SOB-P (2 h) | SOB-Cl (24 h) | SOB-P (24 h) |
|---|---|---|---|---|---|---|---|---|---|
| 018013-A1 FA | DCE | 6.1 | 16.9 | 2.2 | 7.3 | 0.6 | 1.9 | NM | NM |
| 015026-A1 FA | DCE | 5.9 | 16.6 | 2.0 | 7.2 | 0.4 | 1.5 | 0.3 | 1.4 |
| 018001-A2b FA | DCP | 4.6 | 15.9 | 1.9 | 7.1 | 0.8 | 1.9 | NM | NM |
| 002054-A3 FA | DC2OH | 6.5 | 14.3 | 1.6 | 7.1 | NM | NM | NM | NM |
| 011021-A6 FA | DC2OH | 3.0 | 14.3 | 1.5 | 6.1 | 1.2 | 2.0 | NM | NM |
| 002050-A1 FA | ECH | 8.3 | 14.4 | 1.7 | 7.0 | NM | NM | NM | NM |
| 002050-A2 FA | ECH | 8.8 | 14.2 | 1.6 | 7.1 | NM | NM | NM | NM |

SGF, SIB and SOB values expressed in mmol/g dry bead;
NM: not measured

Specific Example of Postcrosslinking of PAH/DCE Preformed Amine Polymer

To a 100 mL round bottom flask, preformed polyamine beads (0.5 g) and DCE (3 mL) were added. The solution was purged with nitrogen and stirred overhead for 5 minutes. Water was added (0.5 g) and the solution was stirred for 20 minutes. The reaction mixture was then heated to 70° C. and stirred for 16 hours. Methanol (5 mL) was added to the reaction mixture, the stirring was stopped, and the solvent decanted off (Table 29).

Specific Example of Postcrosslinking of Polyallyamine/Dichloro-2-Propanol Preformed Amine Polymer To a 20 mL vial, preformed polyamine beads (0.4 g) and methanol (2.8 g) were added. DCP was added (0.5 g for 002064-B4 FA, 0.7 g for 002064-B5 FA). The reaction mixture was then heated to 70° C. and stirred for 16 hours. The temperature was raised to 80° C. for 1 h. Methanol (5 mL) was added to the reaction mixture and the solvent decanted off.

Polyamine beads formed with linear polyallylamine and aqueous-immiscible crosslinkers also have high chloride binding capacity (by SGF) after a second step crosslinking. Furthermore, beads formed with aqueous-immiscible crosslinkers can achieve high SIB-Cl values (>6 mmol/g) after a second step crosslinking (Table 29).

aqueous phase generated has a water content (by weight) 2.42 times the weight of the polyallyamine hydrochloride. A baffled 3 necked flask, equipped with an overhead mechanical stirrer, nitrogen inlet, Dean Stark apparatus with condenser is set up to conduct the suspension reaction. A dichloroethane heptane mixture is prepared, such that there is 3 times by weight dichloroethane to heptane. This dichloroethane, heptane mixed solvent is added to the baffled 3 neck flask. The aqueous solution is added to the flask, such that the ratio is 6.4 dichloroethane to one water by volume. The reaction mixture is stirred and heated to 70° C. for 16 hours. At this point beads are formed. The Dean Stark step is initiated to remove all the water from the beads, while returning the dichloromethane and heptane back to the reaction mixture. Once no more water is removed the reaction mixture is cooled. Water and sodium hydroxide is added back to the reaction mixture at a ratio of 0.25 water to polyallyamine and up to 1 equivalent of sodium hydroxide per chloride on allylamine added (both calculated from polyallyamine hydrochloride added at the beginning of the reaction). The reaction is heated for a further 16 hours at 70° C. The reaction is cooled to room temperature. The beads are purified using a filter frit with the following wash solvents; methanol, water, aqueous solution of HCl, water, aqueous

TABLE 29

| Unique ID | Preformed amine polymer | Step 1 xlinker | Swelling | SGF | SIB-Cl | SIB-P | SOB-Cl (2 h) | SOB-P (2 h) | SOB-Cl (24 h) | SOB-P (24 h) |
|---|---|---|---|---|---|---|---|---|---|---|
| 018022-A2 FA | 018013-A1 FA | DCE | 1.7 | 14.9 | 4.0 | 4.6 | 4.9 | 0.3 | NM | NM |
| 015032-A1 FA | 015026-A1 FA | DCE | 1.4 | 13.2 | 6.1 | 1.5 | 0.5 | 0.0 | 1.9 | 0.1 |
| 015032-B2 FA | 015026-A1 FA | DCE | 1.2 | 13.0 | 6.1 | 1.5 | 1.4 | 0.1 | 2.3 | 0.1 |
| 002064-B4 FA | 002054-A3 FA | DC2OH | 3.1 | 12.1 | 1.7 | 5.6 | 1.3 | 1.4 | NM | NM |
| 002064-B5 FA | 002054-A3 FA | DC2OH | 2.7 | 12.3 | 1.7 | 5.5 | 1.8 | 1.4 | NM | NM |

SGF, SIB and SOB values expressed in mmol/g dry weight;
NM: not measured solution of sodium hydroxide and 3 water washes or until the filtrate measures a pH of 7.

What is claimed is:

1. A process for the preparation of a crosslinked amine polymer, the process comprising (i) swelling a preformed crosslinked amine polymer with a swelling agent, wherein the preformed crosslinked amine polymer is a copolymer comprising the residues of (a) 2-Propen-1-ylamine or a salt thereof and (b) 1,3-Bis(allylamino)propane or a salt thereof and (ii) further crosslinking the preformed crosslinked amine polymer to form the crosslinked amine polymer in a reaction mixture comprising a crosslinking agent and the swelling agent, wherein the preformed crosslinked amine polymer has an absorption capacity for the swelling agent, the amount of swelling agent in the reaction mixture is less than the absorption capacity of the preformed crosslinked amine polymer for the swelling agent, the weight ratio of the swelling agent to the preformed crosslinked amine polymer in the reaction mixture is less than 1:1, and the swelling agent is water, and wherein the crosslinked amine polymer has a chloride ion binding capacity of at least 4 mmol/q, and a phosphate ion binding capacity of less than 2 mmol/g, in a Simulated Small Intestine Buffer ("SIB") assay wherein, in the SIB assay, the crosslinked amine polymer is combined with a SIB buffer consisting of 36 mM NaCl, 20 mM $NaH_2PO_4$ and 50 mM 2-(N-morpholino)ethanesulfonic acid (MES) buffered to pH 5.5 at a concentration of 2.5 mg/ml (25 mg dry mass of the crosslinked amine polymer) in 10 mL of the buffer, and the combination is incubated at 37° C. for 1 hour with agitation on a rotisserie mixer.

2. The process of claim 1 wherein the weight ratio of the swelling agent to the preformed crosslinked amine polymer in the reaction mixture is less than 0.5:1.

3. The process of claim 1 wherein the crosslinking agent is a dichloroalkane.

4. The process of claim 1 wherein the crosslinking agent is dichloroethane or dichloropropane.

5. The process of claim 1 wherein the crosslinked amine polymer has (i) a proton-binding capacity and a chloride binding capacity of at least 5 mmol/g in a Simulated Gastric Fluid ("SGF") assay wherein, in the SGF assay, the crosslinked amine polymer is combined with a SGF buffer consisting of 35 mM NaCl and 63 mM HCl at pH 1.2 at a concentration of 2.5 mg/ml (25 mg dry mass of the crosslinked amine polymer) in 10 mL of the SGF buffer, and the combination is incubated at 37° C. for 12-16 hours with agitation on a rotisserie mixer.

6. The process of claim 1 wherein the crosslinks in the preformed crosslinked amine polymer are primarily carbon-carbon crosslinks and nitrogen-nitrogen crosslinks are primarily formed in the further crosslinking step.

7. The process of claim 1 wherein the preformed crosslinked amine polymer has a chloride binding capacity of at least 10 mmol/g in a Simulated Gastric Fluid ("SGF") assay wherein, in the SGF assay, the preformed crosslinked amine polymer is combined with a SGF buffer consisting of 35 mM NaCl and 63 mM HCl at pH 1.2 at a concentration of 2.5 mg/ml (25 mg dry mass of the crosslinked amine polymer) in 10 mL of the SGF buffer, and the combination is incubated at 37° C. for 12-16 hours with agitation on a rotisserie mixer, and a Swelling Ratio in the range of 2 to 10, and the binding capacity of the crosslinked amine polymer for phosphate in the SIB assay is less than a binding capacity of the preformed crosslinked amine polymer for phosphate in the SIB assay.

8. The process of claim 1 wherein the weight ratio of the swelling agent to the preformed crosslinked amine polymer in the reaction mixture is at least 0.15:1.

9. The process of claim 1 wherein the weight ratio of the swelling agent to the preformed crosslinked amine polymer in the reaction mixture is less than 0.4:1 but at least 0.15:1, respectively.

10. The process of claim 1 wherein the weight ratio of the swelling agent to the preformed crosslinked amine polymer in the reaction mixture is less than 0.3:1 but at least 0.15:1, respectively.

11. The process of claim 1 wherein the reaction mixture comprises a solvent to disperse the preformed crosslinked amine polymer in the reaction mixture, the ratio of the solvent to the preformed crosslinked amine polymer in the reaction mixture is at least 3:1 (milliliters of solvent:grams of preformed crosslinked amine polymer), the crosslinking agent and the solvent are the same, and the swelling agent and the solvent are immiscible.

* * * * *